(12) United States Patent
Curtiss, III et al.

(10) Patent No.: US 9,297,015 B2
(45) Date of Patent: *Mar. 29, 2016

(54) REGULATED EXPRESSION OF ANTIGEN AND/OR REGULATED ATTENTUATION TO ENHANCE VACCINE IMMUNOGENICITY AND/OR SAFETY

(71) Applicants: Roy Curtiss, III, Paradise Valley, AZ (US); Shifeng Wang, Tempe, AZ (US); Soo-Young Wanda, Chandler, AZ (US); Wei Kong, Phoenix, AZ (US)

(72) Inventors: Roy Curtiss, III, Paradise Valley, AZ (US); Shifeng Wang, Tempe, AZ (US); Soo-Young Wanda, Chandler, AZ (US); Wei Kong, Phoenix, AZ (US)

(73) Assignees: Arizona Board of Regents for and on behalf of Arizona State University, Tempe, AZ (US); The Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/789,665

(22) Filed: Mar. 7, 2013

(65) Prior Publication Data

US 2013/0171190 A1    Jul. 4, 2013

Related U.S. Application Data

(63) Continuation of application No. 12/615,872, filed on Nov. 10, 2009, now Pat. No. 8,445,254, which is a continuation-in-part of application No. PCT/US2008/063293, filed on May 9, 2008.

(60) Provisional application No. 60/917,313, filed on May 10, 2007.

(51) Int. Cl.
| | | |
|---|---|---|
| A61K 35/74 | (2015.01) | |
| C12N 15/74 | (2006.01) | |
| C12N 1/36 | (2006.01) | |
| A61K 39/00 | (2006.01) | |

(52) U.S. Cl.
CPC ............... *C12N 15/74* (2013.01); *A61K 35/74* (2013.01); *A61K 39/00* (2013.01); *C12N 1/36* (2013.01); *A61K 2039/522* (2013.01)

(58) Field of Classification Search
USPC .......... 435/252.3, 320.1, 471; 536/23.1, 23.7, 536/24.1, 24.2
See application file for complete search history.

(56) References Cited

U.S. PATENT DOCUMENTS

| | | |
|---|---|---|
| 4,190,495 A | 2/1980 | Curtiss, III |
| 4,888,170 A | 12/1989 | Curtiss, III |
| 4,968,619 A | 11/1990 | Curtiss, III |
| 5,210,035 A | 5/1993 | Stocker |
| 5,294,441 A | 3/1994 | Curtiss, III |
| 5,387,744 A | 2/1995 | Curtiss, III et al. |
| 5,389,368 A | 2/1995 | Gurtiss, III |
| 5,424,065 A | 6/1995 | Curtiss, III et al. |
| 5,468,485 A | 11/1995 | Curtiss, III |
| 5,536,658 A | 7/1996 | Shotts, Jr. et al. |
| 5,654,184 A | 8/1997 | Curtiss, III et al. |
| 5,656,488 A | 8/1997 | Curtiss, III et al. |
| 5,672,345 A | 9/1997 | Curtiss, III |
| 5,679,880 A | 10/1997 | Curtiss, III et al. |
| 5,686,079 A | 11/1997 | Curtiss, III et al. |
| 5,695,983 A | 12/1997 | Miller et al. |
| 5,817,317 A | 10/1998 | Titball et al. |
| 5,827,705 A | 10/1998 | Dean |
| 5,840,483 A | 11/1998 | Curtiss, III |
| 5,855,879 A | 1/1999 | Curtiss III |
| 5,855,880 A | 1/1999 | Curtiss, III et al. |
| 5,888,799 A | 3/1999 | Curtiss, III |
| 5,919,663 A | 7/1999 | Brey et al. |
| 5,961,983 A | 10/1999 | Brey et al. |
| 6,010,705 A | 1/2000 | Thune et al. |
| 6,024,961 A | 2/2000 | Curtiss, III et al. |
| 6,180,614 B1 | 1/2001 | Davis |
| 6,248,329 B1 | 6/2001 | Chandrashekar et al. |
| 6,350,454 B1 | 2/2002 | Thune |
| 6,383,496 B1 | 5/2002 | Curtiss, III et al. |
| 6,399,074 B1 | 6/2002 | Roland |
| 6,403,094 B1 | 6/2002 | Titball et al. |
| 6,610,529 B1 | 8/2003 | Curtiss, III et al. |
| 6,780,405 B1 | 8/2004 | Curtiss, III et al. |
| 6,872,547 B1 | 3/2005 | Curtiss, III |
| 6,969,513 B2 | 11/2005 | Galen |
| 7,083,794 B2 | 8/2006 | Curtiss, III et al. |
| 7,195,757 B2 | 3/2007 | Curtiss, III et al. |
| 7,205,125 B2 | 4/2007 | Castillo et al. |
| 7,341,860 B2 | 3/2008 | Curtiss, III et al. |
| 7,871,604 B1 | 1/2011 | Curtiss, III et al. |
| 7,968,101 B2 | 6/2011 | Kawaoka et al. |
| 8,133,493 B2 | 3/2012 | Curtiss, III |

(Continued)

FOREIGN PATENT DOCUMENTS

| | | |
|---|---|---|
| WO | 88/09669 A1 | 12/1988 |
| WO | 89/03427 A1 | 4/1989 |

(Continued)

OTHER PUBLICATIONS

Song et al (J Bacteriol. Nov. 1997. 179(22): 7025-7032).*

(Continued)

*Primary Examiner* — Jennifer Graser
(74) *Attorney, Agent, or Firm* — Polsinelli PC

(57) ABSTRACT

The invention relates to compositions and methods for making and using recombinant bacteria that are capable of regulated attenuation and/or regulated expression of one or more antigens of interest.

16 Claims, 78 Drawing Sheets

(9 of 78 Drawing Sheet(s) Filed in Color)

(56) References Cited

U.S. PATENT DOCUMENTS

| | | | |
|---|---|---|---|
| 8,445,254 | B2 | 5/2013 | Curtiss, III et al. |
| 8,465,755 | B2 | 6/2013 | Curtiss, III et al. |
| 8,889,121 | B2 | 11/2014 | Curtiss, III et al. |
| 9,040,059 | B2 | 5/2015 | Curtiss, III et al. |
| 9,045,742 | B2 | 6/2015 | Curtiss, III et al. |
| 9,050,285 | B2 | 6/2015 | Curtiss, III et al. |
| 9,062,297 | B2 | 6/2015 | Curtiss, III et al. |
| 2002/0177569 | A1 | 11/2002 | Kaufmann et al. |
| 2003/0031683 | A1 | 2/2003 | Curtiss, III et al. |
| 2003/0175772 | A1 | 9/2003 | Wang |
| 2004/0077556 | A1 | 4/2004 | Chinery |
| 2004/0101531 | A1 | 5/2004 | Curtiss, III et al. |
| 2004/0120962 | A1 | 6/2004 | Curtiss, III et al. |
| 2004/0137003 | A1 | 7/2004 | Curtiss, III |
| 2004/0203039 | A1 | 10/2004 | Hensel et al. |
| 2005/0036987 | A1 | 2/2005 | Pawelek et al. |
| 2005/0106175 | A1 | 5/2005 | Montaines et al. |
| 2005/0106176 | A1* | 5/2005 | Curtis et al. ............... 424/200.1 |
| 2005/0118193 | A1 | 6/2005 | Andino-Pavlovsky et al. |
| 2005/0214911 | A1* | 9/2005 | Marchenko et al. .......... 435/106 |
| 2006/0140975 | A1 | 6/2006 | Curtiss, III et al. |
| 2006/0171917 | A1 | 8/2006 | Campbell et al. |
| 2006/0206961 | A1 | 9/2006 | Cirpus et al. |
| 2006/0233829 | A1 | 10/2006 | Curtiss, III |
| 2006/0234346 | A1 | 10/2006 | Retallack et al. |
| 2006/0275255 | A1 | 12/2006 | Gudkov |
| 2007/0025981 | A1 | 2/2007 | Szalay et al. |
| 2008/0096809 | A1 | 4/2008 | Shai |
| 2008/0248066 | A1 | 10/2008 | Dubensky et al. |
| 2009/0175829 | A1 | 7/2009 | Forbes et al. |
| 2010/0124558 | A1 | 5/2010 | Curtiss, III et al. |
| 2010/0255022 | A1 | 10/2010 | Prescott et al. |
| 2010/0285592 | A1 | 11/2010 | Curtiss, III et al. |
| 2010/0303863 | A1 | 12/2010 | Curtiss, III et al. |
| 2010/0317084 | A1 | 12/2010 | Curtiss, III |
| 2011/0033501 | A1 | 2/2011 | Curtiss, III et al. |
| 2011/0256177 | A1 | 10/2011 | Curtiss, III et al. |
| 2011/0256181 | A1 | 10/2011 | Curtiss, III et al. |
| 2011/0287052 | A1 | 11/2011 | Curtiss, III et al. |
| 2012/0087946 | A1 | 4/2012 | Curtiss, III et al. |
| 2013/0004537 | A1 | 1/2013 | Curtiss, III et al. |
| 2013/0171190 | A1 | 7/2013 | Curtiss, III et al. |
| 2013/0209405 | A1 | 8/2013 | Curtiss, III et al. |
| 2014/0370057 | A1 | 12/2014 | Curtiss, III et al. |
| 2015/0056232 | A1 | 2/2015 | Curtiss, III |

FOREIGN PATENT DOCUMENTS

| | | | |
|---|---|---|---|
| WO | 90/02484 | A1 | 3/1990 |
| WO | 90/11687 | A1 | 10/1990 |
| WO | 90/11688 | A1 | 10/1990 |
| WO | 90/12086 | A1 | 10/1990 |
| WO | 91/06317 | A1 | 5/1991 |
| WO | 92/08486 | A1 | 5/1992 |
| WO | 92/09684 | A1 | 6/1992 |
| WO | 93/04202 | A1 | 3/1993 |
| WO | 94/24291 | A2 | 10/1994 |
| WO | 96/40947 | A1 | 12/1996 |
| WO | 99/25387 | A1 | 5/1999 |
| WO | 01/83785 | A2 | 11/2001 |
| WO | 02/26251 | A1 | 4/2002 |
| WO | 02/30457 | A2 | 4/2002 |
| WO | 02/059292 | A2 | 8/2002 |
| WO | 03/079792 | A1 | 10/2003 |
| WO | 03/096812 | A1 | 12/2003 |
| WO | 03/102160 | A2 | 12/2003 |
| WO | 2004/020643 | A2 | 3/2004 |
| WO | 2005/001069 | A1 | 1/2005 |
| WO | WO2006/061174 | * | 6/2006 |
| WO | 2007/058663 | A2 | 5/2007 |
| WO | 2008/141226 | A2 | 11/2008 |
| WO | 2008/150969 | A1 | 12/2008 |
| WO | 2009/025888 | A2 | 2/2009 |
| WO | 2009/046449 | A1 | 4/2009 |
| WO | 2009/046451 | A1 | 4/2009 |
| WO | 2010/045620 | A1 | 4/2010 |
| WO | 2010/078584 | A1 | 7/2010 |
| WO | 2010/135563 | A1 | 11/2010 |
| WO | 2011/091291 | A1 | 7/2011 |
| WO | 2011/150421 | A2 | 12/2011 |
| WO | 2012/087483 | A1 | 6/2012 |
| WO | 2013/151731 | A1 | 10/2013 |

OTHER PUBLICATIONS

Malley et al., "CD4+ T cells mediate antibody-independent acquired immunity to pneumococcal colonization", PNAS, 2005, pp. 4848-4853, vol. 102, No. 13.

Marshall et al., "Use of the stationary phase inducible promoters, spv and dps, to drive heterologous antigen expression in *Salmonella* vaccine strains", Vaccine, 2000, pp. 1298-1306, vol. 18.

Massin et al., "Cloning of the Chicken RNA Polymerase I Promoter and Use for Reverse Genetics of Influenza A Viruses in Avian Cells", Journal of Virology, 2005, pp. 13811-13816, vol. 79, No. 21.

Matthay et al., "Evaluation of the Opsonic Requirements for Phagocytosis of Streptococcus pneumoniae Serotypes VII, XIV, and XIX by Chemiluminescence Assay", Infection and Immunity, 1981, pp. 228-235, vol. 31, No. 1.

McClelland et al., "Complete genome sequence of *Salmonella enterica* serovar Typhimurium LT2", Nature, 2001, pp. 852-856, vol. 413.

McDaniel et al., "Monoclonal Antibodies Against Protease-Sensitive Pneumococcal Antigens Can Protect Mice from Fatal Infection with Streptococcus pneumoniae", J. Exp. Med., 1984, pp. 368-397, vol. 160.

McDaniel et al., "Use of Insertional Inactivation to Facilitate Studies of Biological Properties of Pneumococcal Surface Protein A (PspA)", J. Exp. Med., 1987, pp. 381-394, vol. 165.

Medina et al., "Use of live bacterial vaccine vectors for antigen delivery: potential and limitations", Vaccine, 2001, pp. 1573-1580, vol. 19.

Mehigh et al., "Expression of the low calcium response in Yersinia pestis", Microbial Pathogenesis, 1989, pp. 203-217, vol. 6.

Mesika et al., "A Regulated, NF κB-Assisted Import of Plasmid DNA into Mammalian Cell Nuclei", Molecular Therapy, 2001, pp. 653-657, vol. 3, No. 5.

Miller et al., "A Novel Suicide Vector and Its Use in Construction of Insertion Mutations: Osmoregulation of Outer Membrane Proteins and Virulence Determinants in Vibrio cholerae Requires toxR", Journal of Bacteriology, 1988, pp. 2575-2583, vol. 170, No. 6.

Miller et al., "Bacteriophage T4 Genome", Microbiology and Molecular Biology Reviews, 2003, pp. 86-156, vol. 67, No. 1.

Molinari et al., "The annual impact of seasonal influenza in the US: Measuring disease burden and costs", Vaccine, 2007, pp. 5086-5096, vol. 25.

Moore et al., "Enhanced protective immunity against pneumococcal infection with PspA DNA and protein", Vaccine, 2006, pp. 5755-5761, vol. 24.

Moreno et al., "*Salmonella* as Live Trojan Horse for Vaccine Development and Cancer Gene Therapy", Current Gene Therapy, 2010, pp. 56-76, vol. 10, No. 1.

Morita et al., "Antibacterial Activity of Bacillus amyloliquefaciencs Phage Endolysin without Holin Conjugation", Journal of Bioscience and Bioengineering, 2001, pp. 469-473, vol. 91, No. 5.

Mossing et al., "Upstream Operators Enhance Repression of the lac Promoter", Science, 1986, pp. 889-892, vol. 233, No. 4766.

Motin et al., "Passive Immunity to Yersiniae Mediated by Anti-Recombinant V Antigen and Protein A-V Antigen Fusion Peptide", Infection and Immunity, 1994, pp. 4192-4201, vol. 62, No. 10.

Muller et al., "Repression of lac Promoter as a Function of Distance, Phase and Quality of an Auxiliary lac Operator", J. Mol. Biol., 1996, pp. 21-29, vol. 257.

Muller-Hill et al., "Mutants That Make More Lac Repressor", Proc. Natl. Acad. Sci. USA, 1968, pp. 1259-1264, vol. 59, No. 4.

Muller-Hill, "Lac Repressor and Lac Operator", Prog. Biophys. Molec. Biol., 1975, pp. 227-252, vol. 30, No. 2-3.

(56) References Cited

OTHER PUBLICATIONS

Mulvey et al., "Regulation of Transcription of katE and katF in *Escherichia coli*", Journal of Bacteriology, 1990, pp. 6713-6720, vol. 172, No. 12.

Murti et al., "Localization of RNA Polymerases on Influenza Viral Ribonucleoproteins by Immunogold Labeling", Virology, 1988, pp. 562-566, vol. 164.

Nabors et al., "Immunization of healthy adults with a single recombinant pneumococcal surface protein A (PspA) variant stimulates broadly cross-reactive antibodies to heterologous PspA molecules", Vaccine, 2000, pp. 1743-1754, vol. 18.

Nagy et al., "Down-Regulation of Key Virulence Factors Makes the *Salmonella enterica* Serovar Typhimurium rfaH Mutant a Promising Live-Attenuated Vaccine Candidate", Infection and Immunity, 2006, pp. 5914-5925, vol. 74, No. 10.

Nakayama et al., "Construction of an Asd+ Expression-Cloning Vector: Stable Maintenance and High Level Expression of Cloned Genes in a Salmonella Vaccine Strain", Bio/Technology, 1988, pp. 693-697, vol. 6.

Nardelli-Haefliger et al., "Human Papillomavirus Type 16 Virus-Like Particles Expressed in Attenuated *Salmonella* typhimurium Elicit Mucosal and Systemic Neutralizing Antibodies in Mice", Infection and Immunity, 1997, pp. 3328-3336, vol. 65, No. 8.

Navasa et al., "Temperature has reciprocal effects on colanic acid and polysialic acid biosynthesis in *E. coli* K92", Appl. Microbiol. Biotechnol., 2009, pp. 721-729, vol. 82.

Nayak et al., "A Live Recombinant Avirulent Oral *Salmonella* Vaccine Expressing Pneumococcal Surface Protein A Induces Protective Responses against Streptococcus pneumoniae", Infection and Immunity, 1998, pp. 3744-3751, vol. 66. No. 8.

Nedialkov et al., "Resistance to Lipopolysaccharide Mediated by the Yersinia pestis V Antigen-Polyhistidine Fusion Peptide: Amplification of Interleukin-10", Infection and Immunity, 1997, pp. 1196-1203, vol. 65, No. 4.

Neumann et al., "RNA Polymerase I-Mediated Expression of Influenza Viral RNA Molecules", Virology, 1994, pp. 477-479, vol. 202.

Neumann et al., "Generation of influenza A viruses entirely from cloned cDNAs", Proc. Natl. Acad. Sci. USA, 1999, pp. 9345-9350, vol. 96.

Neumann et al., "An improved reverse genetics system for influenza A virus generation and its implications for vaccine production", Proc. Natl. Acad. Sci. USA, 2005, pp. 16825-16829, vol. 102, No. 46.

Neutra et al., "Antigen Sampling Across Epithelial Barriers and Induction of Mucosal Immune Responses", Annu. Rev. Immunol., 1996, pp. 275-300, vol. 14.

Nickerson et al., "Role of Sigma Factor RpoS in Initial Stages of *Salmonella* typhimurium Infection", Infection and Immunity, 1997, pp. 1814-1823, vol. 65, No. 5.

Nieto et al., "Complex structure of the nuclear translocation signal of influenza virus polymerase PA subunit", Journal of General Virology, 1994, pp. 29-36, vol. 75.

Noda et al., "Architecture of ribonucleoprotein complexes in influenza A virus particles", Nature, 2006, pp. 490-492, vol. 439.

O'Callaghan et al., "High efficiency transformation of *Salmonella* typhimurium and *Salmonella* typhi by electroporation", Mol Gen Genet, 1990, pp. 156-158, vol. 223.

Oehler et al., "The three operators of the lac operon cooperate in repression", The EMBO Journal, 1990, pp. 973-979, vol. 9, No. 4.

Ogunniyi et al., "Contributions of Pneumolysin, Pneumococcal Surface Protein A (PspA), and PspC to Pathogenicity of Streptococcus pneumoniae D39 in a Mouse Model", Infection and Immunity, 2007, pp. 1843-1851, vol. 75, No. 4.

Olekhnovich et al., "Crucial Roles of Both Flanking Sequences in Silencing of the hilA promoter in *Salmonella enterica*", J. Mol. Biol., 2006, pp. 373-386, vol. 357.

Ortqvist et al., "Randomised trial of 23-valent pneumococcal capsular polysaccharide vaccine in prevention of pneumonia in middle-aged and elderly people", The Lancet, 1998, pp. 399-403, vol. 351.

Osterholm, "Preparing for the Next Pandemic", The New England Journal of Medicine, 2005, pp. 1839-1842, vol. 352, No. 18.

Ozaki et al., "Generation of High-Yielding Influenza a Viruses in African Green Monkey Kidney (Vero) Cells by Reverse Genetics", Journal of Virology, 2004, pp. 1851-1857, vol. 78, No. 4.

Office Action from related U.S. Appl. No. 12/599,655, dated Mar. 12, 2013; 24 pgs.

Office Action from related U.S. Appl. No. 12/599,655, dated Jul. 2, 2012; 18 pgs.

Notice of Allowance from related U.S. Appl. No. 12/615,872, dated Jan. 16, 2013; 6 pgs.

Office Action from related U.S. Appl. No. 12/615,872, dated Mar. 14, 2012; 9 pgs.

Office Action from related U.S. Appl. No. 12/615,872, dated Oct. 23, 2012; 14 pgs.

Galan et al., "Cloning and molecular characterization of genes whose products allow *Salmonella* typhimurium to penetrate tissue culture cells", Proc. Natl. Acad. Sci. USA, 1989, pp. 6383-6387, vol. 86.

Galen et al., "Optimization of Plasmid Maintenance in the Attenuated Live Vector Vaccine Strain *Salmonella* typhi CVD 908-htrA", Infection and Immunity, 1999, pp. 6424-6433, vol. 67, No. 12.

Galen et al., "Can a 'flawless' live vector vaccine strain be engineered?", Trends in Microbiology, 2001, pp. 372-376, vol. 9, No. 8.

Garmory et al., "The Use of Live Attenuated Bacteria as a Delivery System for Heterologous Antigens", Journal of Drug Targeting, 2003, pp. 471-479, vol. 11, No. 8-10.

Garmory et al., "Antibiotic-Free Plasmid Stabilization by Operator-Repressor Titration for Vaccine Delivery by Using Live *Salmonella enterica* Serovar Typhimurium", Infection and Immunity, 2005, pp. 2005-2011, vol. 73, No. 4.

Garzon et al., "recB recJ mutants of *Salmonella* typhimurium are deficient in transductional recombination, DNA repair and plasmid maintenance", Mol. Gen. Genet., 1996, pp. 570-580, vol. 250.

Gay et al., "Positive Selection Procedure for Entrapment of Insertion Sequence Elements in Gram-Negative Bacteria", Journal of Bacteriology, 1985, pp. 918-921, vol. 164, No. 2.

Gentry et al., "Mutational analysis of the *Escherichia coli* spoT gene identifies distinct but overlapping regions involved in ppGpp synthesis and degradation", Molecular Microbiology, 1996, pp. 1373-1384, vol. 19, No. 6.

Gentschev et al., "Delivery of the p67 Sporozoite Antigen of Theileria parva by Using Recombinant *Salmonella* dublin: Secretion of the Product Enhances Specific Antibody Responses in Cattle", Infection and Immunity, 1998, pp. 2060-2064, vol. 66, No. 5.

Gentschev et al., "The *E. coli* α-hemolysin secretion system and its use in vaccine development", Trends in Microbiology, 2002, pp. 39-45, vol. 10, No. 1.

Gerdil, "The annual production cycle for influenza vaccine", Vaccine, 2003, pp. 1776-1779, vol. 21.

Ghany et al., "Candidate Live, Attenuated *Salmonella enterica* Serotype Typhimurium Vaccines with Reduced Fecal Shedding Are Immunogenic and Effective Oral Vaccines", Infection and Immunity, 2007, pp. 1835-1842, vol. 75, No. 4.

Giannella et al., "Gastric Acidity and Cholera", Annals of Internal Medicine, 1973, pg. 780, vol. 78, No. 5.

Gilbert, "The lac repressor and the lac operator", Ciba Found Symp, 1972, pp. 245-259, vol. 7.

Gong et al., "Characterization of the Yersinia pestis Yfu ABC Inorganic Iron Transport System", Infection and Immunity, 2001, pp. 2829-2837, vol. 67, No. 5.

Gor et al., "TH1-TH2: a Procrustean paradigm", Nature Immunology, 2003, pp. 503-505, vol. 4, No. 6.

Greenspan et al., "Defining epitopes: It's not as easy as it seems", Nature Biotechnology, 1999, pp. 936-937, vol. 17.

Greenwood, "The epidemiology of pneumococcal infection in children in the developing world", Phil. Trans. R. Soc. Lond. B, 1999, pp. 777-785, vol. 354.

Grillot-Courvalin et al., "Functional gene transfer from intracellular bacteria to mammalian cells", Nature Biotechnology, 1998, pp. 862-866, vol. 16.

Guerrant et al., "Magnitude and Impact of Diarrheal Diseases", Archives of Medical Research, 2002, pp. 351-355, vol. 33.

Gulig et al., "Plasmid-Associated Virulence of *Salmonella* typhimurium", Infection and Immunity, 1987, pp. 2891-2901, vol. 55, No. 12.

(56) References Cited

OTHER PUBLICATIONS

Gunn, "Mechanisms of bacterial resistance and response to bile", Microbes and Infection, 2000, pp. 907-913, vol. 2.
Guzman et al., "Tight Regulation, Modulation, and High-Level Expression by Vectors Containing the Arabinose PBAD Promoter", Journal of Bacteriology, 1995, pp. 4121-4130, vol. 177, No. 14.
Hall et al., "The Role of Fur in the Acid Tolerance Response of *Salmonella* typhimurium Is Physiologically and Genetically Separable from Its Role in Iron Acquisition", Journal of Bacteriology, 1996, pp. 5683-5691, vol. 178, No. 19.
Hanisch et al., "The Ralstonia eutropha H16 phasin PhaP1 is targeted to intracellular triacylglycerol inclusions in Rhodococcus opacus PD630 and Mycobacterium smegmatis mc2155, and provides an anchor to target other proteins", Microbiology, 2006, pp. 3271-3280, vol. 152.
Hengge-Aronis et al., "Identification and molecular analysis of glgS, a novel growth-phase-regulated and rpoS-dependent gene involved in glycogen synthesis in *Escherichia coli*", Molecular Microbiology, 1992, pp. 1877-1886, vol. 6, No. 14.
Hess et al., "Superior efficacy of secreted over somatic antigen display in recombinant *Salmonella* vaccine induced protection against listeriosis", Proc. Natl. Acad. Sci. USA, 1996, pp. 1458-1463, vol. 93.
Hess et al., "Secretion of different listeriolysin cognates by recombinant attenuated *Salmonella* typhimurium: superior efficacy of haemolytic over non-haemolytic constructs after oral vaccination", Microbes and Infection, 2000, pp. 1799-1806, vol. 2.
Hicks et al., "Incidence of Pneumococcal Disease Due to Non-Pneumococcal Conjugate Vaccine (PCV7) Serotypes in the United States during the Era of Widespread PCV7 Vaccination, 1998-2004", The Journal of Infectious Diseases, 2007, pp. 1346-1354, vol. 196.
Hitchcock et al., "Morphological Heterogeneity Among *Salmonella* Lipopolysaccharide Chemotypes in Silver-Stained Polyacrylamide Gels", Journal of Bacteriology, 1983, pp. 269-277, vol. 154, No. 1.
Hoffmann et al., ""Ambisense" Approach for the Generation of Influenza A Virus: vRNA and mRNA Synthesis from One Template", Virology, 2000, pp. 310-317, vol. 267.
Hohmann et al., "Macrophage-inducible expression of a model antigen in *Salmonella* typhimurium enhances immunogenicity", Proc. Natl. Acad. Sci. USA, 1995, pp. 2904-2908, vol. 92.
Hohmann et al., "Evaluation of a phoP/phoQ-deleted, aroA-deleted live oral *Salmonella* typhi vaccine strain in human volunteers", Vaccine, 1996, pp. 19-24, vol. 14, No. 1.
Hollingshead et al., "Diversity of PspA: Mosaic Genes and Evidence for Past Recombination in Streptococcus pneumoniae", Infection and Immunity, 2000, pp. 5889-5900, vol. 68, No. 10.
Hopkins et al., "A Recombinant *Salmonella* typhimurium Vaccine Induces Local Immunity by Four Different Routes of Immunization", Infection and Immunity, 1995, pp. 3279-3286, vol. 63, No. 9.
Hori et al., "Construction of self-disruptive Bacillus megaterium in response to substrate exhaustion for polyhydroxybutryrate production", Appl Microbiol Biotechnol, 2002, pp. 211-216, vol. 59.
Houghten et al., "Relative Importance of Position and Individual Amino Acid Residues in Peptide Antigen-Antibody Interactions: Implications in the Mechanism of Antigenic Drift and Antigenic Shift", Vaccines, 1986, pp. 21-25, vol. 86.
Houng et al., "Expression of Vi Antigen in *Escherichia coli* K-12: Characterization of ViaB from Citrobacter freundii and Identity of ViaA with RcsB", Journal of Bacteriology, 1992, pp. 5910-5915, vol. 174, No. 18.
Hu et al., "The Inducible lac Operator-Repressor System Is Functional in Mammalian Cells", Cell, 1987, pp. 555-566, vol. 48.
Hu et al., "The inducible lac operator-repressor system is functional for control of expression of injected DNA in Xenopus oocytes", Gene, 1988, pp. 301-313, vol. 62.
Huang et al., "Genome-Wide Screen of *Salmonella* Genes Expressed during Infection in Pigs, Using In Vivo Expression Technology", Applied and Environmental Microbiology, 2007, pp. 7522-7530, vol. 73, No. 23.

Hurme et al., "A Proteinaceous Gene Regulatory Thermometer in *Salmonella*", Cell, 1997, pp. 55-64, vol. 90.
Iannelli et al., "Allelic variation in the highly polymorphic locus pspC of Streptococcus pneumoniae", Gene, 2002, pp. 63-71, vol. 284.
Instructions to Authors, from The Journal of Bacteriology, 2015, pp. 1-18, downloaded from http://journalitas.asm.org/t/49543 on Feb. 13, 2015.
Isoda et al., "Expression of a Porphyromonas gingivalis hemagglutinin on the surface of a *Salmonella* vaccine vector", Vaccine, 2007, pp. 117-126, vol. 25.
Ivancic-Bace et al., "Effects of recJ, recQ, and recFOR Mutations on Recombination in Nuclease-Deficient recB recD Double Mutants of *Escherichia coli*", Journal of Bacteriology, 2005, pp. 1350-1356, vol. 187, No. 4.
Iwasaki et al., "Epitope-specific cytotoxic T lymphocyte induction by minigene DNA immunization", Vaccine, 1999, pp. 2081-2088, vol. 17.
Jin et al., "Multiple amino acid residues confer temperature sensitivity to human influenza virus vaccine strains (FluMist) derived from cold-adapted A/Ann Arbor/6/60", Virology, 2003, pp. 18-24, vol. 306.
International Search Report and Written Opinion from related International Application No. PCT/US08/63303, dated Nov. 26, 2008; 7 pgs.
International Search Report and Written Opinion from related International Application No. PCT/US08/78991, dated Dec. 15, 2008; 7 pgs.
International Search Report and Written Opinion from related International Application No. PCT/US08/78993, dated Dec. 15, 2008; 6 pgs.
International Search Report and Written Opinion from related International Application No. PCT/US08/63293, dated Feb. 12, 2009; 9 pgs.
International Search Report and Written Opinion from related International Application No. PCT/US09/61100, dated Dec. 4, 2009; 8 pgs.
International Search Report and Written Opinion from related International Application No. PCT/US10/20137, dated Mar. 9, 2010; 10 pgs.
International Search Report and Written Opinion from related International Application No. PCT/US10/35630, dated Sep. 29, 2010; 13 pgs.
International Search Report and Written Opinion from related International Application No. PCT/US11/22110, dated Apr. 11, 2011; 8 pgs.
International Search Report and Written Opinion from related International Application No. PCT/US11/38588, dated Nov. 22, 2011; 10 pgs.
International Search Report and Written Opinion from related International Application No. PCT/US2011/061896, dated Apr. 5, 2012; 7 pgs.
International Search Report and Written Opinion from related International Application No. PCT/US13/31592, dated May 22, 2013; 9 pgs.
Kang et al., "Immune Responses to Recombinant Pneumococcal PspA Antigen Delivered by Live Attenuated *Salmonella enterica* Serovar Typhimurium Vaccine", Infection and Immunity, 2002, pp. 1739-1749, vol. 70, No. 4.
Kang et al., "Transduction-Mediated Transfer of Unmarked Deletion and Point Mutations through Use of Counterselectable Suicide Vectors", Journal of Bacteriology, 2002, pp. 307-312, vol. 184, No. 1.
Kang et al., "Immune responses dependent on antigen location in recombinant attenuated *Salmonella* typhimurium vaccines following oral immunization", FEMS Immunology and Medical Microbiology, 2003, pp. 99-104, vol. 37.
Katzman et al., "Invertebrate Connective Tissue. Isolation of D-Arabinose From Sponge Acidic Polysaccharide", Biochem. J., 1970, pp. 17-19, vol. 119.
Kaufmann et al., "Impact of intracellular location of and antigen display by intracellular bacteria: implications for vaccine development", Immunology Letters, 1999, pp. 81-84, vol. 65.

(56) References Cited

OTHER PUBLICATIONS

Kennedy et al., "Attenuation and Immunogenicity of Δcya Δcrp Derivatives of Salmonella choleraesuis in Pigs", Infection and Immunity, 1999, pp. 4628-4636, vol. 67, No. 9.

Khan et al., "Immunogenicity and protective efficacy of DnaJ (hsp40) of Streptococcus pneumoniae against lethal infection in mice", Vaccine, 2006, pp. 6225-6231, vol. 24.

Kilbourne, "Studies on Influenza in the Pandemic of 1957-1958. III. Isolation of Influenza A (Asian Strain) Viruses From Influenza Patients With Pulmonary Complications. Details of Virus Isolation and Characterization of Isolates, With Quantitative Comparison of Isolation Methods", J. Clin. Invest., 1959, pp. 266-274, vol. 38.

Kim et al., "Direct Transcriptional Control of the Plasminogen Activator Gene of Yersinia Pestis by the Cyclic AMP Receptor Protein", Journal of Bacteriology, 2007, pp. 8890-8900, vol. 189, No. 24.
Klumpp et al., "Roles of the influenza virus polymerase and nucleoprotein in forming a functional RNP structure", The EMBO Journal, 1997, pp. 1248-1257, vol. 16, No. 6.
Kolodrubetz et al., "Regulation of the L-Arabinose Transport Operons in *Escherichia coli*", J. Mol. Biol., 1981, pp. 215-227, vol. 151, No. 2.
Kong et al., "Improving DNA Vaccine Vector for Efficient Vaccine Delivery Using Live Attenuated Bacterial Carrier", American Society for Microbiology, General Meeting, Abstract No. T-010, 2008, p. 668, vol. 108.
Kong et al., "Regulated programmed lysis of recombinant *Salmonella* in host tissues to release protective antigens and confer biological containment", PNAS, 2008, pp. 9361-9366, vol. 105, No. 27.
Kong et al., "Regulated Delayed Expression of rfaH in an Attenuated *Salmonella enterica* Serovar Typhimurium Vaccine Enhances Immunogenicity of Outer Membrane Proteins and a Heterologous Antigen", Infection and Immunity, 2009, pp. 5572-5582, vol. 77, No. 12.
Kong et al., "*Salmonella* Synthesizing 1-Monophosphorylated Lipopolysaccharide Exhibits Low Endotoxic Activity while Retaining Its Immunogenicity", The Journal of Immunology, 2011, pp. 412-423, vol. 187.
Konjufca et al., "A Recombinant Attenuated *Salmonella enterica* Serovar Typhimurium Vaccine Encoding Eimeria acervulina Antigen Offers Protection against E. acervulina Challenge", Infection and Immunity, 2006, pp. 6785-6796, vol. 74, No. 12.
Konjufca et al., "Immunogenicity of Recombinant Attenuated *Salmonella enterica* Serovar Typhimurium Vaccine Strains Carrying a Gene That Encodes Eimeria tenella Antigen SO7", Infection and Immunity, 2008, pp. 5745-5753, vol. 76, No. 12.
Kotton et al., "Enteric Pathogens as Vaccine Vectors for Foreign Antigen Delivery", Infection and Immunity, 2004, pp. 5535-5547, vol. 72, No. 10.
Kwon et al., "*Salmonella*-based vaccines for infectious diseases", Expert Review of Vaccines, 2007, pp. 147-152, vol. 6, No. 2.
Lange et al., "Identification of a central regulator of stationary-phase gene expression in *Escherichia coli*", Molecular Microbiology, 1991, pp. 49-59, vol. 5, No. 1.
Lee et al., "Mechanism of araC autoregulation and the domains of two overlapping promoters, PC and PBAD, in the L-arabinose regulatory region of *Escherichia coli*", Proc. Natl. Acad. Sci. USA, 1981, pp. 752-756, vol. 78, No. 2.
Lee et al., "Regulation of L-Arabinose Transport in *Salmonella* typhimurium LT2", Mol Gen Genet, 1982, pp. 136-141, vol. 185.
Lee et al., "The stationary-phase sigma factor σS (RpoS) is required for a sustained acid tolerance response in virulent *Salmonella* typhimurium", Molecular Microbiology, 1995, pp. 155-167, vol. 17, No. 1.
Lee et al., "Surface-displayed viral antigens on *Salmonella* carrier vaccine", Nature Biotechnology, 2000, pp. 645-648, vol. 18, No. 6.
Lee et al., "Trigger Factor Retards Protein Export in *Escherichia coli*", The Journal of Biological Chemistry, 2002, pp. 43527-43535, vol. 277, No. 45.
Lee et al., "Characterization of recent H5 subtype avian influenza viruses from US poultry", Avian Pathology, 2004, pp. 288-297, vol. 33, No. 3.
Lefeber et al., "Th1-Directing Adjuvants Increase the Immunogenicity of Oligosaccharide-Protein Conjugate Vaccines Related to *Streptococcus* pneumoniae Type 3", Infection and Immunity, 2003, pp. 6915-6920, vol. 71, No. 12.
Lefman et al., "Three-Dimensional Electron Microscopic Imaging of Membrane Invaginations in *Escherichia coli* Overproducing the Chemotaxis Receptor Tsr", Journal of Bacteriology, 2004, pp. 5052-5061, vol. 186, No. 15.
Lewis, "The lac repressor", C. R. Biologies, 2005, pp. 521-548, vol. 328.
Li et al., "A sopB Deletion Mutation Enhances the Immunogenicity and Protective Efficacy of a Heterologous Antigen Delivered by Live Attenuated *Salmonella enterica* Vaccines", Infection and Immunity, 2008, pp. 5238-5246, vol. 76, No. 11.
Lobell et al., "AraC-DNA Looping: Orientation and Distance-dependent Loop Breaking by the Cyclic AMP Receptor Protein", J. Mol. Biol., 1991, pp. 45-54, vol. 218.
Lobocka et al., "Organization and Expression of the *Escherichia coli* K-12 dad Operon Encoding the Smaller Subunit of D-Amino Acid Dehydrogenase and the Catabolic Alanine Racemase", Journal of Bacteriology, 1994, pp. 1500-1510, vol. 176, No. 5.
Loessner et al., "Bacteria-mediated DNA transfer in gene therapy and vaccination", Expert Opinion Biol. Ther., 2004, pp. 157-168, vol. 4, No. 2.
Loessner et al., "Differential effect of auxotrophies on the release of macromolecules by *Salmonella enterica* vaccine strains", FEMS Microbiol. Lett, 2006, pp. 81-88, vol. 265.
Loessner et al., "Remote control of tumour-targeted *Salmonella enterica* serovar Typhimurium by the use of L-arabinose as inducer of bacterial gene expression in vivo", Cellular Microbiology, 2007, pp. 1529-1537, vol. 9, No. 6.
Loewen et al., "Genetic Mapping of katF, a Locus That with katE Affects the Synthesis of a Second Catalase Species in *Escherichia coli*", Journal of Bacteriology, 1984, pp. 668-675, vol. 160, No. 2.
Luytjes et al., "Amplification, Expression, and Packaging of a Foreign Gene by Influenza Virus", Cell, 1989, pp. 1107-1113, vol. 59.
Whitfield, "Biosynthesis and Assembly of Capsular Polysaccharides in *Escherichia coli*", Annu. Rev. Biochem., 2006, pp. 39-68, vol. 75.
Whitworth et al., "Expression of the Rickettsia prowazekii pld or tlyC Gene in *Salmonella enterica* Serovar Typhimurium Mediates Phagosomal Escape", Infection and Immunity, 2005, pp. 6668-6673, vol. 73, No. 10.
Wilmes-Riesenberg et al., "Role of Acid Tolerance Response in Virulence of *Salmonella* typhimurium", Infection and Immunity, 1996, pp. 1085-1092, vol. 64, No. 4.
Winter et al., "The *Salmonella enterica* serotype Typhi regulator TviA reduces interleukin-8 production in intestinal epithelial cells by repressing flagellin secretion", Cell Microbiology, 2008, pp. 247-261, vol. 10, No. 1.
Wolf et al., "Evolution of Aminoacyl-tRNA Synthetases-Analysis of Unique Domain Architectures and Phylogenetic Trees Reveals a Complex History of Horizontal Gene Transfer Events", Genome Research, 1999, pp. 689-710, vol. 9.
Wu et al., "The Mechanism Underlying T Cell Help for Induction of an Antigen-Specific in Vivo Humoral Immune Response to Intact *Streptococcus pneumoniae* Is Dependent on the Type of Antigen", The Journal of Immunology, 2002, pp. 5551-5557, vol. 168.
Xiao et al., "Residual Guanosine 3',5' -Bispyrophosphate Synthetic Activity of relA Null Mutants Can Be Eliminated by spoT Null Mutations", The Journal of Biological Chemistry, 1991, pp. 5980-5990, vol. 266, No. 9.
Xin et al., "Analysis of Type II Secretion of Recombinant Pneumococcal PspA and PspC in a *Salmonella enterica* Serovar Typhimurium Vaccine with Regulated Delayed Antigen Synthesis", Infection and Immunity, 2008, pp. 3241-3254, vol. 76, No. 7.
Zahn, "Overexpression of an mRNA Dependent on Rare Codons Inhibits Protein Synthesis and Cell Growth", Journal of Bacteriology, 1996, pp. 2926-2933, vol. 178, No. 10.

(56) References Cited

OTHER PUBLICATIONS

Zahorchak et al., "Effect of Exogenous Nucleotides on Ca2+ Dependence and V Antigen Synthesis in Yersinia pestis", Infection and Immunity, 1982, pp. 953-959, vol. 38, No. 3.
Zhang et al., "Transcription Activation Parameters at ara pBAD", J. Mol. Biol., 1996, pp. 14-24, vol. 258, No. 1.
Zhang et al., "Characterization and Immunogenicity of Salmonella typhimurium SL1344 and UK-1 Δcrp and Δcdt Deletion Mutants", Infection and Immunity, 1997, pp. 5381-5387, vol. 65, No. 12.
Zhang et al., "A One-Plasmid System to Generate Influenza Virus in Cultured Chicken Cells for Potential Use in Influenza Vaccine", Journal of Virology, 2009, pp. 9296-9303, vol. 83, No. 18.
Zinkernagel et al., "Antigen localisation regulates immune responses in a dose- and time-dependent fashion: a geographical view of immune reactivity", Immunological Reviews, 1997, pp. 199-209, vol. 156.
Zobel et al., "RNA polymerase I catalysed transcription of insert viral cDNA", Nucleic Acids Research, 1993, pp. 3607-3614, vol. 21, No. 16.
Rytkonen et al., "SseL, a Salmonella deubiquitinase required for macrophage killing and virulence", PNAS, 2007, pp. 3502-3507, vol. 104, No. 9.
Sadler et al., "A perfectly symmetric lac operator binds the lac repressor very tightly", Proc. Natl. Acad. Sci. USA, 1983, pp. 6785-6789, vol. 80.
Saeland et al., "Serum Samples from Infants Vaccinated with a Pneumococcal Conjugate Vaccine, PncT, Protect Mice against Invasive Infection Caused by Streptococcus pneumoniae Serotypes 6A and 6B", Journal of Infectious Diseases, 2001, pp. 253-260, vol. 183.
Sarubbi et al., "Characterization of the spoT gene of Escherichia coli", The Journal of Biological Chemistry, 1989, pp. 15074-15082, vol. 264, No. 25.
Schleif, "Two Positively Regulated Systems, ara and mal", in Escherichia coli and Salmonella, cellular and molecular biology, eds. F. C. Neidhardt et al. ASM Press, Washington, D.C., pp. 1300-1309.
Schmieger, "Phage P22-Mutants with Increased or Decreased Transduction Abilities", Molec. gen. Genet., 1972, pp. 75-88, vol. 119.
Schmieger et al., "Altered Cotransduction Frequencies Exhibited by HT-Mutants of Salmonella-Phage P22", Molec. gen. Genet., 1976, pp. 307-309, vol. 143.
Schnaitman et al., "Genetics of Lipopolysaccharide Biosynthesis in Enteric Bacteria", Microbiological Reviews, 1993, pp. 655-682, vol. 57, No. 3.
Schödel, "Prospects for Oral Vaccination Using Recombinant Bacteria Expressing Viral Epitopes", Advances in Virus Research, 1992, pp. 409-446, vol. 41.
Schödel, "Recombinant Avirulent Salmonellae as Oral Vaccine Carriers", Infection, 1992, pp. 1-8, vol. 20, No. 1.
Schödel et al., "Hybrid Hepatitis B Virus Core-Pre-S Proteins Synthesized in Avirulent Salmonella typhimurium and Salmonella typhi for Oral Vaccination", Infection and Immunity, 1994, pp. 1669-1676, vol. 62, No. 5.
Schödel et al., "Hybrid Hepatitis B Virus Core Antigen as a Vaccine Carrier Moiety, II. Expression in Avirulent Salmonella spp. for Mucosal Immunization", Adv Exp Med Biol., 1996, pp. 15-21, vol. 397.
Schuchat et al., "Bacterial Meningitis in the United States in 1995", The New England Journal of Medicine, 1997, pp. 970-976, vol. 337, No. 14.
Schulman et al., "Independent Variation in Nature of Hemagglutinin and Neuraminidase Antigens of Influenza Virus: Distinctiveness of Hemagglutinin Antigen of Hong Kong/68 Virus", Proc. Natl. Acad. Sci. USA, 1969, pp. 326-333, vol. 63.
Schwyn et al., "Universal Chemical Assay for the Detection and Determination of Siderophores", Analytical Biochemistry, 1987, pp. 47-56, vol. 160.
Sedgwick et al., "A Solid-Phase Immunoenzymatic Technique for the Enumeration of Specific Antibody-Secreting Cells", Journal of Immunological Methods, 1983, pp. 301-309, vol. 57.
Shalaby, "Short Analytical Review: Development of Oral Vaccines to Stimulate Mucosal and Systemic Immunity: Barriers and Novel Strategies", Clinical Immunology and Immunopathology, 1995, pp. 127-134, vol. 74, No. 2.
Sheehan et al., "Generation and Characterization of Hamster Monoclonal Antibodies That Neutralize Murine Tumor Necrosis Factors", The Journal of Immunology, 1989, pp. 3884-3893, vol. 142.
Siegele et al., "Gene expression from plasmids containing the araBAD promoter at subsaturating inducer concentrations represents mixed populations", Proc. Natl. Acad. Sci. USA, 1997, pp. 8168-8172, vol. 94.
Simonsen et al., "The Impact of Influenza Epidemics on Hospitalizations", The Journal of Infectious Diseases, 2000, pp. 831-837, vol. 181.
Sizemore et al., "Attenuated bacteria as a DNA delivery vehicle for DNA-mediated immunization", Vaccine, 1997, pp. 804-807, vol. 15, No. 8.
Skjot et al., "Comparative Evaluation of Low-Molecular-Mass Proteins from Mycobacterium tuberculosis Identifies Members of the ESAT-6 Family as Immunodominant T-Cell Antigens", Infection and Immunity, 2000, pp. 214-220, vol. 68, No. 1.
Snapper et al., "Distinct types of T-cell help for the induction of a humoral immune response to Streptococcus pneumoniae", Trends in Immunology, 2001, pp. 308-311, vol. 22, No. 6.
Sodeinde et al., "Plasminogen Activator/Coagulase Gene of Yersinia pestis Is Responsible for Degradation of Plasmid-Encoded Outer Membrane Proteins", Infection and Immunity, 1988, pp. 2749-2752, vol. 56, No. 10.
Song et al., "Organization and Regulation of the D-Xylose Operons in Escherichia coli K-12: XylR Acts as a Transcriptional Activator", Journal of Bacteriology, 1997, pp. 7025-7032, vol. 179, No. 22.
Spellberg et al., "Type 1/Type 2 Immunity in Infectious Diseases", Clin. Infect. Dis., 2001, pp. 76-102, vol. 32.
Srinivasan et al., "Oral Immunization with Attenuated Salmonella Expressing Human Sperm Antigen Induces Antibodies in Serum and the Reproductive Tract", Biology of Reproduction, 1995, pp. 462-471, vol. 53.
Steel et al., "Live Attenuated Influenza Viruses Containing NS1 Truncations as Vaccine Candidates against H5N1 Highly Pathogenic Avian Influenza", Journal of Virology, 2009, pp. 1742-1753, vol. 83, No. 4.
Sternberg et al., "Bacteriophage-Mediated Generalized Transduction in Escherichia coli and Salmonella typhimurium", Methods in Enzymology, 1991, pp. 18-43, vol. 204.
Stevens et al., "Immunization with the C-Domain of α-Toxin Prevents Lethal Infection, Localizes Tissue Injury, and Promotes Host Response to Challenge with Clostridium perfringens", Journal of Infectious Diseases, 2004, pp. 767-773, vol. 190.
Straley et al., "Virulence Genes Regulated at the Transcriptional Level by Ca2+ in Yersinia pestis Include Structural Genes for Outer Membrane Proteins", Infection and Immunity, 1986, pp. 445-454, vol. 51, No. 2.
Sun et al., "Highly Efficient Method for Introducing Successive Multiple Scarless Gene Deletions and Markerless Gene Insertions into the Yersinia pestis Chromosome", Applied and Environmental Microbiology, 2008, pp. 4241-4245, vol. 74, No. 13.
Sun et al., "The Role of relA and spoT in Yersinia pestis KIM5+ Pathogenicity", PLoS ONE, 2009, e6720, pp. 1-14, vol. 4, No. 8.
Tacket et al., "Safety and Immunogenicity in Humans of an Attenuated *Salmonella typhi* Vaccine Vector Strain Expressing Plasmid-Encoded Hepatitis B Antigens Stabilized by the Asd-Balanced Lethal Vector System", Infection and Immunity, 1997, pp. 3381-3385, vol. 65, No. 8.
Takaya et al., "The ATP-Dependent Lon Protease of *Salmonella enterica* Serovar Typhimurium Regulates Invasion and Expression of Genes Carried on *Salmonella* Pathogenicity Island 1", Journal of Bacteriology, 2002, pp. 224-232, vol. 184, No. 1.
Taubenberger et al., "1918 Influenza: the Mother of All Pandemics", Emerging Infectious Diseases, 2006, pp. 15-22, vol. 12, No. 1.

(56) References Cited

OTHER PUBLICATIONS

Thompson et al., "The Bacterial Signal Molecule, ppGpp, Mediates the Environmental Regulation of Both the Invasion and Intracellular Virulence Gene Programs of *Salmonella*", The Journal of Biological Chemistry, 2006, pp. 30112-30121, vol. 281, No. 40.
Török et al., "Accumulation of ppGpp in a relA Mutant of *Escherichia coli* during Amino Acid Starvation", The Journal of Biological Chemistry, 1980, pp. 3838-3840, vol. 255, No. 9.
Tu et al., "The PhoP/PhoQ two-component system stabilizes the alternative sigma factor RpoS in *Salmonella enterica*", PNAS, 2006, pp. 13503-13508, vol. 103, No. 36.
Tumpey et al., "Characterization of the Reconstructed 1918 Spanish Influenza Pandemic Virus", Science, 2005, pp. 77-80, vol. 310.
Une et al., "In Vivo Comparison of Avirulent Vwa- and Pgm- or Pstr Phenotypes of Yersiniae", Infection and Immunity, 1984, pp. 895-900, vol. 43, No. 3.
Uzzau et al., "Epitope tagging of chromosomal genes in *Salmonella*", PNAS, 2001, pp. 15264-15269, vol. 98, No. 26.
van Rossum et al., "Host and Bacterial Factors Contributing to the Clearance of Colonization by *Streptococcus pneumoniae* in a Murine Model", Infection and Immunity, 2005, pp. 7718-7726, vol. 73, No. 11.
Van Velkinburgh et al., "PhoP-PhoQ-Regulated Loci Are Required for Enhanced Bile Resistance in *Salmonella* spp.", Infection and Immunity, 1999, pp. 1614-1622, vol. 67, No. 4.
Verjan et al., "Genetic Loci of Major Antigenic Protein Genes of *Edwardsiella tarda*", Applied and Environmental Microbiology, 2005, pp. 5654-5658, vol. 71, No. 9.
Viboud et al., "Yersinia Outer Proteins: Role in Modulation of Host Cell Signaling Responses and Pathogenesis", Annu. Rev. Microbiol., 2005, pp. 69-89, vol. 59.
Waltman et al., "Biochemical Characteristics of *Edwardsiella ictaluri*", Applied and Environmental Microbiology, 1986, pp. 101-104, vol. 51, No. 1.
Wang et al., "Hemagglutinin (HA) Proteins from H1 and H3 Serotypes of Influenza a Viruses Require Different Antigen Designs for the Induction of Optimal Protective Antibody Responses as Studied by Codon-Optimized HA DNA Vaccines", Journal of Virology, 2006, pp. 11628-11637, vol. 80, No. 23.
Wasserman et al., "Two Alanine Racemase Genes in *Salmonella typhimurium* That Differ in Structure and Function", Journal of Bacteriology, 1983, pp. 1439-1450, vol. 153, No. 3.
Webster et al., "Evolution and Ecology of Influenza A Viruses", Microbiological Reviews, 1992, pp. 152-179, vol. 56, No. 1.
Notice of Allowance from related U.S. Appl. No. 12/681,711, dated Oct. 30, 2014; 13 pgs.
Office Action from related U.S. Appl. No. 12/681,711, dated Nov. 28 2012; 14 pgs.
Office Action from related U.S. Appl. No. 12/681,711, dated Jan. 31, 2012; 10 pgs.
Notice of Allowance from related U.S. Appl. No. 121681,721, dated Nov. 21, 2012; 13 pgs.
Office Action from related U.S. Appl. No. 12/681,721, dated May 24, 2012; 13 pgs.
Notice of Allowance from related U.S. Appl. No. 12/759,842, dated Apr. 22, 2015; 7 pgs.
Office Action from related U.S. Appl. No. 12/759,842, dated Nov. 28, 2014; 10 pgs.
Office Action from related U.S. Appl. No. 12/759,842, dated Jun. 7, 2012; 12 pgs.
Office Action from related U.S. Appl. No. 12/759,842, dated Oct. 4, 2011; 9 pgs.
Notice of Allowance from related U.S. Appl. No. 12/789,869, dated Jan. 22, 2015; 8 pgs.
Office Action from related U.S. Appl. No. 12/789,869, dated Oct. 30, 2014; 16 pgs.
Office Action from related U.S. Appl. No. 12/789,869, dated Jun. 3, 2014; 14 pgs.
Office Action from related U.S. Appl. No. 12/789,869, dated Dec. 7, 2011; 27 pgs.
Office Action from related U.S. Appl. No. 12/789,869, dated Mar. 22, 2011; 22 pgs.
Notice of Allowance from related U.S. Appl. No. 131006,072, dated Feb. 13, 2015; 8 pgs.
Office Action from related U.S. Appl. No. 13/006,072, dated Oct. 20, 2014; 15 pgs.
Office Action from related U.S. Appl. No. 13/006,072, dated Dec. 11, 2012; 14 pgs.
Office Action from related U.S. Appl. No. 13/006,072, dated Apr. 19, 2012; 12 pgs.
Notice of Allowance from related U.S. Appl. No. 13/088,141, dated Jan. 28, 2015; 11 pgs.
Office Action from related U.S. Appl. No. 13/088,141, dated Apr. 24, 2014; 11 pgs.
Office Action from related U.S. Appl. No. 13/088,141, dated Dec. 6, 2012; 9 pgs.
Office Action from related U.S. Appl. No. 13/302,575, dated May 1, 2015; 20 pgs.
Office Action from related U.S. Appl. No. 13/302,575, dated Oct. 31, 2014; 23 pgs.
Office Action from related U.S. Appl. No. 13/302,575, dated Jun. 18, 2013; 17 pgs.
Office Action from related U.S. Appl. No. 13/302,575, dated Sep. 25 2012; 13 pgs.
Notice of Allowance from related U.S. Appl. No. 13/574,718, dated Jul. 16, 2014; 7 pgs.
Office Action from related U.S. Appl. No. 13/574,718, dated Apr. 28, 2014; 16 pgs.
Office Action from related U.S. Appl. No. 13/574,718, dated Sep. 6, 2013; 14 pgs.
Office Action from related U.S. Appl. No. 13/700,591, dated Feb. 26, 2015; 24 pgs.
Office Action from related U.S. Appl. No. 13/700,591, dated Apr. 2, 2014; 17 pgs.
Office Action from related U.S. Appl. No. 14,390,306, dated Apr. 23, 2015; 14 pgs.
Park et al., "Engineered viral vaccine constructs with dual specificity: Avian influenza and Newcastle disease", PNAS, 2006, pp. 8203-8208, vol. 103, No. 21.
Pascual et al., "Expression of Recombinant Enterotoxigenic *Escherichia coli* Colonization Factor Antigen I by *Salmonella typhimurium* Elicits a Biphasic T Helper Cell Response", Infection and Immunity, 1999, pp. 6249-6256, vol. 67, No. 12.
Pashine et al., "Th1 dominance in the immune response to live *Salmonella typhimurium* requires bacterial invasiveness but not persistence", International Immunology, 1999, pp. 481-489, vol. 11, No. 4.
Perry et al., "Temperature Regulation of the Hemin Storage (Hms+) Phenotype of Yersinia pestis Is Posttranscriptional", Journal of Bacteriology, 2004, pp. 1638-1647, vol. 186, No. 6.
Petersen et al., "Essential Role for Cyclic AMP and Its Receptor Protein in Yersinia enterocolitica Virulence", Infection and Immunity, 2002, pp. 3665-3672, vol. 70, No. 7.
Peterson et al., "RpoS Proteolysis Is Regulated by a Mechanism That Does Not Require the SprE (RssB) Response Regulator Phosphorylation Site", Journal of Bacteriology, 2004, pp. 7403-7410, vol. 186, No. 21.
Pickard et al., "Characterization of Defined ompR Mutants of *Salmonella typhi*: ompR Is Involved in the Regulation of Vi Polysaccharide Expression", Infection and Immunity, 1994, pp. 3984-3993, vol. 62, No. 9.
Pizarro-Cerda et al., "The bacterial signal molecule, ppGpp, regulates *Salmonella* virulence gene expression", Molecular Microbiology, 2004, pp. 1827-1844, vol. 52, No. 6.
Prouty et al., "*Salmonella enterica* Serovar Typhimurium Invasion Is Repressed in the Presence of Bile", Infection and Immunity, 2000, pp. 6763-6769, vol. 68, No. 12.
Quenee et al., "Yersinia pestis caf1 Variants and the Limits of Plague Vaccine Protection", Infection and Immunity, 2008, pp. 2025-2036, vol. 76, No. 5.
Quinlivan et al., "Attenuation of Equine Influenza Viruses through Truncations of the NS1 Protein", Journal of Virology, 2005, pp. 8431-8439, vol. 79, No. 13.

(56) References Cited

OTHER PUBLICATIONS

Ramarathinam et al., "*Salmonella typhimurium* Induces IFN-γ Production in Murine Splenocytes, Role of Natural Killer Cells and Macrophages", Journal of Immunology, 1993, pp. 3973-3981, vol. 150, No. 9.

Rand, "Crystal violet can be used to visualize DNA bands during gel electrophoresis and to improve cloning efficiency", Technical Tips Online, 1996, pp. 23-24, vol. 1, www.sciencedirect.com.

Raupach et al., "Bacterial virulence, proinflammatory cytokines and host immunity: how to choose the appropriate *Salmonella* vaccine strain?", Microbes and Infection, 2001, pp. 1261-1269, vol. 3.

Reed et al., "The W-Beijing Lineage of Mycobacterium tuberculosis Overproduces Triglycerides and Has the DosR Dormancy Regulon Constitutively Upregulated", Journal of Bacteriology, 2007, pp. 2583-2589, vol. 189, No. 7.

Ribeiro et al., "The role of polyadenylation signal secondary structures on the resistance of plasmid vectors to nucleases", The Journal of Gene Medicine, 2004, pp. 565-573, vol. 6.

Roberts et al., "Oral Vaccination against Tetanus: Comparison of the Immunogenicities of *Salmonella* Strains Expressing Fragment C from the nirB and htrA Promoters", Infection and Immunity, 1998, pp. 3080-3087, vol. 66, No. 7.

Roland et al., "Construction and Evaluation of a Δcya Δcrp *Salmonella typhimurium* Strain Expressing Avian Pathogenic *Escherichia coli* O78 LPS as a Vaccine to Prevent Airsacculitis in Chickens", Avian Diseases, 1999, pp. 429-441, vol. 43.

Romeo et al., "Genetic Regulation of Glycogen Biosynthesis in *Escherichia coli*: In Vitro Effects of Cyclic AMP and Guanosine 5'-Diphosphate 3'-Diphosphate and Analysis of In Vivo Transcripts", Journal of Bacteriology, 1989, pp. 2773-2782, vol. 171, No. 5.

Curtiss III et al., "*Salmonella typhimurium* Deletion Mutants Lacking Adenylate Cyclase and Cyclic AMP Receptor Protein Are Avirulent and Immunogenic", Infection and Immunity, 1987, pp. 3035-3043, vol. 55, No. 12.

Curtiss III et al., "Avirulent *Salmonella typhimurium* Δcya Δcrp oral vaccine strains expressing a streptococcal colonization and virulence antigen", Vaccine, 1988, pp. 155-160, vol. 6, No. 2.

Curtiss III et al., "Stabilization of Recombinant Avirulent Vaccine Strains in vivo", Research in Microbiology, 1990, pp. 797-805, vol. 141.

Curtiss III et al., "Live oral avirulent *Salmonella* vaccines", Veterinary Microbiology, 1993, pp. 397-405, vol. 37.

Curtiss III et al., "Recombinant *Salmonella* Vectors in Vaccine Development", Dev Biol Stand., 1994, pp. 23-33, vol. 82.

Curtiss III et al., "Nonrecombinant and recombinant avirulent *Salmonella* vaccines for poultry", Veterinary Immunology and Immunopathology, 1996, pp. 365-372, vol. 54.

Curtiss III, "Bacterial infectious disease control by vaccine development", The Journal of Clinical Investigation, 2002, pp. 1061-1066, vol. 110, No. 8.

Curtiss III et al., "*Salmonella enterica* Serovar Typhimurium Strains with Regulated Delayed Attenuation in Vivo", Infection and Immunity, 2009, pp. 1071-1082, vol. 77, No. 3.

Curtiss III et al., "New Technologies in Using Recombinant Attenuated *Salmonella* Vaccine Vectors", Critical Reviews in Immunology, 2010, pp. 255-270, vol. 30, No. 3.

Daigle et al., "Identification of *Salmonella typhi* genes expressed within macrophages by selective capture of transcribed sequences (SCOTS)", Molecular Microbiology, 2001, pp. 1211-1222, vol. 41, No. 5.

Darzins et al., "Nucleotide sequence analysis of the phosphomannose isomerase gene (pmi) of Pseudomonas aeruginosa and comparison with the corresponding *Escherichia coli* gene manA", Gene., 1986, pp. 293-302, vol. 42.

Datsenko et al., "One-step inactivation of chromosomal genes in *Escherichia coli* K-12 using PCR products", PNAS, 2000, pp. 6640-6645, vol. 97, No. 12.

Davison, "Towards safer vectors for the field release of recombinant bacteria", Environ. Biosafety Res., 2002, pp. 9-18, vol. 1.

Dean, "Import of Plasmid DNA into the Nucleus Is Sequence Specific", Experimental Cell Research, 1997, pp. 293-302, vol. 230.

De Groote et al., "Homocysteine Antagonism of Nitric Oxide-Related Cytostasis in *Salmonella typhimurium*", Science, 1996, pp. 414-417, vol. 272.

DeKruyff et al., "Induction of immunoglobulin synthesis by CD4+ T cell clones", Seminars in Immunology, 1993, pp. 421-430, vol. 5.

Del Beccaro et al., "Bacteriology of acute otitis media: A new perspective", The Journal of Pediatrics, 1992, pp. 81-84, vol. 120, No. 1.

Deng et al., "Genome Sequence of Yersinia pestis KIM", Journal of Bacteriology, 2002, pp. 4601-4611, vol. 184, No. 16.

Doggett et al., "Delivery of Antigens by Recombinant Avirulent *Salmonella* Strains", Adv. Exp. Med. Biol., 1992, pp. 165-173, vol. 327.

Doggett et al., "Immune Responses to *Streptococcus sobrinus* Surface Protein Antigen A Expressed by Recombinant *Salmonella typhimurium*", Infection and Immunity, 1993, pp. 1859-1866, vol. 61, No. 5.

Doublet et al., "The murI Gene of *Escherichia coli* Is an Essential Gene That Encodes a Glutamate Racemase Activity", Journal of Bacteriology, 1993, pp. 2970-2979, vol. 175, No. 10.

Dubnau, "DNA Uptake in Bacteria", Annual Review of Microbiology, 1999, pp. 217-244, vol. 53.

Dunstan et al., "Comparison of the Abilities of Different Attenuated *Salmonella typhimurium* Strains To Elicit Humoral Immune Responses against a Heterologous Antigen", Infection and Immunity, 1998, pp. 732-740, vol. 66, No. 2.

Dusek et al., "Systemic and Mucosal Immune Responses in Mice Orally Immunized with Avirulent *Salmonella typhimurium* Expressing a Cloned Porphyromonas gingivalis Hemagglutinin", Infection and Immunity, 1994, pp. 1652-1657, vol. 62, No. 5.

Edwards et al., "Improved allelic exchange vectors and their use to analyze 987P fimbria gene expression", Gene, 1998, pp. 149-157, vol. 207.

Egan et al., "A Regulatory Cascade in the Induction of rhaBAD", Journal of Molecular Biology, 1993, pp. 87-98, vol. 234.

Egorov et al., "Transfectant Influenza A Viruses with Long Deletions in the NS1 Protein Grow Efficiently in Vero Cells", Journal of Virology, 1998, pp. 6437-6441, vol. 72, No. 8.

Ellis, "New Technologies for Making Vaccines", Vaccines, 1988, pp. 568-575, Chapter 29, W. B. Saunders Company, US.

Enami et al., "Introduction of site-specific mutations into the genome of influenza virus", Proc. Natl. Acad. Sci. USA, 1990, pp. 3802-3805, vol. 87.

European Search Report from related European Patent Application No. 08825819.9, dated Sep. 28, 2010; 6 pgs.

European Search Report from related European Patent Application No. 08827622.5, dated Jun. 27, 2011; 7 pgs.

European Patent Application No. 08827622.5, Office Action dated Feb. 22, 2012; 5 pgs.

European Search Report from related European Patent Application No. 11735255.9, dated Jun. 26, 2013; 6 pgs.

European Search Report from related European Patent Application No. 13772423.3, dated Aug. 4, 2015; 7 pgs.

Fodor et al., "Rescue of Influenza A Virus from Recombinant DNA", Journal of Virology, 1999, pp. 9679-9682, vol. 73, No. 11.

Folkesson et al., "Components of the peptidoglycan-recycling pathway modulate invasion and intracellular survival of *Salmonella enterica* serovar Typhimurium", Cellular Microbiology, 2005, pp. 147-155, vol. 7, No. 1.

Fooks, "Development of oral vaccines for human use", Current Opinion in Molecular Therapeutics, 2000, pp. 80-86, vol. 2, No. 1.

Formal et al., "Construction of a Potential Bivalent Vaccine Strain: Introduction of Shigella sonnei Form I Antigen Genes into the galE *Salmonella typhi* Ty21a Typhoid Vaccine Strain", Infection and Immunity, 1981, pp. 746-750, vol. 34, No. 3.

Foster et al., "How *Salmonella* Survive Against the Odds", Annu. Rev. Microbiol., 1995, pp. 145-174, vol. 49.

Fraser et al., "The Amino Acid Composition of T3 Bacteriophage", The Journal of Biological Chemistry, 1953, pp. 291-295, vol. 205, No. 1.

(56) References Cited

OTHER PUBLICATIONS

Fu et al., "Dose Dependence of CTL Precursor Frequency Induced by a DNA Vaccine and Correlation with Protective Immunity Against Influenza Virus Challenge", The Journal of Immunology, 1999, pp. 4163-4170, vol. 162.

Alonso et al., "Anti-Polysaccharide Immunoglobulin Isotype Levels and Opsonic Activity of Antisera: Relationships with Protection against *Streptococcus pneumoniae* Infection in Mice", The Journal of Infectious Diseases, 1995, pp. 562-565, vol. 172, No. 2.

Amann et al., "Tightly regulated tac promoter vectors useful for the expression of unfused and fused proteins in *Escherichia coli*", Gene, 1988, pp. 301-315, vol. 69, No. 2.

Anderson et al., "Delivery of the Pertactin/P.69 polypeptide of Bordetella pertussis using an attenuated *Salmonella typhimurium* vaccine strain: expression levels and immune response", Vaccine, 1996, pp. 1384-1390, vol. 14, No. 14.

Aravind et al., "The HD domain defines a new superfamily of metal-dependent phosphohydrolases", Trends Biochem Sci, 1998, pp. 469-472, vol. 23.

Arricau et al., "The RcsB-RcsC regulatory system of *Salmonella typhi* differentially modulates the expression of invasion proteins, flagellin and Vi antigen in response to osmolarity", Molecular Microbiology, 1998, pp. 835-850, vol. 29, No. 3.

Arulanandam et al., "Intranasal Vaccination with Pneumococcal Surface Protein A and Interleukin-12 Augments Antibody-Mediated Opsonization and Protective Immunity against *Streptococcus pneumoniae* Infection", Infection and Immunity, 2001, pp. 6718-6724, vol. 69, No. 11.

Audia et al., "Breaking through the acid barrier: An orchestrated response to proton stress by enteric bacteria", Int. J. Med. Microbiol., 2001, pp. 97-106, vol. 291.

Baek et al., "Leucine-Responsive Regulatory Protein (Lrp) Acts as a Virulence Repressor in *Salmonella enterica* Serovar Typhimurium", Journal of Bacteriology, 2009, pp. 1278-1292, vol. 191, No. 4.

Bang et al., "OmpR Regulates the Stationary-Phase Acid Tolerance Response of *Salmonella enterica* Serovar Typhimurium", Journal of Bacteriology, 2000, pp. 2245-2252, vol. 182, No. 8.

Bang et al., "Autoinduction of the ompR response regulator by acid shock and control of the *Salmonella enterica* acid tolerance response", Molecular Microbiology, 2002, pp. 1235-1250, vol. 44, No. 5.

Bartlett et al., "Influenza A (H5N1): Will It Be the Next Pandemic Influenza? Are We ready?", Annals of Internal Medicine, 2005, pp. 460-462, vol. 143, No. 6.

Bartlett, "Planning for Avian Influenza", Annals of Internal Medicine, 2006, pp. 141-144, vol. 145, No. 2.

Battesti et al., "Acyl carrier protein/SpoT interaction, the switch linking SpoT-dependent stress response to fatty acid metabolism", Molecular Microbiology, 2006, pp. 1048-1063, vol. 62.

Bearson et al., "A Low pH-Inducible, PhoPQ-Dependent Acid Tolerance Response Protects *Salmonella typhimurium* against Inorganic Acid Stress", Journal of Bacteriology, 1998, pp. 2409-2417, vol. 180, No. 9.

Bertani, "Studies on Lysogenesis: I. The Mode of Phage Liberation by Lysogenic *Escherichia Coli*", Journal of Bacteriology, 1951, pp. 293-300, vol. 62, No. 3.

Bittner et al., "RpoS and RpoN are involved in the growth-dependent regulation of rfaH transcription and O antigen expression in *Salmonella enterica* serovar Typhi.", Microb Pathog., 2004, pp. 19-24, vol. 36, No. 1, Abstract Only.

Black et al., "Aspartic β-Semialdehyde Dehydrogenase and Aspartic β-Semialdehyde", Journal of Biological Chemistry, 1955, pp. 39-50, vol. 213.

Blattner et al., "The Complete Genome Sequence of *Escherichia coli* K-12", Science, 1997, pp. 1453-1474, vol. 277.

Branger et al., "Oral Vaccination with Different Antigens from Yersinia pestis KIM Delivered by Live Attenuated *Salmonella typhimurium* Elicits a Protective Immune Response Against Plague", Adv Exp Med Biol, 2007, pp. 387-399, vol. 603.

Briles et al., "PspA, a protection-eliciting pneumococcal protein: immunogenicity of isolated native PspA in mice", Vaccine, 1996, pp. 858-867, vol. 14, No. 9.

Briles et al., "Immunization of Humans with Recombinant Pneumococcal Surface Protein A (rPspA) Elicits Antibodies That Passively Protect Mice from Fatal Infection with *Streptococcus pneumoniae* Bearing Heterologous PspA", The Journal of Infectious Diseases, 2000, pp. 1694-1701, vol. 182.

Briles et al., "The potential for using protein vaccines to protect against otitis media caused by *Streptococcus pneumoniae*", Vaccine, 2001, pp. S87-S95, vol. 19, Suppl 1.

Brooks-Walter et al., "The pspC Gene of *Streptococcus pneumoniae* Encodes a Polymorphic Protein, PspC, Which Elicits Cross-Reactive Antibodies to PspA and Provides Immunity to Pneumococcal Bacteremia", Infection and Immunity, 1999, pp. 6533-6542, vol. 67, No. 12.

Brosius et al., "Spacing of the −10 and −35 Regions in the tac Promoter, Effect on Its in vivo Activity", The Journal of Biological Chemistry, 1985, pp. 3539-3541, vol. 260, No. 6.

Brown et al., "MurA (MurZ), the Enzyme That Catalyzes the First Committed Step in Peptidoglycan Biosynthesis, Is Essential in *Escherichia coli*", Journal of Bacteriology, 1995, pp. 4194-4197, vol. 177, No. 14.

Brubaker, "Interleukin-10 and Inhibition of Innate Immunity to Yersiniae: Roles of Yops and LcrV (V Antigen)", Infection and Immunity, 2003, pp. 3673-3681, vol. 71, No. 7.

Brubaker, "The Vwa+ Virulence Factor of Yersiniae: The Molecular Basis of the Attendant Nutritional Requirement for Ca++", Reviews of Infectious Diseases, 1983, pp. 5748-5758, vol. 5, Suppl 4.

Brumell et al., "*Salmonella* redirects phagosomal maturation", Current Opinion in Microbiology, 2004, pp. 78-84, vol. 7.

Buchanan et al., "IL-12 Enhances Antibody Responses to T-Independent Polysaccharide Vaccines in the Absence of T and NK Cells", The Journal of Immunology, 1998, pp. 5525-5533, vol. 161.

Buchmeier et al., "DNA Repair Is More Important than Catalase for *Salmonella* Virulence in Mice", J. Clin. Invest., 1995, pp. 1047-1053, vol. 95.

Bumann, "Regulated Antigen Expression in Live Recombinant *Salmonella enterica* Serovar Typhimurium Strongly Affects Colonization Capabilities and Specific CD4+-T-Cell Responses", Infection and Immunity, 2001, pp. 7493-7500, vol. 69, No. 12.

Byl et al., "Sequence of the Genome of *Salmonella* Bacteriophage P22", Journal of Bacteriology, 2000, pp. 6472-6481, vol. 182, No. 22.

Cárdenas et al., "Oral Immunization Using Live Attenuated *Salmonella* spp. as Carriers of Foreign Antigens", Clinical Microbiology Reviews, 1992, pp. 328-342, vol. 5, No. 3.

CDC, "Update: Influenza Activity—United States, Sep. 30, 2007-Apr. 5, 2008, and Composition of the 2008-09 Influenza Vaccine", MMWR: Morbidity & Mortality Weekly Report, 2008, pp. 404-409, vol. 57, No. 15.

Charnetzky et al., "RNA Synthesis in Yersinia pestis During Growth Restriction in Calcium-Deficient Medium", Journal of Bacteriology, 1982, pp. 1089-1095, vol. 149, No. 3.

Chatfield et al., "Use of the nirB Promoter to Direct the Stable Expression of Heterologous Antigens in *Salmonella* Oral Vaccine Strains: Development of a Single-Dose Oral Tetanus Vaccine", Bio/Technology, 1992, pp. 888-892, vol. 10.

Chen et al., "Genetic mapping of the cold-adapted phenotype of B/Ann Arbor/1/66, the master donor virus for live attenuated influenza vaccines (FluMist)", Virology, 2006, pp. 416-423, vol. 345.

Cheng et al., "Simultaneous Analyses of Neutral Carbohydrates and Amino Sugars in Freshwaters with HPLC- PAD", Journal of Chromatographic Science, 2003, pp. 434-438, vol. 41.

Chipman et al., "The ACT domain family", Current Opinion in Structural Biology, 2001, pp. 694-700, vol. 11.

Chromy et al., "Proteomic Characterization of Yersinia pestis Virulence", Journal of Bacteriology, 2005, pp. 8172-8180, vol. 187, No. 23.

(56) References Cited

OTHER PUBLICATIONS

Ciabattini et al., "Primary Activation of Antigen-Specific Naive CD4+ and CD8+ T Cells following Intranasal Vaccination with Recombinant Bacteria", Infection and Immunity, 2008, pp. 5817-5825, vol. 76, No. 12.

Collins et al., "Mutations at rfc or pmi Attenuate *Salmonella typhimurium* Virulence for Mice", Infection and Immunity, 1991, pp. 1079-1085, vol. 59, No. 3.

Coombes et al., "SseL Is a *Salmonella*-Specific Translocated Effector Integrated into the SsrB-Controlled *Salmonella* Pathogenicity Island 2 Type III Secretion System", Infection and Immunity, 2007, pp. 574-580, vol. 75, No. 2.

Cornelis et al., "The Virulence Plasmid of Yersinia, an Antihost Genome", Microbiology and Molecular Biology Reviews, 1998, pp. 1315-1352, vol. 62, No. 4.

Curtiss III, "Chromosomal Aberrations Associated with Mutations to Bacteriophage Resistance in *Escherichia coli*", Journal of Bacteriology, 1965, pp. 28-40, vol. 89, No. 1.

\* cited by examiner

ΔrelA196::araC P<sub>BAD</sub> AGGGTGGTGAAT GTG-*lacI* TT
SD

ΔrelA197::araC P<sub>BAD</sub> AGGATGGTGAAT ATG-*lacI* TT
SD

ΔrelA198::araC P<sub>BAD</sub> AGGATGGTGAAT ATG-*lacI*\* TT
SD

ΔendA::araC P_BAD lacI TT

ΔendA19::araC P_BAD AGGGTGGTGAAT GTG-lacI TT
           SD

ΔendA20::araC P_BAD AGGATGGTGAAT ATG-lacI TT
           SD

ΔendA21::araC P_BAD AGGATGGTGAAT ATG-lacI* TT
           SD

```
                              SD-lacI in  endA19 and  relA196    AGG GTG GTG AAT
                              SD-lacI in  endA20 and  relA197    AGG ATG GTG AAT
                              SD-lacI in  endA21 and  relA198    AGG ATG GTG AAT 13/1                                      43/11
GTG AAA CCA GTA ACG TTA TAC GAT GTC GCA GAG TAT GCC GGT GTC TCT TAT CAG ACC GTT
ATG AAA CCA GTA ACG TTA TAC GAT GTC GCA GAG TAT GCC GGT GTC TCT TAT CAG ACC GTT
ATG AAA CCA GTA ACG TTA TAC GAT GTC GCA GAG TAT GCC GGT GTC TCT TAT CAG ACC GTT
 V   K   P   V   T   L   Y   D   V   A   E   Y   A   G   V   S   Y   Q   T   V
73/21                                     103/31
TCC CGC GTG GTG AAC CAG GCC AGC CAC GTT TCT GCG AAA ACG CGG GAA AAA GTG GAA GCG
TCC CGC GTG GTG AAC CAG GCC AGC CAC GTT TCT GCG AAA ACG CGG GAA AAA GTG GAA GCG
TCC CGC GTG GTG AAC CAG GCC AGC CAC GTT TCT GCG AAA ACG CGT GAA AAA GTG GAA GCG
 S   R   V   V   N   Q   A   S   H   V   S   A   K   T   R   E   K   V   E   A
133/41                                    163/51
GCG ATG GCG GAG CTG AAT TAC ATT CCC AAC CGC GTG GCA CAA CAA CTG GCG GGC AAA CAG
GCG ATG GCG GAG CTG AAT TAC ATT CCC AAC CGC GTG GCA CAA CAA CTG GCG GGC AAA CAG
GCG ATG GCG GAG CTG AAT TAC ATT CCG AAC CGC GTG GCA CAA CAA CTG GCG GGC AAA CAG
 A   M   A   E   L   N   Y   I   P   N   R   V   A   Q   Q   L   A   G   K   Q
193/61                                    223/71
TCG TTG CTG ATT GGC GTT GCC ACC TCC AGT CTG GCC CTG CAC GCG CCG TCG CAA ATT GTC
TCG TTG CTG ATT GGC GTT GCC ACC TCC AGT CTG GCC CTG CAC GCG CCG TCG CAA ATT GTC
TCG TTG CTG ATT GGC GTT GCC ACC TCC AGT CTG GCC CTG CAC GCG CCG TCG CAA ATT GTC
 S   L   L   I   G   V   A   T   S   S   L   A   L   H   A   P   S   Q   I   V
253/81                                    283/91
GCG GCG ATT AAA TCT CGC GCC GAT CAA CTG GGT GCC AGC GTG GTG GTG TCG ATG GTA GAA
GCG GCG ATT AAA TCT CGC GCC GAT CAA CTG GGT GCC AGC GTG GTG GTG TCG ATG GTA GAA
GCG GCG ATT AAA TCT CGC GCC GAT CAA CTG GGT GCC AGC GTG GTG GTG TCG ATG GTA GAA
 A   A   I   K   S   R   A   D   Q   L   G   A   S   V   V   V   S   M   V   E
313/101                                   343/111
CGA AGC GGC GTC GAA GCC TGT AAA GCG GCG GTG CAC AAT CTT CTC GCG CAA CGC GTC AGT
CGA AGC GGC GTC GAA GCC TGT AAA GCG GCG GTG CAC AAT CTT CTC GCG CAA CGC GTC AGT
CGT AGC GGC GTC GAA GCC TGT AAA GCG GCG GTG CAC AAT CTT CTC GCG CAA CGC GTC AGT
 R   S   G   V   E   A   C   K   A   A   V   H   N   L   L   A   Q   R   V   S
373/121                                   403/131
GGG CTG ATC ATT AAC TAT CCG CTG GAT GAC CAG GAT GCC ATT GCT GTG GAA GCT GCC TGC
GGG CTG ATC ATT AAC TAT CCG CTG GAT GAC CAG GAT GCC ATT GCT GTG GAA GCT GCC TGC
GGG CTG ATC ATT AAC TAT CCG CTG GAT GAC CAG GAT GCC ATT GCT GTG GAA GCT GCC TGC
 G   L   I   I   N   Y   P   L   D   D   Q   D   A   I   A   V   E   A   A   C
433/141                                   463/151
ACT AAT GTT CCG GCG TTA TTT CTT GAT GTC TCT GAC CAG ACA CCC ATC AAC AGT ATT ATT
ACT AAT GTT CCG GCG TTA TTT CTT GAT GTC TCT GAC CAG ACA CCC ATC AAC AGT ATT ATT
ACT AAT GTT CCG GCG TTA TTT CTT GAT GTC TCT GAC CAG ACA CCG ATC AAC AGT ATT ATT
 T   N   V   P   A   L   F   L   D   V   S   D   Q   T   P   I   N   S   I   I
493/161                                   523/171
TTC TCC CAT GAA GAC GGT ACG CGA CTG GGC GTG GAG CAT CTG GTC GCA TTG GGT CAC CAG
TTC TCC CAT GAA GAC GGT ACG CGA CTG GGC GTG GAG CAT CTG GTC GCA TTG GGT CAC CAG
TTC TCC CAT GAA GAC GGT ACG CGT CTG GGC GTG GAG CAT CTG GTC GCA TTG GGT CAC CAG
 F   S   H   E   D   G   T   R   L   G   V   E   H   L   V   A   L   G   H   Q
553/181                                   583/191
CAA ATC GCG CTG TTA GCG GGC CCA TTA AGT TCT GTC TCG GCG CGT CTG CGT CTG GCT GGC
CAA ATC GCG CTG TTA GCG GGC CCA TTA AGT TCT GTC TCG GCG CGT CTG CGT CTG GCT GGC
CAA ATC GCG CTG TTA GCG GGC CCA TTA AGT TCT GTC TCG GCG CGT CTG CGT CTG GCT GGC
 Q   I   A   L   L   A   G   P   L   S   S   V   S   A   R   L   R   L   A   G
```

FIG. 3

```
613/201                                         643/211
TGG CAT AAA TAT CTC ACT CGC AAT CAA ATT CAG CCG ATA GCG AAA CGG GAA GGC GAC TGG
TGG CAT AAA TAT CTC ACT CGC AAT CAA ATT CAG CCG ATA GCG AAA CGG GAA GGC GAC TGG
TGG CAT AAA TAT CTC ACT CGC AAT CAA ATT CAG CCG ATC GCG GAA CGT GAA GGC GAC TGG
 W   H   K   Y   L   T   R   N   Q   I   Q   P   I   A   E   R   E   G   D   W
673/221                                         703/231
AGT GCC ATG TCC GGT TTT CAA CAA ACC ATG CAA ATG CTG AAT GAG GGC ATC GTT CCC ACT
AGT GCC ATG TCC GGT TTT CAA CAA ACC ATG CAA ATG CTG AAT GAG GGC ATC GTT CCC ACT
AGT GCC ATG TCC GGT TTT CAA CAA ACC ATG CAA ATG CTG AAT GAG GGC ATC GTT CCG ACT
 S   A   M   S   G   F   Q   Q   T   M   Q   M   L   N   E   G   I   V   P   T
733/241                                         763/251
GCG ATG CTG GTT GCC AAC GAT CAG ATG GCG CTG GGC GCA ATG CGC GCC ATT ACC GAG TCC
GCG ATG CTG GTT GCC AAC GAT CAG ATG GCG CTG GGC GCA ATG CGC GCC ATT ACC GAG TCC
GCG ATG CTG GTT GCC AAC GAT CAG ATG GCG CTG GGC GCA ATG CGC GCC ATT ACC GAG TCC
 A   M   L   V   A   N   D   Q   M   A   L   G   A   M   R   A   I   T   E   S
793/261                                         823/271
GGG CTG CGC GTT GGT GCG GAT ATC TCG GTA GTG GGA TAC GAC GAT ACC GAA GAC AGC TCA
GGG CTG CGC GTT GGT GCG GAT ATC TCG GTA GTG GGA TAC GAC GAT ACC GAA GAC AGC TCA
GGG CTG CGC GTT GGT GCG GAT ATC TCG GTA GTG GGT TAC GAC GAT ACC GAA GAC AGC TCA
 G   L   R   V   G   A   D   I   S   V   V   G   Y   D   D   T   E   D   S   S
853/281                                         883/291
TGT TAT ATC CCG CCG TTA ACC ACC ATC AAA CAG GAT TTT CGC CTG CTG GGG CAA ACC AGC
TGT TAT ATC CCG CCG TTA ACC ACC ATC AAA CAG GAT TTT CGC CTG CTG GGG CAA ACC AGC
TGT TAT ATC CCG CCG TTA ACC ACC ATC AAA CAG GAT TTT CGC CTG CTG GGG CAA ACC AGC
 C   Y   I   P   P   L   T   T   I   K   Q   D   F   R   L   L   G   Q   T   S
913/301                                         943/311
GTG GAC CGC TTG CTG CAA CTC TCT CAG GGC CAG GCG GTG AAG GGC AAT CAG CTG TTG CCC
GTG GAC CGC TTG CTG CAA CTC TCT CAG GGC CAG GCG GTG AAG GGC AAT CAG CTG TTG CCC
GTG GAC CGC TTG CTG CAA CTC TCT CAG GGC CAG GCG GTG AAG GGC AAT CAG CTG TTG CCG
 V   D   R   L   L   Q   L   S   Q   G   Q   A   V   K   G   N   Q   L   L   P
973/321                                         1003/331
GTC TCA CTG GTG AAA AGA AAA ACC ACC CTG GCG CCC AAT ACG CAA ACC GCC TCT CCC CGC
GTC TCA CTG GTG AAA AGA AAA ACC ACC CTG GCG CCC AAT ACG CAA ACC GCC TCT CCC CGC
GTC TCA CTG GTG AAA CGT AAA ACC ACC CTG GCG CCG AAT ACG CAA ACC GCC TCT CCG CGC
 V   S   L   V   K   R   K   T   T   L   A   P   N   T   Q   T   A   S   P   R
1033/341                                        1063/351
GCG TTG GCC GAT TCA TTA ATG CAG CTG GCA CGA CAG GTT TCC CGA CTG GAA AGC GGG CAG
GCG TTG GCC GAT TCA TTA ATG CAG CTG GCA CGA CAG GTT TCC CGA CTG GAA AGC GGG CAG
GCG TTG GCC GAT TCA TTA ATG CAG CTG GCA CGT CAG GTT TCC CGT CTG GAA AGC GGG CAG
 A   L   A   D   S   L   M   Q   L   A   R   Q   V   S   R   L   E   S   G   Q
1093/361
TGA
TGA
TGA
 *
```

FIG. 3 (cont.)

ΔasdA::TT araC P<sub>BAD</sub> c2*

ΔasdA18::TT araC P<sub>BAD</sub> <u>AGGAGACTTAACT</u> <u>ATG</u> AAT-c2
                                 SD             Start codon ΔasdA20::TT araC P<sub>BAD</sub> <u>AGGAGACTTAACT</u> <u>ATG</u> AAT-c2*
                                   SD             Start codon ΔasdA21::TT araC P<sub>BAD</sub> <u>TAAGGAGGTTTAACT</u> <u>ATG</u> AAT-c2*
                                   SD             Start codon ΔasdA27::TT araC P<sub>BAD*</sub> <u>TAAGGAGGTTTAACT</u> <u>ATG</u> AAA-c2**
                                   SD             Start codon

```
1/1                                          31/11
ATG AAT ACA CAA TTG ATG GGT GAG CGT ATT  CGC GCT CGA AGA AAA AAA CTC AAG ATT AGA   original
atg aat aca caa ttg atg ggt gag cgt att  cgc gct cgT CgT aaa aaa ctc aag att CgT   optimized
 M   N   T   Q   L   M   G   E   R   I    R   A   R   R   K   K   L   K   I   R
                                                   ──────────────────────────────
61/21                                        91/31
CAA GCC GCT CTT GGT AAG ATG GTG GGA GTG  TCT AAT GTT GCA ATA TCG CAA TGG GAG CGC
caa gcc gct ctt ggt aag atg gtg ggT gtg  tct aat gtt gca atC tcg caa tgg gag cgc
 Q   A   A   L   G   K   M   V   G   V    S   N*  V   A   I   S   Q   W   E   R
─────────────────────────────────────             ──
121/41                                       151/51
TCG GAG ACT GAG CCA AAT GGG GAG AAC CTG  TTG GCA CTT TCG AAG GCT CTT CAG TGC TCC
tcg gag act gag cca aat ggg gag aac ctg  ttg gca ctt tcg aag gct ctt cag tgc tcc
 S   E   T   E   P   N   G   E   N*  L    L   A   L   S   K   A   L   Q   C   S
 ─
181/61                                       211/71
CCT GAC TAT TTG CTG AAA GGA GAT TTA AGC  CAG ACA AAC GTT GCC TAT CAT AGT AGG CAT
cct gac tat ttg ctg aaa ggT gat tta agc  cag aca aac gtt gcc tat cat agt CgT cat
 P   D   Y   L   L   K   G   D   L   S    Q   T   N   V   A   Y   H   S   R   H
241/81                                       271/91
GAG CCA AGA GGA TCA TAC CCT CTT ATC AGT  TGG GTA AGC GCA GGG CAA TGG ATG GAA GCT
gag cca CgT ggT tca tac cct ctt atc agt  tgg gta agc gca ggg caa tgg atg gaa gct
 E   P   R   G   S   Y   P   L   I   S    W   V   S   A   G   Q   W   M   E   A
301/101                                      331/111
GTA GAA CCT TAT CAC AAG CGC GCG ATA GAG  AAC TGG CAC GAC ACC ACT GTA GAT TGT TCA
gta gaa cct tat cac aag cgc gcg atC gag  aac tgg cac gac acc act gta gat tgt tca
 V   E   P   Y   H   K   R   A   I   E    N   W   H   D   T   T   V   D   C   S
361/121                                      391/131
GAA GAT TCA TTT TGG CTT GAT GTC CAA GGT  GAC TCT ATG ACA GCA CCG GCA GGG TTA AGC
gaa gat tca ttt tgg ctt gat gtc caa ggt  gac tct atg aca gca ccg gca ggg tta agc
 E   D   S   F   W   L   D   V   Q   G    D   S   M   T   A   P   A   G   L   S
421/141                                      451/151
ATT CCA GAA GGA ATG ATA ATT CTG GTT GAT  CCC GAA GTC GAA CCA AGA AAC GGC AAG CTG
att cca gaa ggT atg atC att ctg gtt gat  ccG gaa gtc gaa cca CgT aac ggc aag ctg
 I   P   E   G   M   I   I   L   V   D    P   E   V   E   P   R   N   G   K   L
481/161                                      511/171
GTT GTT GCA AAA TTA GAA GGT GAA AAC GAG  GCC ACA TTC AAA AAA TTA GTT ATG GAT GCA
gtt gtt gca aaa tta gaa ggt gaa aac gag  gcc aca ttc aaa aaa tta gtt atg gat gca
 V   V   A   K   L   E   G   E   N   E    A   T   F   K   K   L   V   M   D   A
541/181                                      571/191
GGC CGA AAG TTT TTA AAA CCA TTA AAC CCA  CAA TAT CCG ATG ATA GAA ATC AAC GGA AAC
ggc cgT aag ttt tta aaa cca tta aac cca  caa tat ccg atg atC gaa atc aac ggT aac
 G   R   K   F   L   K   P   L   N   P    Q   Y   P   M   I   E   I   N   G   N
601/201                                      631/211
TGC AAA ATC ATT GGC GTA GTT GTT GAC GCA  AAA CTC GCA AAT CTT CCA TAA
tgc aaa atc att ggc gta gtt gtt gac gca  aaa ctc gca aat ctt cca taa
 C   K   I   I   G   V   V   V   D   A    K   L   A   N   L   P   *
```

FIG. 5

```
                                    P_BAD-35                              -10
Original: TTT ATC CAT AAG ATT AGC GGA TCC TAC CTG ACG CTT TTT ATC GCA ACT CTC TAC TGT
Modified: TTT ATC CAT AAG ATT AGC GGA TCC TAC CTG ACG CTT TTT ATC GCA ACT CTC TAT AAT improved SD
          TTC TCC ATA CCC GTT TTT TTG GGC TAG CCT CGA GGG TACC TAA GGA GGT TTA ACT
          TTC TCC ATA CCC GTT TTT TTG GGC TAG CCT CGA GGG TACC TAA GGA GGT TTA ACT c2 (codon improved)
          ATG AAT ACA CAA TTG ATG GGT GAG CGT ATT CGC GCT CGT CGT AAA AAA CTC AAG ATT CGT
           M   N   T   Q   L   M   G   E   R   I   R   A   R   R   K   K   L   K   I   R
               ↓
          ATG AAA ACA CAA TTG ATG GGT GAG CGT ATT CGC GCT CGT CGT AAA AAA CTC AAG ATT CGT
           K
```

FIG. 6

ΔP_fur::TT araC P_BAD fur a. ΔP_fur33::TT araC P_BAD fur    AG GAC AGA TTC CGC ATG ACT GAC
                                        SD                      M    T    D b. ΔP_fur77::TT araC P_BAD fur    AG GAC AGA TTC CGC GTG ACT GAC
                                        SD                      V    T    D c. ΔP_fur81::TT araC P_BAD fur    AA GGC AGA TTC CGC GTG ACT GAC
                                        SD                      V    T    D

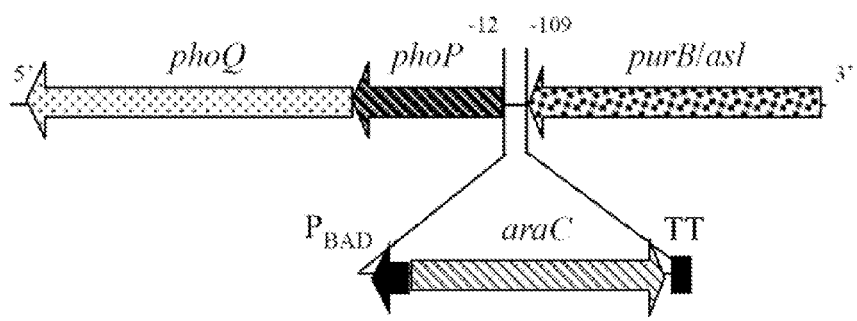

- ΔP_phoPQ107::TT araC P_BAD phoPQ :  AGGGA GAAGAG ATG ATG CGC GTA
                                                    M    M    R    V

- ΔP_phoPQ173::TT araC P_BAD phoPQ :  AGGGA GAAGAG GTG GTG CGC GTA
                                                    V    V    R    V

- ΔP_phoPQ177::TT araC P_BAD phoPQ:   AAGGC GAAGAG GTG GTG CGC GTA
                                                    V    V    R    V

- ΔP_phoPQ174::TT araC P_BAD phoPQ:   AAGGC GAAGAG GTG ATG CGC GTA
                                                    V    M    R    V

- ΔP_phoPQ175::TT araC P_BAD ΔGAG-phoPQ: AAGGC      GAG ATG ATG CGC GTA
                                                        M    M    R    V

- ΔP_phoPQ176::TT araC P_BAD ΩCTC-phoPQ: AAGGC CTCGAAGAG ATG ATG CGC GTA
                                                         M    M    R    V

FIG. 9

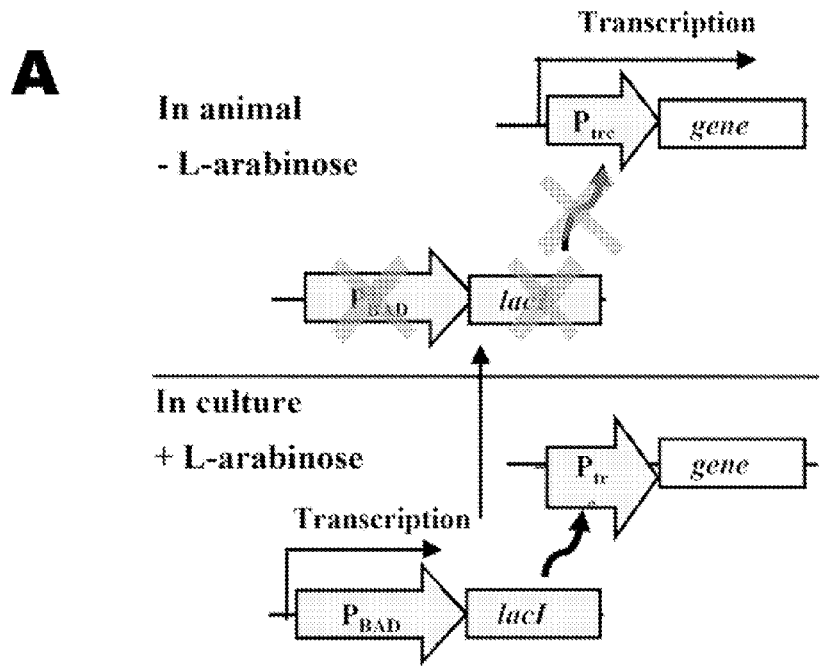
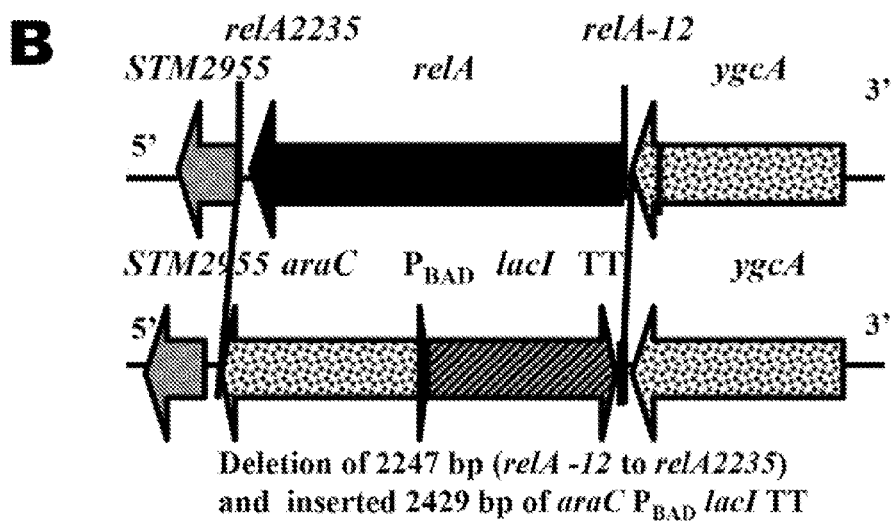
FIG. 19

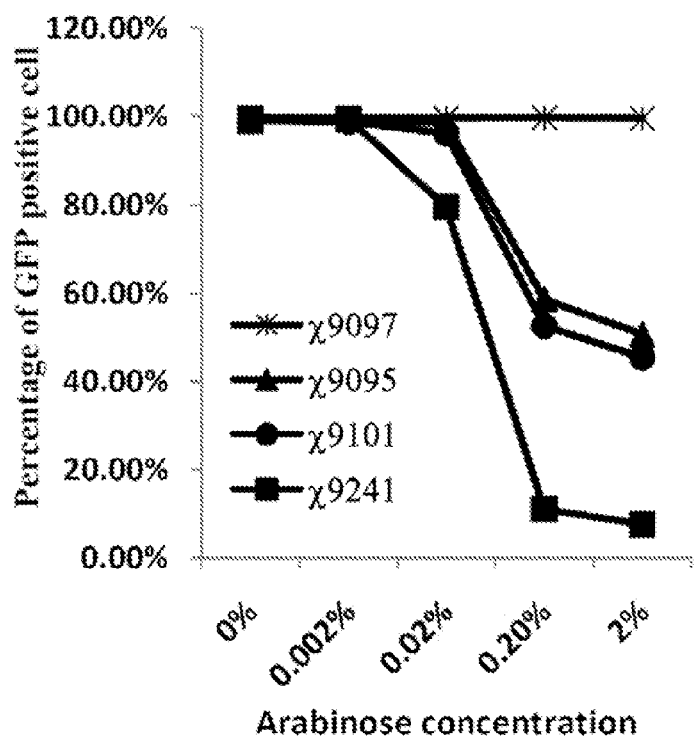
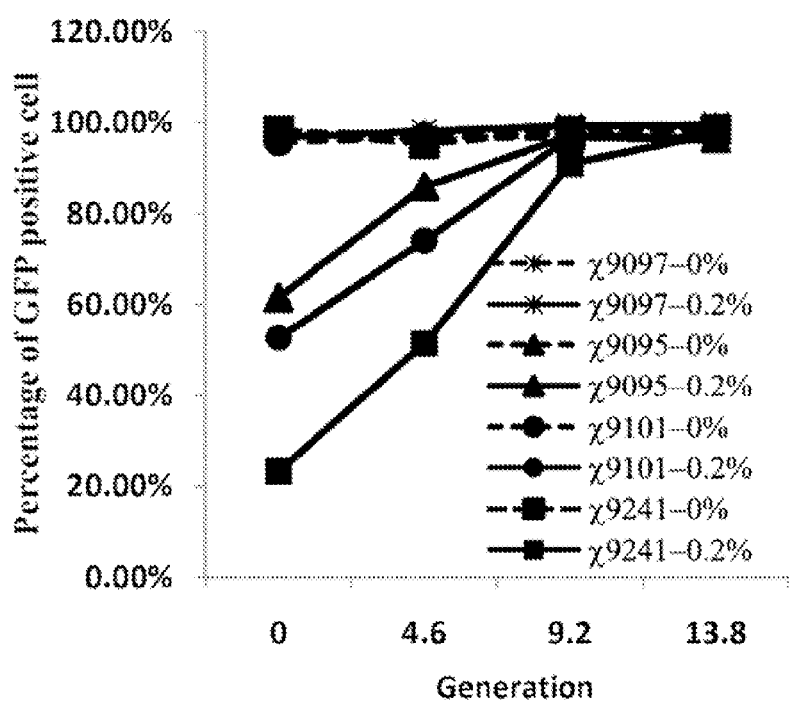
FIG. 21

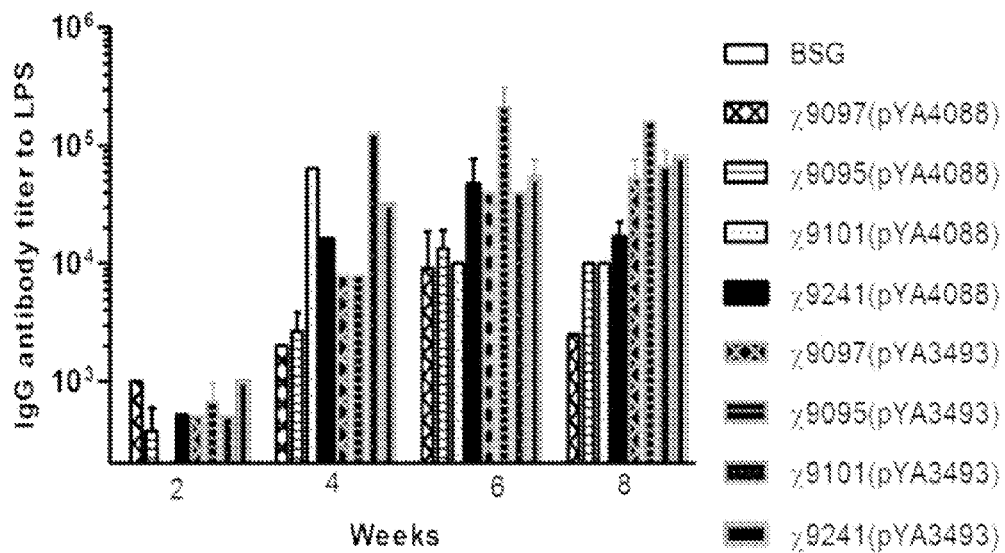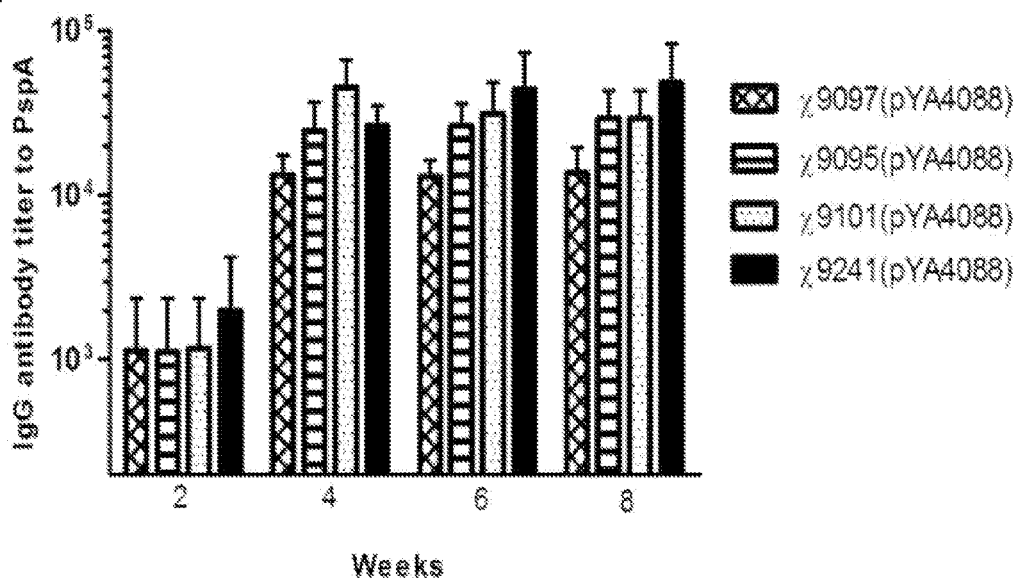
FIG. 23

$\Delta P_{fur33}$::TT $araC$ $P_{BAD}$ $fur$

B ΔP$_{phoPQ107}$::TT *araC* P$_{BAD}$ *phoPQ*
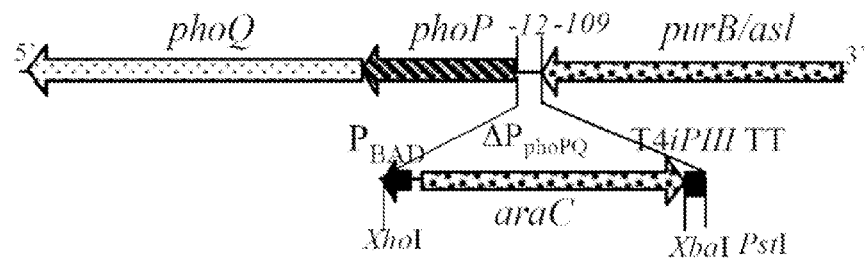
C ΔP$_{rpoS183}$::TT *araC* P$_{BAaD}$ *rpoS*
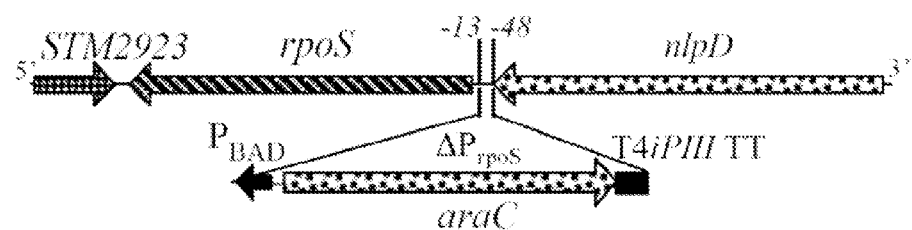
D ΔP$_{crp527}$::TT *araC* P$_{BAD}$ *crp*
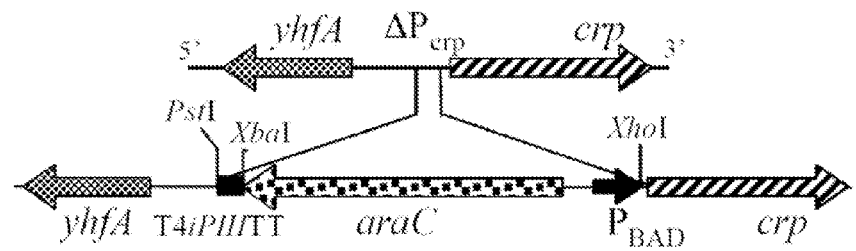
FIG. 25

C          PhoP
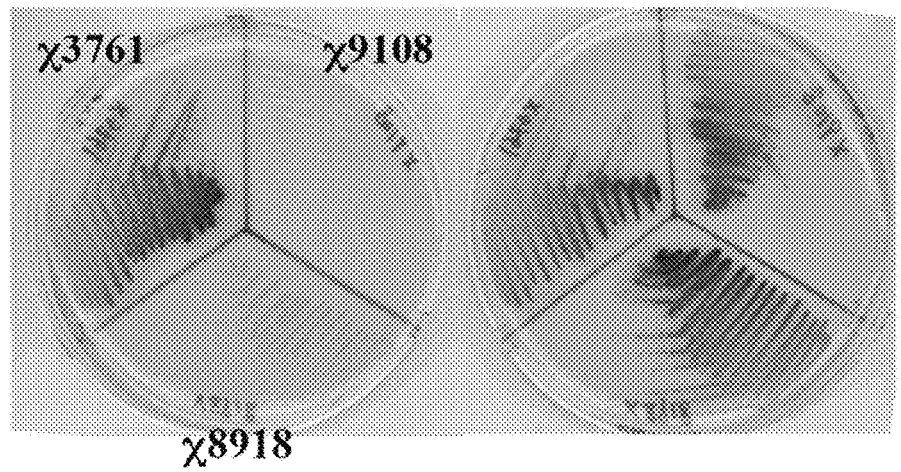
D          RpoS
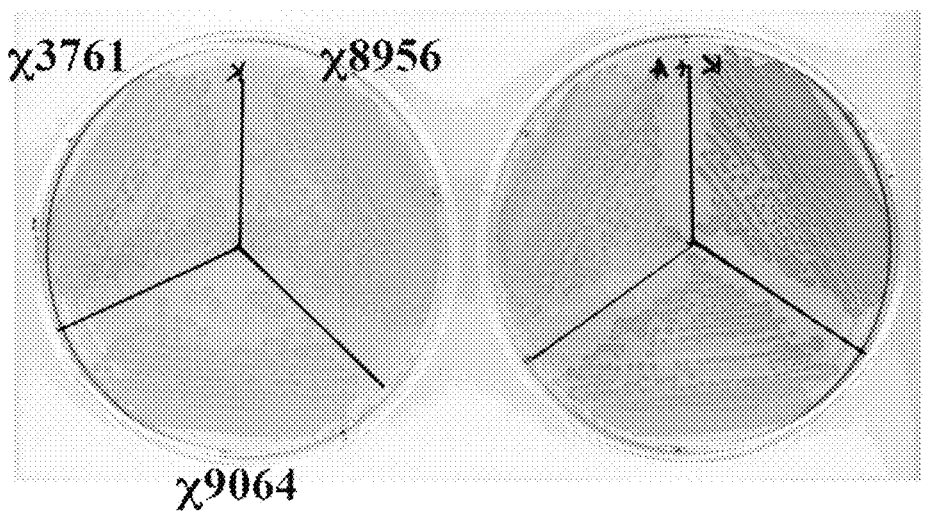
FIG. 26

A Δ*araBAD23*
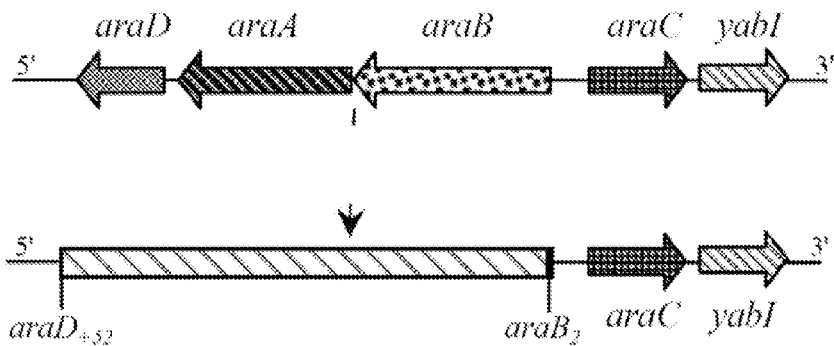
B Δ*araE25*
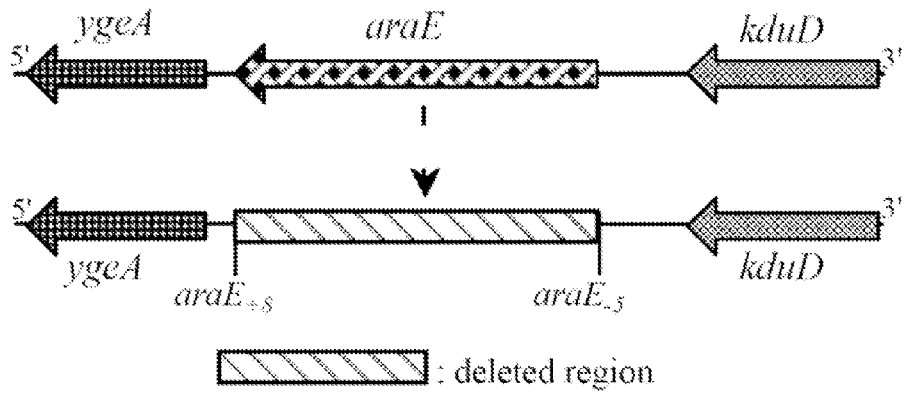
FIG. 27

Δ*pmi-2426*
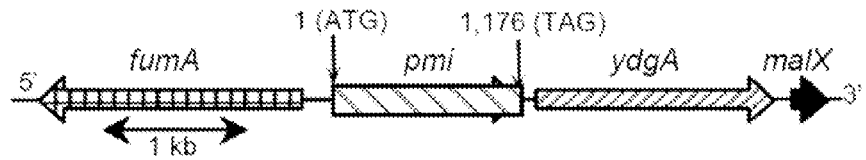
ΔP$_{crp527}$::TT *araC* P$_{BAD}$ *crp*
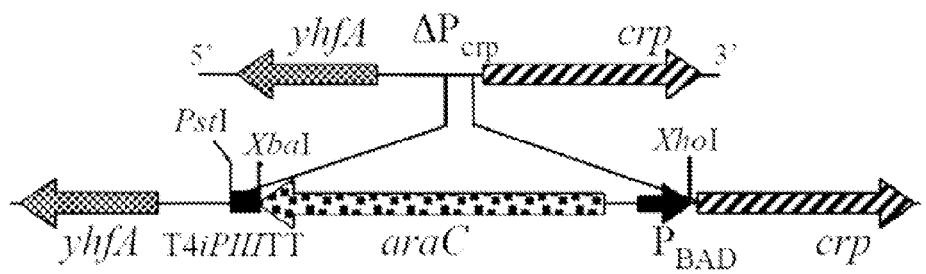
ΔP$_{fur33}$::TT *araC* P$_{BAD}$ *fur*
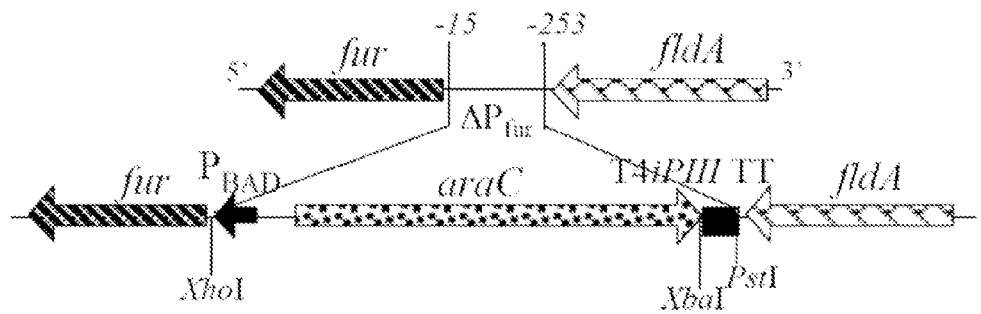
FIG. 31

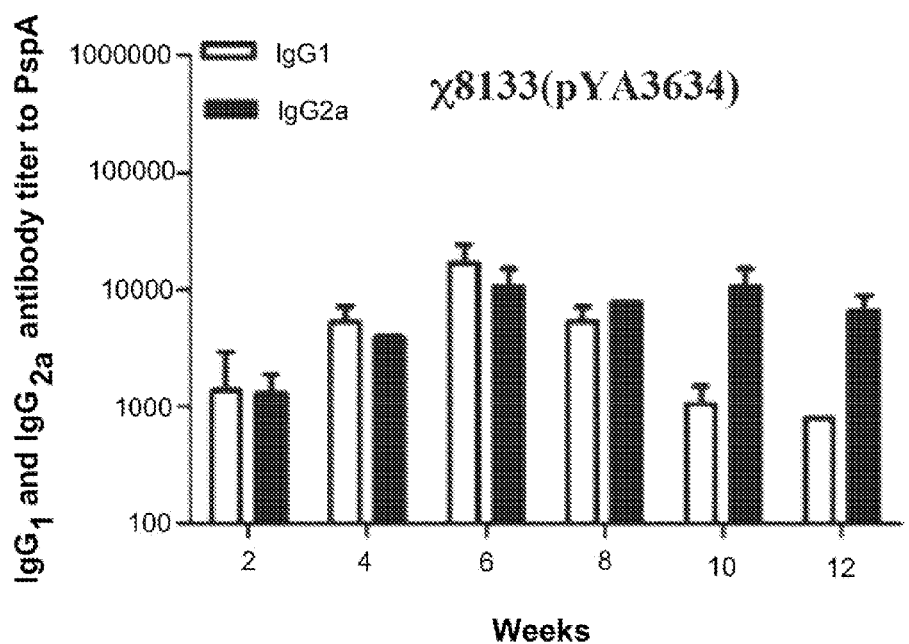
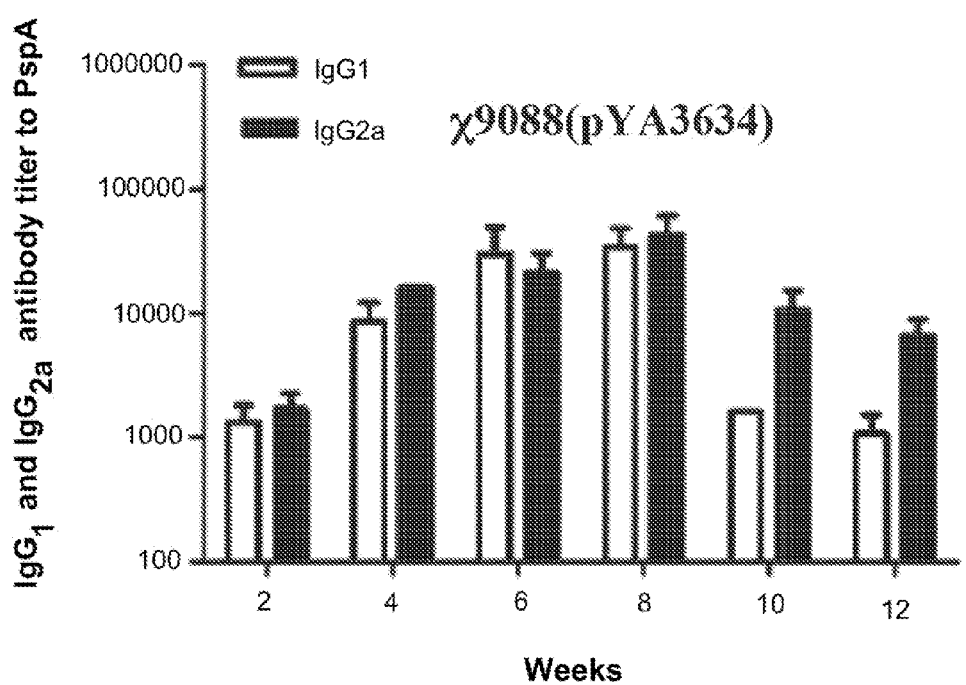
FIG. 34

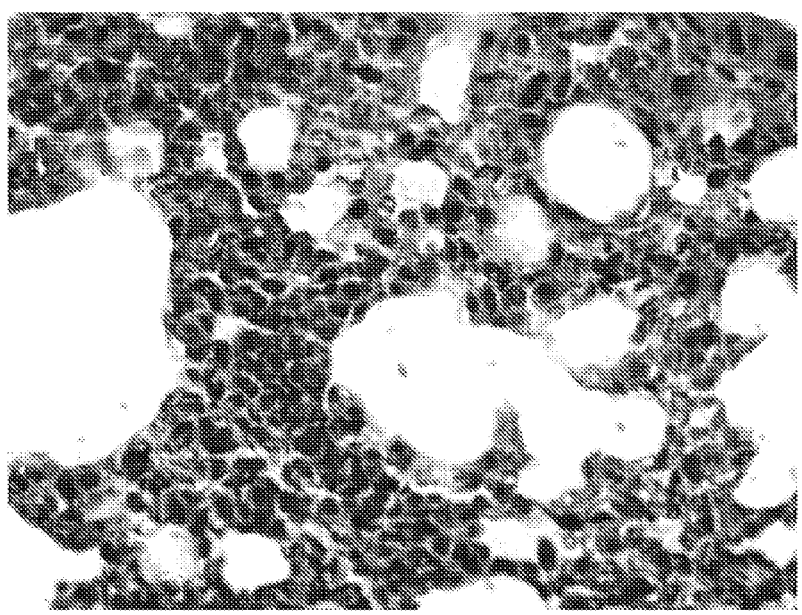
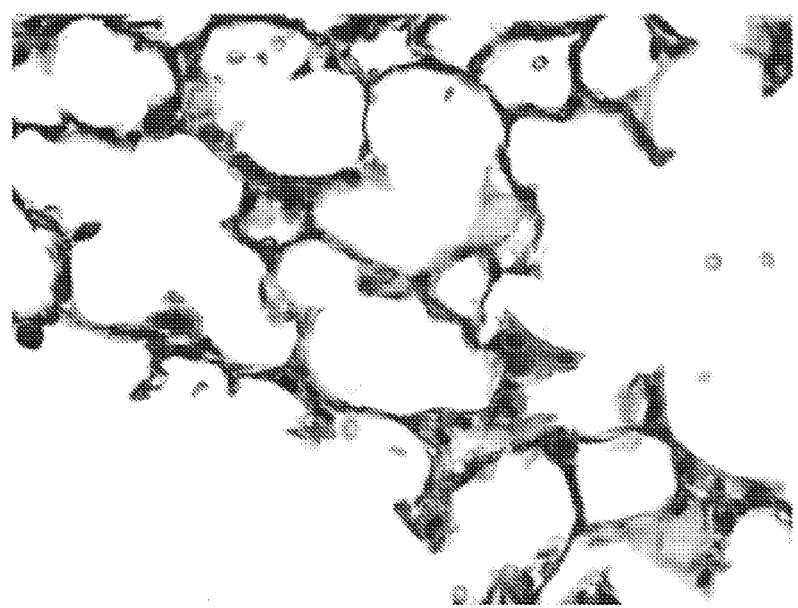
FIG. 36

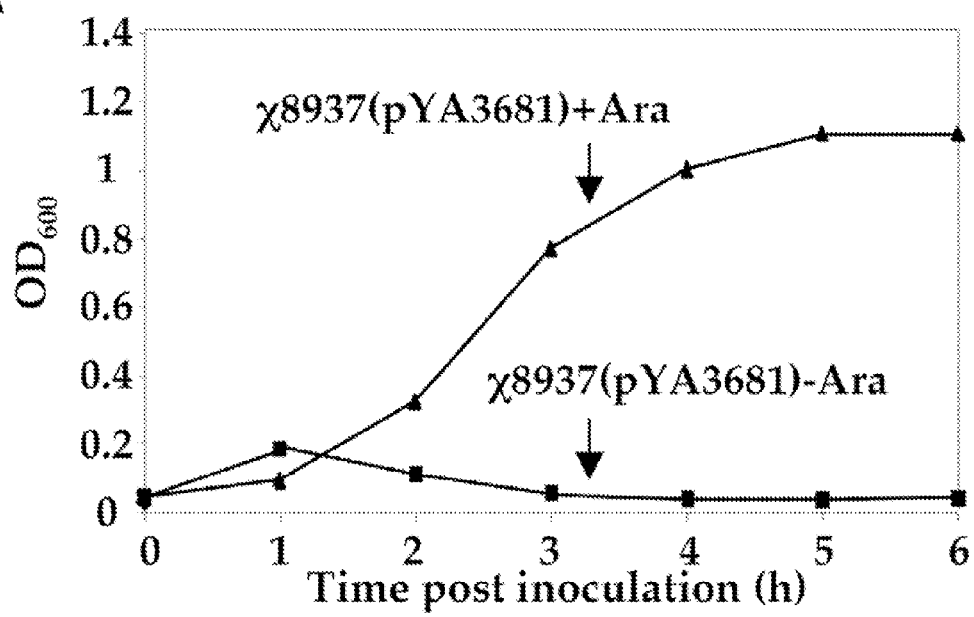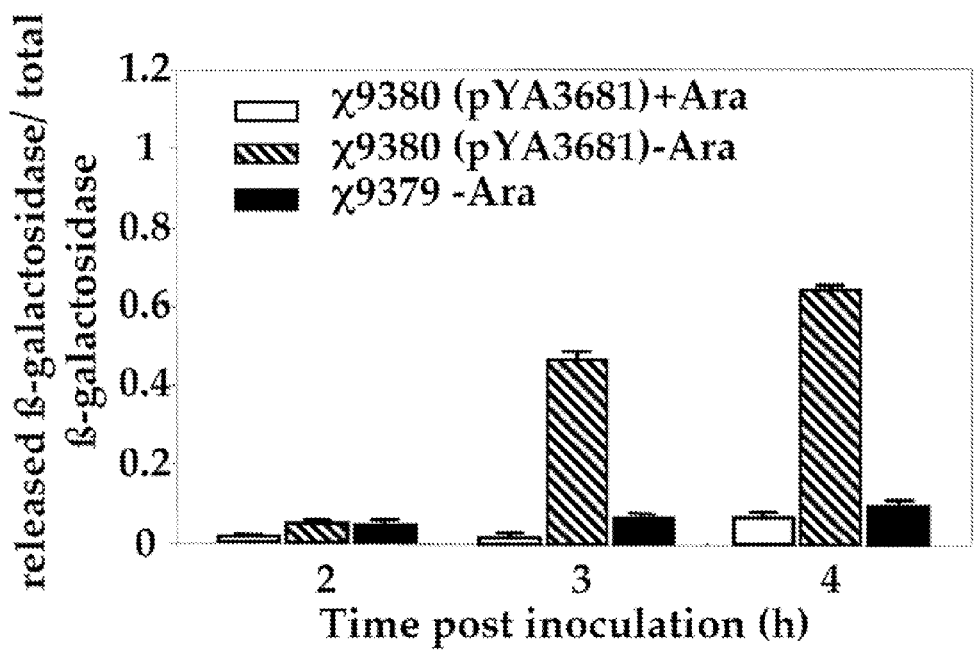
FIG. 40

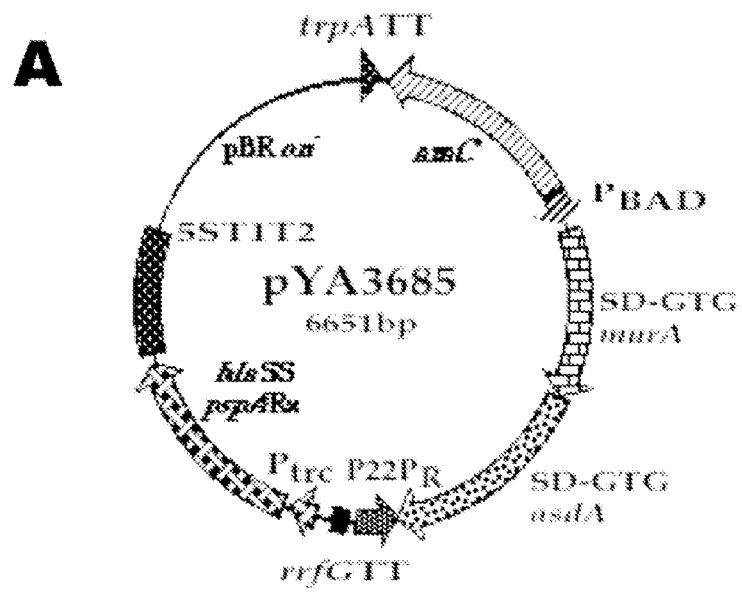
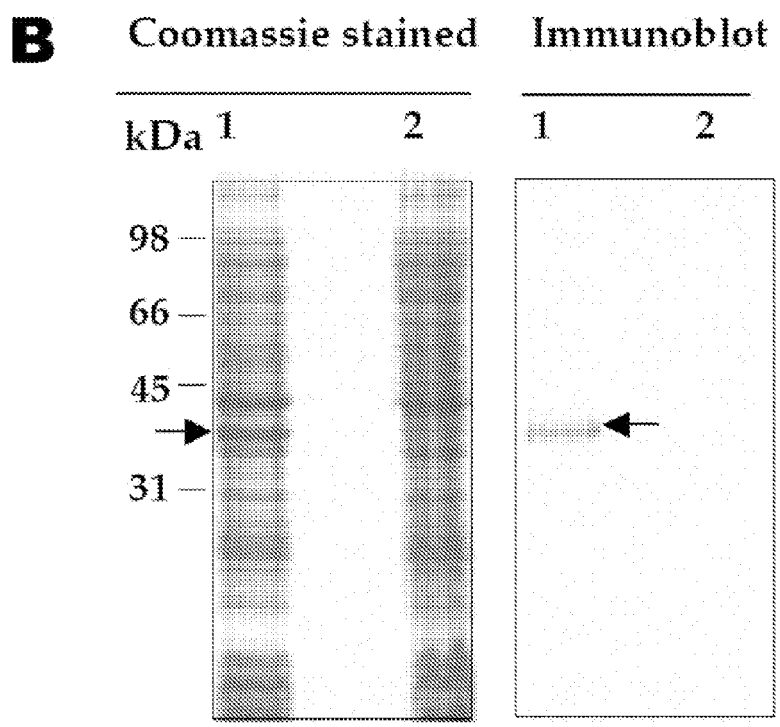
FIG. 41

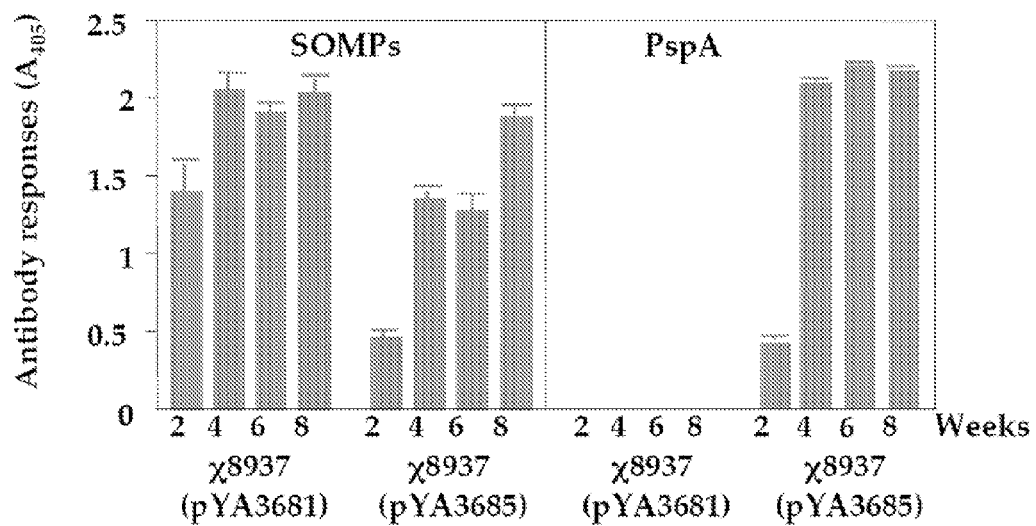
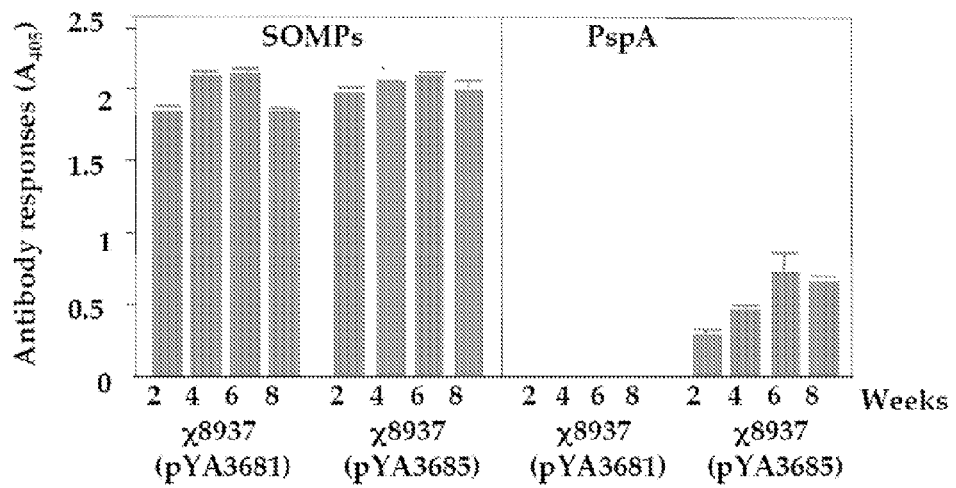
FIG. 42

REGULATED EXPRESSION OF ANTIGEN AND/OR REGULATED ATTENUATION TO ENHANCE VACCINE IMMUNOGENICITY AND/OR SAFETY

CROSS REFERENCE TO RELATED APPLICATIONS

This application is a continuation of U.S. application Ser. No. 12/615,872, filed Nov. 10, 2009, which is a continuation-in part of application number PCT/US2008/063293, filed May 9, 2008, which claims the priority of U.S. provisional application No. 60/917,313, filed May 10, 2007, each of which is hereby incorporated by reference in its entirety.

GOVERNMENTAL RIGHTS

This invention was made with government support under Grant Nos. 5RO1DE006669, 5RO1AI056289, RO1AI24533, and RO1AI057885 awarded by the National institutes of Health, and Grant Nos. 99-35204-8572, 2001-02994, and 2003-35204-13748, awarded by the United States Department of Agriculture. The government has certain rights in the invention.

FIELD OF THE INVENTION

The invention relates to compositions and methods for making and using recombinant bacteria that are capable of regulated attenuation and/or regulated expression of at least one nucleic acid encoding an antigen of interest.

BACKGROUND OF THE INVENTION

Recombinant microorganisms have widespread utility and importance. One use of these microorganisms is as live vaccines to produce an immune response. Live vaccines are most effective when they produce high levels of antigen. However, the synthesis of a recombinant antigen encoded by a highly expressed nucleic acid sequence may be deleterious to the microorganism. Because of this, regulated (as opposed to constitutive) expression systems have been identified and utilized where the recombinant nucleic acid sequence of interest is operably linked to control elements that allow expression of significant amounts of the recombinant nucleic acid sequence only when it is induced, derepressed or activated. Examples include the cspA nucleic acid sequence promoter, the phoA nucleic acid sequence promoter, $P_{BAD}$ (in an araC-$P_{BAD}$ system), the trp promoter, the tac promoter, the trc promoter, $\lambda P_L$, P22 $P_R$, mal promoters, rha promoter, xyl promoter, and the lac promoter. These promoters may mediate transcription at low temperature, at low phosphate levels, in the presence of arabinose, in the presence of at low tryptophan levels, in the presence of rhamnose, in the presence of xylose, and in the presence of lactose (or other lac inducers).

When the recombinant microorganism is used as a vertebrate live vaccine, certain considerations must be taken into account. To provide a benefit beyond that of a nonliving vaccine, the live vaccine microorganism must attach to, invade, and survive in lymphoid tissues of the vertebrate and expose these immune effector sites to antigen for an extended period of time. Through this continual stimulation, the vertebrate's immune system becomes more highly reactive to the antigen than with a nonliving vaccine. Therefore, preferred live vaccines are attenuated pathogens of the vertebrate, particularly pathogens that colonize the gut-associated lymphoid tissue (GALT), nasopharynx-associated lymphoid tissue (NALT) or bronchial-associated lymphoid tissue (BALT). An additional advantage of these attenuated pathogens over non-living vaccines is that these pathogens have elaborate mechanisms to gain access to lymphoid tissues, and thus efficient exposure to the vertebrate's immune system can be expected. In contrast, nonliving vaccines will only provide an immune stimulus if the vaccine is passively exposed to the immune system, or if host mechanisms bring the vaccine to the immune system.

Pathogenic bacteria may be attenuated by mutation so that upon infection, host disease symptomology is not elicited. Most means of attenuation, however, make live vaccine strains more susceptible than wild-type strains to environmental stresses encountered after inoculation into the animal or human host. Consequently, fewer bacteria survive to colonize the GALT, NALT and/or BALT with a reduction in effective immunogenicity of the vaccine. Thus these attenuation mechanisms hyperattenuate the vaccine, precluding the candidate vaccine from either reaching or persisting in lymphoid tissues to a sufficient extent or duration to permit induction of a protective immune response against the wild-type pathogen of interest. Thus, there is a need in the art for methods of regulating the expression of the attenuated phenotype. This allows the live vaccine strain to display abilities similar to a wild-type virulent parental pathogen in order to successfully colonize effector lymphoid tissues prior to the display and imposition of the full attenuated phenotype to preclude induction of disease symptoms.

Since immune responses induced against foreign antigens are proportional to the levels of antigen synthesized by the recombinant attenuated bacterial vaccine (1,3), the placement of the nucleic acid sequence for the foreign antigen on a multi-copy plasmid vector is much preferable to the insertion of the nucleic acid sequence for the foreign antigen into the chromosome of the attenuated bacterial vaccine vector. This is because the level of foreign antigen synthesis is generally proportional to the number of copies of the nucleic acid sequence for the foreign antigen expressed within the attenuated bacterial host.

Since plasmid-containing recombinant attenuated bacterial vaccines overproduce large amounts of antigen that provide no advantage to the vaccine, the plasmid vectors are often lost over time after immunization. In many cases, ten percent or less of the recombinant attenuated bacterial vaccine isolated from the immunized vertebrate retains the plasmid after three or four days. When this plasmid loss occurs, the immune response is directed more against the attenuated bacterial host vaccine itself rather than against the expressed foreign antigen.

As stated above, the level of immune response to a foreign antigen is generally proportional to the level of expression of the nucleic acid sequence encoding the antigen. Encoding the protective antigen on a plasmid vector is important in maximizing the production of that protective antigen, which is very much correlated with the ability to induce high level protective immune responses by production of mucosal and systemic antibodies against the protective antigen. Unfortunately, overexpression of nucleic acid encoding a foreign antigen is often toxic such that it reduces the rate of growth and therefore the ability of the attenuated bacterial vaccine to colonize lymphoid tissues. As a consequence, the ultimate immunogenicity is sharply diminished. For this reason, it is necessary to balance the ability of the vaccine to colonize and grow in lymphoid tissues with the ability to synthesize the foreign antigen.

SUMMARY OF THE INVENTION

One aspect of the present invention encompasses a recombinant bacterium capable of the regulated expression of at least one nucleic acid sequence encoding an antigen of interest, and capable of regulated attenuation. The bacterium comprises at least one chromosomally integrated nucleic acid sequence encoding a repressor operably linked to a regulatable promoter and a vector comprising a nucleic acid sequence encoding at least one antigen of interest operably linked to a promoter regulated by the repressor, such that the expression of the nucleic acid sequence encoding the antigen is repressed during in vitro growth of the bacterium, but the bacterium is capable of high level expression of the nucleic acid sequence encoding the antigen in a host. The bacterium further comprises a regulatable promoter chromosomally integrated so as to replace the native promoter of, and be operably-linked to, at least one nucleic acid sequence of an attenuation protein.

Another aspect of the invention encompasses a recombinant bacterium capable of regulated expression of at least one nucleic acid sequence encoding an antigen of interest. The bacterium comprises at least one chromosomally integrated nucleic acid sequence encoding a repressor operably linked to a regulatable promoter, wherein the nucleic acid sequence encoding the repressor and/or promoter have been modified from the wild-type nucleic acid sequence so as to optimize the expression level of the nucleic acid sequence encoding the repressor, and a vector comprising at least one nucleic acid sequence encoding an antigen of interest operably linked to a promoter regulated by the repressor, such that the expression of the nucleic acid sequence encoding the antigen is repressed during in vitro growth of the bacterium, but the bacterium is capable of high level expression of the nucleic acid sequence encoding the antigen in a host.

Yet another aspect of the invention encompasses a recombinant bacterium capable of regulated attenuation. The bacterium comprises a modified regulatable promoter chromosomally integrated so as to replace the native promoter of, and be operably linked to, at least one nucleic acid sequence encoding an attenuation protein.

Other aspects and iterations of the invention are described more thoroughly below.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3 depicts an illustration of nucleic acid sequence modification analyses of SD-lacI in ΔendA19 and ΔrelA196 (SEQ ID NO:7), SD-lacI in ΔendA20 and ΔrelA197 (SEQ ID NO:8), and SD-lacI in ΔendA21 and ΔrelA198 (SEQ ID NO:9). The amino acid sequence of LacI is included (SEQ ID NO:10).

FIG. 5 depicts an illustration of c2 original sequence (SEQ ID NO:15) aligned with the optimized sequence (SEQ ID NO:16). The amino acid sequence of the optimized sequence is shown (SEQ ID NO:17). According to the actual DNA sequence data, the amino acid at position 49 has been altered to serine (S) from aspartic acid (N) (AAC to AGC).

FIG. 6 depicts an illustration of the original (SEQ ID NO:18) and the modified (SEQ ID NO:19) $P_{BAD}$ region and the original (SEQ ID NO:20) and modified (SEQ ID NO:21) c2 sequence. The original C2 amino acid sequence (SEQ ID NO:22) is compared to the optimized sequence (SEQ ID NO:23).

FIG. 9 depicts an illustration of a chromosomal map of various deletion-insertion mutations of the phoPQ promoter region. The schematic shows the deletion of the phoPQ promoter region (−12 to −109) and the insertion of 1335 bp of $P_{BAD}$ araC TT. The optimized sequences of ΔP$_{phoPQ107}$::TT araC $P_{BAD}$ phoPQ (SEQ ID NO:27), ΔP$_{phoPQ173}$::TT araC $P_{BAD}$ phoPQ (SEQ ID NO:28), and ΔP$_{phoPQ177}$::TT araC $P_{BAD}$ phoPQ (SEQ ID NO:29), ΔP$_{phoPQ174}$::TT araC $P_{BAD}$ phoPQ (SEQ ID NO:30), ΔP$_{phoPQ175}$::TT araC $P_{BAD}$ ΔGAG-phoPQ (SEQ ID NO:31), and ΔP$_{phoPQ176}$::TT araC $P_{BAD}$ ΩCTC-phoPQ (SEQ ID NO:32) show variations of SD sequences and start codons.

FIG. 23 depicts a graph showing antibody titers against LPS and PspA. These strains were transformed with plasmid pYA4088 expressing *S. pneumoniae* PspA Rx1 antigen and vector plasmid pYA3493. Strains were grown with 0.2% arabinose in LB medium before inoculating mice. A) anti-LPS antibody titers; B) anti-PspA antibody titers.

(D) χ8956 with ΔP$_{rpoS183}$::TT araC P$_{BAD}$ rpoS and χ9064 with ΔP$_{rpoS183}$::TT araC P$_{BAD}$ rpoS and ΔP$_{crp527}$::TT araC P$_{BAD}$ crp mutations streaked on glycogen-indicator agar without and with 0.2 percent arabinose and sprayed with iodine indicator solution.

FIG. 27 depicts an illustration of deletion mutations precluding breakdown of arabinose and enhancing retention of arabinose taken up by bacterial cells. (A) The schematic shows the deletion of a total of 4110 bp (araB$_2$ to araD$_{+52}$) and the insertion of 22 bp of SD, NcoI and PmeI at araB2 to create the ΔaraBAD23 mutation. (B) The schematic shows the deletion of a total of 1432 bp (araE−5 to araE+8) to create the ΔaraE25 mutation.

Figure 28:
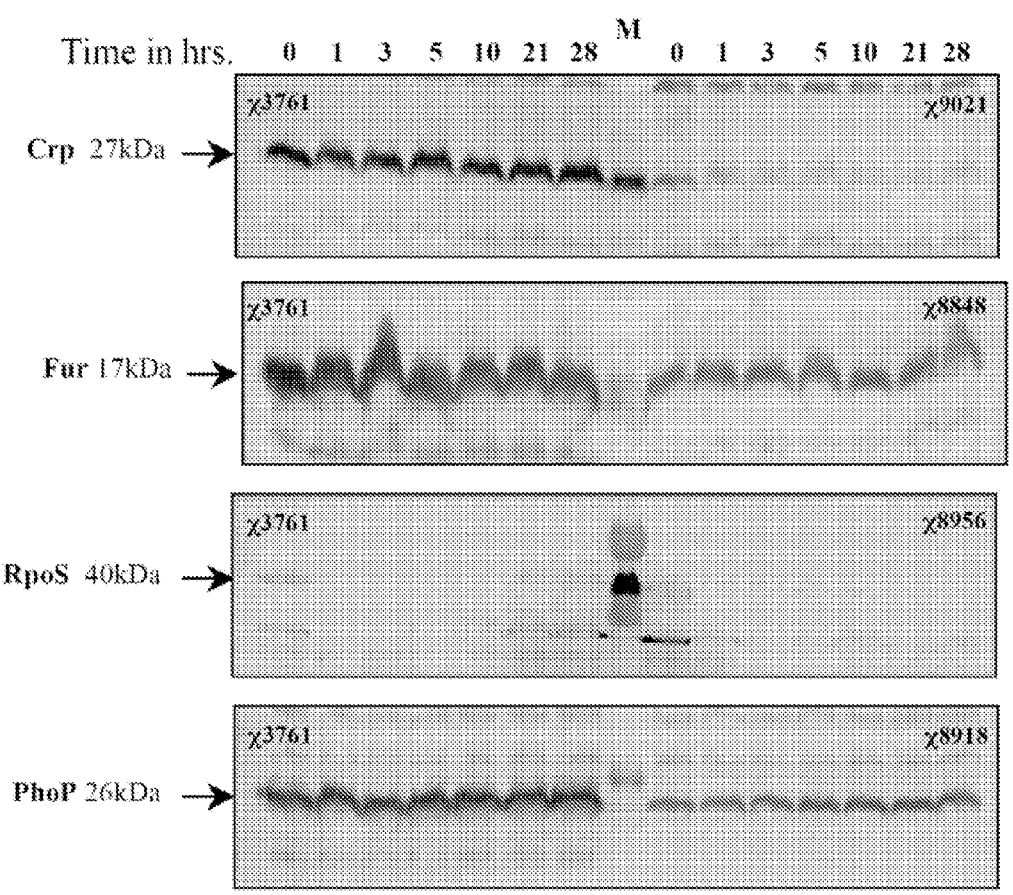

FIG. 28 depicts several photographs illustrating the stability of Crp, Fur, RpoS and PhoP proteins during incubation of cultures induced for synthesis of these proteins prior to addition of 30 and 200 μg chloramphenicol/ml of culture. Rabbit antibodies raised against His-tagged Crp, Fur and PhoP were used for western blot analyses. Mouse monoclonal antibodies for RpoS was purchased from Neoclone. χ9021 (ΔP$_{crp527}$), χ8848 (ΔP$_{fur33}$), χ8956 (ΔP$_{rpoS183}$) and χ8918 (ΔP$_{phoPQ107}$) were grown in LB broth with 0.2 percent arabinose for these studies.

Figure 29:
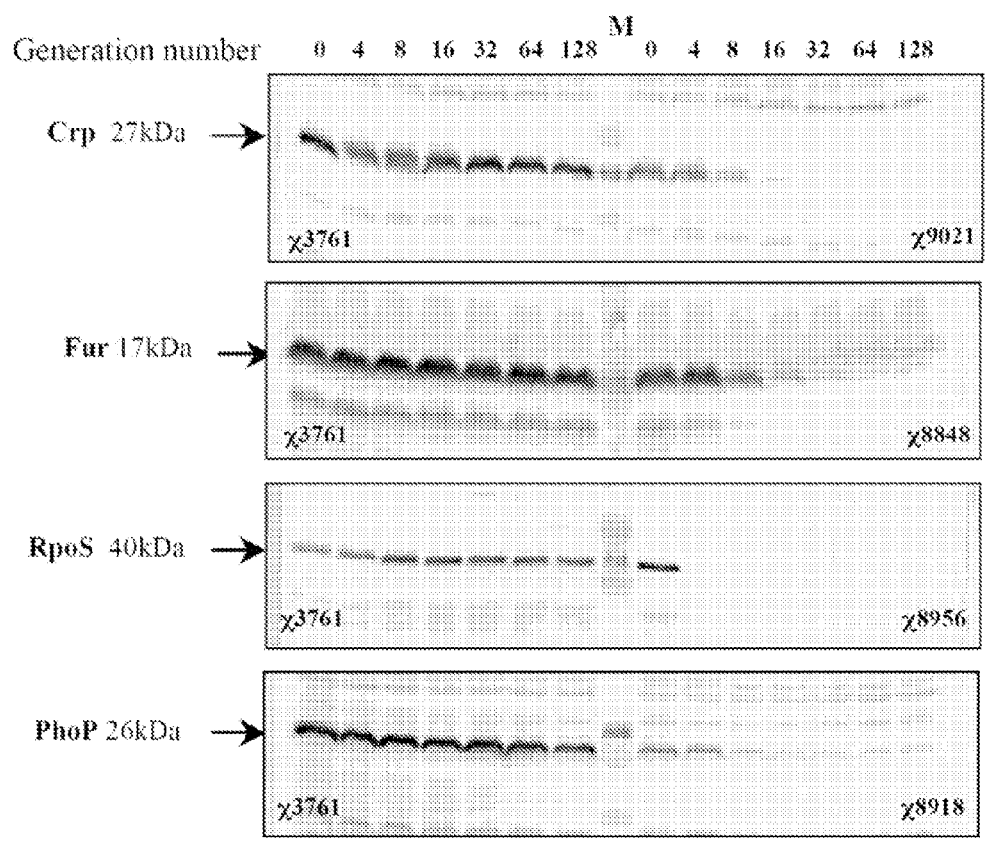

FIG. 29 depicts several photographs illustrating the decrease in amounts of Crp, Fur, RpoS and PhoP proteins as a consequence of growth of χ9021 (ΔP$_{crp527}$), χ8848 (ΔP$_{fur33}$), χ8956 (ΔP$_{rpoS183}$) and χ8918 (ΔP$_{phoPQ107}$) in the absence of arabinose. The same bacterial strains as used for the results shown in FIG. 47, were grown in nutrient broth with 0.2 percent arabinose and at the commencement of sampling to measure the amounts of proteins, the cultures were diluted 1:4 into prewarmed nutrient broth lacking arabinose. Rabbit antibodies raised against His-tagged Crp, Fur and PhoP were used for western blot analyses. Mouse monoclonal antibody against RpoS was purchased from Neoclone. Synthesis of the Crp, Fur and PhoP proteins continues until after the third 1:4 dilution whereas the amount of the RpoS protein decreases considerably after the first 1:4 dilution.

Figure 30:
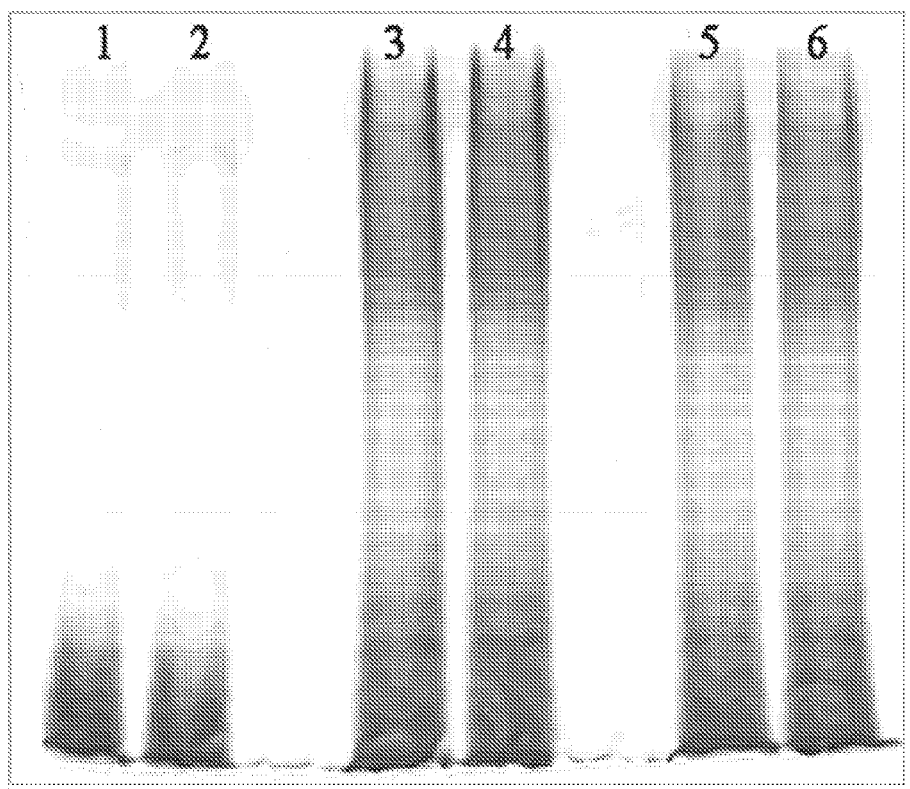

FIG. 30 depicts a photograph of the LPS profiles of vaccine strains in silver-stained SDS-PAGE. Bacteria were lysed with SDS, treated with proteinase K, and analyzed by SDS-PAGE followed by LPS-specific silver staining. Lane 1, χ9088 (pYA3634) (grown in nutrient broth without mannose); Lane 2, χ9558(pYA3634) (grown in nutrient broth without mannose); Lane 3, χ9088(pYA3634) (grown in nutrient broth with 0.5% mannose); Lane 4, χ9558(pYA3634) (grown in nutrient broth with 0.5% mannose); Lane 5, χ9088 (pYA3634) (grown in LB broth); Lane 6, χ9558(pYA3634) (grown in LB broth).

FIG. 31 depicts an illustration showing different regulated delayed attenuation constructs in vaccine strains. To create the Δpmi-2426 mutation, 1176 bp of the pmi nucleic acid sequence was deleted (from ATG to TAG). To create the ΔP$_{crp527}$::TT araC P$_{BAD}$ crp mutation, 95 bp of the crp promoter region (−15 to −109) was deleted and 1335 bp of P$_{BAD}$ araC TT was inserted. To create the ΔP$_{fur33}$::TT araC P$_{BAD}$ fur mutation, 239 bp of the fur promoter region (−15 to −253; including Fur consensus, Crp binding, and OxyR binding sites) was deleted and 1335 bp of P$_{BAD}$ araC TT was inserted.

Figure 32:
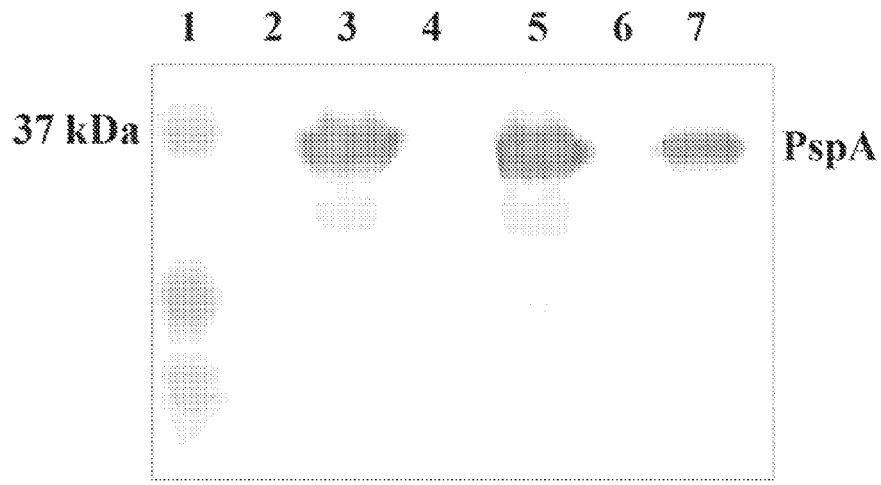

FIG. 32 depicts a photograph showing western blot data of the synthesis of PspA Rx1 by different S. Typhimurium mutants. Cell lysates of S. Typhimurium mutants containing PspA Rx1 were subjected to SDS-PAGE, and the proteins were transferred to nitrocellulose, which was subsequently probed with a polyclonal antibody specific for PspA Lanes: 1, molecular mass markers (positions are indicated in kilodaltons); 2, χ8133(pYA3493); 3, χ8133(pYA3634); 4, χ9088 (pYA3493); 5, χ9088(pYA3634); 6, χ9558(pYA3493); 7, χ9558(pYA3634). Due to the presence of arabinose in LB broth, the PspA synthesis of χ9558(pYA3634) has been suppressed partly.

Figure 33A:
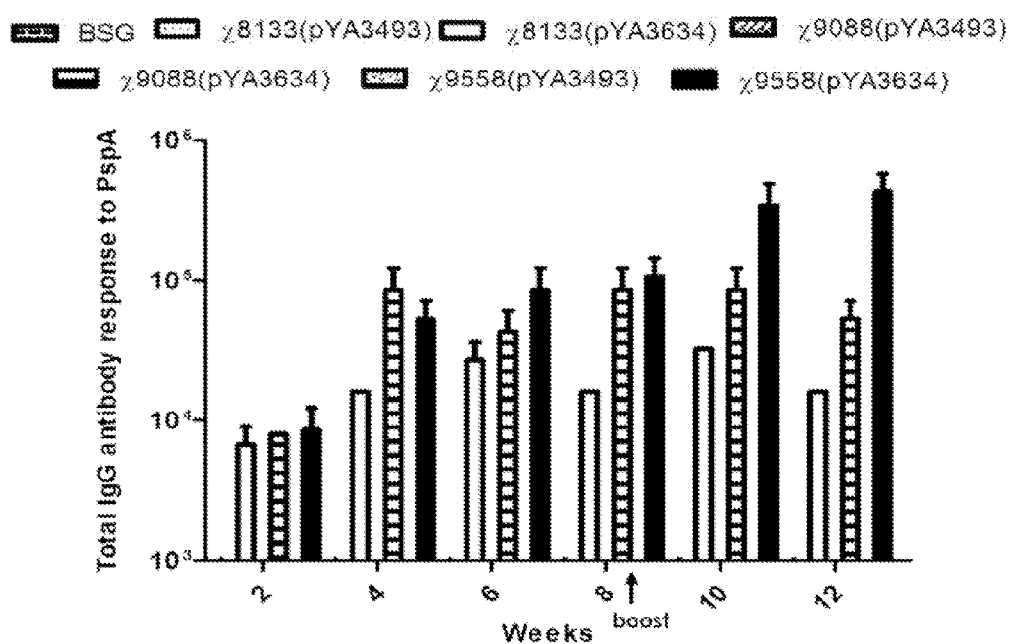
Figure 33:
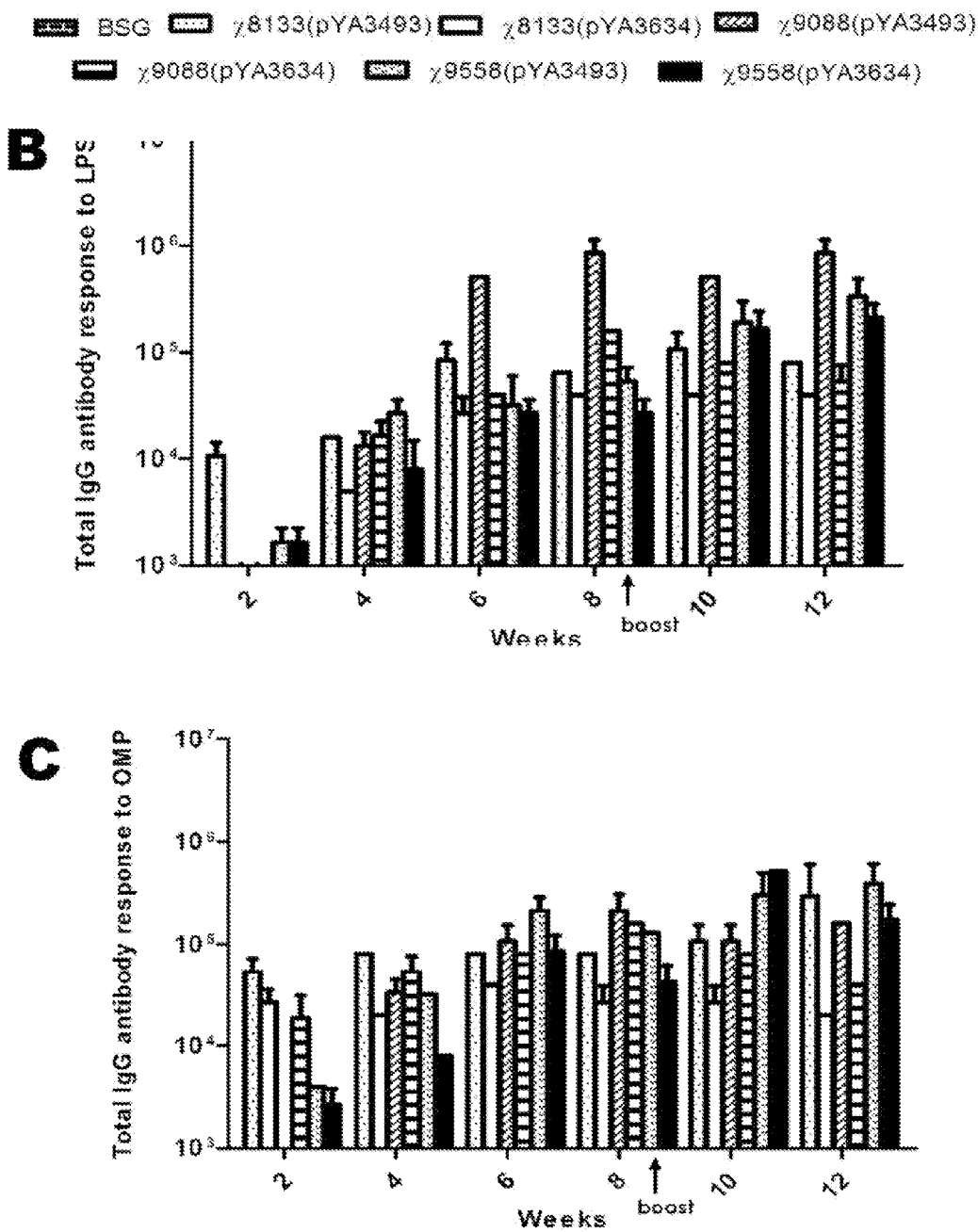

FIG. 33 depicts a series of graphs showing serum IgG responses to rPspA (A) and to S. Typhimurium LPS (B) and SOMPs (C) measured by ELISA. The data represent IgG antibody levels in mice orally immunized with χ8133 (pYA3493) (vector control), χ8133(pYA3634) (expressing rPspA), χ9088(pYA3493) (vector control), χ9088(pYA3634) (expressing rPspA), χ9558(pYA3493) (vector control) and χ9558(pYA3634) (expressing rPspA) at the indicated weeks after immunization. p<0.05 for anti-rPspA serum IgG antibody levels of χ9558(pYA3634) and χ9088(pYA3634) immunized mice with that of the χ8133(pYA3634) immunized mice at week 8. p<0.01 for the anti-rPspA serum IgG antibody levels of χ9558(pYA3634) immunized mice compared to χ8133(pYA3634) immunized mice at week 10 and 12. p<0.05 for the anti-rPspA serum IgG levels of χ9558 (pYA3634) immunized mice compared to χ9088(pYA3634) immunized mice at week 8, 10 and 12.

Figure 34C:
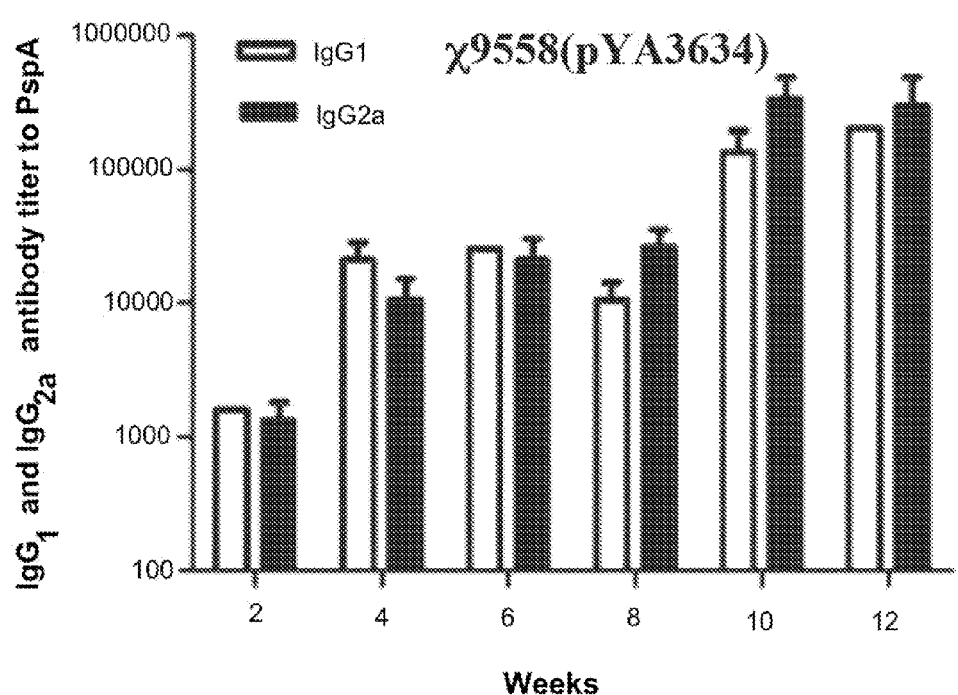

FIG. 34 depicts a series of graphs showing serum IgG2a and IgG1 responses to rPspA measure by ELISA. The data represent IgG2a and IgG1 subclass antibody levels to rPspA in sera of BALB/c mice orally immunized with the indicated strains at various times after immunization. The ratios of IgG1: IgG2a at 12 weeks are 1:8.3 for χ8133(pYA3634) immunized mice (A), 1:9.4 for χ9088(pYA3634) immunized mice (B) and 1:1.5 for χ9558(pYA3634) immunized mice (C).

Figure 35:
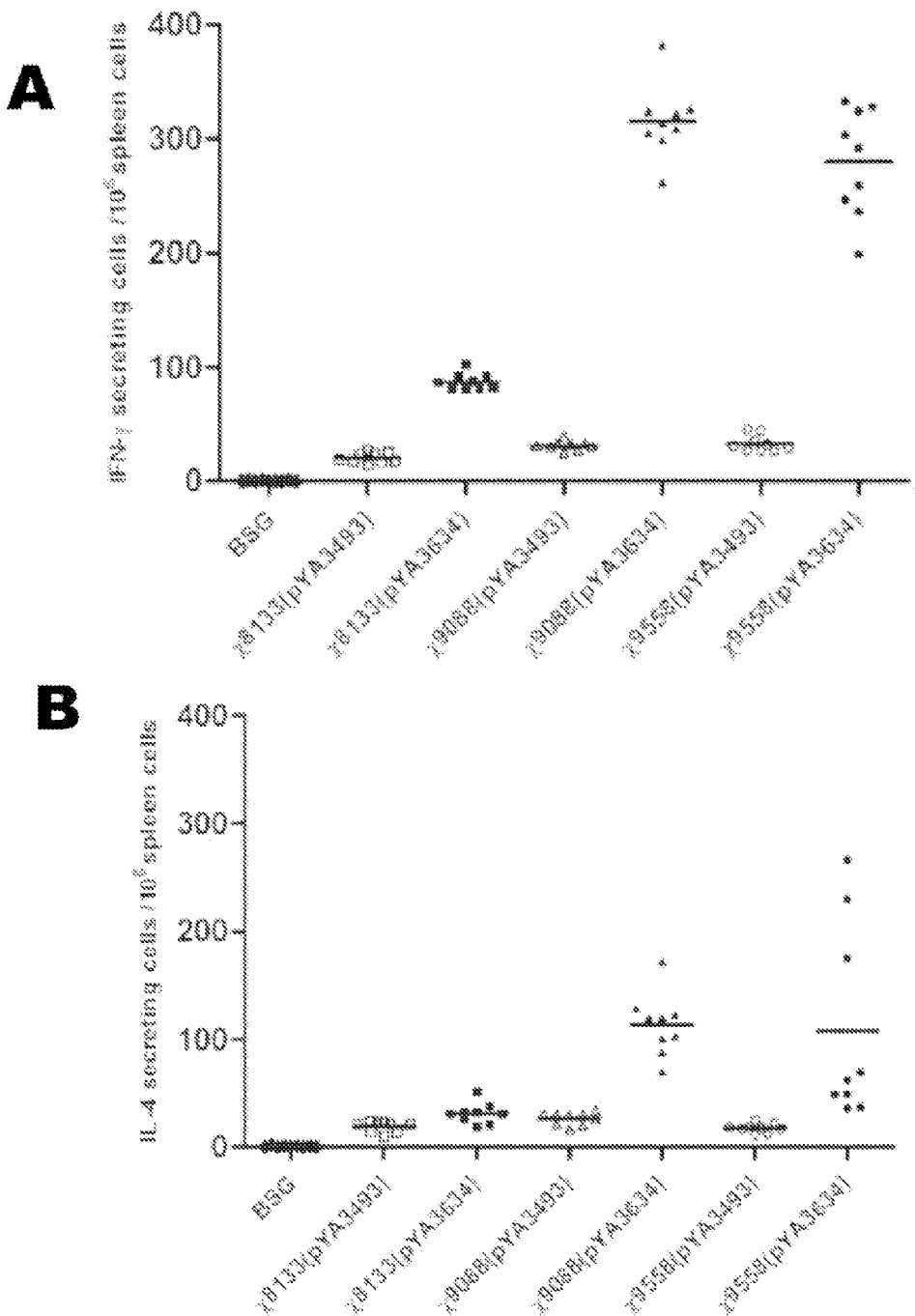

FIG. 35 depicts a series of graphs showing antigen-specific stimulation of IFN-γ (A) or IL-4 (B) production. Splenectomies were performed on euthanized BALB/c mice at 8 weeks following immunization. BSG controls were also included. Splenocytes were harvested from three mice per group. ELISPOT analyses were performed as described in Materials and Methods. The results are presented as ELISPOTS per million splenocytes minus any background ELISPOTS from unpulsed mock controls. One-way ANOVA and LSD methods were adopted to compare the secretion levels of IL-4 or IFN-γ between different groups. p<0.001 when compare χ9558(pYA3634) and χ9088(pYA3634) with χ8133 (pYA3634) for both secretion levels of IL-4 and IFN-γ. p<0.01 when compare χ9558(pYA3634) with χ9088 (pYA3634) for the secretion levels of IFN-γ.

FIG. 36 depicts photomicrographs of conventional light microscopy of H&E-stained lung tissue samples of WU2 challenged mice (10×40). (A) S. pneumoniae caused focal consolidation with extensive mononuclear and polymorphonuclear infiltration and loss of alveolar structure in mice that succumbed to the infection. (B) Lungs from survivors appeared normal without extensive cellular infiltration.

Figure 37:
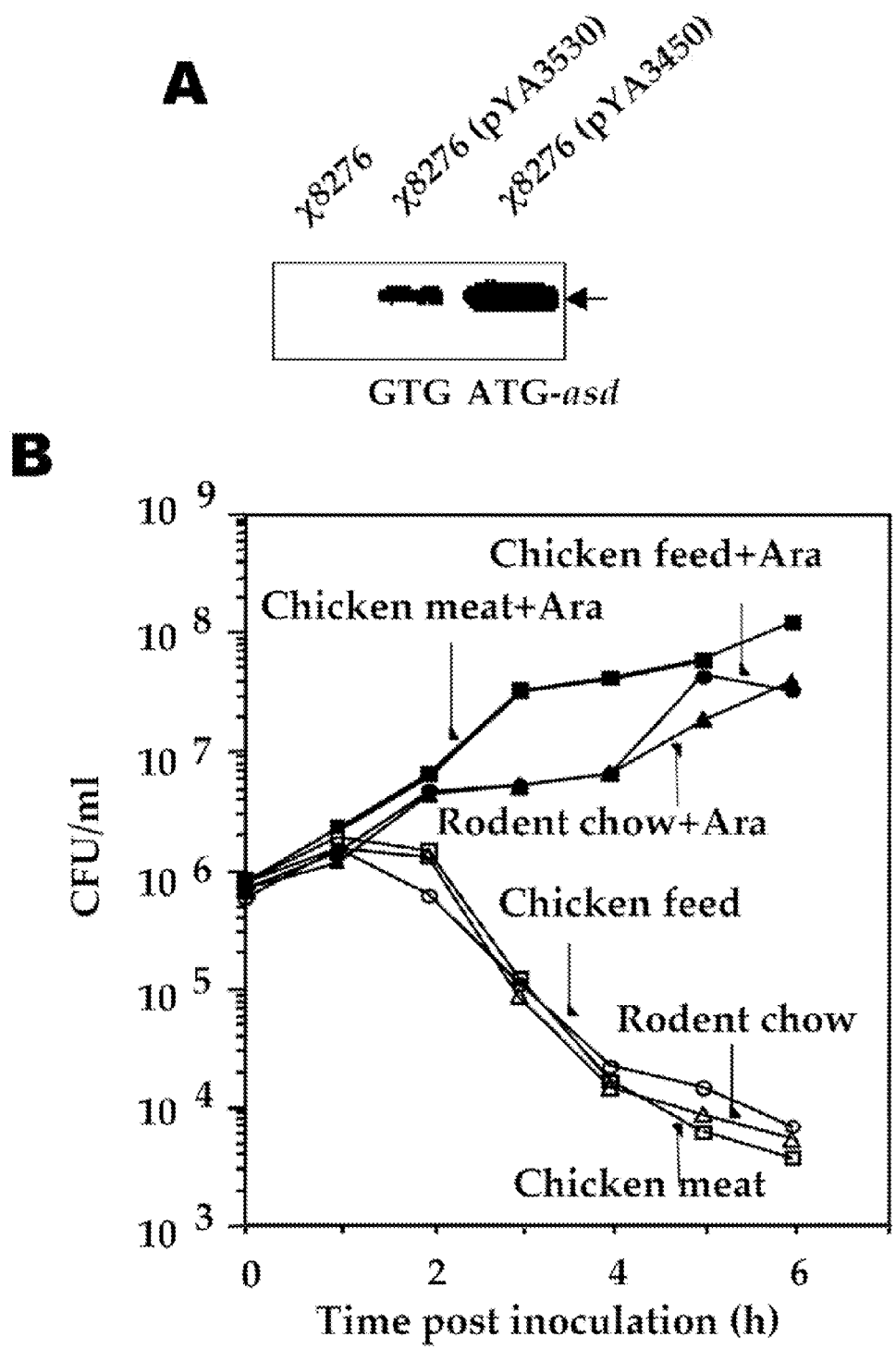

FIG. 37 depicts the synthesis of Asd protein from the asd gene with ATG or GTG start codon and muramic acid-less death assay. (A) The western blot was performed with cell lysates of S. Typhimurium strain χ8276 (ΔasdA16) and its derivatives cultured in LB broth with 0.2% arabinose. DAP was included in the medium for strain χ8276. Asd protein was detected using rabbit anti-Asd serum. The 39 kDa Asd protein is indicated by an arrow. (B) Growth of Salmonella strain χ8645 (ΔP$_{murA7}$::araC P$_{BAD}$ murA) with and without arabinose in the indicated media.

FIG. 38 depicts an illustration and a series of photographs showing the defined deletion mutations of strain χ8937 and nutritional requirements. (A) The defined deletion chromosomal mutations in wild-type Salmonella UK-1 and in strain χ8937. P: promoter, TT: transcriptional terminator. (B) The growth of host strain χ8937 alone or strain χ8937 harboring pYA3681 on LB agar plates with or without supplementations.

Figure 39:
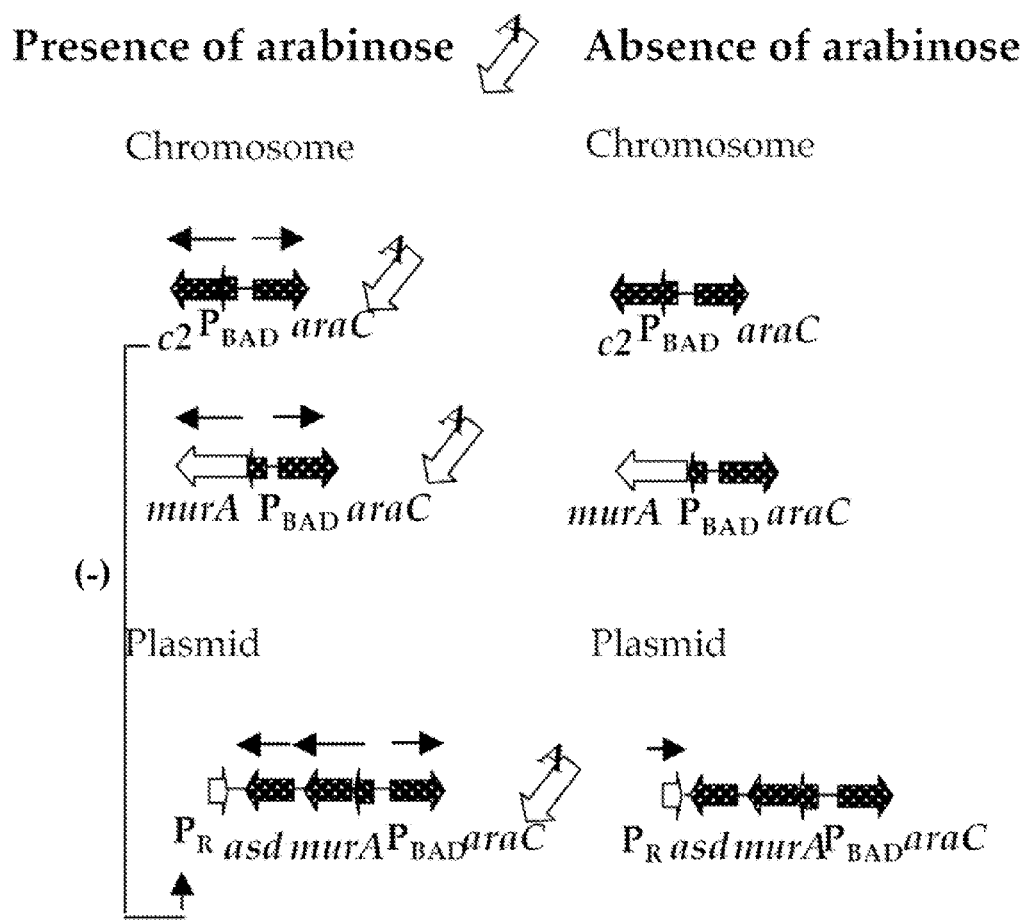

FIG. 39 depicts a diagram illustrating the regulatory interactions in the programmed lysis system.

Figure 40C:
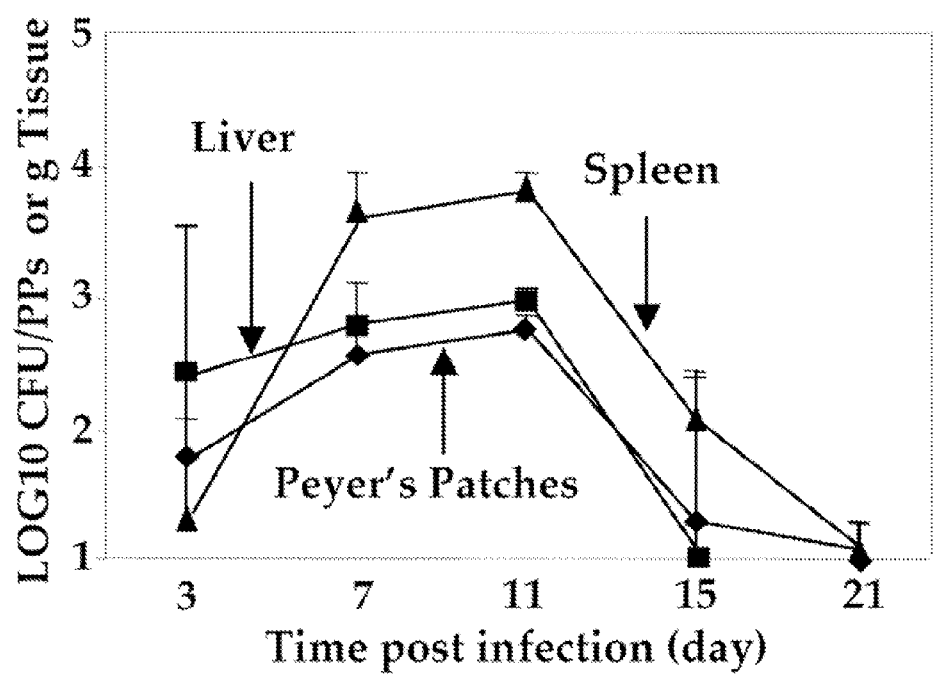

FIG. 40 depicts a series of graphs illustrating the in vitro and in vivo lysis of the programmed lysis system in the absence of arabinose. (A) The growth curves of strain χ8937 (pYA3681) with arabinose-regulated asdA and murA expression in LB broth with or without the addition of 0.02% arabinose. (B) The ratio of released β-galactosidase versus total β-galactosidase when strain χ9380(pYA3681) with arabinose-regulated asdA and murA expression and constitutive lacZ expression was grown in LB broth with or without 0.02% arabinose; the wild-type strain χ9379 modified to express lacZ acts as a non-lysis system control. (C) Colonization of mice with *S. Typhimurium* χ8937(pYA3681) following P.O. inoculation with $10^9$ CFU bacteria. The limits of detection for this assay were 10 CFU/PP or g of tissue.

FIG. 41 depicts the synthesis of PspA Rx1 and arabinose-dependent growth of χ8937(pYA3685). (A) Map of plasmid pYA3685. Plasmid sequences include the trpA, rrfG and 5S ribosomal RNA transcriptional terminators, the $P_{BAD}$, $P_{trc}$ and P22 $P_R$ promoters, the araC gene and start codon-modified murA and asdA genes, and the bla-pspA fusion protein. (B) The synthesis of rPspA Rx1 in the programmed lysis *S. Typhimurium* strain χ8937(pYA3685) grown in LB broth with 0.02% arabinose at 37° C. Aliquots of mid-log phase cultures were subjected to SDS-PAGE or immunoblot analysis. The immunoblot was probed with anti-PspA antibody. PspA proteins are indicated by arrows. Lanes 1 and 2, protein from χ8937(pYA3685) and χ8937(pYA3681), respectively. (C) Growth curves of PspA-producing strain χ8937 (pYA3685) in LB broth with or without the addition of 0.02% arabinose.

FIG. 42 depicts a series of graphs showing Immune responses in mice after oral immunization with χ8937 (pYA3685) (rPspA Rx1) and χ8937(pYA3681) (vector control) as determined by ELISA. (A) IgG antibody against *S. Typhimurium* SOMPs and rPspA Rx1 in a 1:1280 dilution of serum. (B) Anti-SOMP and -rPspA Rx1 IgA antibody levels in a 1:10 dilution of vaginal secretions.

Figure 43:
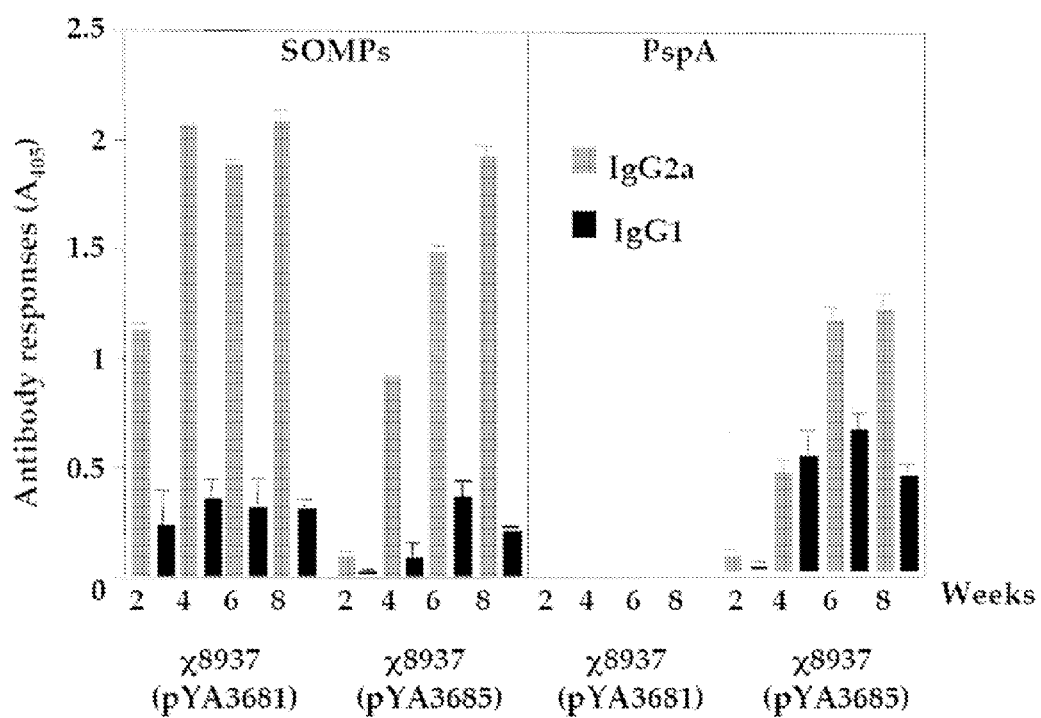

FIG. 43 depicts a graph showing IgG isotype analyses. Serum IgG2a and IgG1 responses to SOMPs and rPspA. IgG2a (gray bars) and IgG1 (dark bars). Serum was diluted 1:400.

Figure 44A:
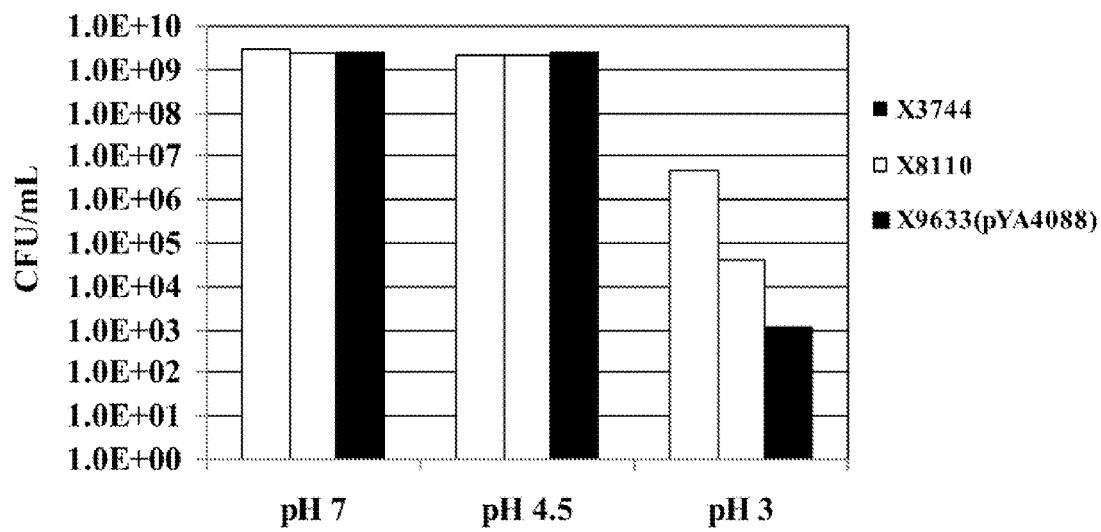
Figure 44B:
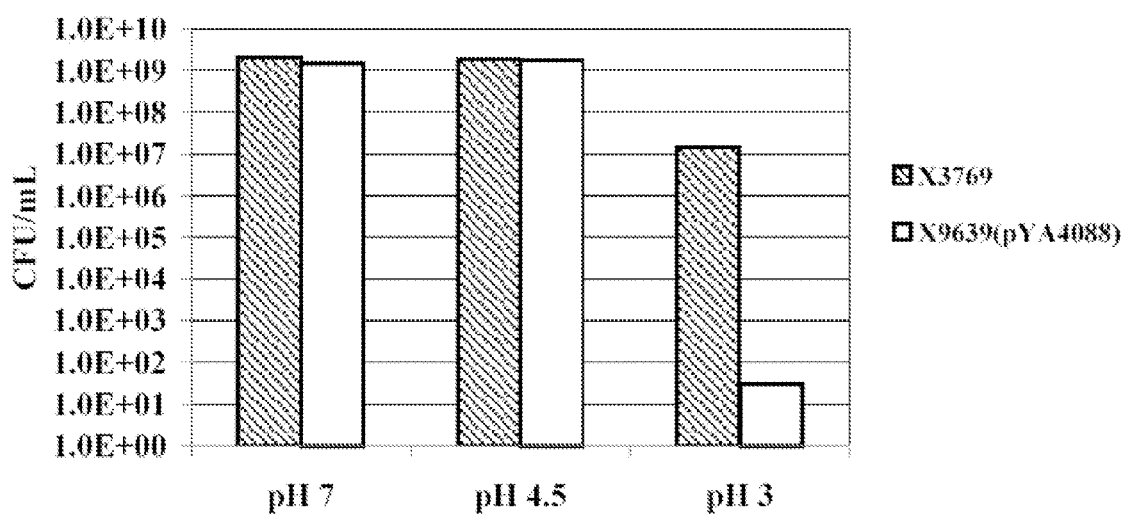
Figure 44C:
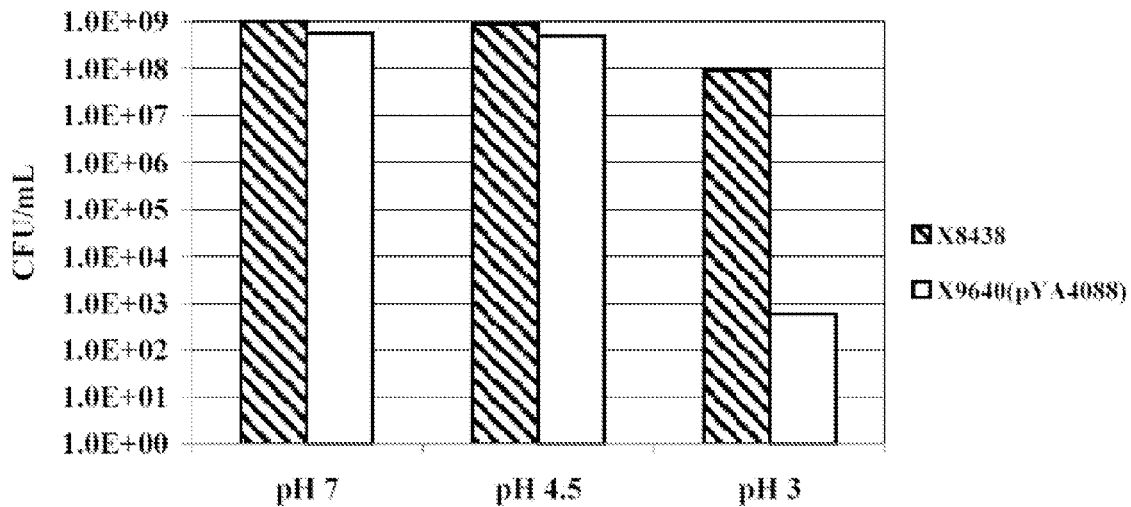

FIG. 44 depicts a series of graphs showing the sensitivity of (A) χ9633(pYA4088), (B) χ9639(pYA4088) and (C) χ9640 (pYA4088) RASV-Sp strains to low pH.

Figure 45:
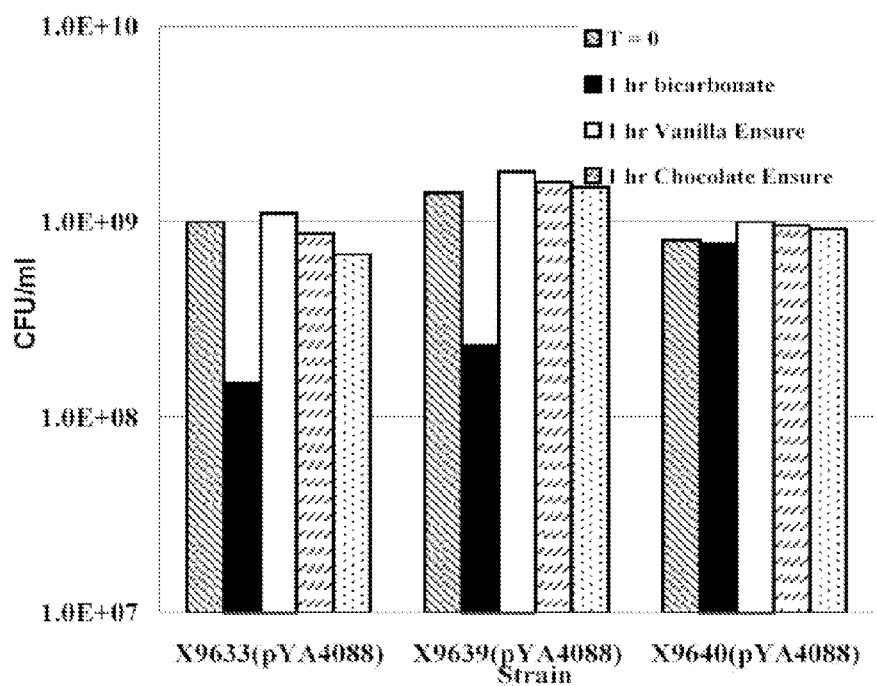

FIG. 45 depicts a graph showing the stability of RASV-Sp vaccine in Ensure nutrition shakes at 37° C.

Figure 46:
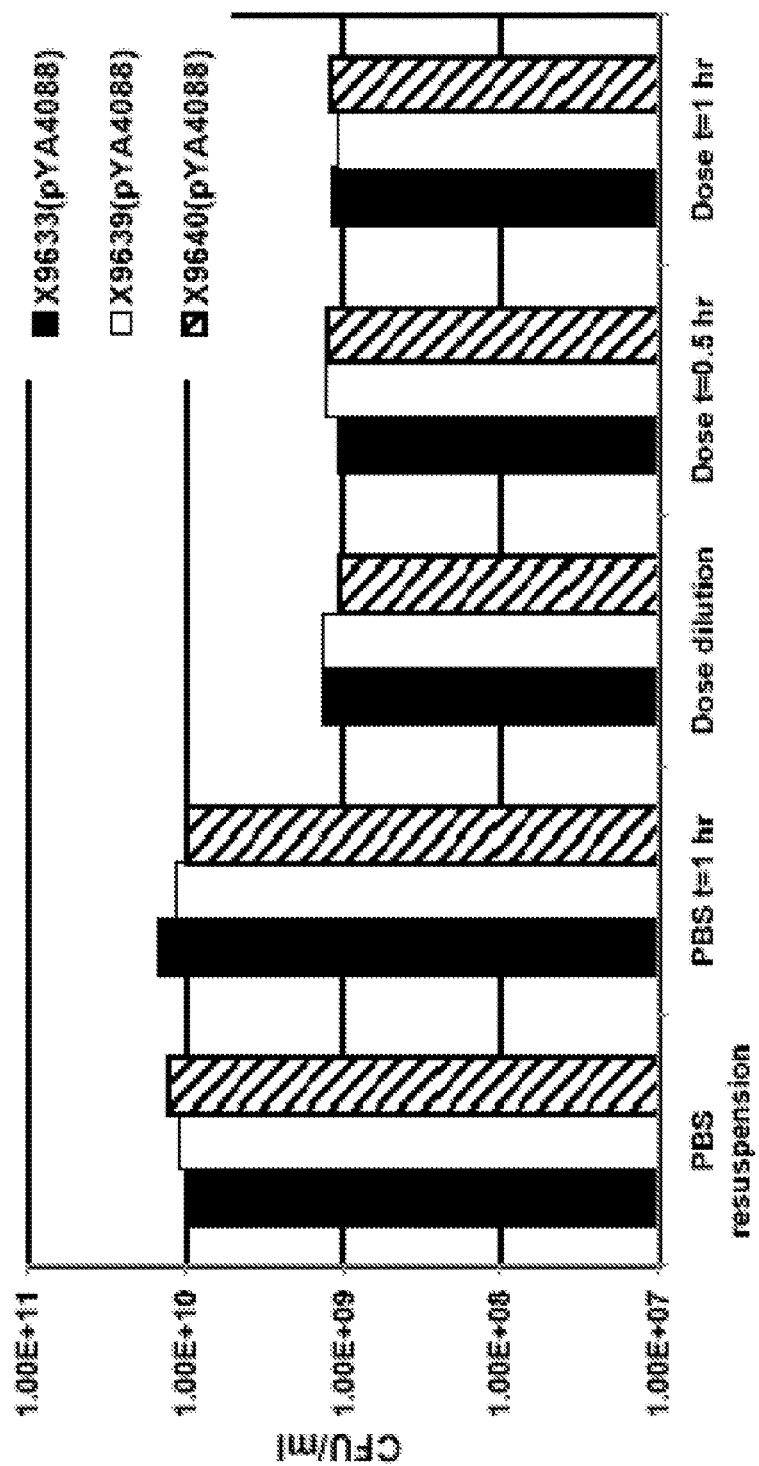

FIG. 46 depicts a graph showing the stability of RASV-Sp strains in PBS at room temperature.

Figure 47A:
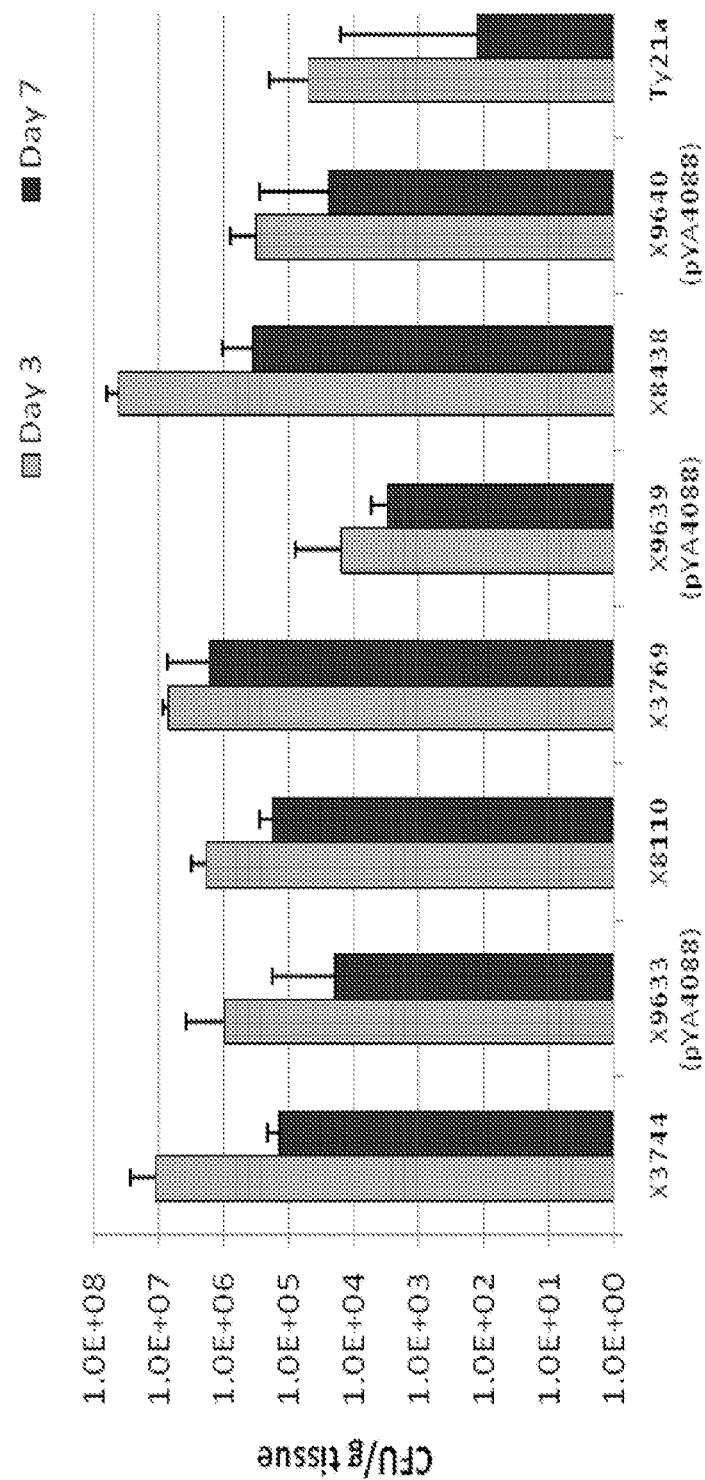
Figure 47B:
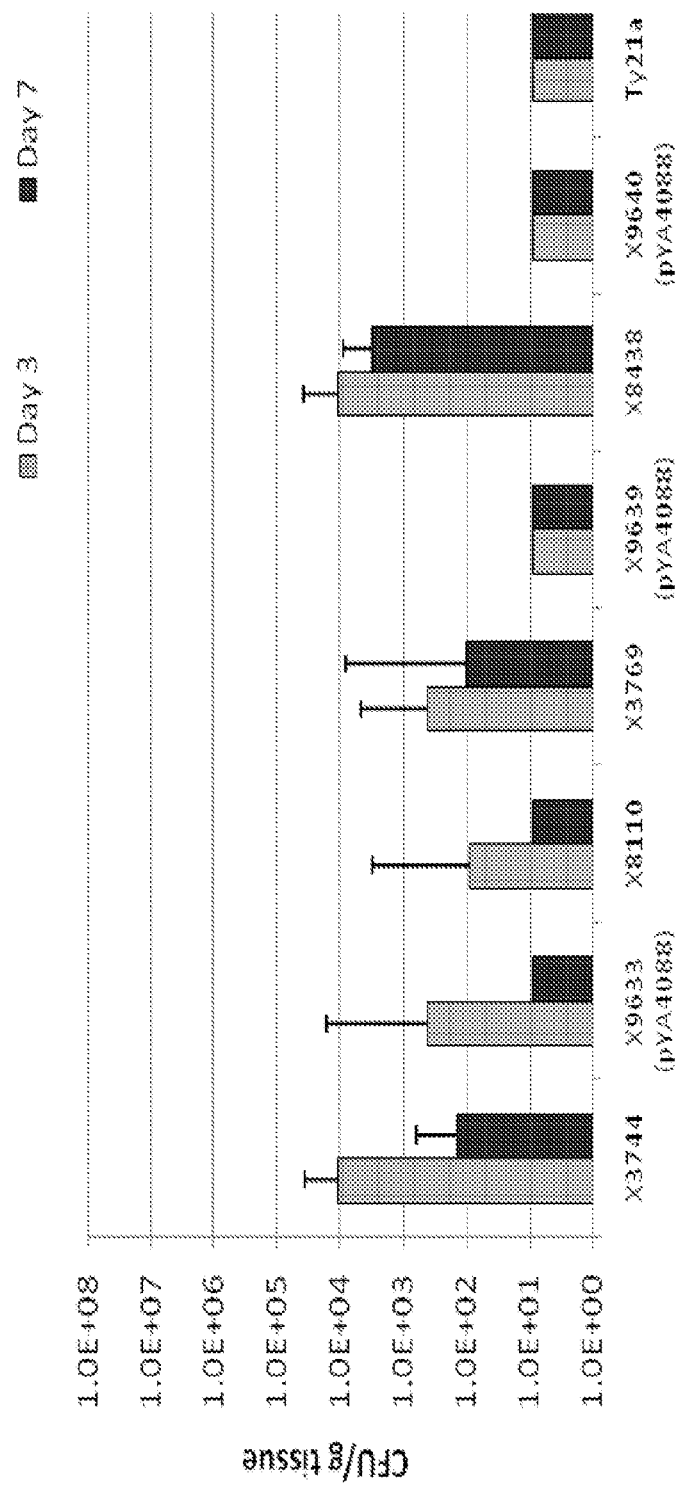
Figure 47C:
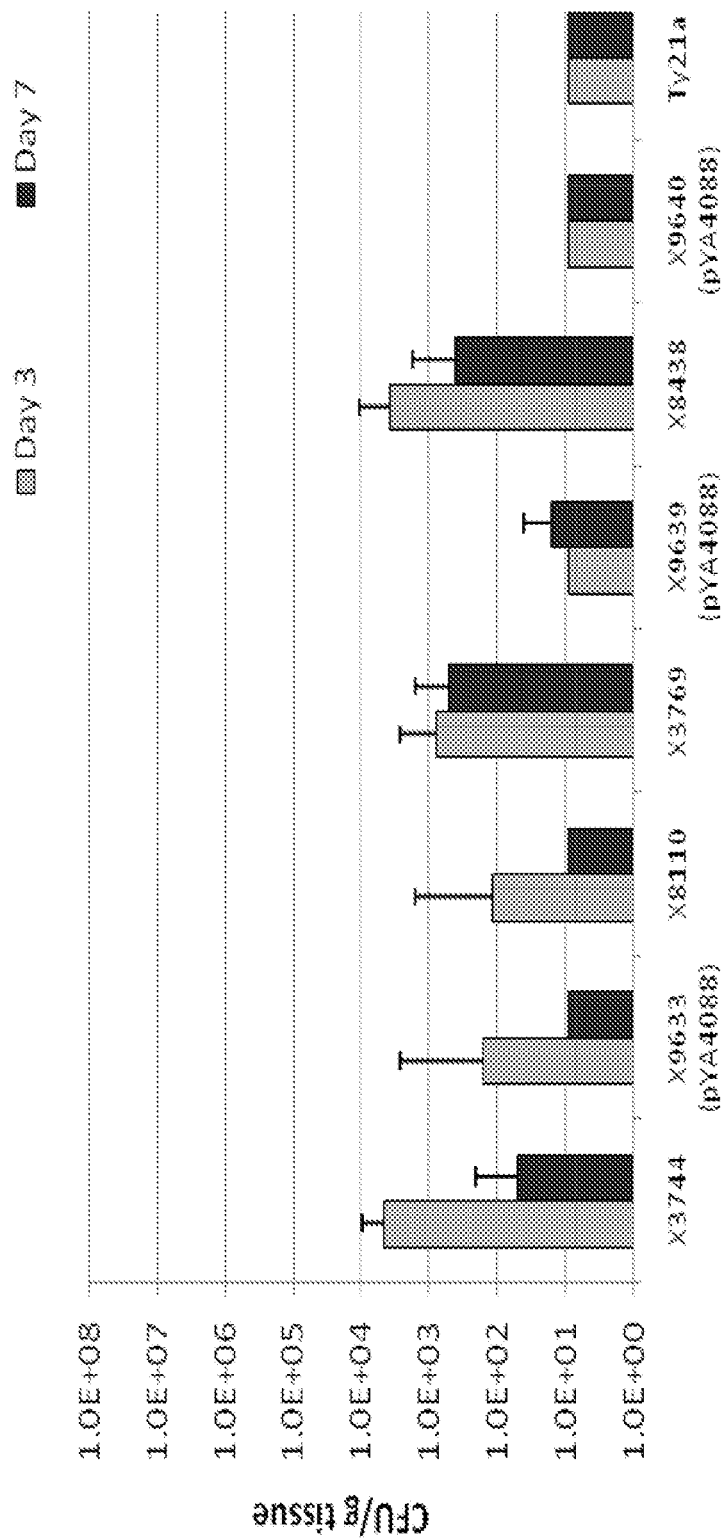

FIG. 47 depicts a series of graphs showing the colonization of the *S. Typhi* strains in (A) intestine, (B) spleen, and (C) liver of newborn mice.

Figure 48A:
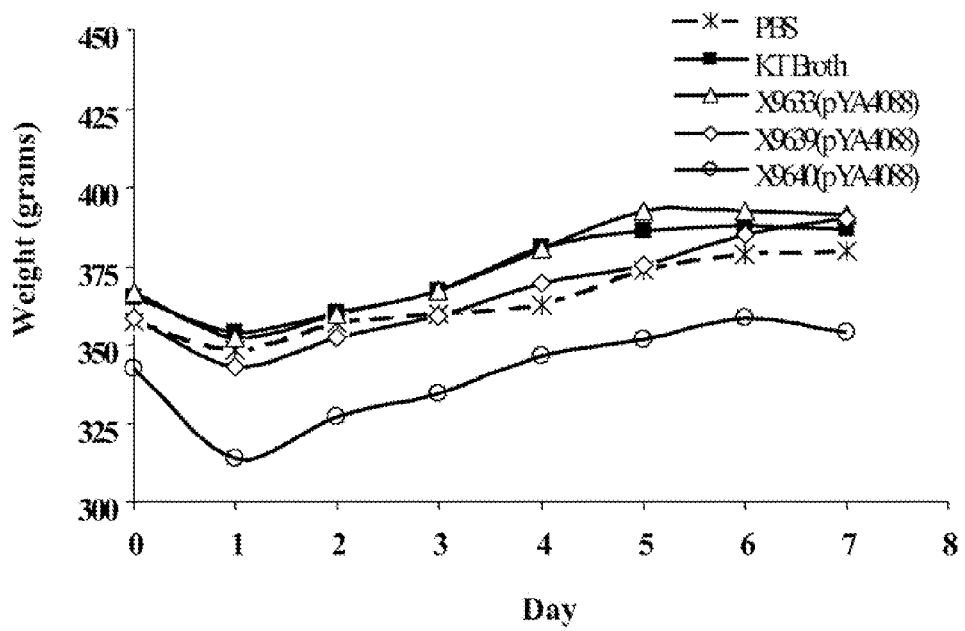
Figure 48B:
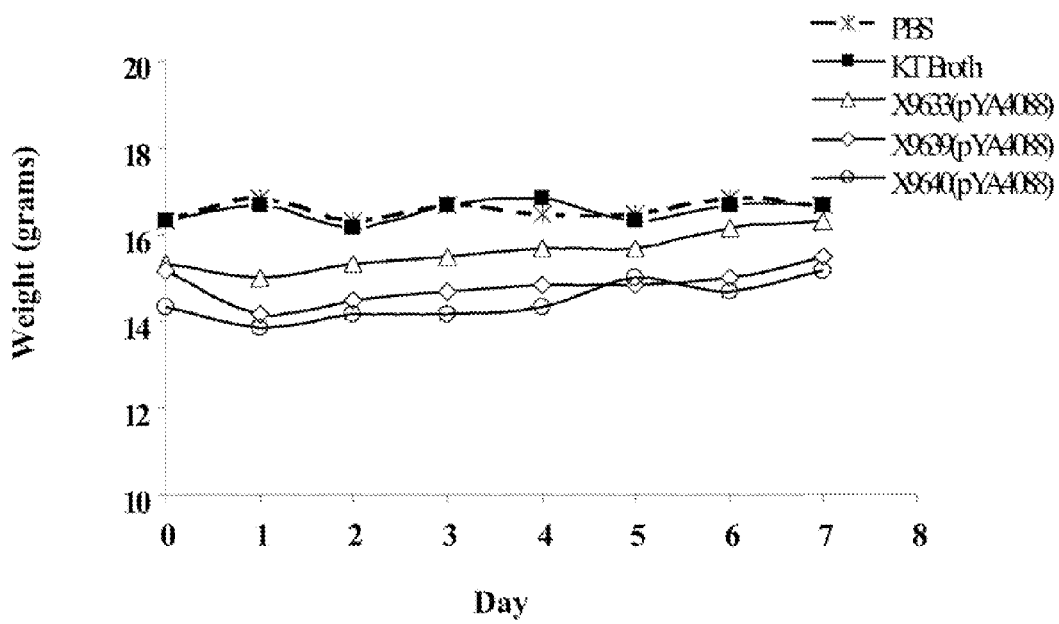

FIG. 48 depicts a series of graphs showing the (A) weights of guinea pigs administered sterile and cell-free PBS wash, and (B) weights of mice administered sterile and cell-free PBS wash.

Figure 49A:
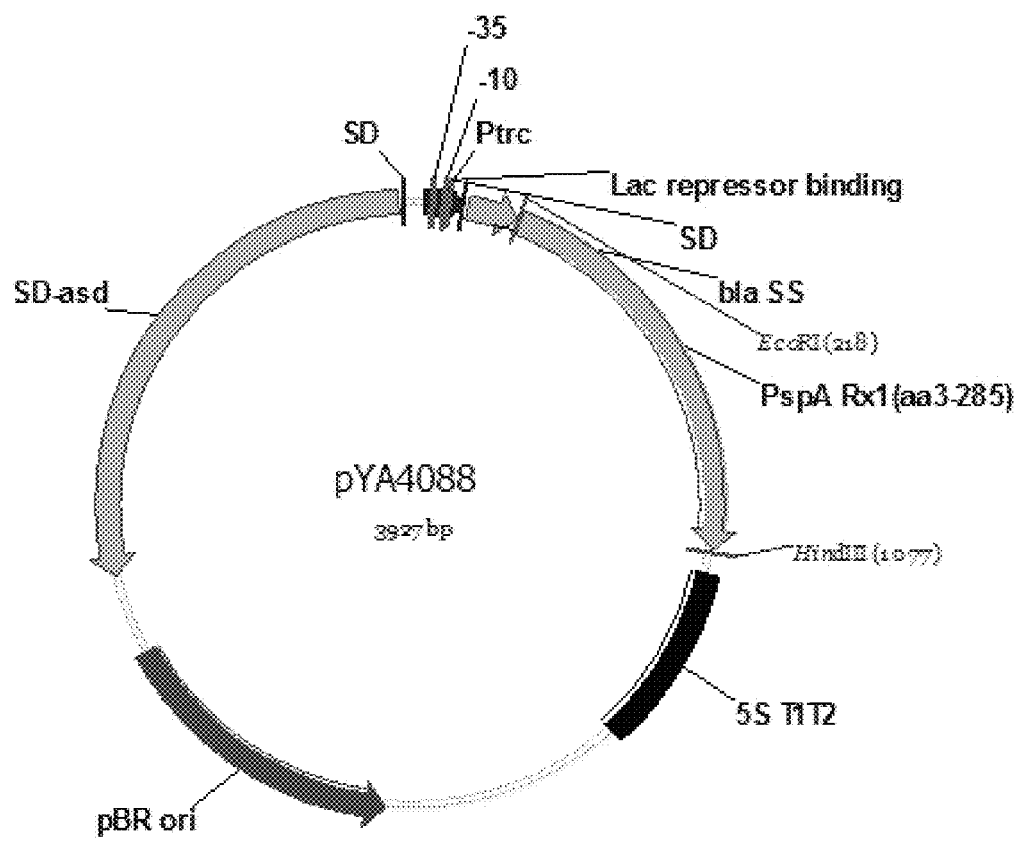
Figure 49B:
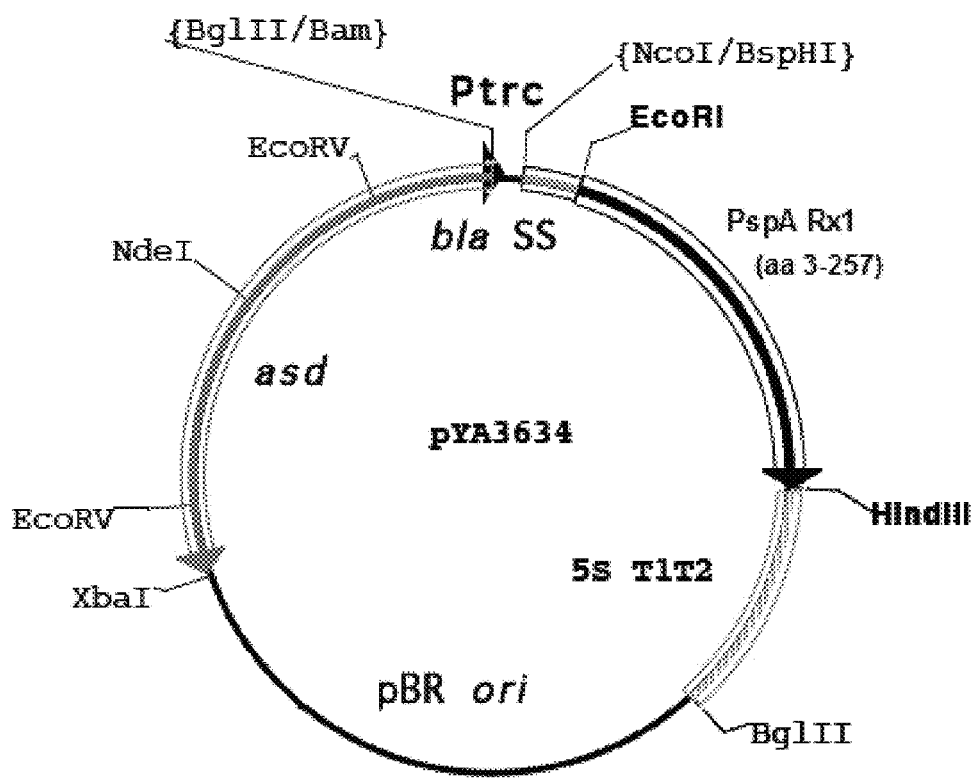
Figure 49C:
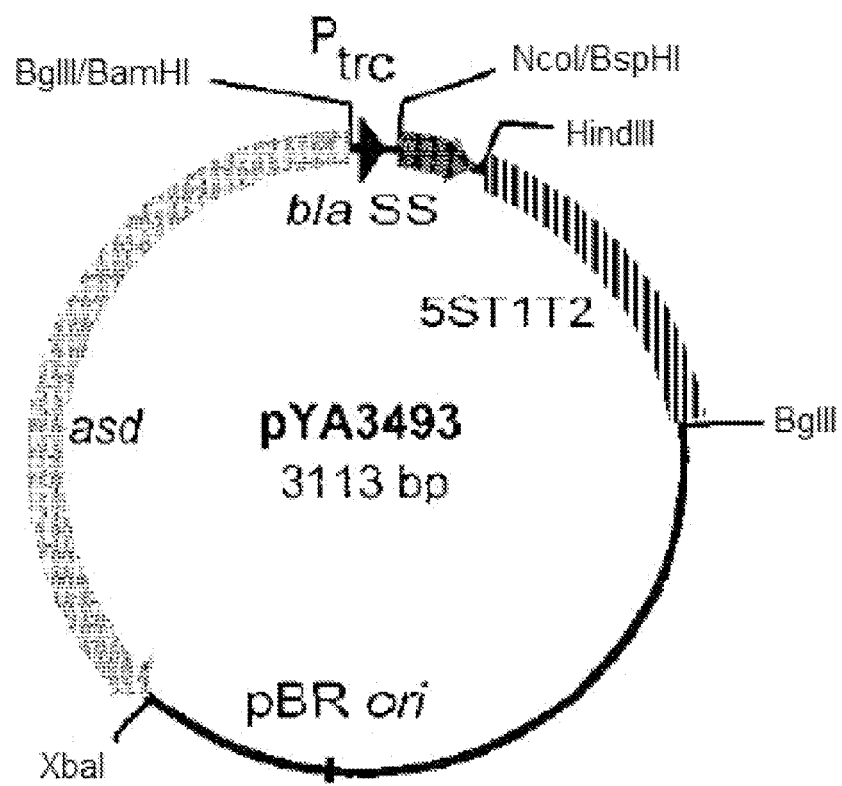

FIG. 49 depicts a schematic of PspA expression plasmids (A) pYA4088 and (B) pYA3634 with empty control vector (C) pYA3493.

Figure 50A:
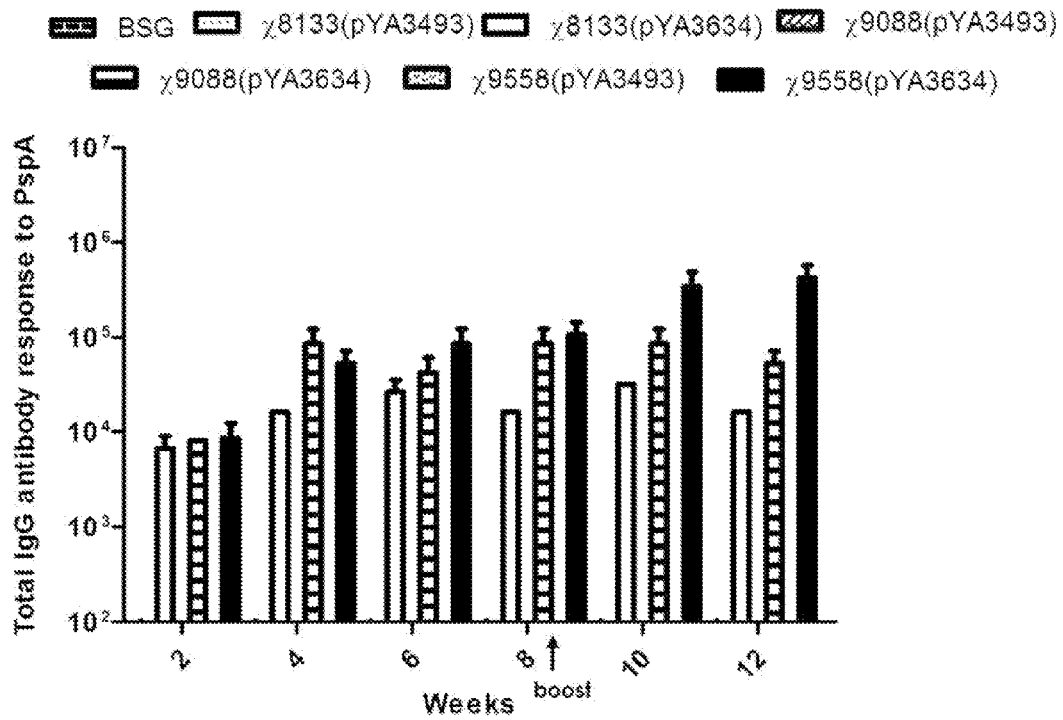
Figure 50B:
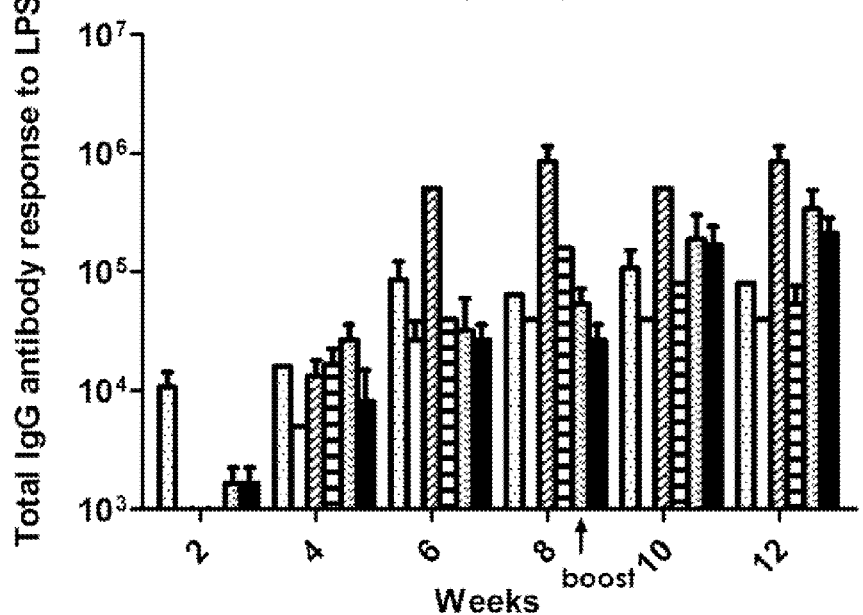

FIG. 50 depicts a series of graphs showing the total serum IgG from mice orally vaccinated with χ8133(pYA3634), χ9088(pYA3634) and χ9558(pYA3634) to (A) PspA and to (B) *S. Typhimurium* LPS.

Figure 51:
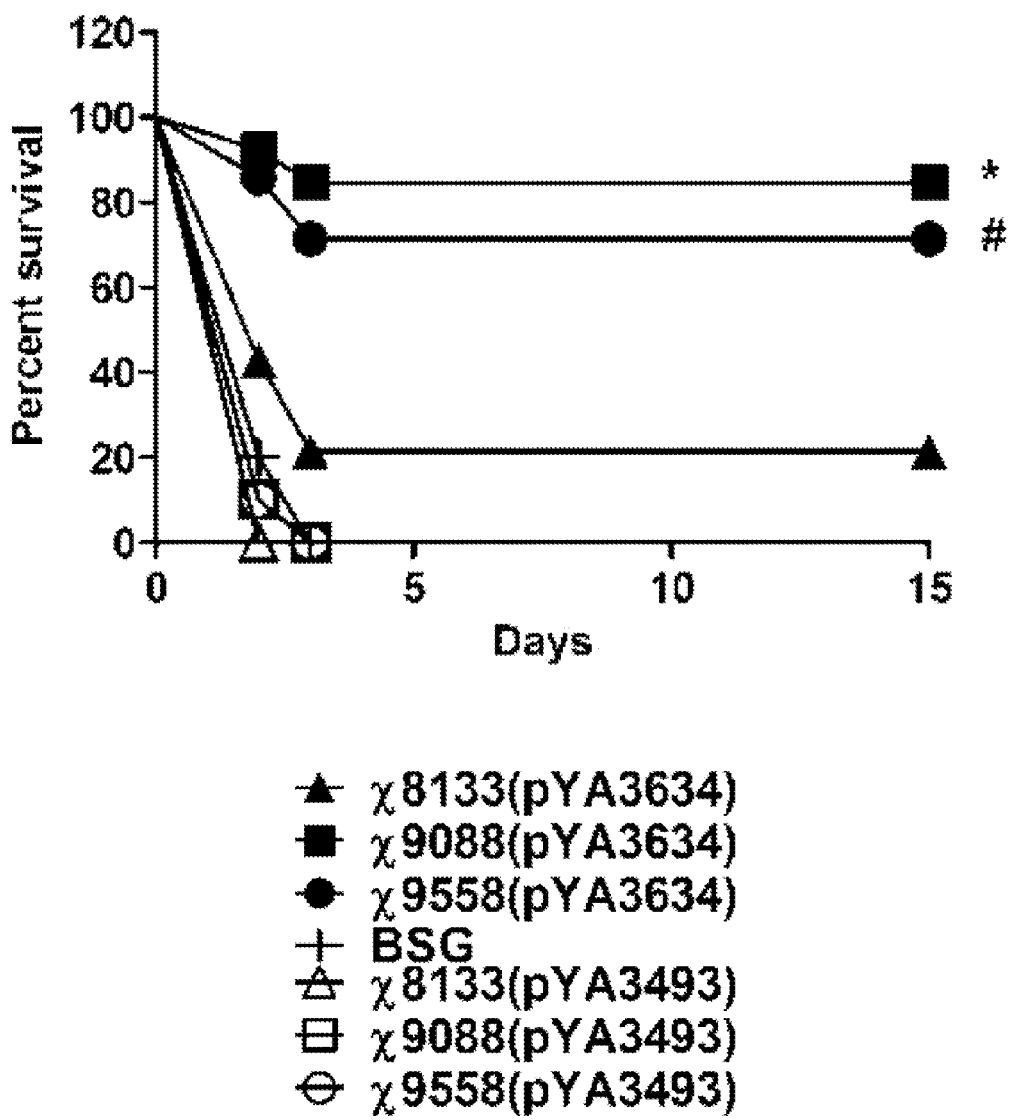

FIG. 51 depicts a graph showing immunization with χ9558 (pYA3634) protects mice against challenge with virulent *S. pneumoniae* strain WU2.

Figure 52A:
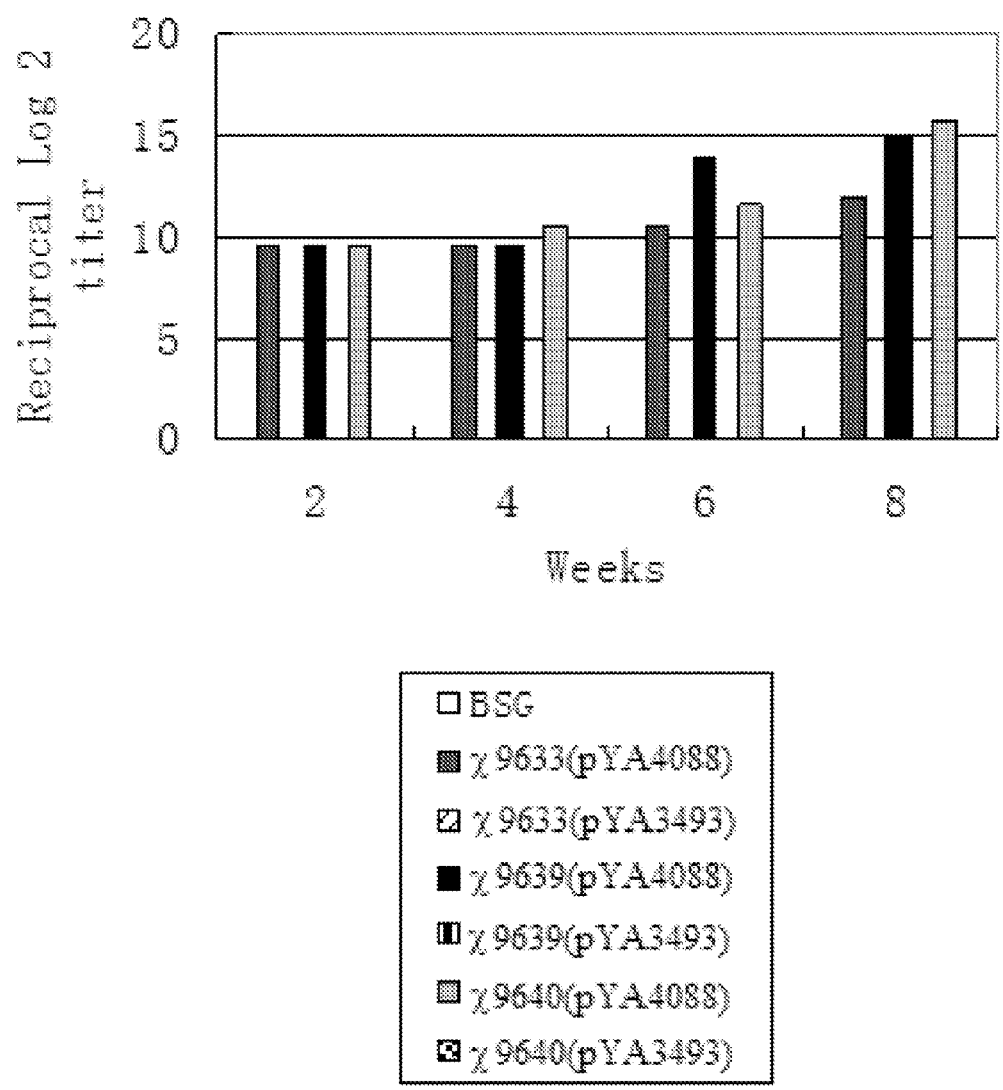
Figure 52B:
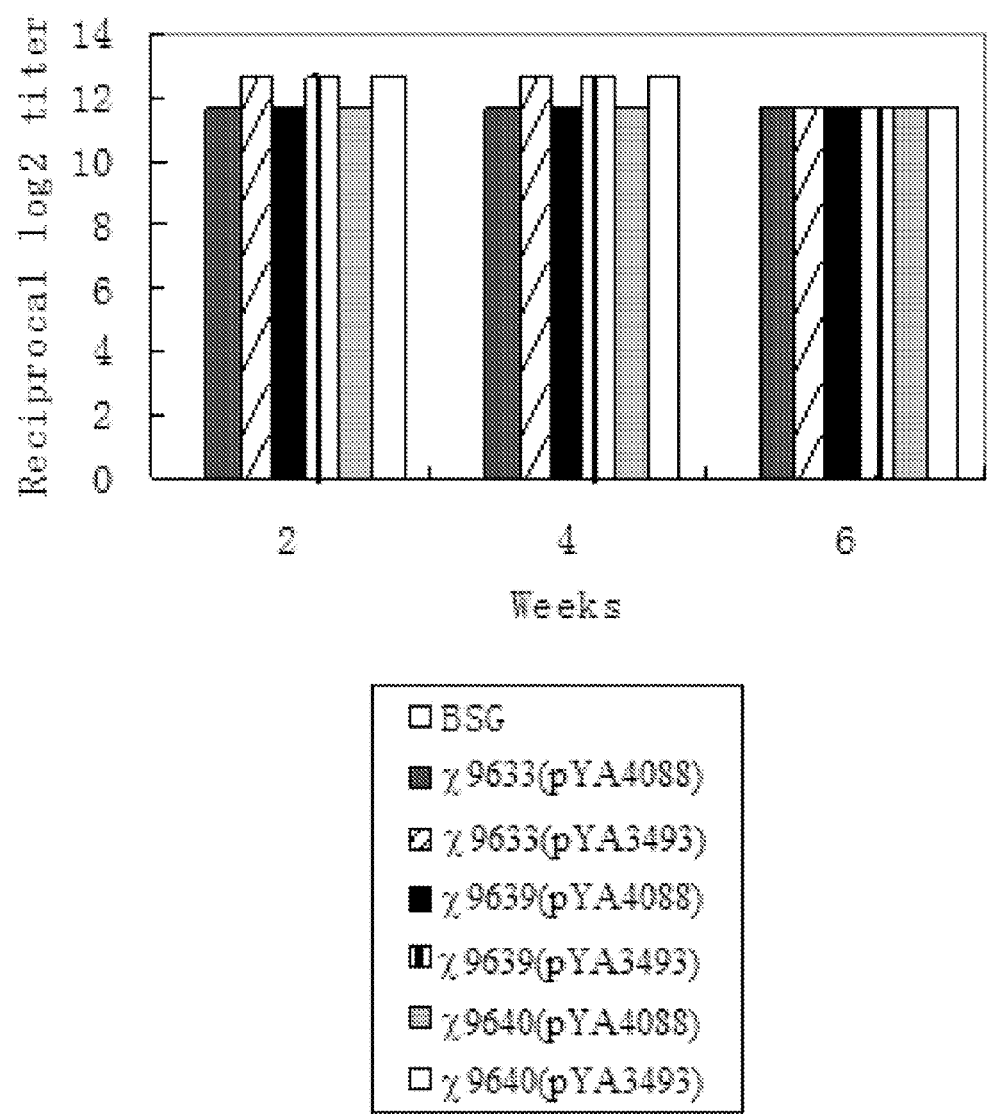
Figure 52C:
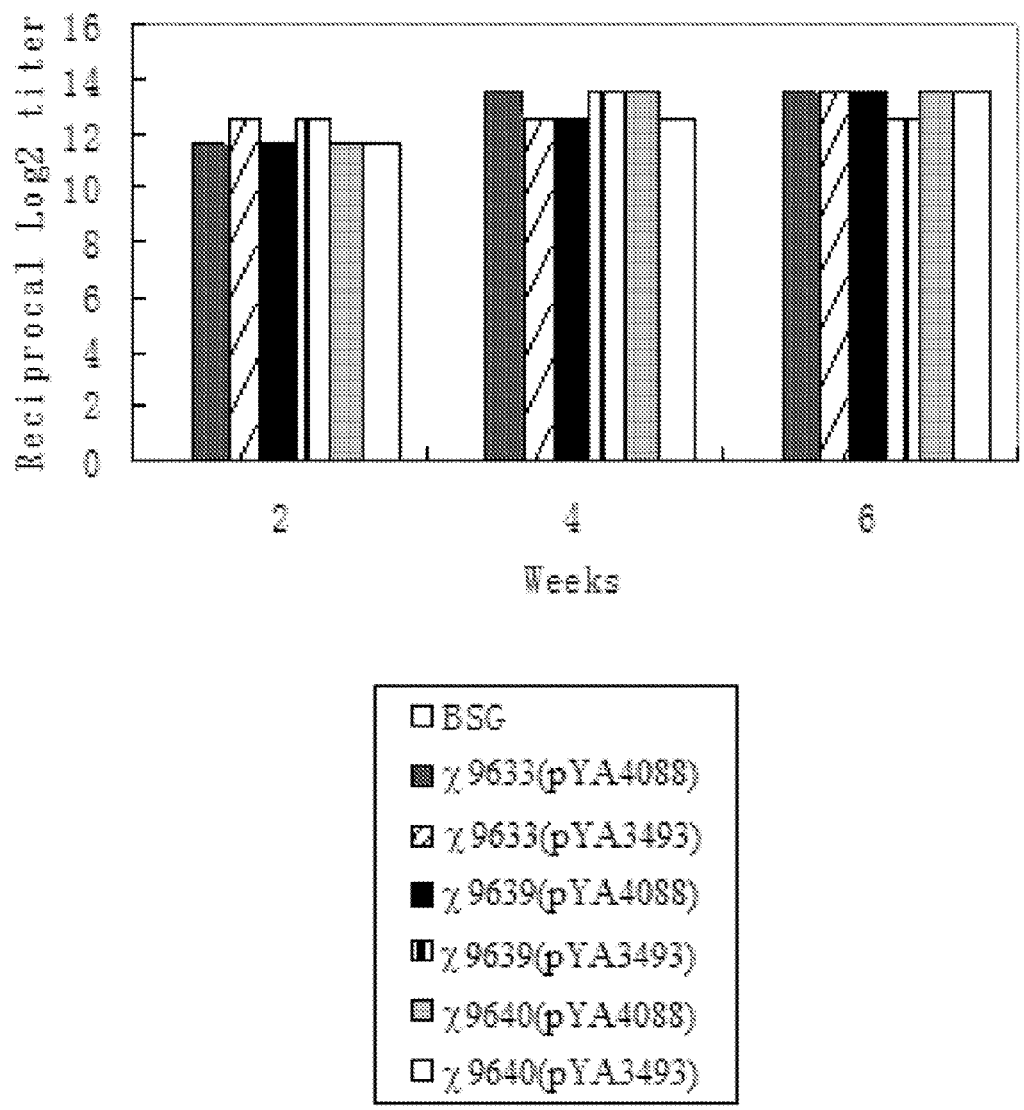

FIG. 52 depicts a series of graphs showing (A) the total IgG antibody response to PspA, (B) the total IgG antibody response to *S. Typhi* LPS, and (C) the total antibody response to *S. Typhi* outer membrane proteins.

Figure 53A:
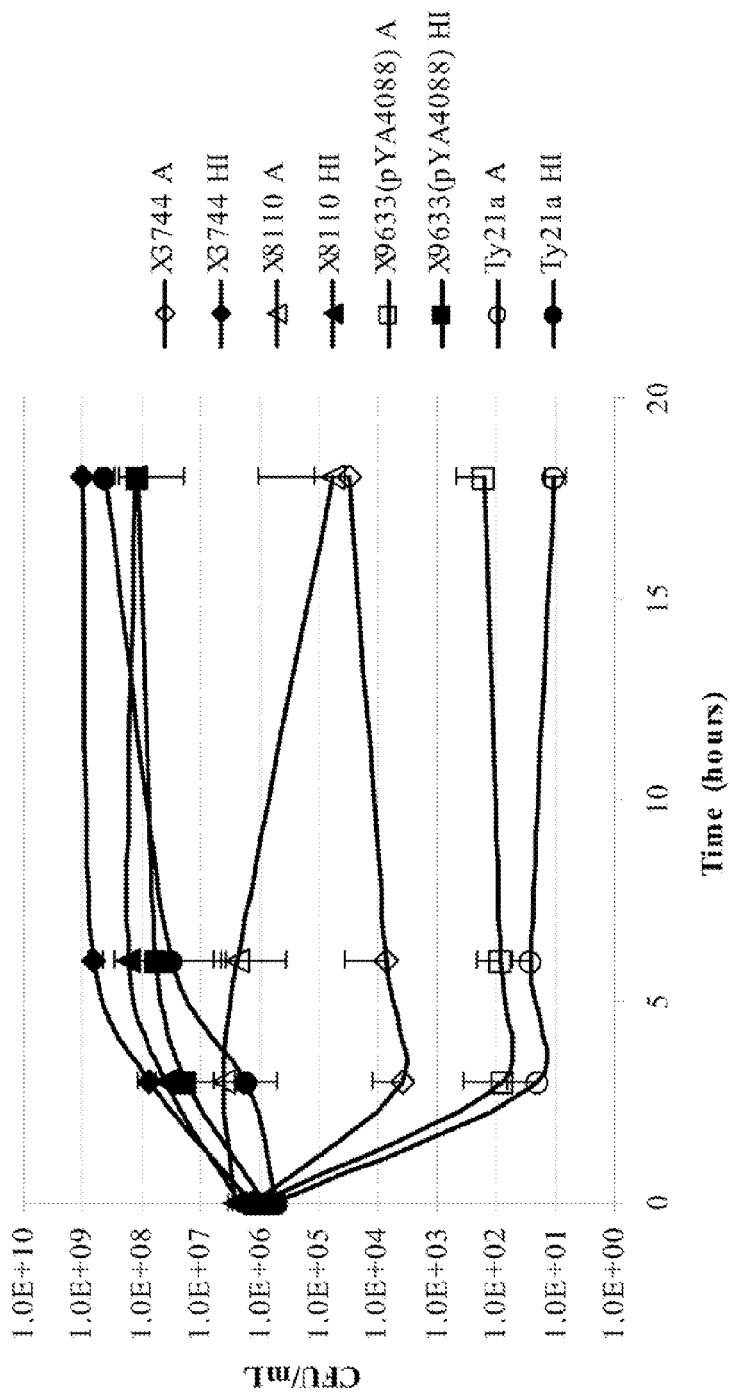
Figure 53B:
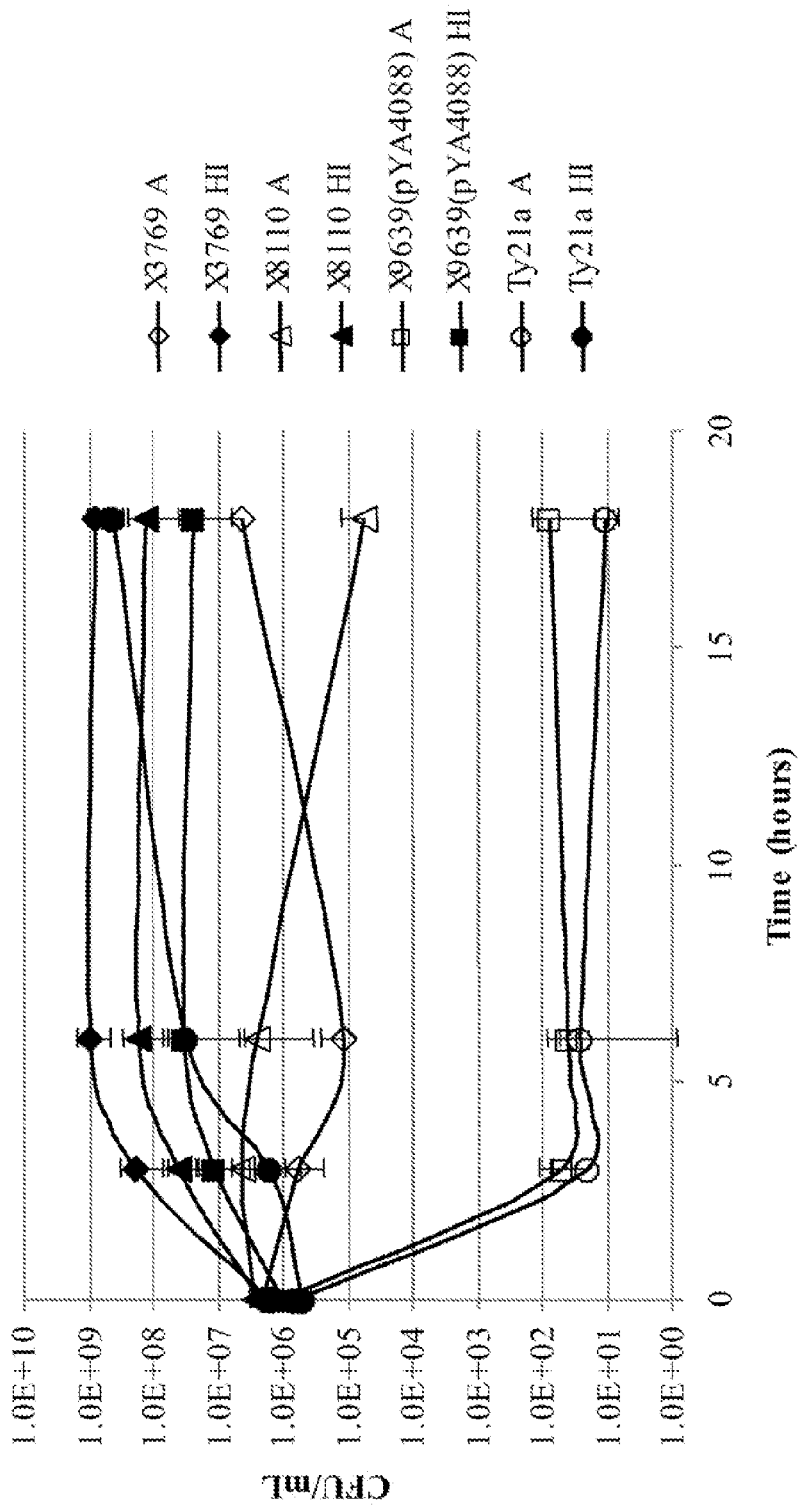
Figure 53C:
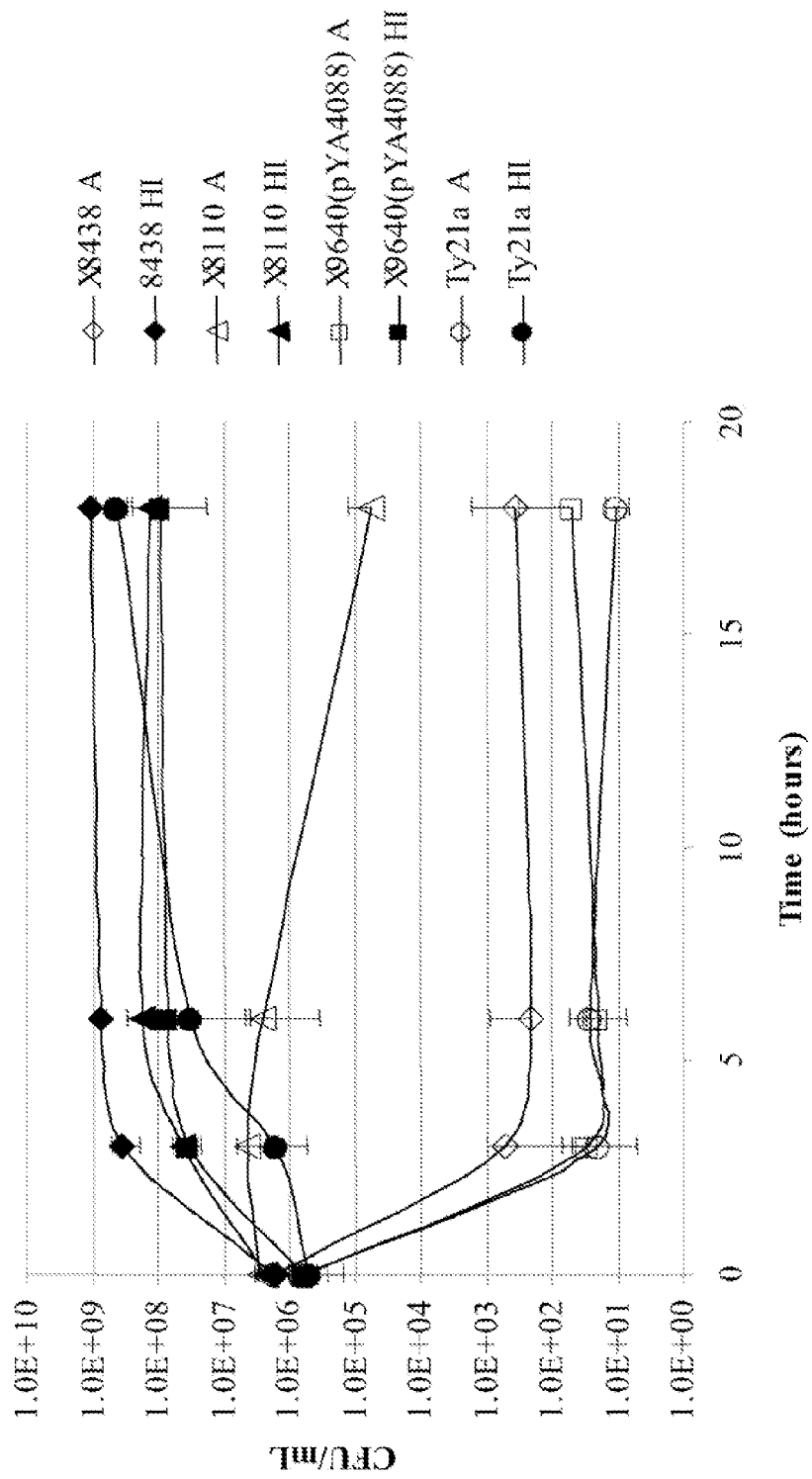

FIG. 53 depicts a series of graphs showing the survival of (A) *S. Typhi* ISP1820 derivatives, (B) Ty2 RpoS⁻ derivatives, and (C) Ty2 RpoS⁺ derivatives in active (A) and heat-inactivated (HI) whole human blood including χ8110 and Ty21a as controls.

Figure 54:
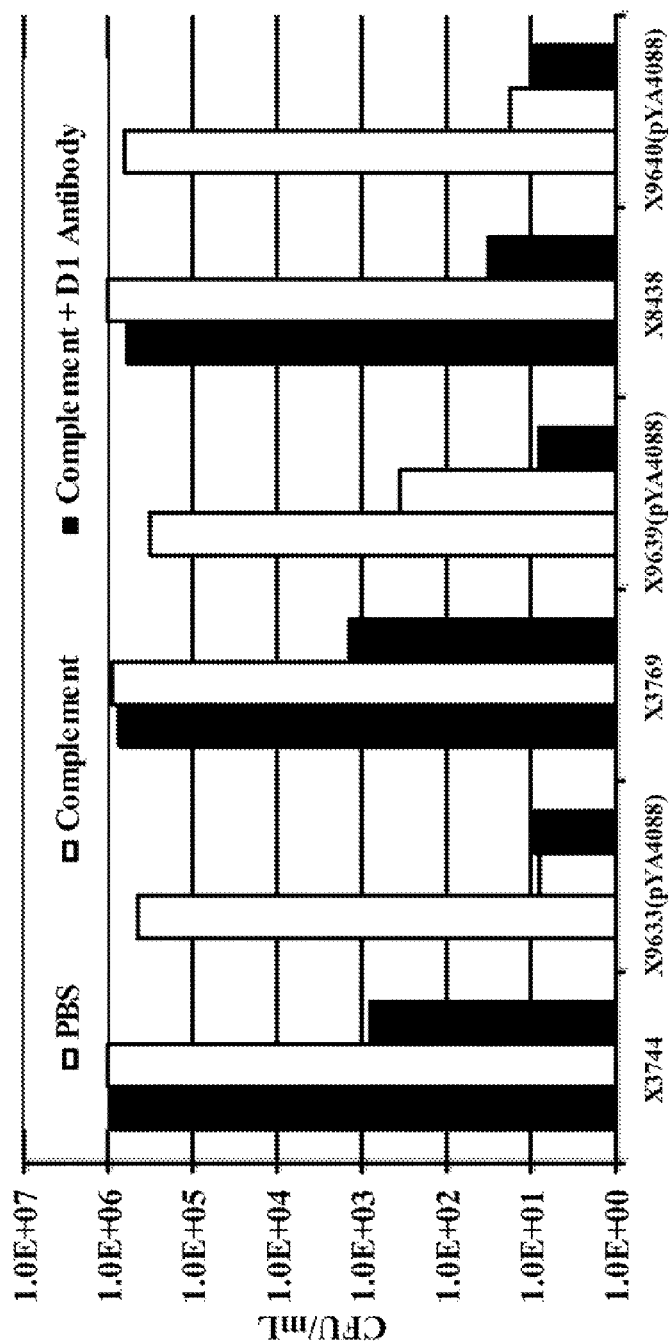

FIG. 54 depicts a graph showing the resistance of RASV-Sp strains compared to wild-type *S. Typhi* strains to guinea pig complement.

FIG. 55 depicts a series of graphs showing the survival of (A) *S. Typhi* ISP1820 derivatives, (B) Ty2 RpoS⁻ derivatives, and (C) Ty2 RpoS⁺ derivatives in peripheral blood mononuclear cells.

Figure 56:
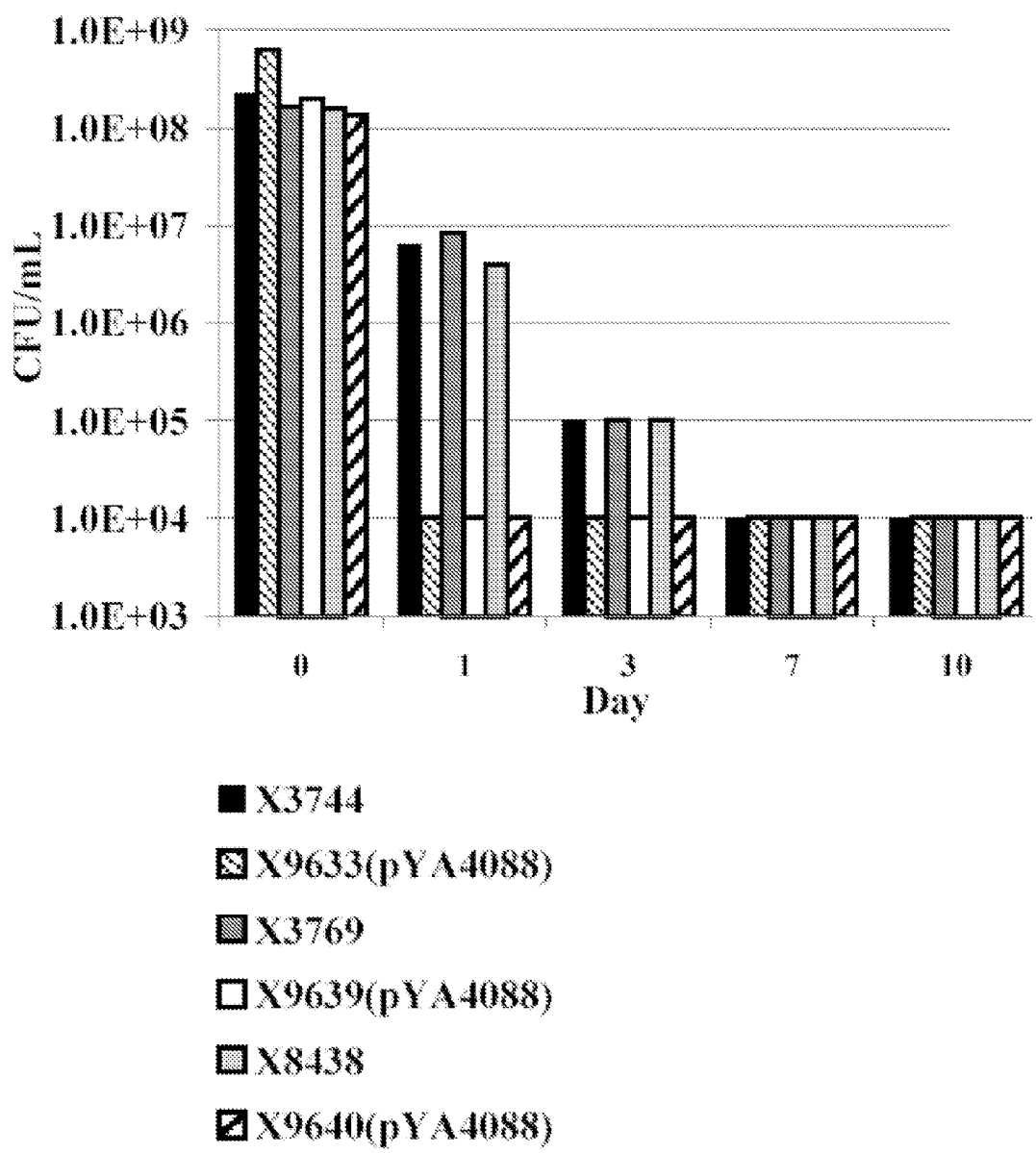

FIG. 56 depicts the survival of *S. Typhi* in human stool.

Figure 57A:
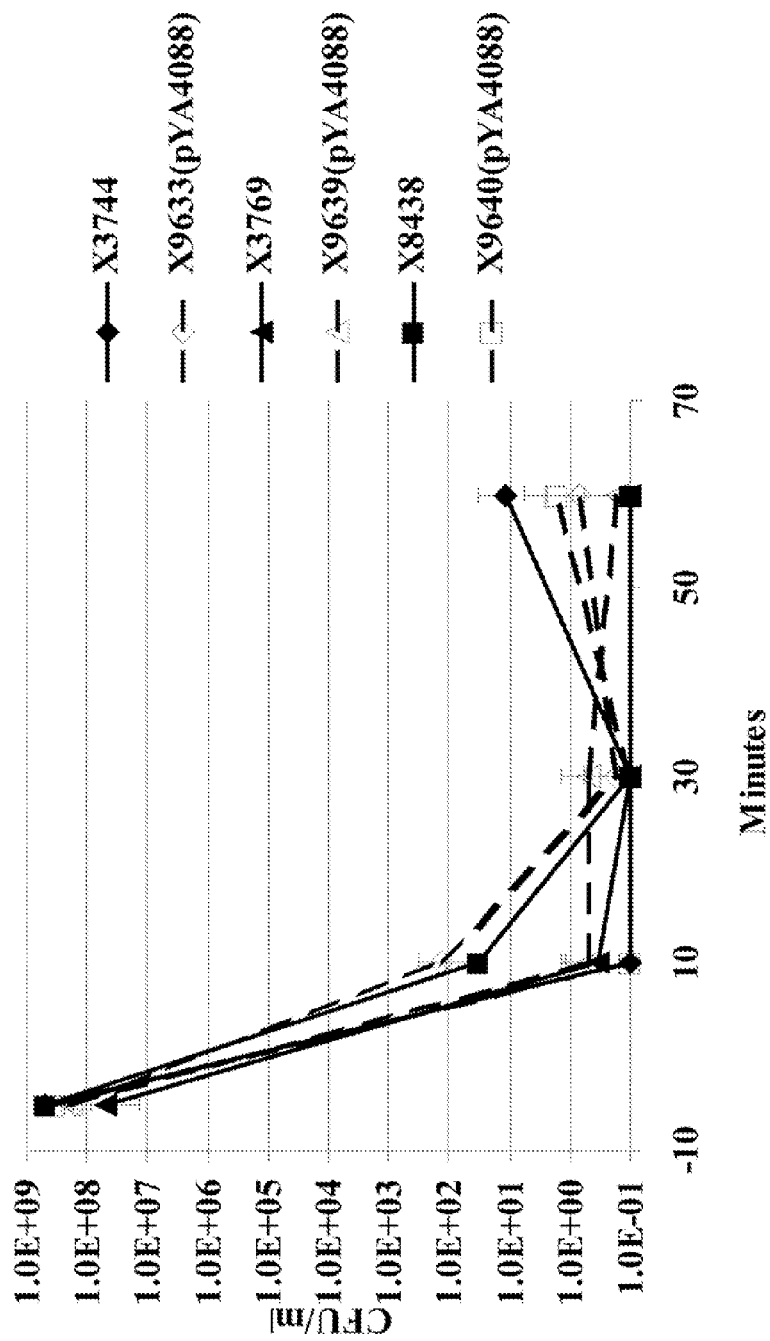
Figure 57B:
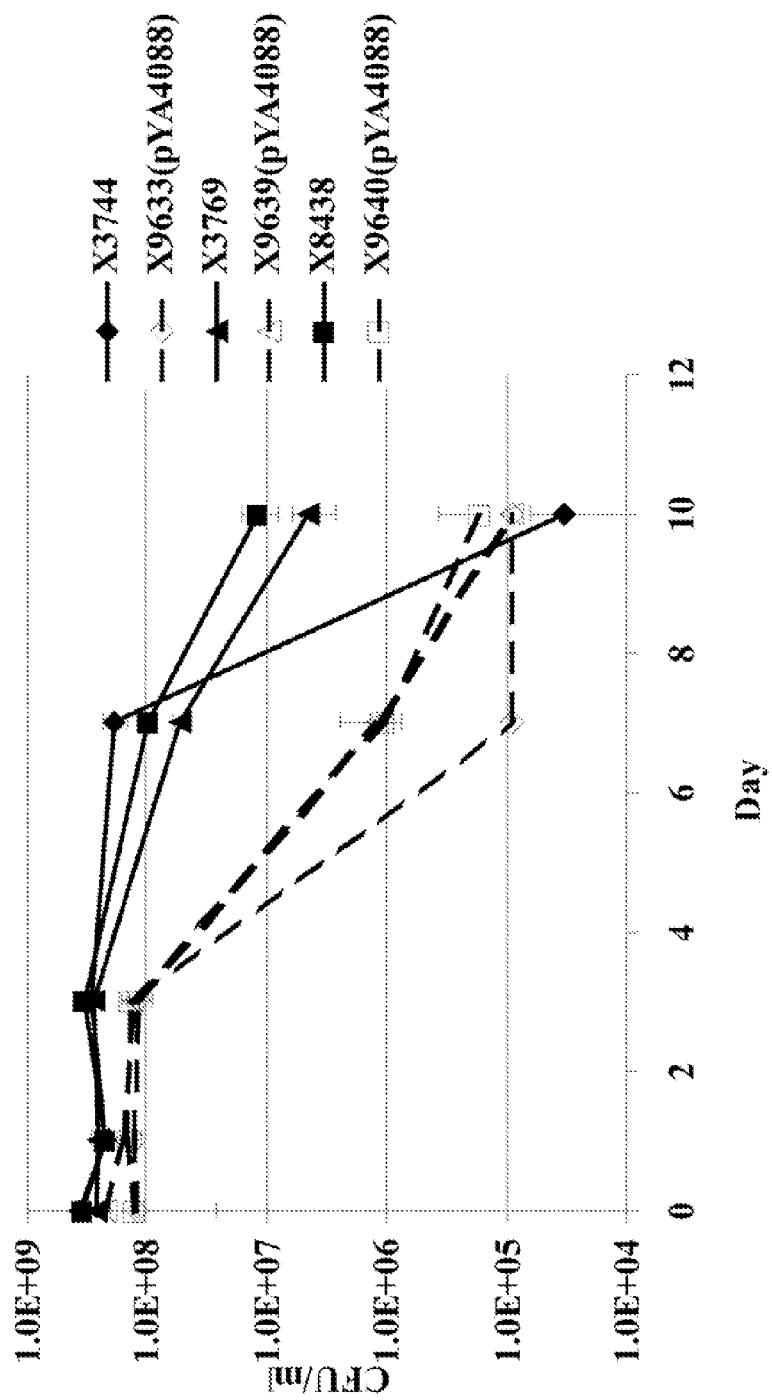
Figure 57C:
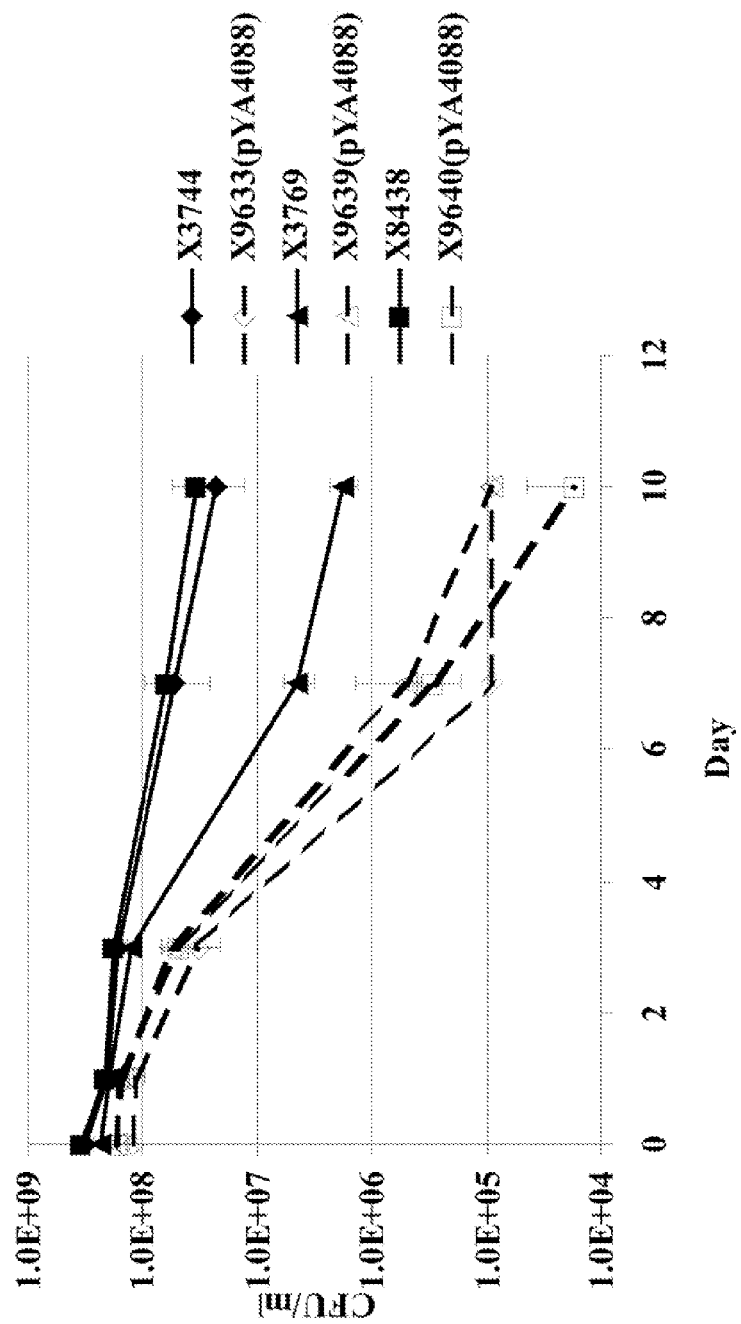

FIG. 57 depicts the survival of RASV-Sp strains and wild-type *S. Typhi* in (A) chlorinated water, (B) untreated canal water, and (c) raw sewage.

FIG. 58 depicts the serum IgG responses to rPspA (A), to *S. Typhi* LPS (B), to OMPs (C) and sIgA (D) in immunized mice. Serum IgG responses against rPspA (A) *S. Typhi* LPS (B), and SOMPS (C) and mucosal IgA responses to rPspA (D) were measured by ELISA using pooled sera from BALB/c mice intranasally immunized with the indicated strains carrying either plasmid pYA3493 (negative control) or pYA4088 (PspA). Error bars represent variation between triplicate wells. Mice were boosted at week 6. Statistical significance was determined at week 8. *, P<0.05; **, P<0.01 for χ9633(pYA4088), χ9639(pYA4088) and χ9640(pYA4088) were compared each other.

Figure 59:
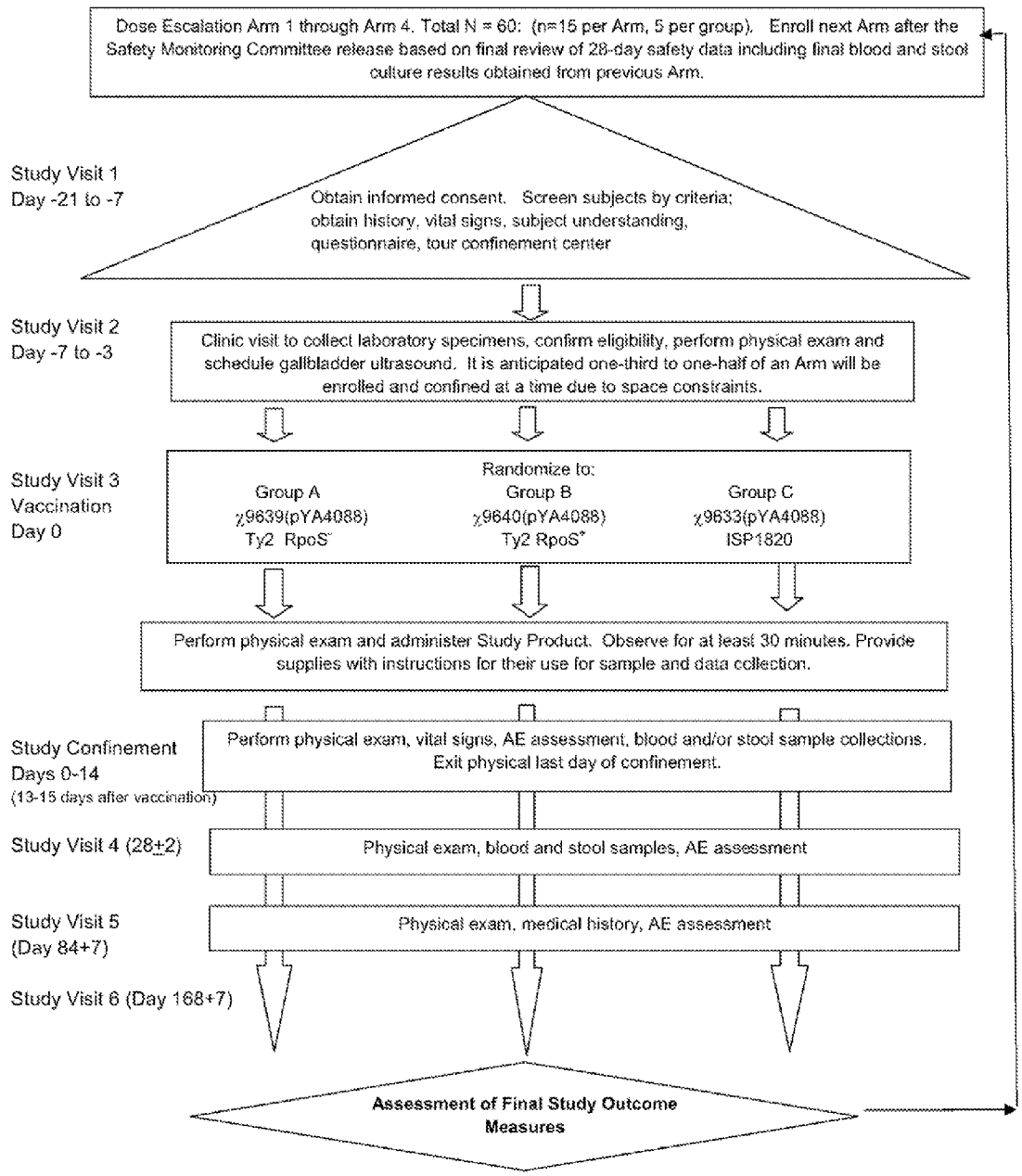

FIG. 59 depicts a schematic of the phase I safety and tolerability clinical study design.

DETAILED DESCRIPTION OF THE INVENTION

The present invention provides, in some embodiments, a recombinant bacterium capable of regulated expression of at least one nucleic acid sequence encoding an antigen of interest. In other embodiments, the invention provides a recombinant bacterium capable of regulated attenuation. In exemplary embodiments, the invention provides a recombinant bacterium capable of both regulated expression of at least one nucleic acid sequence encoding an antigen of interest and regulated attenuation.

In each of the embodiments herein, the recombinant bacterium typically belongs to the Enterobaceteriaceae. The Enterobacteria family comprises species from the following genera: *Alterococcus, Aquamonas, Aranicola, Arsenophonus, Brenneria, Budvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus, Yersinia, Yokenella*. In certain embodiments, the recombinant bacterium is typically a pathogenic species of the Enterobaceteriaceae. Due to their clinical significance, *Escherichia coli, Shigella, Edwardsiella, Salmonella, Citrobacter, Klebsiella, Enterobacter, Serratia, Proteus, Morganella, Providencia* and *Yersinia* are considered to be particularly useful.

In other embodiments, the recombinant bacterium may be a species or strain commonly used for a vaccine.

Some embodiments of the instant invention comprise a species or subspecies of the *Salmonella* genera. For instance, the recombinant bacterium may be a *Salmonella enterica* serovar. In an exemplary embodiment, a bacterium of the invention may be derived from *S. typhimurium, S. typhi, S. paratyphi, S. gallinarum, S. enteritidis, S. choleraesius, S. arizona,* or *S. dublin.*

A recombinant bacterium of the invention derived from *Salmonella* may be particularly suited to use as a vaccine. Infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus the use of recombinant *Salmonella* for oral immunization stimulates all three branches of the immune system, which is particularly important for immunizing against infectious disease agents that colonize on and/or invade through mucosal surfaces.

In an alternative embodiment, a bacterium of the invention may be a bacterium included in Table 1 below.

TABLE 1

| Strain | Genotype or relevant characteristics |
|---|---|
| *Escherichia coli* | |
| χ289 | F$^-$ λ$^-$ glnV42 T3$^r$ |
| χ6097 | F$^-$ araD139 Δ(proAB-lac) λ$^-$ φ80dlacZΔM15 rpsL ΔasdA4 Δ(zhf-2::Tn10) thi-1 |
| χ6212 | F$^-$ Δ(argF-lacZYA)-U169 glnV44 λ$^-$ deoR φ80dlacZΔM15 gyrA96 recA1 relA1 endA1 ΔasdA4 Δ(zhf-2::Tn 10) thi-1 hsdR17 |
| χ7213 | thr-1 leuB6 fhuA21 lacY1 glnV44 recA1 ΔasdA4 Δ(zhf-2::Tn 10) thi-1 RP4-2-Tc::Mu [λpir]; Km$^r$ |
| χ7232 | endA1 thr-1 hsdR17(r$_K^-$, m$_K^+$) supE44 gyrA recA1 ΔrelA1 Δ(argF-lacZYA)-U169 [λpir] deoR Φ80dlacZΔM15 |
| χ7370 | F$^-$ araD139 Δ(ara-leu)-7697 ΔlacX74 Δlon-4 galK deoR |
| | ΔcsgA4 mcrA galU ⟩ 80dlacZΔM15 ΔfliC38 Δ(wcaL-wza)-19 recA1 endA1 nupG rpsl Δ(fimA-H) Δ(mcrBC-hsdRMS-mrr) |
| χ7385 | F$^-$ araD139 Δ(ara-leu)-7697 Δ(lacAYZOPI)-X74 Δlon-4 ΔompT0523::TT araC P$_{BAD}$ T7 pol TT galK deoR ΔcsgA4 mcrA galU φ80dlacZΔM15 ΔfliC38 Δ(wcaL-wza)-19 recA1 endA1 nupG rpsL Δ(fimA-H) Δ(mcrBC-hsdRMS-mrr) ΔasdA99 |
| BL21 (DE3) | F$^-$ ompT hsdS$_B$(r$_B^-$, m$_B^-$) gal dcm (DE3) |
| Top 10 | F$^-$ mcrA Δ(mrr-hsdRMS-mcrBC) φ80dlacZΔM15 ΔlacX74 recA1 araD139 Δ(ara-leu)7697 galU galK rpsL (Str$^r$) endA1 nupG |
| XL1-blue | recA1 endA1 gyrA96 thi-1 hsdR17 supE44 relA1 lac [F' proAB lacI$^q$ZΔM15 Tn 10 (Tet$^r$)]. |
| *Salmonella enterica* Typhimurium UK-1 | |
| χ3761 | UK-1 wild type |
| χ8060 | ΔpabA1516 |
| χ8133 | Δcya-27 Δcrp-27 ΔasdA16 |
| χ8276 | ΔasdA16 |
| χ8289 | ΔasdA19::TTaraC P$_{BAD}$ c2 |
| χ8442 | ΔpabA1516 ΔpabB232 |
| χ8477 | ΔaraE25 |
| χ8645 | ΔP$_{murA7}$::TT araC P$_{BAD}$ murA |
| χ8767 | ΔaraBAD23 |
| χ8831 | Δ(gmd-fcl)-26 |
| χ8844 | ΔendA2311 |
| χ8848 | ΔP$_{fur33}$::TT araC P$_{BAD}$ fur |
| χ8854 | ΔendA2311 Δasd479::TT araC P$_{BAD}$ c2 |
| | ΔP$_{murA7}$::TT araC P$_{BAD}$ murA ΔaraE25 ΔaraBAD1923 |
| χ8882 | ΔrelA1123 |
| χ8914 | ΔpabA1516 ΔpabB232 ΔasdA16 |
| χ8918 | ΔP$_{phoPQ107}$::TT araC P$_{BAD}$ phoPQ |
| χ8937 | ΔasdA19::araC P$_{BAD}$ c2 ΔP$_{murA7}$::araC P$_{BAD}$ murA Δ(gmd-fcl)-26 ΔrelA1123 ΔendA2311 |
| χ8956 | ΔP$_{rpoS183}$::TT araC P$_{BAD}$ rpoS |
| χ8960 | ΔasdA18::TT araC P$_{BAD}$ c2 |
| χ8989 | ΔendA419::araC P$_{BAD}$ lacI TT |
| χ8990 | ΔrelA196::araC P$_{BAD}$ lacI TT |
| χ9000 | ΔP$_{fur33}$::TT araC P$_{BAD}$ fur ΔP$_{phoPQ107}$::TT araC P$_{BAD}$ phoPQ |
| χ9021 | ΔP$_{crp527}$::TT araC P$_{BAD}$ crp |
| χ9064 | ΔP$_{rpoS183}$::TT araC P$_{BAD}$ rpoS ΔP$_{crp527}$::TT araC P$_{BAD}$ crp |
| χ9080 | ΔrelA197::araC P$_{BAD}$ lacI TT |
| χ9088 | Δpmi-2426 Δ(gmd-fcl)-26 ΔP$_{fur33}$::TT araC P$_{BAD}$ fur ΔasdA33 |
| χ9095 | ΔpabA1516 ΔpabB232 ΔasdA16 ΔrelA196::araC P$_{BAD}$ lacI TT ΔaraBAD23 |
| χ9097 | ΔpabA1516 ΔpabB232 ΔasdA16 ΔaraBAD23 |
| χ9101 | ΔpabA1516 ΔpabB232 ΔasdA16 ΔrelA197::araC P$_{BAD}$ lacI TT ΔaraBAD23 |

TABLE 1-continued

| Strain | Genotype or relevant characteristics |
|---|---|
| χ9107 | $\Delta P_{fur33}$::TT araC $P_{BAD}$ fur $\Delta P_{crp527}$::TT araC $P_{BAD}$ crp |
| χ9108 | $\Delta P_{phoPQ107}$::TT araC $P_{BAD}$ phoPQ $\Delta P_{crp527}$::TT araC $P_{BAD}$ crp |
| χ9109 | $\Delta P_{fur33}$::TT araC $P_{BAD}$ fur $\Delta P_{phoPQ107}$::TT araC $P_{BAD}$ phoPQ $\Delta P_{crp527}$::TT araC $P_{BAD}$ crp |
| χ9225 | $\Delta$endA21::araC $P_{BAD}$ lacI TT |
| χ9226 | $\Delta$relA198::araC $P_{BAD}$ lacI TT |
| χ9241 | $\Delta$pabA1516 $\Delta$pabB232 $\Delta$asdA16 $\Delta$araBAD23 $\Delta$relA198::araC $P_{BAD}$ lacI TT |
| χ9269 | $\Delta P_{fur81}$::TT araC $P_{BAD}$ fur |
| χ9273 | $\Delta P_{fur77}$::TT araC $P_{BAD}$ fur |
| χ9275 | $\Delta$asdA21::TT araC $P_{BAD}$ c2 |
| χ9302 | $\Delta$asdA20::TT araC $P_{BAD}$ c2 |
| χ9339 | $\Delta$sifA26 $\Delta$asdA18::TT araC $P_{BAD}$ c2 $\Delta P_{crp527}$::TT araC $P_{BAD}$ crp $\Delta$araBAD23 |
| χ9340 | $\Delta$alr-3 $\Delta$dadB4 $\Delta P_{phoPQ107}$::TT araC $P_{BAD}$ phoPQ $\Delta$recJ1516 $\Delta$recF126 $\Delta$asdA18::TT araC $P_{BAD}$ c2 |
| χ9362 | $\Delta$pmi-2426 $\Delta$(gmd-fcl)-26 $\Delta P_{phoPQ107}$::TT araC $P_{BAD}$ phoPQ $\Delta P_{crp527}$::TT araC $P_{BAD}$ crp $\Delta$asdA18::TT araC $P_{BAD}$ c2 $\Delta$araE25 $\Delta$araBAD23 $\Delta$relA198::araC $P_{BAD}$ lacI TT |
| χ9371 | $\Delta P_{phoPQ173}$::TT araC $P_{BAD}$ phoPQ |
| χ9372 | $\Delta P_{phoPQ177}$::TT araC $P_{BAD}$ phoPQ |
| χ9373 | $\Delta$pmi-2426 $\Delta$(gmd-fcl)-26 $\Delta P_{fur81}$::TT araC $P_{BAD}$ fur $\Delta P_{crp527}$::TT araC $P_{BAD}$ crp $\Delta$asdA21::TT araC $P_{BAD}$ c2 $\Delta$araE25 $\Delta$araBAD23 $\Delta$relA198::araC $P_{BAD}$ lacI TT |
| χ9379 | χ3761 $\Delta$atrB13::MudJ |
| χ9380 | χ9379 $\Delta$atrB13::MudJ |
| χ9382 | $\Delta P_{phoPQ173}$::TT araC $P_{BAD}$ phoPQ $\Delta$araBAD23 |
| χ9383 | $\Delta P_{phoPQ177}$::TT araC $P_{BAD}$ phoPQ $\Delta$araBAD23 |
| χ9402 | $\Delta$pmi-2426 $\Delta$(gmd-fcl)-26 $\Delta P_{fur81}$::TT araC $P_{BAD}$ fur $\Delta P_{crp527}$::TT araC $P_{BAD}$ crp $\Delta$asdA21::TT araC $P_{BAD}$ c2 $\Delta$araE25 $\Delta$araBAD23 $\Delta$relA198::araC $P_{BAD}$ lacI TT $\Delta$sopB1925 |
| χ9412 | $\Delta$pmi-2426 $\Delta$(gmd-fcl)-26 $\Delta P_{fur81}$::TT araC $P_{BAD}$ fur $\Delta P_{crp527}$::TT araC $P_{BAD}$ crp $\Delta$asdA21::TT araC $P_{BAD}$ c2 $\Delta$araE25 $\Delta$araBAD23 $\Delta$relA198::araC $P_{BAD}$ lacI TT $\Delta P_{murA7}$::TT araC $P_{BAD}$ murA |
| χ9413 | $\Delta$pmi-2426 $\Delta$(gmd-fcl)-26 $\Delta P_{phoPQ107}$::TT araC $P_{BAD}$ phoPQ $\Delta P_{crp527}$::TT araC $P_{BAD}$ crp $\Delta$asdA18::TT araC $P_{BAD}$ c2 $\Delta$araE25 $\Delta$araBAD23 $\Delta$relA198::araC $P_{BAD}$ lacI TT $\Delta P_{murA7}$::TT araC $P_{BAD}$ murA |
| χ9442 | $\Delta P_{murA12}$::TT araC $P_{BAD}$ murA |
| χ9443 | $\Delta$(araC $P_{BAD}$)-5::P22 $P_R$ araBAD |
| χ9444 | $\Delta$ asdA34::TT |
| χ9477 | $\Delta$ asdA27::TT araC $P_{BAD}$ c2 |
| χ9509 | $\Delta$ relA198::araC $P_{BAD}$ lacI TT $\Delta$ araBAD23 |
| χ9521 | $\Delta P_{murA12}$::TT araC $P_{BAD}$ murA $\Delta$ (araC $P_{BAD}$)-5::P22 $P_R$ araBAD |
| χ9527 | $\Delta P_{fur77}$::TT araC $P_{BAD}$ fur $\Delta$ (araC $P_{BAD}$)-5::P22 $P_R$ araBAD |
| χ9533 | $\Delta P_{crp527}$::TT araC $P_{BAD}$ crp $\Delta$ (araC $P_{BAD}$)-5::P22 $P_R$ araBAD |
| χ9541 | $\Delta P_{phoPQ176}$::TT araC $P_{BAD}$ phoPQ |
| χ9542 | $\Delta P_{phoPQ175}$::TT araC $P_{BAD}$ phoPQ |
| χ9543 | $\Delta P_{phoPQ174}$::TT araC $P_{BAD}$ phoPQ |
| χ9548 | $\Delta P_{phoPQ175}$::TT araC $P_{BAD}$ phoPQ $\Delta$ araBAD23 |
| χ9549 | $\Delta P_{phoPQ174}$::TT araC $P_{BAD}$ phoPQ $\Delta$ araBAD23 |
| χ9550 | $\Delta P_{fur77}$::TT araC $P_{BAD}$ fur $\Delta P_{crp527}$::TT araC $P_{BAD}$ crp |
| χ9551 | $\Delta$ asdA34::TT $\Delta P_{phoPQ107}$::TT araC $P_{BAD}$ phoPQ |
| χ9552 | $\Delta$ asdA34::TT $\Delta P_{phoPQ173}$::TT araC $P_{BAD}$ phoPQ |
| χ9553 | $\Delta$ asdA34::TT $\Delta P_{phoPQ177}$::TT araC $P_{BAD}$ phoPQ |
| χ9558 | $\Delta$pmi-2426 $\Delta$(gmd-fcl)-26 $\Delta P_{fur81}$::TT araC $P_{BAD}$ fur $\Delta P_{crp527}$::TT araC $P_{BAD}$ crp $\Delta$asdA27::TT araC $P_{BAD}$ c2 $\Delta$araE25 $\Delta$araBAD23 $\Delta$relA198::araC $P_{BAD}$ lacI TT $\Delta$sopB1925 $\Delta$agfBAC811 |
| χ9569 | $\Delta$ endA20::araC $P_{BAD}$ lacI TT |

*Salmonella enterica* Typhi ISP1820

| | |
|---|---|
| χ9421 | $\Delta P_{crp527}$::TT araC $P_{BAD}$ crp $\Delta P_{fur81}$::TT araC $P_{BAD}$ fur $\Delta P_{phoPQ107}$::TT araC $P_{BAD}$ phoPQ $\Delta$ pmi-2426 $\Delta$ (gmd-fcl)-26 $\Delta$ sopB1925 $\Delta$ relA198::araC $P_{BAD}$ lacI TT $\Delta$ araE25 $\Delta$araBAD23 $\Delta$ tviABCDE10 $\Delta$ agfBAC811 |
| χ9633 | $\Delta P_{crp527}$::TT araC $P_{BAD}$ crp $\Delta P_{fur81}$::TT araC $P_{BAD}$ fur $\Delta$pmi-2426 $\Delta$(gmd-fcl)-26 $\Delta$sopB1925 $\Delta$relA198::araC $P_{BAD}$ lacI TT $\Delta$araE25 $\Delta$araBAD23 $\Delta$tviABCDE10 $\Delta$agfBAC811 PhoP$^+$ $\Delta$asdA33 |

*Salmonella enterica* Typhi Ty2

| | |
|---|---|
| χ9205 | $\Delta P_{crp527}$::TT araC $P_{BAD}$ crp $\Delta P_{fur33}$::TT araC $P_{BAD}$ fur RpoS$^-$ |
| χ9114 | $\Delta P_{phoPQ107}$::TT araC $P_{BAD}$ phoPQ $\Delta P_{crp527}$::TT araC $P_{BAD}$ crp RpoS$^-$ |
| χ9213 | $\Delta P_{crp527}$::TT araC $P_{BAD}$ crp $\Delta P_{fur33}$::TT araC $P_{BAD}$ fur $\Delta P_{phoPQ107}$::TT araC $P_{BAD}$ phoPQ RpoS$^-$ |
| χ9369 | $\Delta P_{crp527}$::TT araC $P_{BAD}$ crp $\Delta P_{fur33}$::TT araC $P_{BAD}$ fur $\Delta P_{phoPQ107}$::TT araC $P_{BAD}$ phoPQ $\Delta$ pmi-2426 $\Delta$ gmd-fcl-26 $\Delta$ relA198::araC $P_{BAD}$ lacI TT RpoS$^-$ |

TABLE 1-continued

| Strain | Genotype or relevant characteristics |
|---|---|
| χ9639 | $\Delta P_{crp527}$::TT araC $P_{BAD}$ crp $\Delta P_{fur81}$::TT araC $P_{BAD}$ fur $\Delta$pmi-2426 $\Delta$(gmd-fcl)-26 $\Delta$sopB1925 $\Delta$relA198::araC $P_{BAD}$ lacI TT $\Delta$araE25 $\Delta$tviABCDE10 $\Delta$gfBAC811 PhoP$^+$ $\Delta$asdA33 RpoS$^-$ |
| χ9640 | $\Delta P_{crp527}$::TT araC $P_{BAD}$ crp $\Delta P_{fur81}$::TT araC $P_{BAD}$ fur $\Delta$pmi-2426 $\Delta$(gmd-fcl)-26 $\Delta$sopB1925 $\Delta$relA198::araC $P_{BAD}$ lacI TT $\Delta$araE25 $\Delta$tviABCDE10 $\Delta$agfBAC811 PhoP$^+$ RpoS$^+$ $\Delta$asdA33 |
| *Salmonella enterica* Paratyphi A | |
| χ9515 | $\Delta P_{crp527}$::TT araC $P_{BAD}$ crp $\Delta P_{fur81}$::TT araC $P_{BAD}$ fur $\Delta P_{phoPQ107}$::TT araC $P_{BAD}$ phoPQ $\Delta$ pmi-2426 $\Delta$ (gmd-fcl)-26 $\Delta$ sopB1925 $\Delta$ agfBAC811 $\Delta$ relA198::araC $P_{BAD}$ lacI TT |
| χ9608 | $\Delta P_{crp527}$::TT araC $P_{BAD}$ crp $\Delta P_{fur81}$::TT araC $P_{BAD}$ fur $\Delta P_{phoPQ107}$::TT araC $P_{BAD}$ phoPQ $\Delta$ pmi-2426 $\Delta$ (gmd-fcl)-26 $\Delta$agfBAC811 $\Delta$ relA198::araC $P_{BAD}$ lacI TT $\Delta$ sopB1925 $\Delta$araE25 $\Delta$araBAD23 $\Delta$asdA33 |
| χ9651 | $\Delta P_{crp527}$::TT araC $P_{BAD}$ crp $\Delta P_{fur81}$::TT araC $P_{BAD}$ fur $\Delta P_{phoPQ107}$::TT araC $P_{BAD}$ phoPQ $\Delta$pmi-2426 $\Delta$(gmd-fcl)-26 $\Delta$agfBAC811 $\Delta$relA198::araC $P_{BAD}$ lacI TT $\Delta$sopB1925 $\Delta$araE25 $\Delta$(araC $P_{BAD}$)-5::P22 $P_R$ araBAD |
| χ9763 | $\Delta P_{crp527}$::TT araC $P_{BAD}$ crp $\Delta P_{fur81}$::TT araC $P_{BAD}$ fur $\Delta$ pmi-2426 $\Delta$ (gmd-fcl)-26 $\Delta$ agfBAC811 $\Delta$ relA198::araC $P_{BAD}$ lacI TT $\Delta$ sopB1925 $\Delta$araE25 $\Delta$araBAD23 PhoP$^+$ |
| χ9857 | $\Delta P_{crp527}$::TT araC $P_{BAD}$ crp $\Delta P_{fur81}$::TT araC $P_{BAD}$ fur $\Delta$ pmi-2426 $\Delta$ (gmd-fcl)-26 $\Delta$ agfBAC811 $\Delta$ relA198::araC $P_{BAD}$ lacI TT $\Delta$ sopB1925 $\Delta$araE25 $\Delta$araBAD23 PhoP$^+$ $\Delta$asdA33 |
| *Streptococcus pneumoniae* | |
| Rx1 | PspA Clade 2, Capsule Type Rough |
| WU2 | PspA Clade 2, Capsule Type 3 |
| D39 | PspA Clade 2, Capsule Type 2 |

$\Delta$ = deletion
P = promoter
p = plasmid
TT = transcription terminator

I. Regulated Expression

The present invention encompasses a recombinant bacterium capable of regulated expression of at least one nucleic acid sequence encoding an antigen of interest. Generally speaking, the bacterium comprises a chromosomally integrated nucleic acid sequence encoding a repressor and a vector. Each is discussed in more detail below.

(a) Chromosomally Integrated Nucleic Acid Sequence Encoding a Repressor

A recombinant bacterium of the invention that is capable of the regulated expression of at least one nucleic acid sequence encoding an antigen comprises, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the relA nucleic acid sequence. In another embodiment, the nucleic acid sequence encoding a repressor may be integrated into the endA nucleic acid sequence.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

i. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

The choice of a repressor depends, in part, on the species of the recombinant bacterium used. For instance, the repressor is usually not derived from the same species of bacteria as the recombinant bacterium. For instance, the repressor may be derived from *E. coli* if the recombinant bacterium is from the genus *Salmonella*. Alternatively, the repressor may be from a bacteriophage.

Suitable repressors are known in the art, and may include, for instance, LacI of *E. coli*, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI. In another embodiment, the repressor is C2. In yet another embodiment, the repressor is C1.

ii. Regulatable Promoter

The chromosomally integrated nucleic acid sequence encoding a repressor is operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system which has been shown to work as a strong promoter induced by the addition of low levels of arabinose (5). The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araC araBAD system from E. coli. For example, there is homology at the amino acid sequence level between the E. coli and the S. Typhimurium AraC proteins, and less homology at the DNA level. However, there is high specificity in the activity of the AraC proteins. For example, the E. coli AraC protein activates only E. coli $P_{BAD}$ (in the presence of arabinose) and not S. Typhimurium $P_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid encodes MalT, a positive regulator of four maltose-responsive promoters ($P_K$, $P_{EFG}$, $P_{KBM}$, and $P_S$). The combination of malT and a mal promoter creates a tightly regulated expression system that has been shown to work as a strong promoter induced by the addition of maltose (6). Unlike the araC-$P_{BAD}$ system, malT is expressed from a promoter ($P_T$) functionally unconnected to the other mal promoters. $P_T$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as $P_{KBM}$, and the portion of the malEFG-malKBM promoter that mediates expression of the malEFG nucleic acid sequence, and that is controlled by the malT nucleic acid sequence product, is referred to herein as $P_{EFG}$. Full induction of $P_{KBM}$ requires the presence of the MalT binding sites of $P_{EFG}$. For use in the vectors and systems described herein, a cassette with the malT nucleic acid sequence and one of the mal promoters may be used. This cassette is referred to herein as malT-$P_{mal}$. In the presence of maltose, the MalT protein is a positive regulatory element that allows expression from $P_{mal}$.

In still other embodiments, the promoter may be sensitive to the level of rhamnose in the environment. Analogous to the araC-$P_{BAD}$ system described above, the rhaRS-$P_{rhaB}$ activator-promoter system is tightly regulated by rhamnose. Expression from the rhamnose promoter ($P_{rha}$) is induced to high levels by the addition of rhamnose, which is common in bacteria but rarely found in host tissues. The nucleic acid sequences rhaBAD are organized in one operon that is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the P rhaRS promoter and activates the production of RhaR and RhaS. RhaS together with L-rhamnose in turn binds to the $P_{rhaBAD}$ and the $P_{rhaT}$ promoter and activates the transcription of the structural nucleic acid sequences (7). Full induction of rhaBAD transcription also requires binding of the Crp-cAMP complex, which is a key regulator of catabolite repression (7).

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC $P_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the $P_{rhaBAD}$ promoter.

In still other embodiments, the promoter may be sensitive to the level of xylose in the environment. The xylR-$P_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-$P_{BAD}$ system described above, the xylR-$P_{xylAB}$ and/or xylR-$P_{xylFGH}$ regulatory systems may be used in the present invention. In these embodiments, xylR $P_{xylAB}$ xylose interacting with the XylR protein activates transcription of nucleic acid sequences operably-linked to either of the two $P_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

iii. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation (see the Examples). Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of the nucleic acid encoding an antigen of interest, and is substantially not synthesized in a non-permissive environment, thereby allowing expression of the nucleic acid encoding an antigen of interest.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lacI may be altered, the SD sequence may be altered, and the codons of lacI may be optimized.

Methods of modifying the nucleic acid sequence encoding the repressor and/or the regulatable promoter are known in the art and detailed in the examples.

iv. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

(b) Vector

A recombinant bacterium of the invention that is capable of the regulated expression of at least one nucleic acid sequence encoding an antigen comprises, in part, a vector. The vector comprises a nucleic acid sequence encoding at least one antigen of interest operably linked to a promoter. The promoter is regulated by the chromosomally encoded repressor, such that the expression of the nucleic acid sequence encoding an antigen is repressed during in vitro growth of the bacterium, but the bacterium is capable of high level synthesis of the antigen in an animal or human host.

As used herein, "vecto0r" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR on or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

i. Antigen

As used herein, "antigen" refers to a biomolecule capable of eliciting an immune response in a host. In some embodiments, an antigen may be a protein, or fragment of a protein, or a nucleic acid. In an exemplary embodiment, the antigen elicits a protective immune response. As used herein, "protective" means that the immune response contributes to the lessening of any symptoms associated with infection of a host with the pathogen the antigen was derived from or designed to elicit a response against. For example, a protective antigen from a pathogen, such as *Mycobacterium*, may induce an immune response that helps to ameliorate symptoms associated with *Mycobacterium* infection or reduce the morbidity and mortality associated with infection with the pathogen. The use of the term "protective" in this invention does not necessarily require that the host is completely protected from the effects of the pathogen.

Antigens may be from bacterial, viral, mycotic and parasitic pathogens, and may be designed to protect against bacterial, viral, mycotic, and parasitic infections, respectively. Alternatively, antigens may be derived from gametes, provided they are gamete specific, and may be designed to block fertilization. In another alternative, antigens may be tumor antigens, and may be designed to decrease tumor growth. It is specifically contemplated that antigens from organisms newly identified or newly associated with a disease or pathogenic condition, or new or emerging pathogens of animals or humans, including those now known or identified in the future, may be expressed by a bacterium detailed herein. Furthermore, antigens for use in the invention are not limited to those from pathogenic organisms. The selection and recombinant synthesis of antigens has been previously described by Schodel (9) and Curtiss (10). Immunogenicity of the bacterium may be augmented and/or modulated by constructing strains that also express sequences for cytokines, adjuvants, and other immunomodulators.

Some examples of microorganisms useful as a source for antigen are listed below. These may include microoganisms for the control of plague caused by *Yersinia pestis* and other *Yersinia* species such as *Y. pseudotuberculosis* and *Y. enterocolitica*, for the control of gonorrhea caused by *Neisseria gonorrhoeae*, for the control of syphilis caused by *Treponema pallidum*, and for the control of venereal diseases as well as eye infections caused by *Chlamydia trachomatis*. Species of *Streptococcus* from both group A and group B, such as those species that cause sore throat or heart diseases, *Erysipelothrix rhusiopathiae, Neisseria meningitidis, Mycoplasma pneumoniae* and other *Mycoplasma*-species, *Hemophilus influenza, Bordetella pertussis, Mycobacterium tuberculosis, Mycobacterium leprae*, other *Bordetella* species, *Escherichia coli, Streptococcus equi, Streptococcus pneumoniae, Brucella abortus, Pasteurella hemolytica* and *P. multocida, Vibrio cholera, Shigella* species, *Borrellia* species, *Bartonella* species, *Heliobacter pylori, Campylobacter* species, *Pseudomonas* species, *Moraxella* species, *Brucella* species, *Francisella* species, *Aeromonas* species, *Actinobacillus* species, *Clostridium* species, *Rickettsia* species, *Bacillus* species, *Coxiella* species, *Ehrlichia* species, *Listeria* species, and *Legionella pneumophila* are additional examples of bacteria within the scope of this invention from which antigen nucleic acid sequences could be obtained. Viral antigens may also be used. Viral antigens may be used in antigen delivery microorganisms directed against viruses, either DNA or RNA viruses, for example from the classes Papovavirus, Adenovirus, Herpesvirus, Poxvirus, Parvovirus, Reovirus, Picornavirus, Myxovirus, Paramyxovirus, Flavivirus or Retrovirus. Antigens may also be derived from pathogenic fungi, protozoa and parasites.

Certain embodiments encompass an allergen as an antigen. Allergens are substances that cause allergic reactions in a host that is exposed to them. Allergic reactions, also known as Type I hypersensitivity or immediate hypersensitivity, are vertebrate immune responses characterized by IgE production in conjunction with certain cellular immune reactions. Many different materials may be allergens, such as animal dander and pollen, and the allergic reaction of individual hosts will vary for any particular allergen. It is possible to induce tolerance to an allergen in a host that normally shows an allergic response. The methods of inducing tolerance are well-known and generally comprise administering the allergen to the host in increasing dosages.

It is not necessary that the vector comprise the complete nucleic acid sequence of the antigen. It is only necessary that the antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In another alternative, a vector may comprise a long sequence of nucleic acid encoding several nucleic acid sequence products, one or all of which may be antigenic. In some embodiments, a vector of the invention may comprise a nucleic acid sequence encoding at least one antigen, at least two antigens, at least three antigens, or more than three antigens. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein.

In certain embodiments, an antigen of the invention may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tenus toxin fragment C, CT-B, LT-B and hepatitis virus B core are particularly useful for these purposes, although other epitope presentation systems are well known in the art.

In further embodiments, a nucleic acid sequence encoding an antigen of the invention may comprise a secretion signal. In other embodiments, an antigen of the invention may be toxic to the recombinant bacterium.

ii. Promoter Regulated by Repressor

The vector comprises a nucleic acid sequence encoding at least one antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence encoding the antigen, such that expression of the nucleic acid sequence encoding an antigen is repressed when the repressor is synthesized (i.e. during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding an antigen after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding an antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

iii. Expression of the Nucleic Acid Sequence Encoding an Antigen

As detailed above, generally speaking the expression of the nucleic acid sequence encoding the antigen should be repressed when the repressor is synthesized. For instance, if the repressor is synthesized during in vitro growth of the bacterium, expression of the nucleic acid sequence encoding the antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependant T cell populations or antigen-dependant cytokine levels are known in the art, and methods of measuring levels of expression of antigen encoding sequences by measuring levels of mRNA transcribed or by quantitating the level of antigen synthesis are also known in the art. For more details, see the examples.

(c) Crp Cassette

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above.

(d) Attenuation

In each of the above embodiments, a recombinant bacterium of the invention capable of regulated expression may also be attenuated. "Attenuated" refers to the state of the bacterium wherein the bacterium has been weakened from its wild type fitness by some form of recombinant or physical manipulation. This includes altering the genotype of the bacterium to reduce its ability to cause disease. However, the bacterium's ability to colonize the gut (in the case of Salmonella) and induce immune responses is, preferably, not substantially compromised.

In an exemplary embodiment, a recombinant bacterium may be attenuated as described in section II below. In which case, both regulated attenuation and regulated expression of an antigen encoding sequence may be dependent upon an arabinose regulatable system. Consequently, the concentration of arabinose needed for optimal expression of the regulated antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fur and phoPQ, so that the production levels of Fur and PhoPQ are optimal for both the regulated attenuation phenotype and the regulated expression when growing strains with a given concentration of arabinose. One of skill in the art will appreciate that other nucleic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

Other methods of attenuation are known in the art. For instance, attenuation may be accomplished by altering (e.g., deleting) native nucleic acid sequences found in the wild type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

In another embodiment, the recombinant bacterium may contain one and in some embodiments, more than one, deletion and/or deletion-insertion mutation present in the strains listed in Table 1 above. Furthermore, suicide vectors, as listed in Table 2, and ss described in the Examples below, along with other plasmid vectors, may be used to introduce these deletion and deletion-insertion mutations into strains during their construction.

TABLE 2

| Plasmid | Properties |
|---|---|
| | Suicide vector |
| pMEG-375 | sacRB mobRP4 R6K ori Cm$^r$ Ap$^r$ |
| pMEG-443 | ΔasdA16 |
| pRE112 | SacB mobRP4 R6K ori Cm$^r$ |
| pYA3438 | ΔpabB232 in pMEG-375 |
| pYA3485 | ΔaraE25 in pMEG-375 |

TABLE 2-continued

| Plasmid | Properties |
|---|---|
| pYA3599 | ΔaraBAD23 in pMEG-375 |
| pYA3629 | Δ(gmd-fcl)-26 in pMEG-375 |
| pYA3652 | ΔendA2311 in pMEG-375 |
| pYA3679 | ΔrelA1123 in pMEG-375 |
| pYA3722 | ΔP$_{fur33}$::TT araC P$_{BAD}$ fur in pMEG-375 |
| pYA3723 | ΔP$_{phoPQ107}$::TT araC P$_{BAD}$ phoPQ in pRE112 |
| pYA3735 | ΔP$_{rpoS183}$::TT araC P$_{BAD}$ rpoS in pRE112 |
| pYA3736 | ΔasdA33 in pRE112 |
| pYA3737 | ΔasdA18::TT araC P$_{BAD}$ P22 c2 in pRE112 |
| pYA3783 | pRE112 derived suicide vector to generate GTG-lacI, ΔendA19::araC P$_{BAD}$ lacI TT mutation, Cm$^r$ |
| pYA3784 | pRE112 derived suicide vector to generate GTG-lacI, ΔrelA196::araC P$_{BAD}$ lacI TT mutation, Cm$^r$ |
| pYA3832 | ΔP$_{crp527}$::TT araC P$_{BAD}$ crp in pRE112 |
| pYA3871 | pRE112 derived suicide vector to generate ATG-lacI, ΔendA20::araC P$_{BAD}$ lacI TT mutation, Cm$^r$ |
| pYA3879 | pRE112 derived suicide vector to generate ATG-lacI, ΔrelA197::araC P$_{BAD}$ lacI TT mutation, Cm$^r$ |
| pYA4062 | ΔP$_{phoPQ173}$::TT araC P$_{BAD}$ phoPQ in pRE112 |
| pYA4063 | pRE112 derived suicide vector to generate improved SD ATG-lacI, ΔendA21::araC P$_{BAD}$ lacI (improved codon) TT mutation, Cm$^r$ |
| pYA4064 | pRE112 derived suicide vector to generate codon optimized lacI, ΔrelA198::araC P$_{BAD}$ lacI TT mutation, Cm$^r$ |
| pYA4109 | ΔP$_{phoPQ177}$::TT araC P$_{BAD}$ phoPQ in pRE112 |
| pYA4138 | ΔasdA27::TT araC P$_{BAD}$ P22 c2 in pRE112 |
| pYA4177 | ΔasdA21::TT araC P$_{BAD}$ P22 c2 in pRE112 |
| pYA4180 | ΔP$_{fur77}$::TT araC P$_{BAD}$ fur in pRE112 |
| pYA4181 | ΔP$_{fur81}$::TT araC P$_{BAD}$ fur in pRE112 |
| pYA4213 | ΔasdA20::TT araC P$_{BAD}$ P22 c2 in pRE112 |
| pYA4235 | ΔP$_{murA12}$::TT araC P$_{BAD}$ murA in pRE112 |
| pYA4280 | Δ(araC P$_{BAD}$)-5: P22 P$_R$ araBAD in pRE112 |
| pYA4343 | ΔP$_{phoPQ176}$::TT araC P$_{BAD}$ phoPQ in pRE112 |
| pYA4344 | ΔP$_{phoPQ175}$::TT araC P$_{BAD}$ phoPQ in pRE112 |
| pYA4345 | ΔP$_{phoPQ174}$::TT araC P$_{BAD}$ phoPQ in pRE112 |
| | Recombinant vector |
| pGEM-3Z | Ap$^r$, Cloning vector, pUC ori |
| pYA3342 | pBR ori Asd$^+$, 3012 bp |
| pYA3450 | p15A ori araC $^§$ P$_{BAD}$ SD-ATG asdA |
| pYA3493 | pBR ori bla SS, Asd$^+$, 3113 bp, |
| pYA3530 | p15A ori araC $^§$ P$_{BAD}$ SD-GTG asdA |
| pYA3552 | Asd$^+$ vector expression gfp3, pBR ori |
| pYA3620 | pBR ori Asd$^+$, bla SS bla CT, 3169 bp |
| pYA3624 | Plasmid with tightly regulated araC P$_{BAD}$ cassette, p15A ori |
| pYA3634 | pBR ori bla SS, Asd$^+$ PspA Rx1 aa 3-257 |
| pYA3635 | pBR ori bla SS, Asd$^+$ PspA Rx1 aa 3-257 (codon optimized) |
| pYA3681 | pBR ori araC P$_{BAD}$ SD-GTG asdA SD-GTG murA P22 P$_R$ anti-sense mRNA |
| pYA3685 | pBR ori araC P$_{BAD}$ SD-GTG asdA SD-GTG murA P22 P$_R$ anti-sense mRNA, rPspA Rx1 |
| pYA3698 | pGEM-3Z with T4 iplII transcription terminator, Ap$^r$ |
| pYA3699 | pGEM-3Z with araC P$_{BAD}$ cassette, Ap$^r$ |
| pYA3700 | AraC P$_{BAD}$ TT cassette plasmid, Ap$^r$ |
| pYA3782 | P$_{BAD}$ regulated lacI (GTG) in pYA3700-PCR-Topo-Blunt II |
| pYA3789 | Runaway vector harboring araC P$_{BAD}$ P22 c2, GTG-MurA$^+$, GTG-Asd$^+$, P$_{trc}$, pSC101 ori, pUC ori |
| pYA3856 | pBAD-HisA with GTG start codon lacI, His-tagged, Ap$^r$ |
| pYA4050 | pUC ori araC P$_{BAD}$ SD-GTG murA SD-GTF asd, P22P$_R$ antisense RNA with DNA nuclear Targeting sequence and poly A from SV40, 6941 bp |
| pYA4088 | pBR ori bla SS, Asd$^+$ PspA Rx1 aa 3-285 (codon optimized) |
| pYA4090 | Asd$^+$ vector, P$_{trc}$ gfp3, pBR ori | p = plasmid
P = promoter
SD = Shine-Dalgarno sequence
araC $^§$ P$_{BAD}$ = *E. coli* B/r
aa = amino acid
SS = signal sequence
Ap$^r$ = ampicillin resistance
Cm$^r$ = chloramphenicol resistance The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asd. Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall Yet another balanced-lethal host-vector system comprises modifying the bacterium such that the synthesis of an essential constituent of the rigid layer of the bacterial cell wall is dependent on a nutrient (e.g., arabinose) that can be supplied during the growth of the microorganism. For example, a bacterium may be comprise the $\Delta P_{murA}$::TT araC $P_{BAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the bacterium in vitro.

However, when arabinose is absent as it is in an animal or human host, the essential constituent of the peptidoglycan layer of the cell wall is not synthesized. This mutation represents an arabinose dependant lethal mutation. In the absence of arabinose, synthesis of muramic acid ceases and lysis of the bacterium occurs because the peptidoglycan layer of the cell wall is not synthesized. It is not possible to generate ΔmurA mutations because they are lethal. The necessary nutrient, a phosphorylated muramic acid, can not be exogenously supplied because enteric bacteria cannot take the nutrient up from the media. Recombinant bacteria with a $\Delta P_{murA}$::TT araC $P_{BAD}$ murA deletion-insertion mutation grown in the presence of arabinose exhibit effective colonization of effector lymphoid tissues after oral vaccination prior to undergoing lysis due to the inability to synthesize muramic acid.

Figure 13:
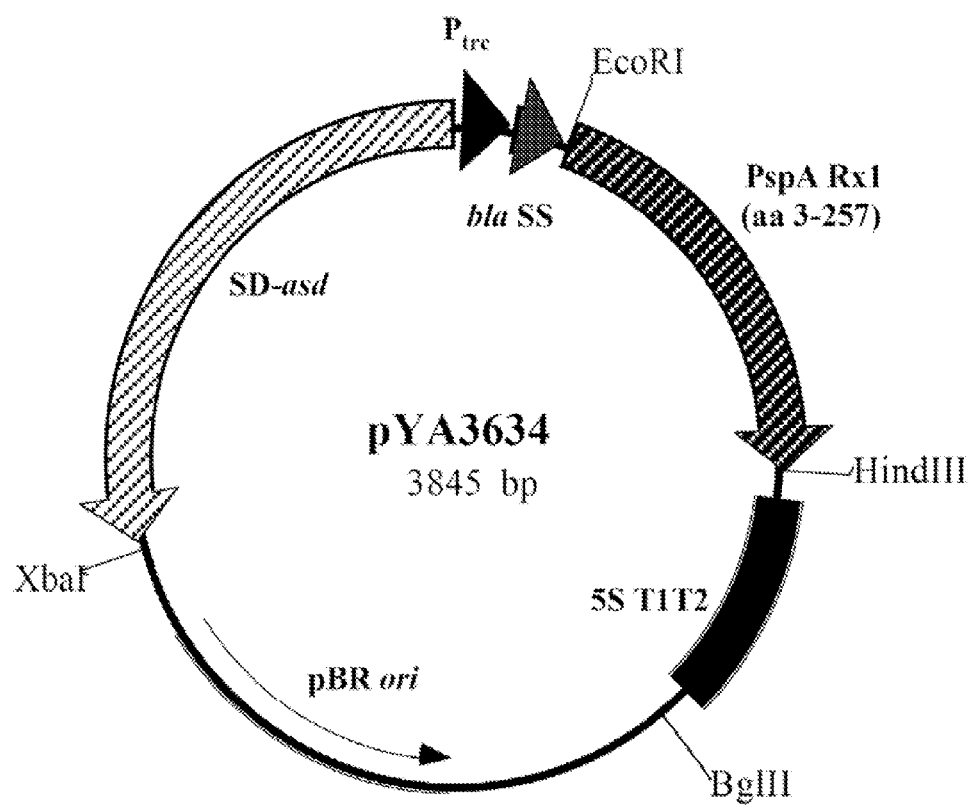
FIG. 13 depicts an illustration of the pYA3634 plasmid.

Similarly, various embodiments may comprise the araC $P_{BAD}$ c2 cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above. The vector enables the regulated expression of an antigen encoding sequence through the repressible promoter. For instance, in one embodiment shown in FIG. 13, pYA3634 has the Asd⁺ vector specifying the antigen PspA Rx1.

Figure 1:
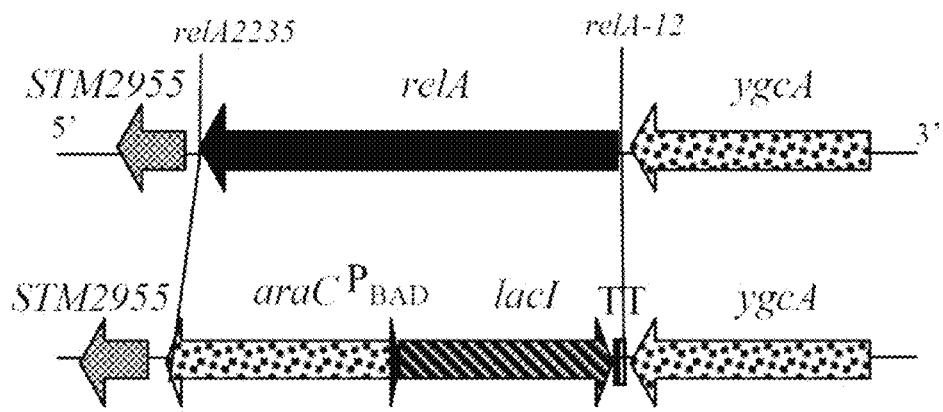
FIG. 1 depicts an illustration of various deletion-insertion mutations of relA and various embodiments of lacI optimization. The schematic shows the deletion of 2247 bp (relA-12 to relA 2235/2235) and insertion of 2429 bp of araC $P_{BAD}$ lacI TT. The optimized sequences of ΔrelA196::araC $P_{BAD}$ lacI TT (SEQ ID NO:1), ΔrelA197::araC $P_{BAD}$ lacI TT (SEQ ID NO:2), and ΔrelA198::araC $P_{BAD}$ (SEQ ID NO:3) lacI*TT show variations of SD sequences and start codons. lacI*: codon optimized.
Figure 2:
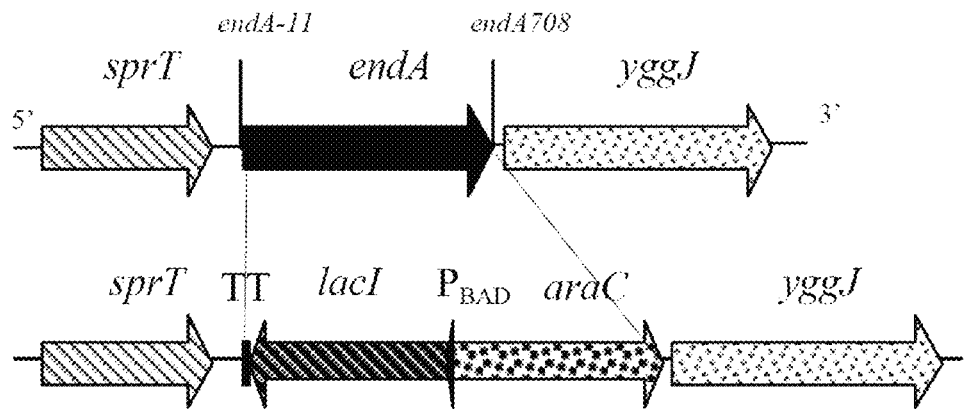
FIG. 2 depicts an illustration of a chromosomal map of the deletion-insertion mutation of endA and various embodiments of lacI optimization. The schematic shows the deletion of 719 bp (endA −11 to endA 708/708) and insertion of 2429 bp of araC $P_{BAD}$ lacI TT. The optimized sequences of ΔendA19::araC $P_{BAD}$ lacI TT (SEQ ID NO:4), ΔendA20:: araC $P_{BAD}$ lacI TT (SEQ ID NO:5), and ΔendA21::araC $P_{BAD}$ lacI* TT (SEQ ID NO:6) show variations of SD sequences and start codons.
Figure 4:
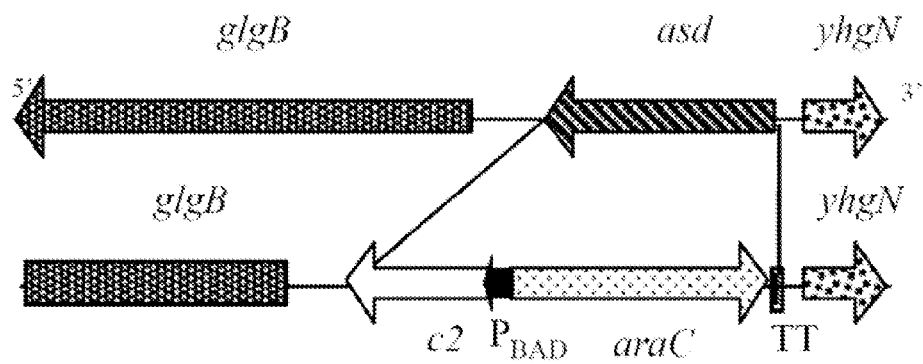
FIG. 4 depicts an illustration of a chromosomal map of various deletion-insertion mutations of asdA and various embodiments of c2 optimization. The schematic shows the deletion of 1104 bp from the asd nucleic acid sequence (1 to 1104 not including TAG stop codon) and the insertion of 1989 bp of c2 $P_{BAD}$ araC TT. The optimized sequences of ΔasdA18::TT araC $P_{BAD}$ c2 (SEQ ID NO:11), ΔasdA20::TT araC $P_{BAD}$ c2* (SEQ ID NO:12), ΔasdA21::TT araC $P_{BAD}$ c2* (SEQ ID NO:13), and ΔasdA27::TT araC $P_{BAD}$* c2** (SEQ ID NO:14) show variations of SD sequences and start codons. $P_{BAD}$*: the −10 sequence is improved from TACTGT to TATAAT; c2*: SD-codon optimized; c2**: SD-codon optimized and second codon is modified to AAA from AAT.

In one embodiment shown in FIG. 4, ΔasdA271::TT araC $P_{BAD}$ c2 has an improved SD sequence and a codon optimized c2 nucleic acid sequence (FIG. 5). The C2 repressor synthesized in the presence of arabinose is used to repress nucleic acid sequence expression from P22 $P_R$ and $P_L$ promoters. In another embodiment shown in FIG. 4, ΔasdA27::TT araC $P_{BAD}$ c2 (the preferred embodiment) has the 1104 base-pair asd nucleic acid sequence deleted (1 to 1104, but not including the TAG stop codon) and the 1989 base-pair fragment containing T4 ipIII TT araC $P_{BAD}$ c2 inserted. The c2 nucleic acid sequence in ΔasdA27::TT araC $P_{BAD}$ c2 has a SD sequence that was optimized to TAAGGAGGT. It also has an improved $P_{BAD}$ promoter such that the −10 sequence is improved from TACTGT to TATAAT. Furthermore, it has a codon optimized c2 nucleic acid sequence, in which the second codon was modified from AAT to AAA (FIG. 6).

Figure 14:
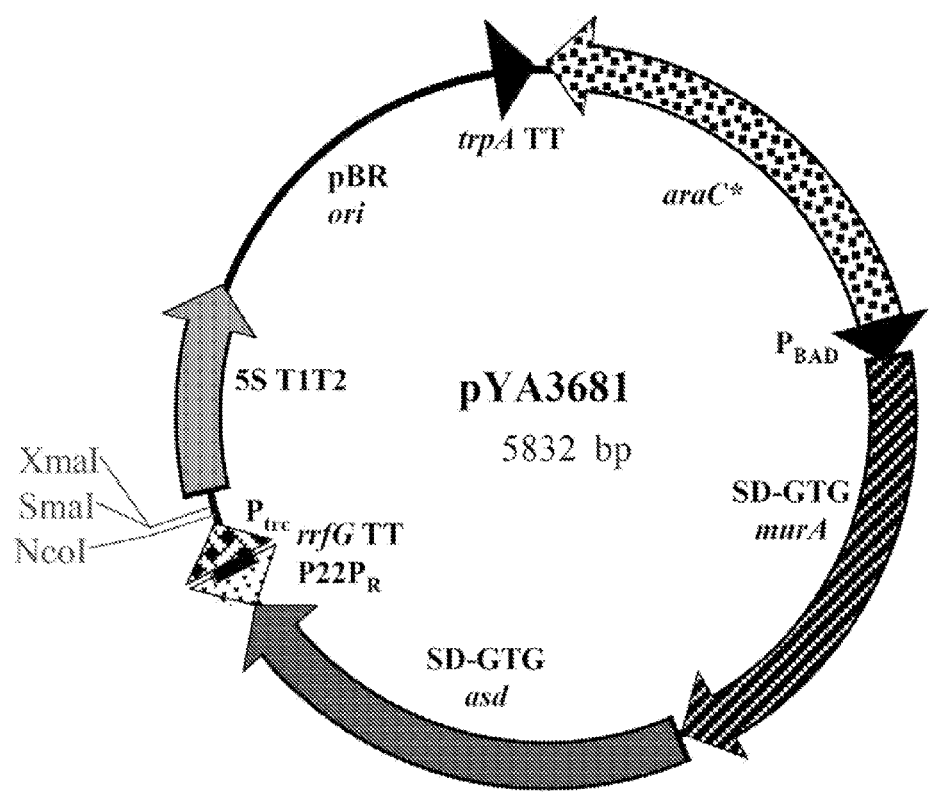
FIG. 14 depicts an illustration of the pYA3681 plasmid.
Figure 15:
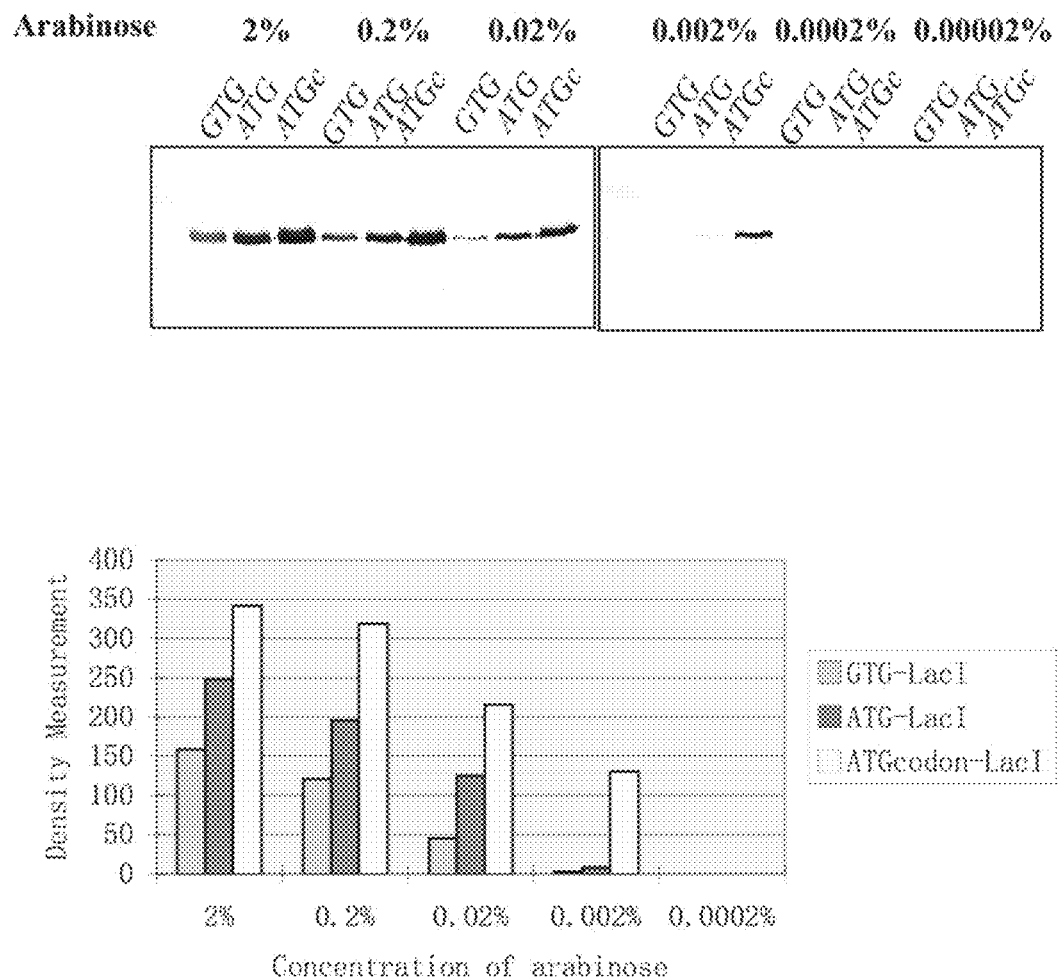
FIG. 15 depicts a photograph and a graph showing results from a western blot analysis on *Salmonella* UK-1 ΔrelA:: araC $P_{BAD}$ lacI (GTG vs ATG vs ATG codon) TT mutations using rabbit LacI antiserum.
Figure 16:
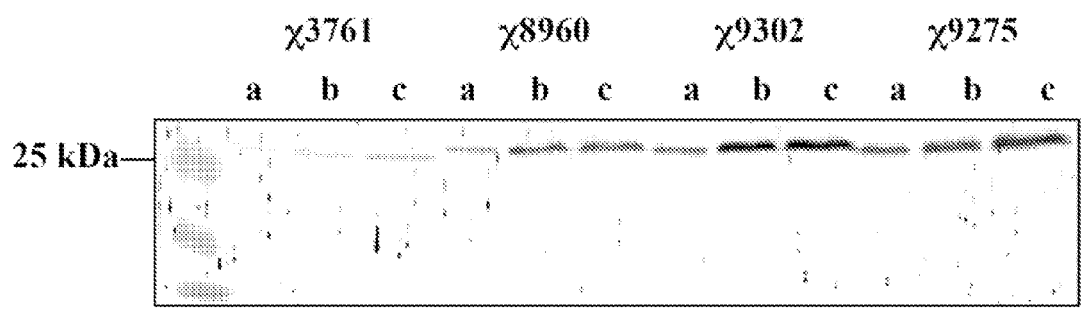
FIG. 16 depicts a photograph showing results from a western blot analysis on *Salmonella* UK-1 ΔasdA::TT araC $P_{BAD}$ c2 mutants using polyclonal C2 antiserum.
Figure 17:
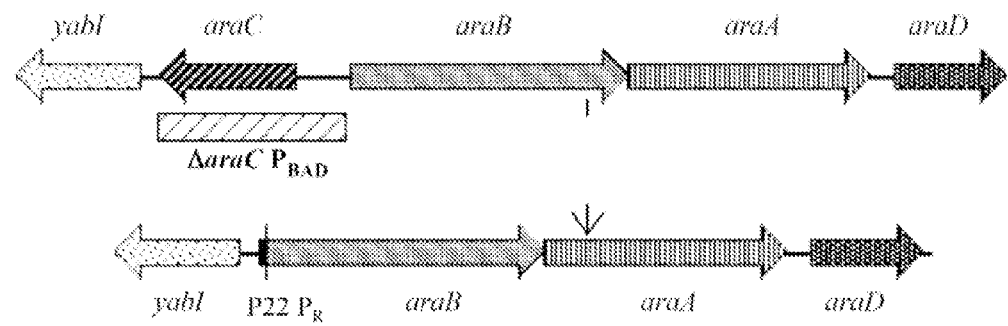
FIG. 17 depicts an illustration of a chromosomal map of the deletion-insertion mutation of the araC $P_{BAD}$ region and the DNA sequence of P22 $P_R$ araB region (SEQ ID NO: 33). The schematic shows the deletion of 1169 bp including 846 bp of araC and 323 bp of the $P_{BAD}$ region and the insertion of 91 bp of P22 $P_R$ sequence.
Figure 18:
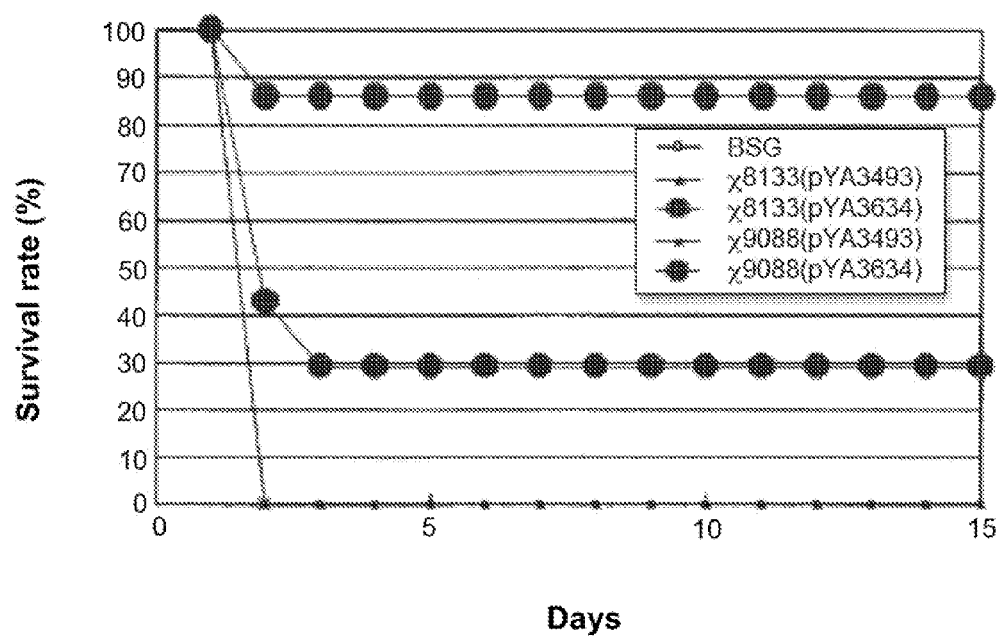
FIG. 18 depicts a graph showing survival after *S. pneumoniae* challenge.

In further embodiments, the bacterium may be attenuated by regulating the murA nucleic acid sequence encoding the first enzyme in muramic acid synthesis and the asd nucleic acid sequence essential for DAP synthesis. These embodiments may comprise the chromosomal deletion-insertion mutations ΔasdA19::TT araC $P_{BAD}$ c2 or ΔasdA27::TT araC $P_{BAD}$ c2 and $\Delta P_{murA7}$::TT araC $P_{BAD}$ murA or $\Delta P_{murA12}$::TT araC $P_{BAD}$ murA. This host-vector grows in LB broth with 0.1% L-arabinose, but is unable to grow in or on media devoid of arabinose since it undergoes cell wall-less death by lysis. In some embodiments of the invention, the recombinant bacterium may comprise araBAD and araE mutations to preclude breakdown and leakage of internalized arabinose such that asd and murA nucleic acid sequence expression continues for a cell division or two after oral immunization into an environment that is devoid of external arabinose. (For example a strain with the $\Delta P_{murA7}$::TT araC $P_{BAD}$ murA deletion-insertion mutation undergoes about two cell divisions and then commences to lyse in media made of mouse or chicken feed or chicken breast meat, unless they are supplemented with arabinose.) Either GTG or TTG start codons for the murA and asd nucleic acid sequences are important to decrease translation efficiency on multi-copy plasmids. This embodiment is illustrated by FIG. 14, which shows the plasmid vector pYA3681. This vector contains the murA nucleic acid sequence (with altered start codon sequences to decrease translation efficiency) under the control of an araC $P_{BAD}$ promoter. Also the second nucleic acid sequence under the direction of this promoter is the asd nucleic acid sequence (with altered start codon sequences to decrease translation efficiency). The P22 $P_R$ promoter is in the anti-sense direction of both the asd nucleic acid sequence and the murA nucleic acid sequence. The P22 $P_R$ is repressed by the C2 repressor made during growth of the strain in media with arabinose (due to the ΔasdA19::TT araC $P_{BAD}$ c2 deletion-insertion). However C2 concentration decreases due to cell division in vivo to cause $P_R$ directed synthesis of anti-sense mRNA to further block translation of asd and murA mRNA. The araC $P_{BAD}$ sequence is also not from E. coli B/r as originally described (5) but represents a sequence derived from E. coli K-12 strain χ289 with tighter control and less leakiness in the absence of arabinose. In the preferred embodiment, transcription terminators (TT) flank all of the domains for controlled lysis, replication, and expression so that expression in one domain does not affect the activities of another domain. As a safety feature, the plasmid asd nucleic acid sequence does not replace the chromosomal asd mutation since they have a deleted sequence in common, consequently, the E. coli murA nucleic acid sequence was used in the plasmid instead of using the Salmonella murA nucleic acid sequence. The recombinant bacterium of this embodiment is avirulent at oral doses in excess of $10^9$ CFU to BALB/c mice. In addition to being fully attenuated, this construction exhibits complete biological containment with no in vivo recombinant bacteria survivors detectable after 21 days and no recombinant bacteria survivors during or after excretion. This property enhances vaccine safety and minimizes the potential for vaccination of individuals not intended for vaccination.

II. Regulated Attenuation

The present invention also encompasses a recombinant bacterium capable of regulated attenuation. Generally speaking, the bacterium comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In each of the above embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section I above.

(a) Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RpoS, PhoPQ, OmpR, Fur, and Crp proteins. In other embodiments, the protein may be a necessary component of the cell wall of the bacterium, such as the protein encoded by murA. In still other embodiments, the protein may be listed in Section I(d) above.

The native promoter of at least one, two, three, four, five, or more than five attenuation proteins may be replaced by a regulatable promoter as described herein. In one embodiment, the promoter of one of the proteins selected from the group comprising RpoS, PhoPQ, OmpR, Fur, and Crp may be replaced. In another embodiment, the promoter of two, three, four or five of the proteins selected from the group comprising RpoS, PhoPQ, OmpR, Fur, and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

(b) Regulatable Promoter

The native promoter of a nucleic acid encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

In certain embodiments, a recombinant bacterium of the invention may comprise any of the following: $\Delta P_{fur}$::TT araC $P_{BAD}$ fur, $\Delta P_{crp}$::TT araC $P_{BAD}$ crp, $\Delta P_{phoPQ}$::TT araC $P_{BAD}$ phoPQ, or a combination thereof. (P stands for promoter and TT stands for transcription terminator). Growth of such strains in the presence of arabinose leads to transcription of the fur, phoPQ, and/or crp nucleic acid sequences, but nucleic acid sequence expression ceases in a host because there is no free arabinose. Attenuation develops as the products of the fur, phoPQ, and/or the crp nucleic acid sequences are diluted at each cell division. Strains with the $\Delta P_{fur}$ and/or the $\Delta P_{phoPQ}$ mutations are attenuated at oral doses of $10^9$ CFU, even in three-week old mice at weaning. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as ΔaraBAD or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as ΔaraBAD23, which prevents use of arabinose retained in the cell cytoplasm at the time of oral immunization, and/or ΔaraE25 that enhances retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

(c) Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed above with respect to repressors in Section I.

In some embodiments, more than one modification may be performed to optimize the attenuation of the bacterium. For instance, at least one, two, three, four, five, six, seven, eight or nine modifications may be performed to optimize the attenuation of the bacterium.

Figure 8:
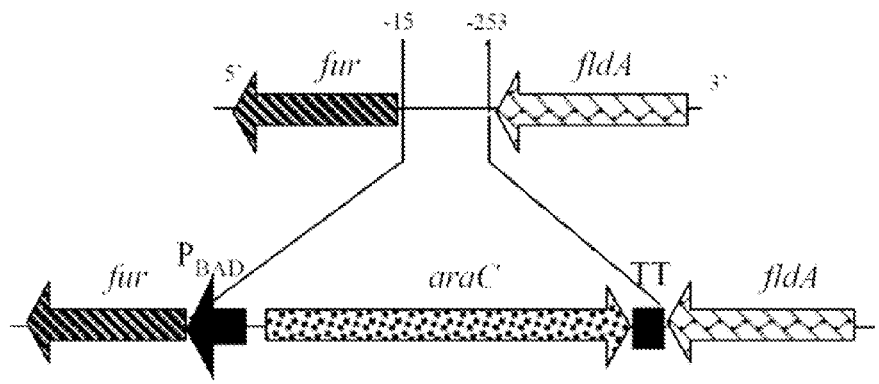
FIG. 8 depicts an illustration of a chromosomal map of various deletion-insertion mutations of the fur promoter region. The schematic shows the deletion of the fur promoter region (−15 to −253; including Fur consensus, Crp binding, and OxyR binding sites) and the insertion of 1335 bp of $P_{BAD}$ araC TT. The optimized sequences of ΔP$_{fur33}$::TT araC $P_{BAD}$ fur (SEQ ID NO:24), ΔP$_{fur77}$::TT araC $P_{BAD}$ fur (SEQ ID NO:25), and ΔP$_{fur81}$::TT araC $P_{BAD}$ fur (SEQ ID NO:26) show variations of SD sequences and start codons.
Figure 10:
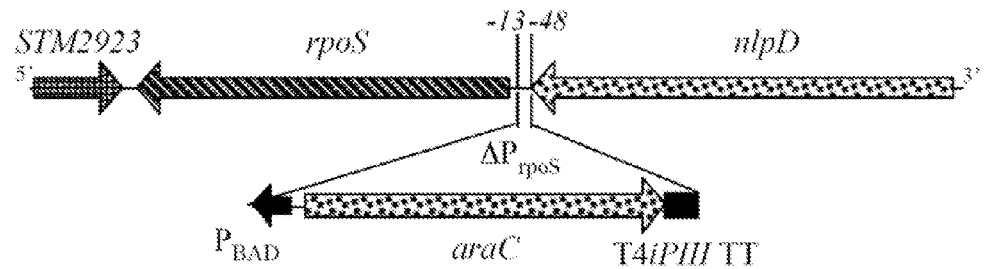
FIG. 10 depicts an illustration of a chromosomal map of the deletion-insertion mutation of the rpoS promoter region. The schematic shows the deletion of 36 bp of the rpoS promoter region (rpoS-13 to −48) and the insertion of 1335 bp of $P_{BAD}$ araC TT.
Figure 11:
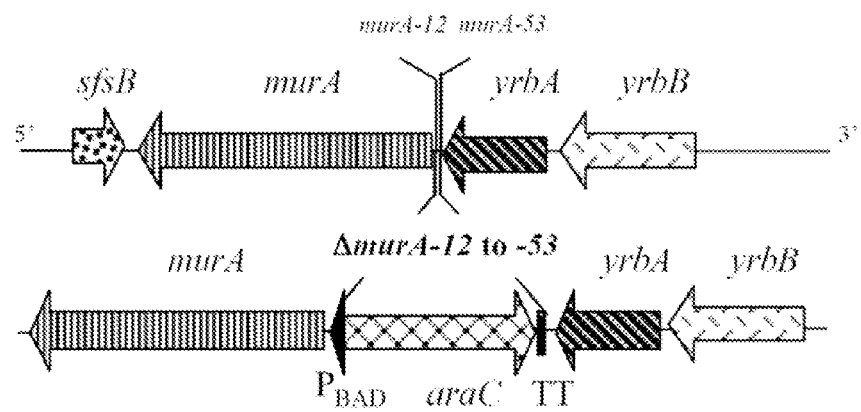
FIG. 11 depicts an illustration of a chromosomal map of the deletion-insertion mutation of the murA promoter region. The schematic shows the deletion of 42 bp between murA and yrbA and the insertion of 1335 bp of $P_{BAD}$ araC TT.
Figure 12:
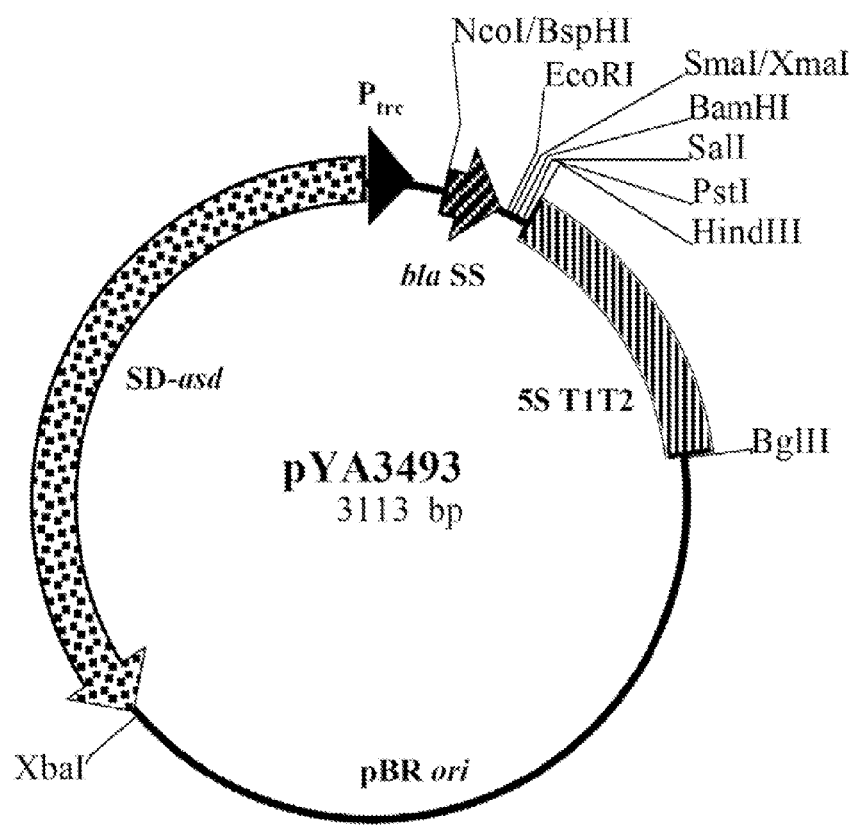
FIG. 12 depicts an illustration of pYA3493 plasmid.

In various exemplary embodiments of the invention, the SD sequences and/or the start codons for the fur and/or the phoPQ virulence nucleic acid sequences may be altered so that the production levels of these nucleic acid products are optimal for regulated attenuation. FIG. 8 depicts $\Delta P_{fur77}$::TT araC $P_{BAD}$ fur, whose start codon is changed from ATG to GTG, and $\Delta P_{fur81}$::TT araC $P_{BAD}$ fur, that has a weakened SD sequence as well as the start codon changed from ATG to GTG. FIG. 9 depicts $\Delta P_{phopQ173}$::TT araC $P_{BAD}$ phoPQ, that has modifications to the start codon as well as the second codon, which was changed from ATG to GTG. FIG. 9 also depicts $\Delta P_{phoPQ177}$::TT araC $P_{BAD}$ phoPQ, wherein the SD sequence has been changed to the weaker AAGG sequence, the start codon was modified, and the second codon was modified from ATG to GTG.

(d) Crp Cassette

Figure 7:
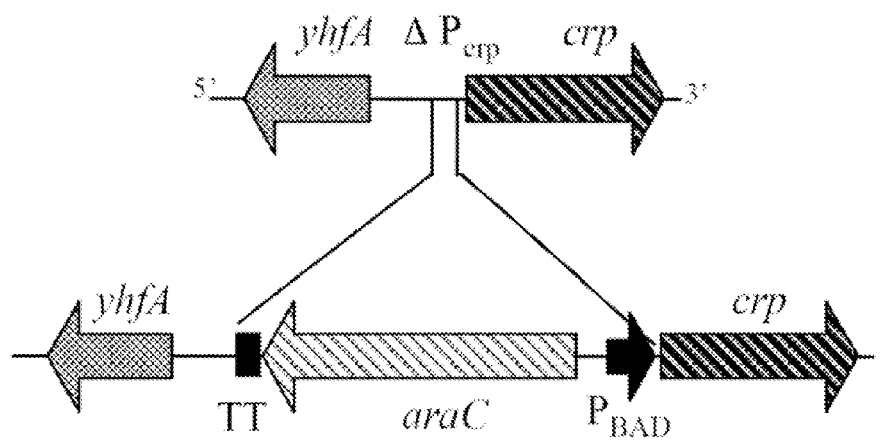
FIG. 7 depicts an illustration of a chromosomal map of the deletion-insertion mutation of the crp promoter region. The schematic shows the deletion of the crp promoter region (−15 to −109) and the insertion of 1335 bp of TT araC $P_{BAD}$. TT: T4 ipIII Transcription Terminator

In some embodiments, a recombinant bacterium of the invention may also comprise a $\Delta P_{crp}$::TT araC $P_{BAD}$ crp deletion-insertion mutation (FIG. 7), as described above. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional control on the expression of the nucleic acid sequence encoding an attenuation protein.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above (e) Regulated Expression In each of the above embodiments, a bacterium capable of regulated attenuation may also be capable of regulated expression of at least one nucleic acid encoding an antigen as detailed in section I above.

For instance, various embodiments of the present invention may encompass a recombinant pathogenic Enterobacteriaceae species comprising deletion-insertion mutations conferring regulated attenuation and regulated expression of a nucleic acid sequence encoding an antigen. In some embodiments, the recombinant bacterium may further comprise at least one chromosomal nucleic acid sequence containing a mutation conferring a lethal phenotype. The mutated chromosomal nucleic acid sequence may be complemented by a plasmid vector containing a functional nucleic acid sequence corresponding to the mutated chromosomal nucleic acid sequence.

III. Vaccine Compositions and Administration

A recombinant bacterium of the invention may be administered to a host as a vaccine composition. As used herein, a vaccine composition is a composition designed to elicit an immune response to the recombinant bacterium, including any antigens that may be expressed by the bacterium. In an exemplary embodiment, the immune response is protective, as described above. Immune responses to antigens are well studied and widely reported. A survey of immunology is given by aul, W E, Stites D et. al. and Ogra P L. et. al. (11-13). Mucosal immunity is also described by Ogra P L et. al. (14).

Vaccine compositions of the present invention may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. The vaccine can be administered as a prophylactic or for treatment purposes.

In exemplary embodiments, the recombinant bacterium is alive when administered to a host in a vaccine composition of the invention. Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response. In exemplary embodiments, the use of a live attenuated recombinant bacterium may act as a natural adjuvant. The vaccine compositions may further comprise additional components known in the art to improve the immune response to a vaccine, such as T cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

(b) Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

IV. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

V. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against an antigen in a host. The method comprises administering to the host an effective amount of a composition comprising a recombinant bacterium of the invention In still another embodiment, a recombinant bacterium of the invention may be used in a method for eliciting an immune response against a pathogen in an individual in need thereof. The method comprises administrating to the host an effective amount of a composition comprising a recombinant bacterium as described herein. In a further embodiment, a recombinant bacterium described herein may be used in a method for ameliorating one or more symptoms of an infectious disease in a host in need thereof. The method comprises administering an effective amount of a composition comprising a recombinant bacterium as described herein.

REFERENCES (TO PREVIOUS ABOVE TEXT)

1. Doggett T A, Jagusztyn-Krynicka E K, & Curtiss R, III. (1993) Immune responses to *Streptococcus sobrinus* surface protein antigen A expressed by recombinant *Salmonella typhimurium*. Infect Immun 61: 1859-1866.
2. Schoedel F, Kelly S M, Peterson D L, Milich D R, & Curtiss R, III. (1994) Hybrid hepatitis B virus core-pre-S proteins synthesized in avirulent *Salmonella typhimurium* and *Salmonella typhi* for oral vaccination. Infect Ummun 62: 1669-1676.
3. Srinivasan J, Tinge S, Wright R, Herr J C, & Curtiss R, III. (1995) Oral immunization with attenuated *Salmonella* expressing human sperm antigen induces antibodies in serum and the reproductive tract. Biol Reprod 53: 462-471.
4. Curtiss R, III, Goldschmidt R M, Fletchall N B, & Kelly S M (1988) Avirulent *Salmonella typhimurium* delta cya delta crp oral vaccine strains expressing a streptococcal colonization and virulence antigen. Vaccine 6: 155-160.
5. Guzman L M, Belin D, Carson M J, & Beckwith J (1995) Tight regulation, modulation, and high-level expression by vectors containing the arabinose PBAD promoter. J Bacteriol 177: 4121-4130.
6. Schleif R F (1996) in *Escherichia coli* and *Salmonella*, cellular and molecular biology, eds. F. C. Neidhardt, R. Curtiss III, J. L. Ingraham, E. C. C. Lin, K. B. Low, B. Magasanik, W. S. Reznikoff, M. Riley, Schaechter M, & Umbarger H E (ASM Press, Washington, D.C.), pp. 1300-1309.
7. Egan S M & Schleif R F (1993) A regulatory cascade in the induction of rhaBAD. J Mol Biol 234: 87-98.
8. Song S & Park C (1997) Organization and regulation of the D-xylose operons in *Escherichia coli* K-12: XylR acts as a transcriptional activator. J Bacteriol 179: 7025-7032.
9. Schodel F (1992) Recombinant avirulent Salmonellae as oral vaccine carriers. Infection 20:1-8.
10. Curtiss R, III, Galan J E, Nakayama K, & Kelly S M (1990) Stabilization of recombinant avirulent vaccine strains in vivo. Res Microbiol 141: 797-805.
11. Paul W E (1999) Fundamental immunology (Lippincott-Raven, Philadelphia).
12. Stites D P & Stobo J D (1994) Basic & clinical immunology (Lange Medical Publications, Los Altos, Calif.).
13. Ogra P L (1994) Handbook of mucosal immunology (Academic Press, Inc., San Diego).
14. Ogra P L (1999) Mucosal immunology (Academic Press, San Diego).

EXAMPLES

The following examples illustrate various iterations of the invention.

Example 1

Regulated Expression of Antigen Encoding Nucleic Acid Sequences

Antigens, delivered by recombinant attenuated *Salmonella* vaccine strains (RASVs), induce strong systemic and mucosal immune responses that are dependent on several factors including route of immunization [1, 2], expression level [3], cellular location [4], presentation [5], strain background [6, 7] and the inherent immunogenic properties of antigen. Generally, achieving maximal immune responses to the foreign antigen is directly correlated with the amount of the antigen produced [3, 8], thus it is important that the immunizing bacterial strain produce adequate levels of antigen. However, for RASV, this need must be weighed against the fact that high level antigen production can be a drain on the energy resources of the bacterium, leading to reduced growth rates and a compromised ability to colonize and stimulate effector lymphoid tissues [9]. In addition, some antigens are inherently toxic to vaccine strains for other reasons, leading to a severe inhibition of growth rate and host colonizing potential and, in some cases, death of the RASV. Sometimes, overexpression of foreign proteins can also result in mutations in the promoter or coding sequence of the nucleic acid sequence encoding the antigen, leading to unwanted changes in the level of antigen synthesis or character, thus reducing or compromising the desired immune response. Several approaches have been used to address this problem, including adopting in vivo inducible promoters, including those from the pagC [13], nirB [14], spy and dps [15] nucleic acid sequences. In principle, the advantage of using inducible promoters is that only low levels of antigen are produced during in vitro growth and the initial stages of infection. These promoters then upregulate antigen expression once the bacteria reach immunocompetent sites within the host, thus inducing the desired antigen-specific immune response. However, inducible promoters, as they are presently known in the art, are often either too weak in vivo or too strong in vitro, and may be limited by the mode of attenuation [14, 16]. Therefore, there is a need in the art for a system with a promoter that is weakly active in vitro, is capable of strong expression in vivo and whose function is not influenced by the mode of attenuation.

In this example, the construction of such a system is described utilizing the strong $P_{trc}$ promoter for antigen expression and attenuated *Salmonella enterica* serovar *Typhimurium* strains expressing different levels of LacI under the control of an arabinose-regulated promoter. Two test antigens were used to evaluate the system. The green fluorescent protein (GFP) was used for in vitro evaluation of the system and the α-helical fragment of the *Streptococcus pneumoniae* pspA nucleic acid sequence [4, 17, 18] was used as the test antigen for immunogenicity studies. *Salmonella* strains were constructed and evaluated for level of LacI synthesis, antigen synthesis and the ability to induce a protective immune response in mice.

Materials and Methods for Example 1

Bacterial Strains, Plasmids, Media and Growth Conditions:

Bacterial strains and plasmids used are listed in above Table 1 and Table 2, respectively. Bacteria were grown statically overnight at 37° C. in LB broth [19], 3XD broth, a buffered Casamino acids medium that includes glycerol as the carbon source [20] or nutrient broth (Difco) as indicated. The second day, the cultures were diluted 1:100 into prewarmed media with aeration at 37° C. When required, antibiotics and supplements were added at the following concentrations: chloramphenicol, 30 µg/ml; Diaminopimelic acid (DAP), 50 µg/ml [21]; p-aminobenzoic acid (pABA), 10 µg/ml. LB agar without NaCl and containing 5% sucrose was used for sacB nucleic acid sequence-based counter selection in allelic exchange experiments [22]. *S. pneumoniae* WU2 was cultured on brain heart infusion agar containing 5% sheep blood or in Todd-Hewitt broth plus 0.5% yeast extract [17].

General DNA Procedures:

DNA manipulations were carried out as described by Sambrook et al. [51]. Transformation of bacterial strains was routinely done by electroporation [52] using Nucleic acid sequence Pulser Xcell System (BioRad, Hercules, Calif.). Transformants containing $Asd^+$ plasmids were selected on LB agar plates without DAP. Only clones containing the recombinant plasmids were able to grow under these conditions. Suicide vector and P22-mediated transduction was used to generate defined deletion/deletion-insertion mutation [53, 54]. Transfer of recombinant suicide plasmids to *Salmonella* was accomplished by conjugation using *E. coli* χ7213 (Asd⁻) as the plasmid donor [48]. Bacteriophage P22HT int-mediated general transduction was performed by standard methods [55]. PCR amplification was employed to obtain DNA fragments for cloning and for verification of chromosomal deletion mutations. Nucleotide sequencing reactions were performed by the DNA lab in Arizona State University.

Construction of Plasmid pYA3700:

Plasmid pYA3700 carried a tightly regulated araC $P_{BAD}$ TT cassette. To construct this plasmid, two oligonucleotides, 5'-CCT<u>GGTACCTAGGCCTCTAGA</u>TA-AATAAAAGCAGTTTACAACTCCTAGAATTGTGAA TATATTATCACAATTCTAGGATAGAATAATAAA <u>AGATCTCTGCAG</u>GGC-3' (SEQ ID NO:34) and its complement, corresponding to the T4 ipIII transcription terminator [56] and additional enzyme site (underlined) were annealed, cut with KpnI-PstI, and cloned into pGEM3Z cut with the same enzymes to create plasmid pYA3698 (Table 2). The araC $P_{BAD}$ cassette was amplified using plasmid pYA3624 [57] as template with primer pair 1pBADaraCKpnI (5'-AGAGGTACCCTCGAGGCTAGCCCAAAAAAACGGG-3') (SEQ ID NO:35) and 1pBADaraCXbaI (5'-TGGTCTA-GAGTCAAGCCGTCAATTGTCTGATTCG-3') (SEQ ID NO:36). The PCR fragment was cut with KpnI-XbaI and cloned into plasmid pGEM3Z to generate plasmid pYA3699 and into pYA3698 to generate the plasmid pYA3700.

Construction of Suicide Vector pYA3784:

The GTG-lacI nucleic acid sequences were amplified from the χ289 genome using the primer pairs, lacI EcoRI-3'(5'-GGAATTCTCACTGCCCGCTTTCCAGTCGGG-3') (SEQ ID NO:37) and GTG lacI XhoI-5' (5'-CCGCTCGAG AGGGTGGTGAATGTGAAACCAGTAACGTT-3') (SEQ ID NO:38). The resulting 1.1 kb PCR fragment was cloned into pCR-Blunt II-TOPO to create pCR-Blunt II-TOPO-LacI (E-X). The relA upstream homology region from the χ 3761 genome was amplified using the primer pairs RelA N-HindIIISacI-5' (5'-CCCAAGCTTGAGCTCGAGGGCGTTC-CGGCGCTGGTAGAA-3') (SEQ ID NO:39) and RelA N-BglII-3' (5'-GAAGATCTAAGGGACCAGGCCTAC-CGAAG-3') (SEQ ID NO:40). The fragment was cut with HindIII-BglII and ligated into plasmid pYA3700 at the same restriction sites to generate plasmid pGEM3Z-pBADaraCT4ipIIIrelA-N. Plasmid pYA3700 was cut with XhoI-XbaI and ligated into pCR-Blunt II-TOPO-LacI(E-X) to generate the plasmid pCR-BluntII-TOPO-LacIpBA-DaraC. This plasmid was cut with EcoRI, blunted with Mungbean nuclease and then cut with HindIII. Plasmid pGEM3Z-pBADaraCT4ipIIIrelA-N was cut with XbaI, blunted with Mungbean nuclease and then cut with HindIII. These two fragments were ligated to form the plasmid pCR-Blunt II-TOPO-LacI(GTG)pBADaraC-relAN. The relA downstream homology region was amplified from χ3761 genome using the primer pairs RelA C-EcoRI-5' (5'-CGGAATTCAC-CCCAGACAGTAATCATGTAGCGGCT-3') (SEQ ID NO:41) and RelA C-KpnI-3' (5'-CGGGTACCCCA-GATATTTTCCAGATCTTCAC-3') (SEQ ID NO:42). The fragment was ligated with the pCR-BluntII-TOPO-LacI (GTG)pBADaraC-relAN, cut with XbaI and blunted with Mungbean nuclease, to generate plasmid pYA3782. The relA::araC $P_{BAD}$ lacI TT cassette was cut with KpnI-SacI and cloned into pRE112 to generate the suicide plasmid pYA3784 harboring the GTG-lacI. The ATG-lacI was amplified using primers pairs, lacI EcoRI-3' (5'-GGAATTCTCACTGC-CCGCTTTCCAGTCGGG-3') (SEQ ID NO:43) and XhoI SD*-ATG lacI-5' (5'-CCGCTCGAG <u>AGGATGGTGAATATGAAACCAGTAACGTT</u>-3') (SEQ ID NO:44) and cloned into pCR-Blunt-II-Topo vector. The codon optimization of ATG-lacI was done by the PCR method. Briefly, 22 pairs of overlapping primers covering 15 non-optimized codons used in the lacI nucleic acid sequence were PCR amplified. The overlapping PCR products were used as template to be amplified again to get codon optimized ATG-lacI. The 15 codons are 35th CGG to CGT, 49th CCC to CCG, 101th CGA to CGT, 155th CCC to CCG, 168th CGA to CGT, 213th ATA to ATC, 216th CGG to CGT, 239th CCC to CCG, 272th GGA to GGT, 320th CCC to CCG, 326th AGA to CGT, 332th CCC to CCG, 339th CCC to CCG, 351th CGA to CGT and 355th CGA to CGT. The codon optimized ATG-lacI was also cloned into the pCR-Blunt-II-Topo plasmid. Then the similar strategies were used to generate suicide plasmid pYA3789 with the ATG-lacI and suicide plasmid pYA4064 with codon optimized lacI.

Construction of Expression Plasmid pYA4088:

Plasmid pYA3494 carries amino acids 3-257 of native pspA Rx1 fused to the first 23 amino acids of bla [23]. Nine codons that are rare in *Salmonella* were converted to highly used codons without changing the amino acid sequence to create plasmid pYA3635 using PCR methods [58]. The 9 codons are 2nd CCC to CCG, 57th CTA to CTG, 77th CTA to CTG, 95th ATA to ATC, 113th CGA to CGT, 144th CTA to CTG, 185th AGA to CGT, 186th CTA to CTG, 221st CTA to CTG. Two additional codons, 23rd GCG to GCT and 124th GCT to GCG were also changed to keep the GC content the same. Generally, the overlapping primers covering the 9 non-optimized codons used in the pspA Rx1 nucleic acid sequence were PCR amplified. The overlapping PCR products were used as template to be amplified again to get the codon optimized pspA Rx1. The final PCR product was cloned into pYA3493 to generate pYA3635. Using pYA3635 as the starting material, the optimized pspA sequence was extended an additional 28 amino acids to include a recently identified B cell epitope (S. Hollingshead, personal communication). The extended codon-optimized pspA Rx-1 nucleic acid sequence was constructed in 3 steps. First, the optimized pspA sequence was amplified using primer set PspA Rx1 forward (5'-TCTCCGGTAGCCAGTCAGTCTAAAGCT-GAG-3') (SEQ ID NO:45) and PspA RX1-a1 (5'-CTAAT-TCAGCTTTTTTAGCAGCAAT-AGTTTTCTCTAAACCTTCTTTAAAGTAGTCTTC TACATTATTGTTTTCTTC-3') (SEQ ID NO:46). The resulting 820-bp PCR fragment was used as template in a second PCR reaction using primer set PspA Rx1 forward (5'-TCTC-CGGTAGCCAGTCAGTCTAAAGCTGAG-3') (SEQ ID NO:47) and PspA Rx1-a2 (5'-TGCTTTCTTAAGGT-CAGCTTCAGTTTTTTCTAAT-TCAGCTTTTTTAGCAGCAATAGTT TTCTC-3') (SEQ ID NO:48) PspA Rx1-EcoRI-s. The resulting 849-bp PCR product was used as template for a third amplification with the primer set PspA Rx1-EcoRI-s (5'-GGAATTCTCTCCGG-TAGCCAGTCAGTCT-3') (SEQ ID NO:49) and PspA Rx1-HindIII-a (5'-TTCAAGCTTATTATGCTTTCTTAAGGT-CAGCTTC-3') (SEQ ID NO:50). The 869-bp PCR product from that reaction was cloned into plasmid pYA3493 [23] using EcoRI-HindIII restriction sites to generate pYA4088. The sequence was verified by sequencing and enzyme digestion.

Construction of Plasmid pYA4090:

Plasmid pYA3552 comprises the gfp3 nucleic acid sequence, which is a kind gift from Dr. Ho-Young Kang. Plasmid pYA4090 was constructed by PCR amplification of the 740-bp gfp3 nucleic acid sequence using plasmid pYA3552 as template with the primer set GFP-EcoRI-s (5'-GGGAATTCCGATGAGTAAAGGAGAAGAACTTTTC-3') (SEQ ID NO:51) and GFP-HindIII-a (5'-CGGTG-CAAGCTTATTATTTGTATAGTTCATCCATG-3') (SEQ ID NO:52) and then cloned into pYA3342 using EcoRI-HindIII.

Construction of Plasmid pYA3438:

The plasmid containing the 1.5 kb pabB nucleic acid homology was cloned into the XbaI-BamHI site of pMEG375. The pabB nucleic acid sequence had 106 bp deleted between the two internal EcoRV sites.

Construction of plasmid pYA3599: The suicide plasmid pYA3599 was used to delete the araBAD operon. A 360 bp fragment of the 3' end of araD was generated by PCR using primers araD-BamHI (5'-CGGGATCCTGGTAGGGAAC-GAC-3'; add BamHI underlined) (SEQ ID NO:53) and araD-NcoI (5'-GATG CCATGGTTTAAACTATATTCAGCAAATGCG-3'; add NcoI underlined) (SEQ ID NO:54), and a 500 bp fragment of 5' end of the araB nucleic acid sequence was nucleic acid generated by PCR using primers araC-NcoI (5'-GATG CCATGGTCTGTTTCCTCGTCTTACTCCATCC-3'; add NcoI underlined) (SEQ ID NO:55) and araC-SphI (5'-ACAT GCATGCGGACGATCGATAA-3'; add SphI underlined) (SEQ ID NO:56). These two fragments were cloned into the BamHI and SphI site of pMEG-375 to result in the suicide vector pYA3599.

Construction of χ9097:

The strain χ8060 is from Megan Health, Inc. and harbors a pabA1516 mutation. The χ8442 strain was constructed by conjugation of χ7213, harboring plasmid pYA3599, with χ8060. The χ8914 strain was constructed by conjugation of χ7213, harboring plasmid pMEG-443, with χ8060. The χ8767 was constructed by conjugation of χ7213 harboring plasmid pYA3599. The P22 lysate was made on the single cross over by conjugation χ7213, harboring plasmid pYA3599, with χ8767 according to Kang's method [59]. The ΔaraBAD23 mutation was introduced into strain χ8914 bp P22 transduction from (χ8767:pYA3599) to generate strain χ9097. The mutation was verified by PCR and formation of a white colony phenotype on MacConkey agar supplemented with 1% arabinose. Minimal agar with/without pABA was used to detect the phenotype associated with the pabA pabB mutations. The presence of the asdA mutation in *Salmonella* was confirmed by its dependence on DAP for growth [21]. The presence of the 3.3 kb deletion-insertion of relA was confirmed by PCR with primer set RelA N-HindIII SacI-5' (5'-CCCAAGCTTGAGCTCGAGGGCGTTCCG-GCGCTGGTAGAA-3') (SEQ ID NO:57) and RelA C-KpnI-3' (5'-CGGGTACCCCAGATATTTTCCAGATCTTCAC-3') (SEQ ID NO:58) and western-blot using anti-LacI antiserum as described below. Lipopolysaccharide (LPS) profiles of *Salmonella* strains were examined as described [60].

Construction of Vectors and Strains:

Similar strategies to those described above were used to construct pYA3789 and pYA4064 to generate the ATG-lacI mutation ΔrelA197::araC $P_{BAD}$ lacI TT and the codon optimized ATG-lacI mutation ΔrelA198::araC $P_{BAD}$ lacI TT, respectively. Plasmid pYA3342 is an Asd+ expression vector with promoter $P_{trc}$ [23]. Plasmid pYA4090 is a pYA3342 derivative that codes for gfp3 expression from the $P_{trc}$ promoter. Details for the construction of plasmid pYA4090 are described herein. Plasmid pYA3493 is a pYA3342 derivative that encodes the first 23 amino acids of β-lactamase [23]. Plasmid pYA4088, derived from pYA3493, carries a cloned fragment of the *S. pneumoniae* pspA nucleic acid sequence, encoding aa 3-285, that has been codon-optimized for expression in *Salmonella*, and fused to the nucleic acid sequence encoding amino acids 1-23 of β-lactamase.

Construction and Phenotypic Characterization of S. Typhimurium Vaccine Strains:

The ΔrelA196::araC $P_{BAD}$ lacI TT, ΔrelA197::araC $P_{BAD}$ lacI TT and ΔrelA198::araC $P_{BAD}$ lad TT mutations were introduced into the S. Typhimurium strain χ3761 by allelic exchange using χ7213 harboring the suicide vectors pYA3784, pYA3789 and pYA4064 to yield χ8990, χ9080 and χ9226, respectively, and into RASV strain χ9097 to generate χ9095, χ9101 and χ9241. The presence of the 3.3 kb deletion-insertion was confirmed by PCR and western-blot as described below.

Western Blot Analysis:

Protein samples were prepared from equal numbers of cells, separated on a 12% SDS-PAGE gel, and transferred to a nitrocellulose membrane using Trans-Blot SD Semi-Dry Transfer Cell (Bio Rad). LacI, PspA and GroEL were detected using rabbit polyclonal anti-LacI, anti-PspA and anti-GroEL primary antiserum, respectively, at 1:10,000 dilutions, and a secondary anti-rabbit alkaline phosphatase-conjugated antibody (Sigma, St Louis, Mo.) at 1:10,000 dilution. Bands were visualized using NBT/BCIP (Sigma). The bands were scanned and densitometry was measured using Quantity One software (Bio-Rad).

Growth Curves:

Standing overnight 37° C. cultures of RASV strains χ9095, χ9097, χ9101 and χ9241, with and without plasmid pYA4088, were grown in LB or LB plus DAP, respectively, containing 0.2% arabinose. The culture was adjusted to the same OD with pre-warmed medium, and then diluted 1:100 into pre-warmed LB or LB-DAP broth with 0.2% arabinose. The optical density at 600 nm ($OD_{600}$) was measured every 40 min. At the final time point, samples of each strain were taken and used for western blot analysis with anti-LacI and/or anti-PspA antisera.

Protein Stability Analysis:

S. Typhimurium strains χ8990, χ9080 and χ9226 were grown in 3XD medium containing 0.2% arabinose and E. coli strain XL1-Blue was grown in LB without arabinose. Standing overnights of each strain were grown at 37° C., diluted 1:100 into fresh media and grown with aeration to an $OD_{600}$ of 0.6. Cells were washed 2 times with fresh medium. Chloramphenicol was added to 50 µg/ml. Samples taken before adding chloramphenicol (pre 0), just after adding chloramphenicol (O), and at 1, 2, 4, 6, 8, 24 h were analyzed by western blot. The samples were normalized by cell number before loading onto the gel.

Flow Cytometry Analysis:

Standing overnight cultures of χ9095(pYA4090), χ9097 (pYA4090), χ9101(pYA4090) and χ9241(pYA4090) were grown at 37° C. in Nutrient Broth without arabinose. Then, 3×10$^5$ CFU of each strain were added to 3 ml of fresh medium containing 0%, 2%, 0.2%, 0.02% or 0.002% arabinose and grown to an $OD_{600}$ of 0.4. The cultures were diluted 1:10 in PBS and subjected to flow cytometry analysis using Cytomics FC500 (Beckman Coulter, Inc., Fullerton, Calif., USA). The data were analized by CXP analysis software (Beckman Coulter, Inc.)

Kinetics of LacI Loss and Antigen Synthesis in Pre-Induced Cultures Grown without Arabinose:

Overnight cultures of strains χ9095, χ9097, χ9101 and χ9241 carrying either plasmid pYA4088 or plasmid pYA4090 were grown in Nutrient broth with or without 0.2% arabinose. Each culture was adjusted to $OD_{600}$=0.6 and diluted 1:100 into the same pre-warmed medium at 37° C. When cultures reached an $OD_{600}$ of 0.6, the cultures were washed once with nutrient broth without arabinose and diluted 1:100 (for plasmid pYA4090) or 1:10 (for plasmid pYA4088) into pre-warmed nutrient broth without arabinose and grown to an $OD_{600}$=0.6. The cultures were diluted into fresh media and the process was repeated twice (for pYA4090 cultures) or three times more (for pYA4088 cultures). Samples were taken at the end of each growth cycle. Samples of strains χ9095(pYA4088), χ9097(pYA4088), χ9101 (pYA4088) and χ9241(pYA4088) were normalized according to cell number and analyzed by western blot. Bands were scanned and densitometry was measured using Quantity One software (Bio-Rad, Hercules, Calif.). Samples of strains χ9095(pYA4090), χ9097(pYA4090), χ9101(pYA4090) and χ9241(pYA4090) were analyzed by flow cytometry.

Tests of Immunogenicity and Protection in Mice:

Strains were grown in LB medium supplemented with 0.2% arabinose to an $OD_{600}$ of 0.8, sedimented by room temperature centrifugation at 6,000×g for 15 minutes and resuspended in phosphate-buffered saline containing gelatin (BSG) [24]. Groups of female BALB/c mice were orally immunized with 10$^9$ CFU of the RASV. Food and water was removed 4 h before inoculation and restored 30 min after inoculation. The inoculum was diluted for titer determination on LB agar plates. Mice were bled at 0, 2, 4, 6, and 8 weeks. Anti-LPS and anti-PspA Rx1 serum IgG was evaluated by ELISA. Mice were challenged by intraperitoneal injection with 250 $LD_{50}$ of virulent S. pneumoniae WU2 eight weeks after immunization. The mice were observed daily for 21 days after challenge. All animal protocols were approved by ASU IACUC and complied with rules and regulations by American Association for Accreditation of Laboratory Animal Care.

ELISA:

rPspA Rx1 protein was purified as described by Kang et al. [23]. S. Typhimurium LPS was obtained from Sigma. The procedure for ELISA has been described [23]. Briefly, polystyrene 96-well flat-bottom microtiter plates (Nunc, Roskilde, Denmark) were coated with 100 ng/well of either S. Typhimurium LPS or rPspA Rx1 in 100 ml sodium carbonate-bicarbonate coating buffer (pH 9.6). The sera were serially diluted in two-fold steps for detection of IgG. A 100 ml of diluted sample was added to triplicate wells. Plates were treated with biotinylated goat anti-mouse IgG (Southern Biotechnology Inc., Birmingham) and then alkaline phosphatase-labeled streptavidin (Southern Biotechnology Inc., Birmingham). After adding p-nitrophenylphosphate substrate solution in diethanolamine buffer (pH 9.8) (Sigma, St. Louis, Mo.), absorbance was read at 405 nm.

Statistics:

Statistical analyses were performed by using the SPSS software package (SPSS, Chicago, Ill.). p values of 50.05 were considered significant. Antibody titers were expressed as means±standard error. The means were evaluated with One-way Anova and the LSD tests were used for multiple comparisons among groups.

Rationale for the Regulated Delayed Antigen Synthesis System

The $P_{trc}$ promoter is commonly used for constitutive expression of nucleic acid sequences encoding antigens [25, 26]. $P_{trc}$ is a strong promoter in vivo [27], constitutive under most environmental conditions, and is more transcriptionally active both anaerobically and aerobically than the nirB promoter [14]. Although the $P_{trc}$ promoter has been widely used in bacterial expression vectors and in mammalian cell expression systems [28-30], it has been reported that constitutive antigen expression from the similar $P_{tac}$ promoter can affect the colonization capability of RASV [16]. Thus regulating antigen expression from $P_{trc}$ would be beneficial. The $P_{trc}$ promoter can be repressed by LacI. In Escherichia coli, the LacI repressor is typically produced at approximately 8 copies per cell [31, 32] and regulates expression of the lactose metabolic nucleic acid sequences [33] by binding to the lacO operator sequence, blocking RNA polymerase from binding to the lac promoter. Generally, induction of expression from LacI-repressed promoters is accomplished by the addition of chemical agents, either lactose or IPTG which bind to LacI causing an allosteric change in the protein that leads to its release from lacO. However, this is not a practical method of induction for RASVs. Instead, the production of LacI was regulated by placing it under the control of the regulated arabinose-inducible promoter $P_{BAD}$ (FIG. 19A). Transcription from $P_{BAD}$ can be regulated by varying the concentration of arabinose [34, 35]. When the RASV is grown in culture and arabinose is added to the growth medium, LacI is produced which represses transcription from $P_{trc}$. Once in the host, the transcription from $P_{BAD}$ would cease because free arabinose is very rarely encountered in animal tissues [36], and subsequently, no additional LacI would be produced. The concentration of LacI should then decrease by dilution as the RASV cells divide and antigen production would increase to levels high enough to induce the desired immune response.

Construction of Strains with High Expression of LacI

Figure 19C:
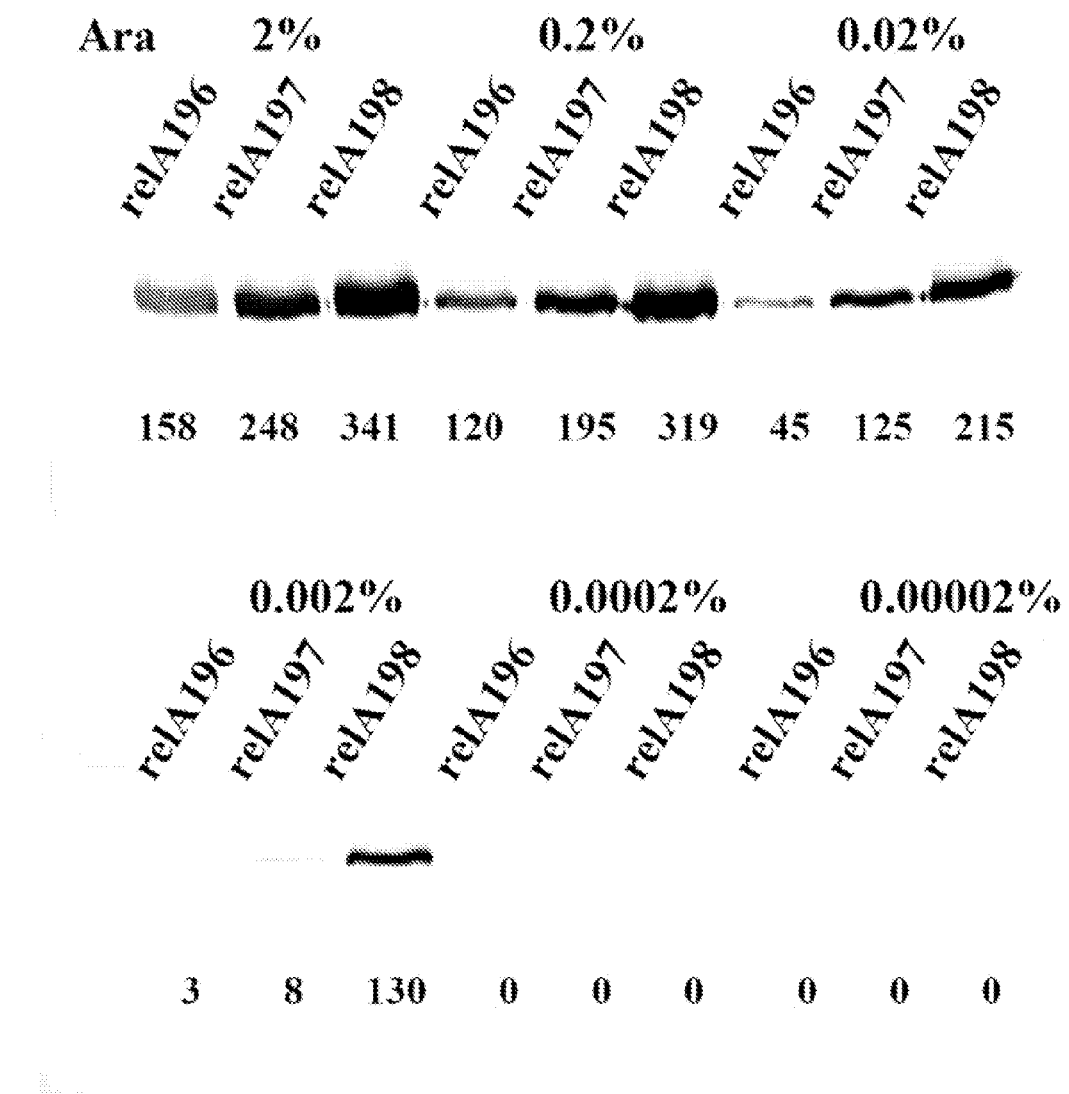
FIG. 19 depicts principle of regulated delayed expression and constructions of strains with ΔrelA::araC $P_{BAD}$ lacI TT cassette. (A) Principle of regulated delayed expression. This system includes a chromosomal repressor gene, lacI, expressed from the arabinose-regulated araC $P_{BAD}$ promoter. LacI regulates expression from a plasmid promoter, $P_{trc}$ that directs antigen synthesis. In the presence of arabinose, LacI is produced which binds to $P_{trc}$, blocking antigen encoding sequence expression. In host tissues, an arabinose poor environment, the concentration of LacI will decrease with each cell division allowing increased antigen synthesis, thus inducing an immune response. (B) Strains with different levels of LacI encoding sequence expression due to altered SD-sequence, start codon and codon usage in the lacI gene were inserted into the relA gene site of the *Salmonella* genome. The deletion-insertion deleted 2247 bp in relA (relA −12 to relA 2235) and inserted 2429 bp of araC $P_{BAD}$ lacI TT cassette. These mutations were also introduced into strains with the ΔpabA ΔpabB ΔasdA ΔaraBAD genotype to provide attenuation, selection for a balanced-lethal vector (Asd+) and to block arabinose metabolism. (C) Western blot analysis of ΔrelA::araC $P_{BAD}$ lacI (GTG vs. ATG vs. ATG codon optimized) mutations using rabbit anti-LacI antiserum. The strains were grown in 3×D media with different concentrations of arabinose. The samples were normalized by cell number. Densitometry was measured by Quantityone software. The number shows the relative densitometry.

Based on this concept, a tightly-regulated araC $P_{BAD}$ lacI TT cassette was integrated into the chromosome in the relA nucleic acid sequence (FIG. 19B), nucleic acid sequencing defining the relA196 allele in strain, $\chi$8990. relA was chosen as the integration site because the relA mutation is not attenuating nor does it have an effect on colonization [37, 38]. The native lacI nucleic acid sequence has a GTG start codon and an AGGG Shine-Dalgarno sequence, leading to expression of only 5-10 molecules each generation [31] and the functional form of LacI repressor is a tetramer [32]. Plasmids with a ColE1 (pBR) replicon are present at 20-30 copies per cell. Thus, it was estimated that at least 80-120 copies of LacI are needed to repress the operator sequences in the expression plasmid to achieve adequate repression. Therefore, in addition to strain $\chi$8990, which encodes the native lacI sequence (GTG-lacI), the start codon of lacI was modified from GTG to ATG, and the SD sequence was modified from AGGG to the canonical ribosome binding site sequence, AGGA, resulting in the relA197 allele in strain $\chi$9080. This modification increased LacI levels about 2 fold (FIG. 19C). To enhance expression further, the codons of lacI were optimized according to the codon usage for highly expressed nucleic acid sequences in Salmonella, yielding the relA198 allele in strain $\chi$9226. This modification increased LacI levels approximately 4-8 fold over relA196 (FIG. 19C). The expression levels of LacI for GTG-lacI, ATG-lacI, and codon optimized-lacI were proportional to the arabinose concentration (FIG. 19C). It is anticipated that different antigens may require different levels of repression, so these constructs provide the flexibility needed to produce different amounts of repressor to meet varied requirements.

High Expression of LacI does not Affect Growth.

Figure 20:
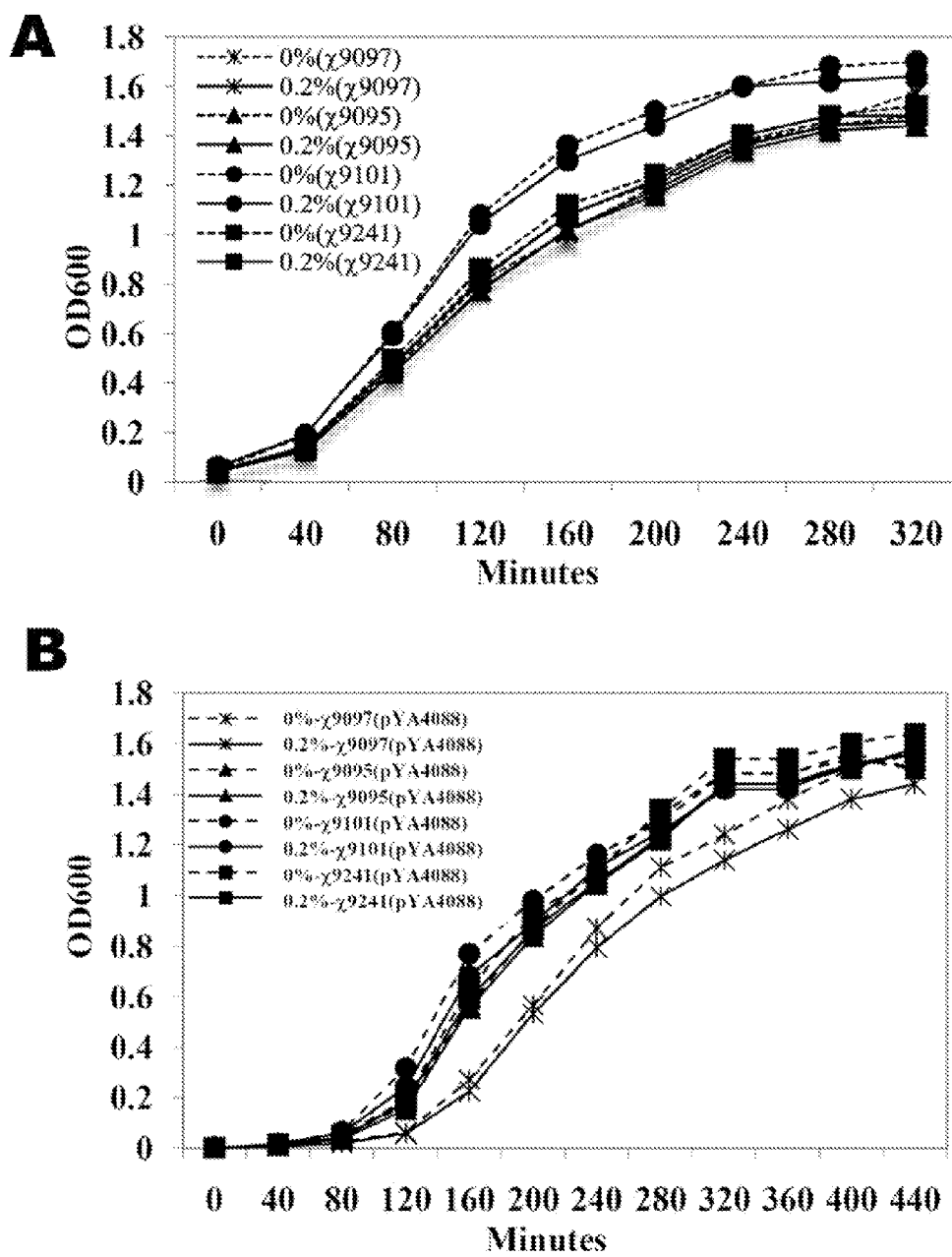
FIG. 20 depicts two graphs showing that higher expression of LacI encoding sequence does not change growth. The strains were grown in LB media with 0% (dashed line) and 0.2% arabinose (solid line). The $OD_{600}$ was measured at 40 min intervals. *, χ9097, ▲, χ9095, ●, χ9101, ■, χ9241 (a) Strains without antigen encoding sequence expression plasmid. DAP was included in the growth medium for these strains. (b) Strains with antigen encoding sequence expression plasmid pYA4088.

The Salmonella chromosome does not encode the lac operon. Consequently, the effect of LacI production or overproduction on growth was investigated, because this might translate to a reduction in immunogenicity. The growth of all three of the above strains was evaluated in LB broth with or without 0.2% arabinose, and compared to a strain that does not produce LacI. All four strains had similar growth rates, including strain $\chi$9241 (relA198), which produces the most LacI (FIG. 20). Although one of the LacI-producing strains, $\chi$9101 (relA197), grew better than the other strains, there were no large differences in doubling times. Growth at lower concentrations of arabinose gave similar results, but 2% arabinose led to reduced growth of all the LacI-producing strains.

Codon Optimized LacI Provides the Highest Repression

To evaluate the relationship between antigen synthesis and arabinose concentration, plasmid pYA4090, which encodes the gfp3 nucleic acid sequence under transcriptional control of $P_{trc}$, was introduced into S. Typhimurium strains $\chi$9097, $\chi$9095, $\chi$9101 and $\chi$9241. Transformants were grown in LB at varying arabinose concentrations and subjected to FACS analysis. The $P_{BAD}$ promoter is subject to autocatalytic regulation, and therefore we were able to evaluate the fraction of cells expressing GFP as a measure of induction [39]. As expected, there was no effect of arabinose on gfp3 nucleic acid expression in strain $\chi$9097(pYA4090), which does not encode lacI (FIG. 21A). When strains $\chi$9095(pYA4090), $\chi$9101(pYA4090) and $\chi$9241(pYA4090) were grown without arabinose, nearly all the cells expressed GFP. No decrease in the number of GFP-positive cells was observed when 0.002% arabinose was included in the growth medium but repression was evident at 0.02% arabinose for all strains. As the arabinose concentration was increased, the number of GFP positive cells dropped substantially for all strains with arabinose-regulated expression of lacI. The greatest level of repression was seen in strain $\chi$9241 (relA198), with only 7.6% GFP positive cells in the presence of 2% arabinose. These results are consistent with the expectation that antigen synthesis should be inversely proportional to arabinose concentration and inversely proportional to LacI synthesis (FIG. 21A). Although the lacI constructs in $\chi$9095 (relA196) and $\chi$9101 (relA197) produced different amounts of LacI (FIG. 19), there was no difference in gfp nucleic acid expression between the two strains.

LacI is a Stable Protein

Figure 22:
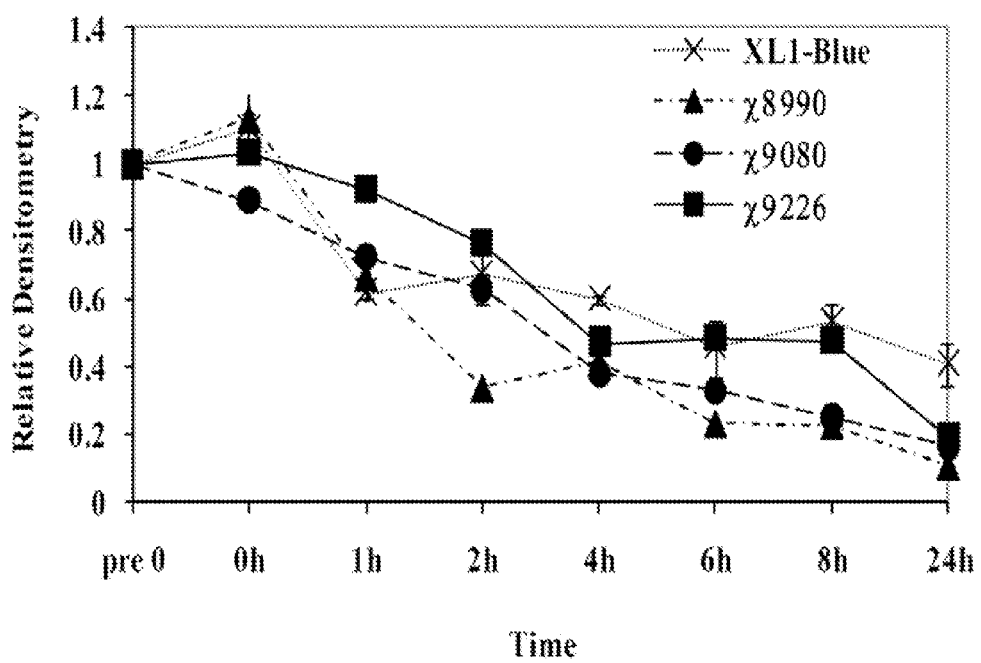
FIG. 22 depicts a graph showing the stability of LacI protein in different strains. XL1-Blue (lacI$^q$ *E. coli*) was grown in LB media. Strains χ8990, χ9080 and χ9226 were grown in 3×D media with 0.2% arabinose to $OD_{600}$ of 0.6 and washed 2 times with 3×D media without arabinose. Chloramphenicol were added to 50 μg/ml. Samples were taken before washing (pre0), just after adding chloramphenicol (0), and at 1, 2, 4, 6, 8, 24 h and subjected to western blot analysis. The samples were normalized by cell number. The densitometry was measured by Quantityone software.

Because LacI is not normally synthesized in S. Typhimurium and in E. coli it is only expressed at low levels and because of the central role LacI plays in the system, the stability of LacI was investigated in these strains, as that could have an impact on the timing of antigen synthesis in vivo. Chloramphenicol was added to mid-exponential phase cultures of Salmonella strains $\chi$8990, $\chi$9080 and $\chi$9226 and E. coli strain XL1-Blue. The stability of LacI was similar for all strains (FIG. 22). The amount of LacI declined by 50% over the first 2-4 hours in all strains, after which the amount declined very slowly, reaching approximately 20% of the starting levels by 24 hours for the S. Typhimurium strains and 40% for the E. coli strain. These results indicate that LacI stability is essentially the same in S. Typhimurium and E. coli, and that the protein is relatively stable. Thus it is expected that the concentration of LacI in these strains, in the absence of arabinose, will decrease primarily due to dilution as a result of cell division.

Time Course for the Induction of GFP Synthesis.

To evaluate the kinetics of the induction of antigen synthesis after growth in arabinose, the GFP-producing strains were grown in nutrient broth with 0.2% arabinose. Nutrient broth was chosen as the growth medium because it is derived from animal tissue and should mimic the low arabinose conditions found in host tissues better than LB broth. The arabinose-grown cells were diluted 1:100 into fresh nutrient broth without arabinose and grown to an $OD_{600}$ of 0.6. The cells were diluted and grown twice more in the same way. Each round of growth represented approximately 4.3 cell divisions, for a total of 13.8 nucleic acid sequencerations of growth in the absence of arabinose. Samples were taken at the end of each growth cycle and analyzed by FACS (FIG. 21B). The results indicated that although some strains were not fully repressed by growth in arabinose, the kinetics of induction was similar in all strains leading to nearly full induction for synthesis of GFP by 9.2 nucleic acid sequencerations of growth.

Time Course for the Induction of PspA Antigen Synthesis

As shown above, the system worked as expected using gfp3 as a model. The system was next evaluated in the context of a vaccine with a clinically relevant antigen, the *S. pneumoniae* PspA Rx1 protein that has been shown to be a potent and protective immunogen [23]. Plasmid pYA4088 was introduced into the strains and their growth rates in LB broth were compared. All of the LacI-producing strains had a growth advantage over strain χ9097(pYA4088) in the presence of 0.2% arabinose (FIG. 20B), indicating that repressing the expression of the nucleic acid sequence encoding antigen results in faster growth. The LacI-producing strains also grew faster than χ9097(pYA4088) in the absence of added arabinose. This may be due to trace amounts of arabinose present in the yeast extract used to prepare the LB broth medium, approximately 0.0034% (K. Ameiss, personal communication). Although the amount of LacI produced under these conditions was undetectable by western blot (FIG. 19C), there may have been sufficient LacI present to account for the observed growth advantage.

Figure 21C:
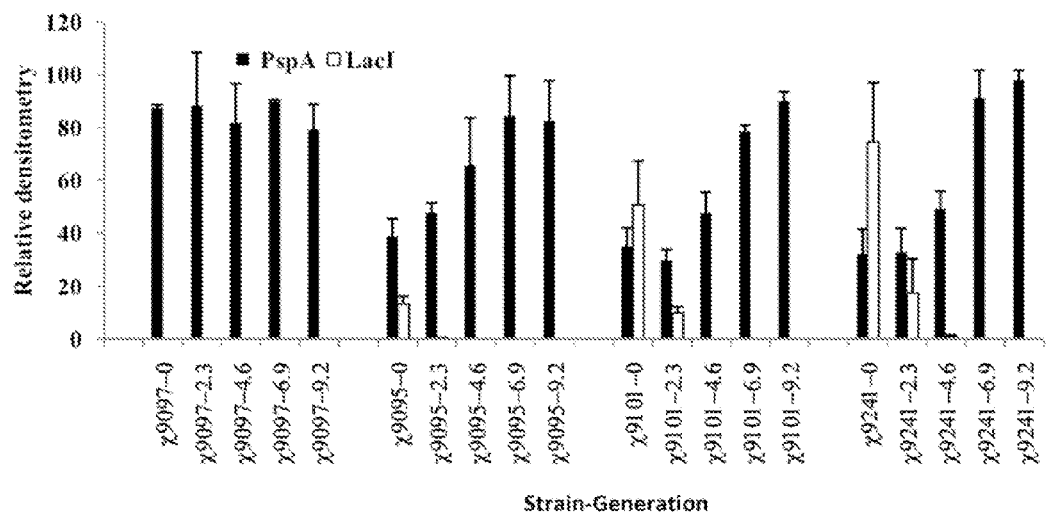
FIG. 21 depicts a series of graphs illustrating the effect of arabinose on gfp expression and the kinetics of LacI decrease and PspA antigen increase. (A) Different repression levels of GFP synthesis achieved by varied concentrations of arabinose. These strains have plasmid pYA4090 expressing GFP with $P_{trc}$ promoter. Overnight nutrient broth cultures grown without arabinose were diluted 1:100 into pre-warmed nutrient broth with 2%, 0.2%, 0.02%, 0.002% and 0% arabinose. When $OD_{600}$ reached 0.4, samples were diluted 1:100 into PBS and subjected to FACS analysis. (B) Kinetics of GFP synthesis. Overnight cultures with different concentrations of arabinose were diluted 1:100 into pre-warmed nutrient broth with arabinose; grown to OD600 of 0.6, and diluted 1:100 into the same pre-warmed media without arabinose. The process was repeated two more times. At each time point of $OD_{600}$ about 0.6, samples were diluted 1:200 into PBS and subjected to FACS analysis. (C) Kinetics of LacI decrease and PspA antigen increase. Overnight cultures with 0.2% arabinose were diluted 1:100 into pre-warmed LB media with 0.2% arabinose, grown to an $OD_{600}$ of 0.6, and then diluted 1:10 into pre-warmed LB media without arabinose. The process was repeated four times. At each time point of $OD_{600}$ about 0.6, equal numbers of samples were taken for western blot analysis using anti-LacI and anti-PspA antisera. The densitometry was measured by Quantityone software.

Next LacI and PspA synthesis were directly evaluated in cells grown in 0.2% arabinose. This concentration was chosen because there was only a small difference in repression levels between 2% and 0.2% arabinose, (FIG. 21A) and the addition of 2% arabinose resulted in a growth rate reduction. The amount of PspA synthesis was inversely correlated with LacI synthesis, as expected (FIG. 21C). PspA synthesis levels in strain χ9241(pYA4088), which produced the most LacI, were approximately 8-fold less than the χ9097(pYA4088) control. The kinetics of induction was evaluated as described above for the GFP-producing strains and it was found that all of the strains produced the same amount of PspA as χ9097 (pYA4088) after 9.2 nucleic acid sequencerations of growth, indicating full derepression of $P_{trc}$ (FIG. 21C). For most strains, the maximum PspA synthesis was achieved by 6.9 nucleic acid generations.

Regulated Delayed Expression Provides Better Protection than Constitutive Expression Strains χ9097(pYA4088), χ9095(pYA4088), χ9101 (pYA4088) and χ9241(pYA4088) were then evaluated for immunogenicity in mice in two separate experiments. The results of both experiments were similar, so the results were pooled. After a single dose, all immunized mice developed high titers against *S. Typhimurium* LPS (FIG. 23A). Compared with vector controls, the strains synthesizing PspA elicited lower LPS titers, although the synthesis of LacI abrogated this effect somewhat. While all the RASV strains carrying pYA4088 induced a strong anti-PspA serum IgG response (FIG. 23B), those strains, χ9095, χ9101 and χ9241 that produced LacI induced significantly higher anti-PspA titers than strain χ9097(pYA4088) ($p<0.05$). Strain χ9241 (pYA4088) vaccinates produced higher anti-PspA antibodies than the other strains at 6 and 8 weeks ($p<0.05$). Overall, the serum antibody response was roughly proportional to the amount of LacI produced by each strain. No anti-PspA antibody response was detected in mice vaccinated with the vector only controls.

Figure 24:
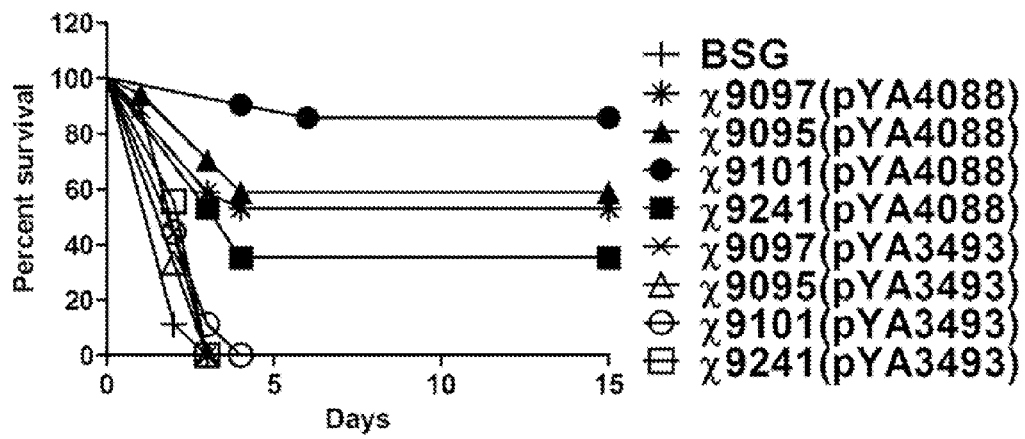
FIG. 24 depicts a graph showing a survival curve after challenge with virulent *S. pneumonia* WU2 strain. Female BALB/c mice were immunized with a single dose of the indicated strains grown in LB containing 0.2% arabinose. Eight weeks after immunization, mice were challenged with 250 $LD_{50}$ of virulent *S. pneumoniae* WU2. All mice immunized with PspA-expressing strains were significantly protected (p<0.05). Mice vaccinated with strain χ9101 (pYA4088) showed significantly higher protection than mice vaccinated with the other strains (p<0.05). The remaining vaccinated groups were not significantly different from each other (p>0.05).

When vaccinated mice were challenged with virulent *S. pneumoniae* WU2, all groups that received PspA-producing strains were protected ($p<0.01$; FIG. 24). Among the protected groups, mice vaccinated with strain χ9101(pYA4088) showed significantly higher protection than mice vaccinated with the other strains ($p<0.05$). The remaining vaccinated groups were not significantly different from each other ($p>0.05$). Interestingly, χ9241(pYA4088), the strain that induced the highest anti-PspA antibody titer (FIG. 23B), provided the poorest protection. These results illustrate the need to optimize the amount of LacI and antigen to attain an optimal immune response and indicate that protection may not be closely correlated with induced antibody titer levels.

Discussion for Example 1

A regulated delayed expression system has been developed to minimize the negative effects of antigen expression on the host strain and to enhance immunity. An araC $P_{BAD}$ lacI TT cassette was engineered to synthesize different levels of LacI when grown in the presence of arabinose (FIG. 19C). The amount of LacI produced by the strains was proportional to the amount of arabinose present in the medium, up to 2%, the maximum concentration tested (FIG. 19C). These results differ from what has been observed in *E. coli* where protein synthesis from $P_{BAD}$ reached a maximum at 0.2% arabinose [34]. There are several possible reasons for this difference. First, the source of the araC $P_{BAD}$ promoter/activator cassette was *E. coli* K-12, while in the previous studies, the promoter was derived from *E. coli* B/r. Tighter regulation has been observed with a K-12 cassette than with a B/r cassette. Additionally, the previous studies were performed using plasmid copies of $P_{BAD}$, while herein the $P_{BAD}$ was chromosomally integrated. Moreover, differences in regulation have been observed for a number of promoters when they are present in multiple copies (Kenneth Roland, personal communication). Finally, differences in the arabinose-transport system between *E. coli* and *Salmonella* may have also played a role. *Salmonella* only has one L-arabinose transport system encoded by araE [40, 41], which has a low affinity for arabinose, while *E. coli* has both araE and the high affinity transport system encoded by araFGH [40, 42]. Therefore, in *Salmonella*, higher concentrations of arabinose are likely to be required for full $P_{BAD}$ promoter induction than in *E. coli* [40].

Although 2% arabinose can induce the maximum LacI synthesis, repression of antigen synthesis was not complete (FIG. 21). One reason for this problem is undoubtedly the fact that the $P_{trc}$ promoter is present on a multicopy plasmid, while LacI is specified by a single nucleic acid sequence on the chromosome. Another reason may be that the binding affinity of the lactose operator sequence in $P_{trc}$ is 10-fold less than the ideal one [43]. An additional consideration is that in the native *E. coli* lac operon, there are 3 adjacent operator sequences, facilitating cooperative binding interactions between three LacI tetramers [44], while there is only one operator in our plasmid [45-47]. Consistent with this hypothesis is the fact that only in strain χ9241, which produced 3-4 times the amount of LacI as the other strains, was antigen expression nearly shut off completely. Thus it is likely possible to improve the efficiency of antigen repression by modifying lacO for tighter repressor binding. In addition, one can also modify the system by adjusting the amount of arabinose in the growth medium, thereby varying the amount of LacI in the cell.

In this example, three strains were developed with the idea that different antigens may require more or less LacI to achieve an appropriate balance between the health of the RASV and the optimal antigen expression required for induction of protective immune responses. Antigen expression was reduced in vitro, which led to a faster growth rate by the RASV (FIG. 20). While all the RASV strains described in this example grew faster than the control strain that constitutively expressed PspA, the results from each strain were different with respect to the serum immune response and protective immunity (FIG. 23, FIG. 24). It was anticipated that strain χ9241 with the relA198 allele would elicit the highest antibody titers and provide the best protection. This strain did, in fact, yield the highest anti-PspA serum IgG titers (FIG. 23), but it did the poorest job of providing protection against *S. pneumoniae* challenge (FIG. 24). This may be a reflection of differences in the amount of antigen produced by each strain and the timing of the induction of antigen synthesis or that other factors such as cellular immunity might be more important than antibodies for conferring protective immunity.

In conclusion, a regulated delayed antigen expression system has been developed. This system reduces the negative effects of antigen expression during in vitro growth thereby improving the overall health of the vaccine strain, while allowing for maximum antigen expression in host tissues. This technology should be particularly useful for inducing immune responses to antigens that are toxic to the vaccine strain synthesizing them.

REFERENCES FOR EXAMPLE 1

1. Fooks, A. R., Development of oral vaccines for human use. Curr Opin Mol Ther, 2000. 2(1): p. 80-6.
2. Shalaby, W. S., Development of oral vaccines to stimulate mucosal and systemic immunity: barriers and novel strategies. Clin Immunol Immunopathol, 1995. 74(2): p. 127-34.
3. Anderson, R., G. Dougan, and M. Roberts, Delivery of the Pertactin/P.69 polypeptide of *Bordetella pertussis* using an attenuated *Salmonella typhimurium* vaccine strain: expression levels and immune response. Vaccine, 1996. 14(14): p. 1384-90.
4. Kang, H. Y. and Curtiss, R., III, Immune responses dependent on antigen location in recombinant attenuated *Salmonella typhimurium* vaccines following oral immunization. FEMS Immunol Med Microbiol, 2003. 37(2-3): p. 99-104.
5. Neutra, M. R., E. Pringault, and J. P. Kraehenbuhl, Antigen sampling across epithelial barriers and induction of mucosal immune responses. Annu Rev Immunol, 1996. 14: p. 275-300.
6. Dusek, D. M., A. Progulske-Fox, and T. A. Brown, Systemic and mucosal immune responses in mice orally immunized with avirulent *Salmonella typhimurium* expressing a cloned *Porphyromonas gingivalis* hemagglutinin. Infect Immun, 1994. 62(5): p. 1652-7.
7. Lee, J. S., et al., Surface-displayed viral antigens on *Salmonella* carrier vaccine. Nat Biotechnol, 2000. 18(6): p. 645-8.
8. Zinkernagel, R. M., et al., Antigen localisation regulates immune responses in a dose- and time-dependent fashion: a geographical view of immune reactivity. Immunol Rev, 1997. 156: p. 199-209.
9. Galen, J. E. and M. M. Levine, Can a 'flawless' live vector vaccine strain be engineered? Trends Microbiol, 2001. 9(8): p. 372-6.
10. Isoda, R., et al., Expression of a *Porphyromonas gingivalis* hemagglutinin on the surface of a *Salmonella* vaccine vector. Vaccine, 2007. 25(1): p. 117-26.
11. Zahn, K., Overexpression of an mRNA dependent on rare codons inhibits protein synthesis and cell growth. J Bacteriol, 1996. 178(10): p. 2926-33.
12. Gentschev, I., G. Dietrich, and W. Goebel, The *E. coli* alpha-hemolysin secretion system and its use in vaccine development. Trends Microbiol, 2002. 10(1): p. 39-45.
13. Hohmann, E. L., et al., Macrophage-inducible expression of a model antigen in *Salmonella typhimurium* enhances immunogenicity. Proc Natl Acad Sci USA, 1995. 92(7): p. 2904-8.
14. Chatfield, S. N., et al., Use of the nirB promoter to direct the stable expression of heterologous antigens in *Salmonella* oral vaccine strains: development of a single-dose oral tetanus vaccine. Biotechnology (NY), 1992. 10(8): p. 888-92.
15. Marshall, D. G., et al., Use of the stationary phase inducible promoters, spv and dps, to drive heterologous antigen expression in *Salmonella* vaccine strains. Vaccine, 2000. 18(14): p. 1298-306.
16. Bumann, D., Regulated antigen expression in live recombinant *Salmonella enterica* serovar *Typhimurium* strongly affects colonization capabilities and specific CD4(+)-T-cell responses. Infect Immun, 2001. 69(12): p. 7493-500.
17. Briles, D. E., et al., PspA, a protection-eliciting pneumococcal protein: immunogenicity of isolated native PspA in mice. Vaccine, 1996. 14(9): p. 858-67.
18. Nayak, A. R., et al., A live recombinant avirulent oral *Salmonella* vaccine expressing pneumococcal surface protein A induces protective responses against *Streptococcus pneumoniae*. Infect Immun, 1998. 66(8): p. 3744-51.
19. Bertani, G., Studies on lysonucleic acid sequencesis. I. The mode of phage liberation by lysogenic *Escherichia coli*. J Bacteriol, 1951. 62(3): p. 293-300.
20. Fraser, D. and E. A. Jerrel, The amino acid composition of T3 bacteriophage. J Biol Chem, 1953. 205(1): p. 291-5.
21. Nakayama, K., M. Kelly, and Curtiss, R., III, Construction of an Asd+ expression-cloning vector: stable maintenance and high level expression of cloned nucleic acid sequences in a *Salmonella* vaccine strain. BioTechnology 1988. 6: p. 693-697.
22. Gay, P., et al., Positive selection procedure for entrapment of insertion sequence elements in gram-negative bacteria. J Bacteriol, 1985. 164(2): p. 918-21.
23. Kang, N. Y., J. Srinivasan, and Curtiss, R., III, Immune responses to recombinant pneumococcal PspA antigen delivered by live attenuated *Salmonella enterica* serovar *Typhimurium* vaccine. Infect Immun, 2002. 70(4): p. 1739-49.
24. Curtiss, R., III, Chromosomal Aberrations Associated with Mutations to Bacteriophage Resistance in *Escherichia Coli*. J Bacteriol, 1965. 89: p. 28-40.
25. Nakayama, K., M. Kelly, and Curtiss, R. III., Construction of an Asd+ expression-cloning vector: stable maintenance and high level expression of cloned nucleic acid sequences in a *Salmonella* vaccine strain. BioTechnology, 1988. 6: p. 693-697.
26. Schodel, F., et al., Hybrid hepatitis B virus core-pre-S proteins synthesized in avirulent *Salmonella typhimurium* and *Salmonella typhi* for oral vaccination. Infect Immun, 1994. 62(5): p. 1669-76.
27. Brosius, J., M. Erfle, and J. Storella, Spacing of the −10 and −35 regions in the tac promoter. Effect on its in vivo activity. J Biol Chem, 1985. 260(6): p. 3539-41.
28. Amann, E., B. Ochs, and K. J. Abel, Tightly regulated tac promoter vectors useful for the expression of unfused and fused proteins in *Escherichia coli*. Nucleic acid sequence, 1988. 69(2): p. 301-15.
29. Hu, M. C. and N. Davidson, The inducible lac operator-repressor system is functional in mammalian cells. Cell, 1987. 48(4): p. 555-66.
30. Hu, M. C. and N. Davidson, The inducible lac operator-repressor system is functional for control of expression of injected DNA in *Xenopus oocytes*. Nucleic acid sequence, 1988. 62(2): p. 301-13.
31. Muller-Hill, B., L. Crapo, and W. Gilbert, Mutants that mke more lac repressor. Proc Natl Acad Sci USA, 1968. 59(4): p. 1259-64.
32. Muller-Hill, B., Lac repressor and lac operator. Prog Biophys Mol Biol, 1975. 30(2-3): p. 227-52.
33. Lewis, M., The lac repressor. C R Biol, 2005. 328(6): p. 521-48.
34. Guzman, L. M., et al., Tight regulation, modulation, and high-level expression by vectors containing the arabinose $P_{BAD}$ promoter. J Bacteriol, 1995. 177(14): p. 4121-30.
35. Zhang, X., T. Reeder, and R. Schleif, Transcription activation parameters at ara pBAD. J Mol Biol, 1996. 258(1): p. 14-24.
36. Katzman, R. L., E. Lisowska, and R. W. Jeanloz, Invertebrate connective tissue. Isolation of D-arabinose from sponge acidic polysaccharide. Biochem J, 1970. 119(1): p. 17-9.
37. Pizarro-Cerda, J. and K. Tedin, The bacterial signal molecule, ppGpp, regulates *Salmonella* virulence nucleic acid sequence expression. Mol Microbiol, 2004. 52(6): p. 1827-44.

38. Huang, Y., et al., Genome-wide screen of *Salmonella* nucleic acid sequences expressed during infection in pigs, using in vivo expression technology. Appl Environ Microbiol, 2007. 73(23): p. 7522-30.
39. Siegele, D. A. and J. C. Hu, Nucleic acid sequence expression from plasmids containing the araBAD promoter at subsaturating inducer concentrations represents mixed populations. Proc Natl Acad Sci USA, 1997. 94(15): p. 8168-72.
40. Lee, J. H., et al., Regulation of L-arabinose transport in *Salmonella typhimurium* LT2. Mol Gen Nucleic acid sequencet, 1982. 185(1): p. 136-41.
41. McClelland, M., et al., Complete genome sequence of *Salmonella enterica* serovar *Typhimurium* LT2. Nature, 2001. 413(6858): p. 852-6.
42. Kolodrubetz, D. and R. Schleif, Regulation of the L-arabinose transport operons in *Escherichia coli*. J Mol Biol, 1981. 151(2): p. 215-27.
43. Sadler, J. R., H. Sasmor, and J. L. Betz, A perfectly symmetric lac operator binds the lac repressor very tightly. Proc Natl Acad Sci USA, 1983. 80(22): p. 6785-9.
44. Gilbert, W., The lac repressor and the lac operator. Ciba Found Symp, 1972. 7: p. 245-59.
45. Muller, J., S. Oehler, and B. Muller-Hill, Repression of lac promoter as a function of distance, phase and quality of an auxiliary lac operator. J Mol Biol, 1996. 257(1): p. 21-9.
46. Mossing, M. C. and M. T. Record, Jr., Upstream operators enhance repression of the lac promoter. Science, 1986. 233(4766): p. 889-92.
47. Oehler, S., et al., The three operators of the lac operon cooperate in repression. EMBO J, 1990. 9(4): p. 973-9.
48. Roland, K., Curtiss, R. III., and D. Sizemore, Construction and evaluation of a delta cya delta crp *Salmonella typhimurium* strain expressing avian pathogenic *Escherichia coli* 078 LPS as a vaccine to prevent airsacculitis in chickens. Avian Dis, 1999. 43(3): p. 429-41.
49. Curtiss, R., III, Colonization Control of Human Bacterial Enteropathogens in Poultry, J. Bailey, Cox N A, Stern N J. Meinersmann R J, Editor. 1991, Academic Press, New York p. 169-198.
50. Curtiss, R., III. and S. A. Tinge, Regulated antigen delivery system (RADS), in U.S. Pat. No. 6,780,405. 2004: US.
51. Sambrook, J. and D. W. Russell, Molecular cloning: a laboratory manual. 3rd ed. 2001, Cold Spring Harbor, N.Y.: Cold Spring Harbor Laboratory Press.
52. O'Callaghan, D. and A. Charbit, High efficiency transformation of *Salmonella typhimurium* and *Salmonella typhi* by electroporation. Mol Gen Nucleic acid sequencet, 1990. 223(1): p. 156-8.
53. Schmieger, H. and H. Backhaus, Altered cotransduction frequencies exhibited by HT-mutants of *Salmonella*-phage P22. Mol Gen Nucleic acid sequencet, 1976. 143(3): p. 307-9.
54. Edwards, R. A., L. H. Keller, and D. M. Schifferli, Improved allelic exchange vectors and their use to analyze 987P fimbria nucleic acid sequence expression. Nucleic acid sequence, 1998. 207(2): p. 149-57.
55. Sternberg, N. L. and R. Maurer, Bacteriophage-mediated nucleic acid sequenceralized transduction in *Escherichia coli* and *Salmonella typhimurium*. Methods Enzymol, 1991. 204: p. 18-43.
56. Miller, E. S., et al., Bacteriophage T4 genome. Microbiol Mol Biol Rev, 2003. 67(1): p. 86-156,
57. Curtiss, R., III. and W. Kong, Regulated bacterial lysis for nucleic acid sequence vaccine vector delivery and antigen release, in United States 20060140975. 2006.
58. Curtiss, R., III. and H. Y. Kang, Immunogenic compositions and vaccines comprising carrier bacteria that secrete antigens, in United States Patent Application Publication 20040101531, 2004: US.
59. Kang, H. Y., et al., Transduction-mediated transfer of unmarked deletion and point mutations through use of counterselectable suicide vectors. J Bacteriol, 2002. 184 (1): p. 307-12.
60. Hitchcock, P. J. and T. M. Brown, Morphological heteronucleic acid sequenceity among *Salmonella* lipopolysaccharide chemotypes in silver-stained polyacrylamide gels. J Bacteriol, 1983. 154(1): p. 269-77.

Example 2

Regulated Attenuation

Attenuation of *Salmonella* vaccine vectors should decrease, if not eliminate, undesirable disease symptoms, but the nutritional status and health of the population to be vaccinated should be considered. The attenuation should be (i) an inherent property of the vaccine and not depend on fully functional host defenses and immune responses, (ii) not be reversible by diet or by host or microbial modification of diet constituents, and (iii) not permit development of a persistent carrier state. The attenuated vaccine should be sufficiently invasive and persistent to stimulate both strong primary and lasting memory immune responses and should be designed to minimize unnecessary tissue damage. As even attenuated vaccines may cause disease in unlucky individuals, the vaccine should be susceptible to clinically useful antibiotics. Many means to attenuate *Salmonella* vaccines make them less able to tolerate stresses encountered after oral administration including exposure to acid, bile, increasing osmolarity and iron, and decreasing $O_2$, and/or reduced invasion of the gut associated lymphoid tissue (GALT). The doses of recombinant *Salmonella* vaccines to elicit maximal immune responses are lower for intranasal immunization than they are for oral immunization (1,2). This may be due, in part, to killing of orally administered vaccines by the acid stress of the stomach (3) quickly followed by exposure to bile in the duodenum. We have determined that these two stresses in succession are more effective in causing bacterial cell death than the sum of killing by each stress alone. *Salmonella* possesses a large constellation of genes that confer acid tolerance and resistance to acid stress (4,5) and inactivation of these genes or their inability to be expressed by induction, reduces virulence (6). In this regard, the regulatory proteins RpoS (7), Fur (8), PhoPQ (9) and OmpR (10, 11) are all necessary to confer resistance to acid stress and/or shock in *S. Typhimurium*. Similarly, many genes are turned on in response to exposure to bile and some of these gene products transiently repress invasion while bacteria reside in the intestinal lumen (12-14).

It is important to have mutations contributing to attenuation or other beneficial vaccine attributes that do not impair the abilities of the vaccine to adjust to and/or withstand a diversity of stresses encountered at any location within the gastrointestinal tract if administered orally or in the respiratory tract if administered intranasally. Likewise, the vaccine strain should have wild-type abilities not compromised by attenuating or other mutations to penetrate through mucin, to attach to cells in the mucosal epithelium and be invasive into those cells. To achieve these objectives, means have been developed herein to achieve regulated delayed attenuation in vivo such that the vaccine at the time of immunization exhibits almost the same abilities as a fully virulent wild-type strain to contend with stresses and successfully reach effector lymphoid tissues before display of attenuation to preclude onset of any disease symptoms. The means described herein confer high-level attenuation and superior immunogenicity compared to traditional mutationally attenuated strains.

Materials and Methods for Example 2

Bacterial strains, media and bacterial growth: All strains for testing in mice are derived from the highly virulent *S.*

*Typhimurium* strain UK-1 (15). All bacterial strains for this example are listed above in Table 1. LB broth and agar (16) are used as complex media for propagation and plating of bacteria. Nutrient broth and agar (Difco), which are devoid of arabinose and mannose, and minimal salts medium and agar (17) were also used. Some studies were done with bacterial strains grown in tissue culture medium to simulate environments to be encountered in vivo. MacConkey agar with 0.5% lactose (Lac), 0.2 or 0.5% arabinose (Ara) or 0.5% maltose (Mal) were used to indicate fermentation of sugars and enumerate bacteria from mice. CAS plates (Schwyn B, Neilands J B, 1987. Universal chemical assay for the detection and determination of siderophores. Anal Biochem. 1987 January; 160(1):47-56), which were used to determine siderophore production, were made by addition of chrome azurol S mixed with $Fe^{+3}$ and hexadecyltrimethyl ammonium bromide (HDTMA) to MOPS basal agar. X-P plates to detect phosphatase activity were made by addition of 50 mg/ml of 5-bromo-4-chloro-3-indolyl-phosphate (BCIP or XP) to Nutrient agar. Kornberg agar medium plates were prepared as a glycogen indicator agar (18-20). Selenite broth, with or without supplements, was used for enrichment of *Salmonella* from tissues, although later results demonstrated that enrichment with tetrathionate broth gave better results when vaccine strains had multiple mutations. Bacterial growth was monitored spectrophotometrically and by plating for colony counts.

Molecular and Genetic Procedures:

Methods for DNA isolation, restriction enzyme digestion, DNA cloning and use of PCR for construction and verification of vectors are standard (21). DNA sequence analysis was performed in the DNA Sequence Laboratory in the School of Life Sciences at ASU. All oligonucleotide and/or gene segment syntheses were done commercially. Overlapping PCR amplification with primers designed for specific modifications was used to optimize codons for translational efficiency in *Salmonella* or to alter promoter, ribosome binding/Shine-Dalgarno (SD) and start codon sequences. Conjugational transfer of suicide vectors for generation of unmarked deletion and deletion-insertion mutations was performed by standard methods (22, 23) using the suicide vector donor strain χ7213 (Table 1). Since live vaccine strains cannot display resistance to antibiotics, means were used to generate defined deletion mutations using suicide vector technologies that did not use drug-resistance markers or leave molecular scars. Subsequently, these unmarked defined deletion mutations with and without specific insertions were introduced into strains using P22HTint (24, 25) transduction of suicide vectors integrated into the deletion or deletion-insertion mutation followed by selection for sucrose resistance as described (26). Whenever insertion of a regulatory sequence might adversely effect expression of an adjoining gene, a transcription terminator (TT) was included to prevent such consequences. Strong TTs from bacteriophages were generally used. Plasmid constructs were evaluated by DNA sequencing, ability to complement various *S. Typhimurium* mutant strains (Table 1) and for ability to specify synthesis of proteins using gel electrophoresis and western blot analyses. His- or GST-tagged proteins have been produced and used to obtain anti-protein rabbit antisera for western blot analyses.

Strain Characterizations:

Exquisite care was taken in strain construction and complete biochemical and genetic characterizations were performed after every step in strain construction. This includes running an LPS gel to make sure rough variants were not selected. Comparative growth analyses were conducted since the objective is to have single and multiple mutant strains grow at similar rates and to the same density as the wild-type parental strains when grown under permissive conditions. Vaccine strain stability was also evaluated, due to possible recombinational and/or mutational events as described below. Strains are also evaluated for biochemical and metabolic attributes, sensitivity to antibiotics and drugs, serological properties and resistance compared to wild-type parental strains to stresses associated with exposure to acid and bile.

Cell Biology:

The ability of various constructed *Salmonella* strains to attach to, invade into and survive in various murine and human epithelial and/or macrophage cell lines are quantitated by well established methods (27, 28) that are used routinely.

Animal Experimentation:

BALB/c and C57BL/6 female mice, six to eight weeks of age, were used for most experiments. Mice are held in quarantine one-week before use in experiments. They are deprived of food and water 6 h before oral immunization. No bicarbonate is administered. Food and water are returned 30 min after immunization. Candidate vaccine strains are quantitatively enumerated in various tissues as a function of time after inoculation (29, 30). The inoculation procedures are the same as in the immunization studies. All animals are housed in BL2 containment with filter bonnet covered cages. If high immunogenicity is observed in initial tests after primary immunization, subsequent studies are done to determine the lowest level of vaccine inocula to induce a significant protective immune response to oral or intraperitoneal challenge with the wild-type *S. Typhimurium* UK-1 parental strain χ3761.

Construction of Deletion-Insertion Mutations to Achieve Regulated Delayed Attenuation.

Figure 25A:
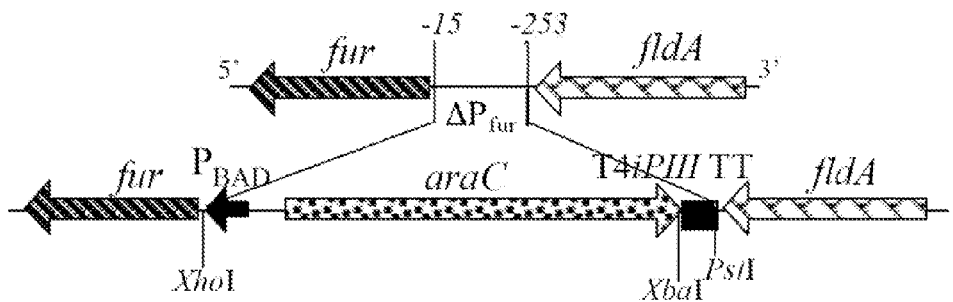
FIG. 25 depicts schematics illustrating different deletion-insertion mutations resulting in arabinose-regulated virulence trait. (A) The schematic shows the deletion of the fur promoter region (−15 to −253; including Fur consensus, Crp binding, and OxyR binding sites) and the insertion of 1335 bp of $P_{BAD}$ araC TT to create the $\Delta P_{fur33}$::TT araC $P_{BAD}$ fur insertion-deletion mutation. (B) The schematic shows the deletion of the phoPQ promoter region (−12 to −109) and the insertion of 1335 bp of $P_{BAD}$ araC TT to create the. $\Delta P_{phoPQ107}$::TT araC $P_{BAD}$ phoPQ deletion-insertion mutation. (C) The schematic shows the deletion of 36 bp of the rpoS promoter region (−13 to −48) and the insertion of 1335 bp of $P_{BAD}$ araC TT to create the $\Delta P_{rpoS183}$::TT araC $P_{BAD}$ rpoS deletion-insertion mutation. (D) The schematic shows the deletion of the crp promoter region (−15 to −109) and the insertion of 1335 bp of TT araC $P_{BAD}$ to create the $\Delta P_{crp527}$:: TT araC $P_{BAD}$ crp insertion-mutation.

Four means are described to permit a regulated delayed attenuation phenotype so that vaccine strains at the time of immunization exhibit nearly wild-type attributes for survival and colonization of lymphoid tissues and after five to ten cell divisions become avirulent. These means to achieve regulated delayed attenuation rely on using an araC $P_{BAD}$ activator-promoter that is more tightly regulated by arabinose (31) than the original sequence from the *E. coli* B/r strain (32). The promoter was deleted, including all sequences that interact with activator or repressor proteins, for the fur, phoPQ, rpoS and crp nucleic acid sequences and substituted by insertion of the improved araC $P_{BAD}$ cassette (31) to yield *Salmonella* strains with the $\Delta P_{fur33}$::TT araC $P_{BAD}$ fur, $\Delta P_{phoPQ107}$::TT araC $P_{BAD}$ phoPQ, $\Delta P_{rpoS183}$::TT araC $P_{BAD}$ rpoS and $\Delta P_{crp527}$::TT araC $P_{BAD}$ crp deletion-insertion mutations (P stands for promoter and TT stands for transcription terminator). The suicide vectors used to generate these four deletion-insertion mutations are depicted in FIG. 25 and are listed in Table 2. A strong phage-derived TT was included at the 3' end of the araC nucleic acid sequence in all these constructions since its transcription in the presence of arabinose could often lead to altered over expression of downstream adjacent nucleic acid sequences with the same transcriptional orientation as the araC nucleic acid sequence or to diminished expression when the downstream adjacent nucleic acid sequence is in opposite orientation resulting in synthesis of anti-sense mRNA from $P_{araC}$.

Phenotypic Characterization of Mutant Strains.

Figure 26:
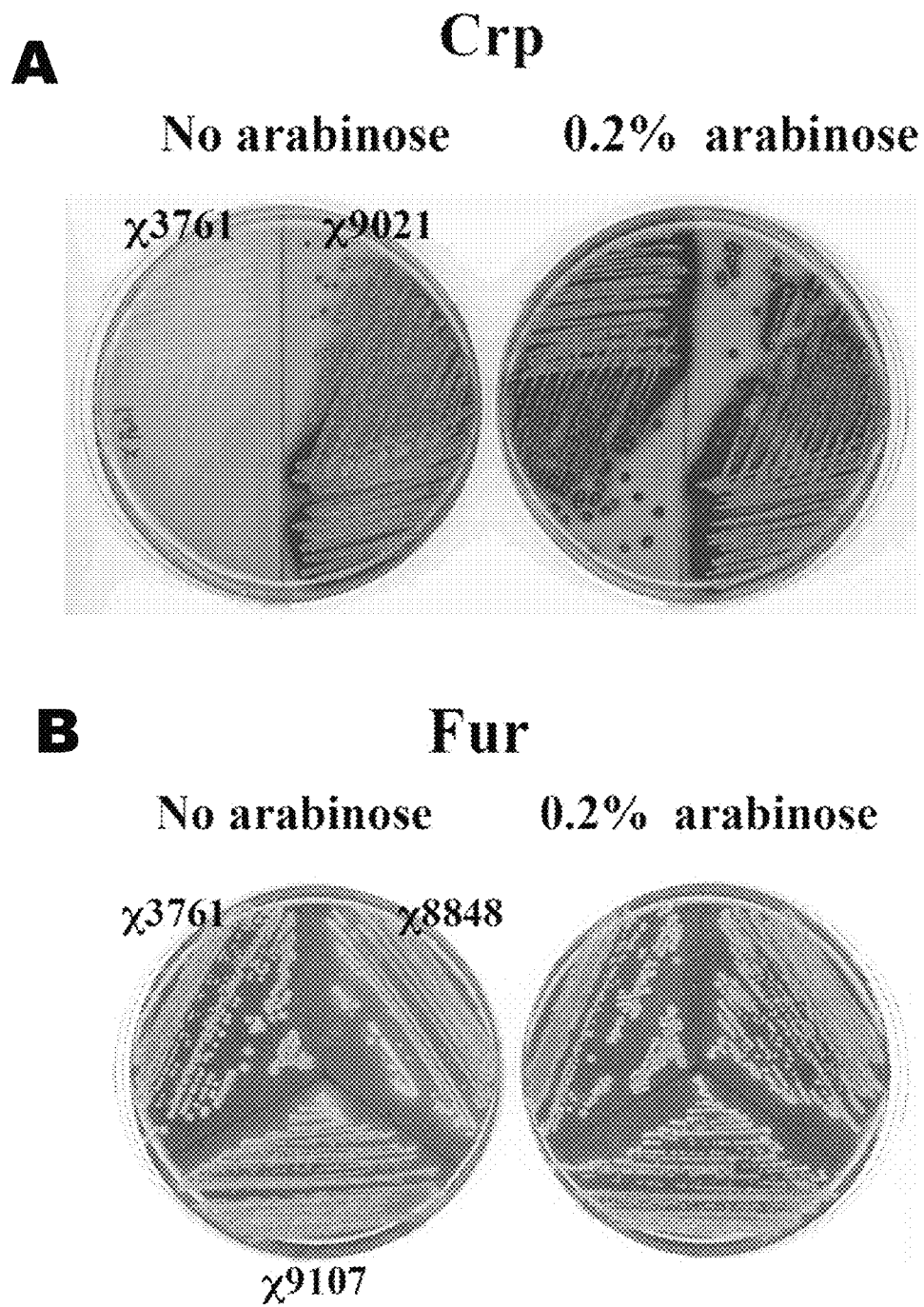
FIG. 26 depicts several photographs illustrating the phenotypes of strains with deletion-insertion mutations to enable arabinose-dependent expression of virulence traits. (A) χ9021 with $\Delta P_{crp527}$::TT araC $P_{BAD}$ crp mutation streaked on MacConkey maltose agar without and with 0.2 percent arabinose. (B) χ8848 with $\Delta P_{fur33}$::TT araC $P_{BAD}$ fur and χ9107 with $\Delta P_{fur33}$::TT araC $P_{BAD}$ fur and $\Delta P_{crp527}$::TT araC $P_{BAD}$ crp mutations spotted on CAS agar plates without and with 0.2 percent arabinose to visualize siderophore production. (C) χ8918 with $\Delta P_{phoPQ107}$::TT araC $P_{BAD}$ phoPQ and χ9108 with $\Delta P_{phoPQ107}$::TT araC $P_{BAD}$ phoPQ and $\Delta P_{crp527}$::TT araC $P_{BAD}$ crp mutations streaked on X-P plates without and with 0.2 percent arabinose to reveal acid phosphatase activity.

Growth of these strains in the presence of arabinose leads to transcription of the fur, phoPQ, rpoS and/or crp nucleic acid sequences but nucleic acid sequence expression ceases in the absence of arabinose. These activities can be readily observed by appropriate tests. Thus χ9021 with the $\Delta P_{crp527}$::TT araC $P_{BAD}$ crp deletion-insertion mutation can only ferment maltose when grown in the presence of arabinose and not in the absence of arabinose as revealed by streaking cultures on MacConkey maltose agar without and with 0.2 percent arabinose (FIG. 26A). Similarly, χ8848 with the $\Delta P_{fur33}$::TT araC $P_{BAD}$ fur and χ9107 with $\Delta P_{fur33}$::TT araC $P_{BAD}$ fur and $\Delta P_{crp527}$::TT araC $P_{BAD}$ crp mutations reveal siderophore production when streaked on CAS plates without arabinose and no siderophore production when grown in the presence of arabinose (FIG. 26B). χ8918 with the $\Delta P_{phoPQ107}$::TT araC $P_{BAD}$ phoPQ and χ9108 with the $\Delta P_{phoPQ107}$::TT araC $P_{BAD}$ phoPQ and $\Delta P_{crp527}$::TT araC $P_{BAD}$ crp mutations when streaked on X-P plates without and with 0.2 percent arabinose reveal acid phosphatase activity due to expression of the PhoP-activated phoN nucleic acid sequence only when grown in the presence of arabinose (FIG. 26C). χ8956 with the $\Delta P_{rpoS183}$::TT araC $P_{BAD}$ rpoS and χ9064 with the $\Delta P_{rpoS183}$::TT araC $P_{BAD}$ rpoS and $\Delta P_{crp527}$::TT araC $P_{BAD}$ crp mutations reveal glycogen accumulation when streaked on glycogen-indicator agar with 0.2 percent arabinose and sprayed with iodine indicator solution (FIG. 26D). The presence or absence of RpoS in these strains can also be revealed by adding hydrogen peroxide to cultures to detect the activity of the RpoS-dependant catalase, KatE, (33-36) when arabinose is present during strain growth. Since Crp positively enhances transcription from $P_{BAD}$, the inclusion of the $\Delta P_{crp527}$::TT araC $P_{BAD}$ crp mutation with other araC $P_{BAD}$ regulated nucleic acid sequences causes a tighter cessation of transcription in the absence of arabinose. This is seen by close examination of the photographs in FIG. 26. For this reason, the $\Delta P_{crp527}$::TT araC $P_{BAD}$ crp mutation is included in all vaccine strains when using araC $P_{BAD}$ regulation of virulence nucleic acid sequences.

Stability of Crp, Fur, RpoS and PhoP Proteins and their Decline During Growth in the Absence of Arabinose.

Growth of strains with araC $P_{BAD}$ regulated nucleic acid sequences in the presence of arabinose results in acid production that can cause cessation of growth. We have therefore included the ΔaraBAD23 mutation (FIG. 27) that prevents use of arabinose. Inclusion of this mutation also prevents breakdown of arabinose retained in the cell cytoplasm at the time of oral immunization and inclusion of the ΔaraE25 mutation (FIG. 27), which enhances retention of arabinose further delays cessation in expression of araC $P_{BAD}$ regulated nucleic acid sequences for an additional cell division or so. The suicide vectors for introducing the ΔaraBAD23 and ΔaraE25 mutations are listed in Table 2.

The stability of virulence gene products in strains with each of the araC $P_{BAD}$ regulated virulence genes was determined by growing cultures to an $OD_{600}$ of 0.8 in LB broth with 0.2 percent arabinose and then adding 30 µg chloramphenicol/ml (37) for Crp, Fur and PhoP and 200 µg chloramphenicol/ml for RpoS (38) to arrest further protein synthesis. As can be seen by the results presented in FIG. 28, the Crp, Fur and PhoP proteins are very stable and not significantly degraded, whereas the RpoS protein displays no stability in the log phase (39). However, the RpoS protein seemed to be stable when 50 µg chloramphenicol/ml was added to saturated overnight stationery phase cultures. When these mutant strains were grown in Nutrient broth with 0.2 percent arabinose to an $OD_{600}$ of 0.8 and then diluted 1 to 4 into Nutrient broth with no added arabinose and these 1 to 4 dilutions continued after each culture again reached an $OD_{600}$ of 0.8, we observed no significant reductions in the amounts of Crp, Fur and PhoP proteins until a final dilution of 1 to 16 with an arabinose concentration of 0.0125 percent or until a final dilution of 1 to 64 with an arabinose concentration of 0.003125 percent. Thereafter the amount of these proteins decreased by a factor of four for each subsequent 1 to 4 dilution of the culture (FIG. 29). In the case of RpoS protein, we observed a significant amount of reduction within a dilution of 1 to 4 with an arabinose concentration of 0.05 percent (FIG. 29). The decline in the amounts of these proteins in vivo would be expected to be more accelerated since there is no arabinose present in tissues upon invasion of *Salmonella* into the GALT. In other experiments, strains grown in Nutrient broth with 0.2 percent arabinose were sedimented by centrifugation and resuspended at a density one-fourth of the original culture. In this case after growth to the original density, the amounts of each of the four virulence gene proteins was three to four times less than in the culture grown with arabinose. In other experiments, it was determined that the levels of Fur, PhoP, RpoS and Crp synthesis were nearly the same when mutant cultures were grown in LB broth with either 0.05 percent or 0.2 percent arabinose.

Attenuation of Mutant Strains in Orally Immunized Female BALB/c Mice.

Levels of attenuation were evaluated in *S. Typhimurium* UK-1 strains with different araC $P_{BAD}$ regulated virulence nucleic acid sequences by oral inoculation of female BALB/c mice with doses approximating $10^7$, $10^8$ and $10^9$ CFU from cultures grown in LB broth with 0.0, 0.05 and 0.2 percent arabinose. It should be noted, that LB broth contains arabinose in the yeast extract equivalent to a concentration of 0.003 percent based on mass spec analysis. The collective results presented in Table 3 indicate that the strains with the $\Delta P_{phoPQ107}$::TT araC $P_{BAD}$ phoPQ, $\Delta P_{rpoS183}$::TT araC $P_{BAD}$ rpoS and $\Delta P_{crp527}$::TT araC $P_{BAD}$ crp deletion-insertion mutations were highly attenuated whereas the strain with the $\Delta P_{fur33}$::TT araC $P_{BAD}$ fur mutation was less attenuated. In this regard, a higher level of attenuation was noted when χ8848 was grown in LB broth with no added arabinose and a greater virulence when grown in LB broth with 0.2 percent arabinose. It is evident, however, from the collective results (Table 3) that attenuation develops as the products of the fur, phoPQ, rpoS and/or crp nucleic acid sequences are diluted at each cell division.

TABLE 3

Attenuation of mutant strains in orally immunized female BALB/c mice [a]

| Strain | Genotype | Dose [b] range | Survivors/ total | Percent/ survivors |
|---|---|---|---|---|
| χ8848 | $\Delta P_{fur33}$ | $9.0 \times 10^6$-$2.2 \times 10^9$ | 138/189 | 73.0 |
| χ8918 | $\Delta P_{phoPQ107}$ | $9.0 \times 10^6$-$1.2 \times 10^9$ | 182/185 | 98.4 |
| χ8956 | $\Delta P_{rpoS183}$ | $9.4 \times 10^6$-$1.5 \times 10^9$ | 179/184 | 97.3 |
| χ9021 | $\Delta P_{crp527}$ | $9.5 \times 10^6$-$1.5 \times 10^9$ | 163/164 | 99.4 |

[a] Mice were seven to eight weeks of age. Bacterial strains were grown in LB broth with 0, 0.05 or 0.2 percent arabinose that did not have a significant effect on levels of attenuation on strains with the $\Delta P_{phoPQ107}$::TT araC $P_{BAD}$ phoPQ, $\Delta P_{rpoS183}$::TT araC $P_{BAD}$ rpoS and $\Delta P_{crp527}$::TT araC $P_{BAD}$ crp deletion-insertion mutations but did effect the results for χ8848 with the $\Delta P_{fur33}$::TT araC $P_{BAD}$ fur mutation (see Results).
[b] Doses are in CFU.

Abilities of Orally Administered Strains with araC $P_{BAD}$ Regulated Virulence Nucleic Acid Sequences to Induce Protective Immunity to Oral Challenge with Wild-Type *S. Typhimurium* UK-1.

Strains with each of the araC $P_{BAD}$ regulated virulence nucleic acid sequences were next evaluated for induction of protective immunity against a challenge with the highly virulent *S. Typhimurium* UK-1 strain χ3761 (oral $LD_{50}$ of 1-2× $10^4$ CFU). The results in Table 4 reveal that χ8848 with the $\Delta P_{fur33}$::TT araC $P_{BAD}$ fur mutation displayed some virulence even at low doses when grown in LB broth with 0.2 percent arabinose. However, for immunizing doses of $10^7$ CFU and higher 100 percent of the survivors developed protective immunity to challenges with $10^8$ and $10^9$ CFU doses of χ3761. Thus the $\Delta P_{fur33}$::TT araC $P_{BAD}$ fur mutation while displaying moderate attenuation is highly immunogenic. This is a very important attribute of an attenuating mutation to include in a vaccine strain. It was previously reported (40) that χ8848 with the $\Delta P_{fur33}$::TT araC $P_{BAD}$ fur mutation was completely attenuated even at high $10^9$ CFU doses when grown in LB broth with no added arabinose. This observation implies that production of too much Fur protein may diminish attenuation.

TABLE 4

Oral immunization of mice with χ8848 (ΔP$_{fur33}$) and with survivors challenged orally with wild-type χ3761 thirty days later [a]

| Immunizing dose [b] | | Survivors/ total | | Challenge dose [b] | | Survivors/ total | |
| --- | --- | --- | --- | --- | --- | --- | --- |
| Exp. 1 | Exp. 2 | Exp. 1 | Exp. 2 | Exp. 1 | Exp. 2 | Exp. 1 | Exp. 2 |
| $9.0 \times 10^8$ | $1.1 \times 10^9$ | 6/10 | 4/10 | $1.0 \times 10^9$ | $1.5 \times 10^9$ | 3/3 | 2/2 |
| | | | | $1.0 \times 10^8$ | $1.5 \times 10^8$ | 3/3 | 2/2 |
| $9.0 \times 10^7$ | $1.1 \times 10^8$ | 7/10 | 7/10 | $1.0 \times 10^9$ | $1.5 \times 10^9$ | 2/2 | 4/4 |
| | | | | $1.0 \times 10^8$ | $1.5 \times 10^8$ | 5/5 | 3/3 |
| $9.0 \times 10^6$ | $1.1 \times 10^7$ | 7/10 | 5/10 | $1.0 \times 10^9$ | $1.5 \times 10^9$ | 4/4 | 2/2 |
| | | | | $1.0 \times 10^8$ | $1.5 \times 10^8$ | 3/3 | 3/3 |
| $9.0 \times 10^5$ | $1.1 \times 10^6$ | 5/10 | 8/10 | $1.0 \times 10^9$ | $1.5 \times 10^9$ | 1/2 | 1/4 |
| | | | | $1.0 \times 10^8$ | $1.5 \times 10^8$ | 0/3 | 2/4 |
| $9.0 \times 10^4$ | $1.1 \times 10^5$ | 10/10 | 7/10 | $1.0 \times 10^9$ | $1.5 \times 10^9$ | 0/5 | 2/4 |
| | | — | — | $1.0 \times 10^8$ | $1.5 \times 10^8$ | 0/5 | 3/3 |
| Total (all doses) | | | 66/100 | | | | 45/66 |
| | | | | | | | 68.2% |
| Total ($10^7 - 10^9$ doses) | | | 36/60 | | | | 36/36 |
| | | | | | | | 100% |

[a] Female BALB/c mice were six to eight weeks of age. χ8848 was grown in LB broth with 0.2% arabinose.
[b] Doses are in CFU.

The results in Table 5 reveal that χ8918 with the ΔP$_{phoPQ107}$::TT araC P$_{BAD}$ phoPQ deletion-insertion mutation is very attenuated but displays more moderate immunogenicity in regard to inducing protection against challenge with χ3761. These results suggest that some of the attenuation may be due to a reduced ability of χ8918 to effectively colonize lymphoid tissues, quite possibly due to the over expression of the phoPQ nucleic acid sequences when χ8918 is grown in LB broth with 0.2 percent arabinose. In accord with this expectation, χ8918 is better able to colonize Peyer's patches, mesenteric lymph nodes and spleens in orally immunized mice when grown in LB broth without added arabinose than when grown in LB broth with 0.2 percent arabinose. Nevertheless, χ8918 is still less capable of colonizing these lymphoid tissues than χ9021 with the ΔP$_{crp527}$::TT araC P$_{BAD}$ crp deletion-insertion mutation, which colonizes equally well independent of arabinose concentration in the LB broth.

The results in Table 6 confirm the oral avirulence of χ8956 with the ΔP$_{rpoS183}$::TT araC P$_{BAD}$ rpoS deletion-insertion mutation. However, the two experiments give very different results on the ability of this strain to induce protective immunity to oral challenge with wild-type S. Typhimurium. We therefore repeated the experiment giving oral doses of χ8956 (ΔP$_{rpoS183}$) of $1.4 \times (10^7, 10^8$ and $10^9)$ CFU with 15 survivors at each dose and after challenge with $3.1 \times 10^9$ CFU of χ3761 observed 13, 13 and 14 survivors, respectively, out of 15 mice challenged. It thus appears that the data in the second experiment in Table 6 are more indicative of the correct attenuating and immunogenic phenotype. No differences in results were observed when χ8956 (ΔP$_{rpoS183}$) was grown in LB broth with or without arabinose.

TABLE 5

Oral immunization of mice with χ8918 (ΔP$_{phoPQ107}$) and with survivors challenged orally with wild-type χ3761 thirty days later [a]

| Immunizing dose [b] | | Survivors/ total | | Challenge dose [b] | | Survivors/ total | |
| --- | --- | --- | --- | --- | --- | --- | --- |
| Exp. 1 | Exp. 2 | Exp. 1 | Exp. 2 | Exp. 1 | Exp. 2 | Exp. 1 | Exp. 2 |
| $9.0 \times 10^8$ | $1.2 \times 10^9$ | 10/10 | 9/10 | $1.0 \times 10^9$ | $1.5 \times 10^9$ | 4/5 | 5/5 |
| | | | | $1.0 \times 10^8$ | $1.5 \times 10^8$ | 4/5 | 4/4 |
| $9.0 \times 10^7$ | $1.2 \times 10^8$ | 10/10 | 10/10 | $1.0 \times 10^9$ | $1.5 \times 10^9$ | 3/5 | 4/5 |
| | | | | $1.0 \times 10^8$ | $1.5 \times 10^8$ | 3/5 | 5/5 |
| $9.0 \times 10^6$ | $1.2 \times 10^7$ | 10/10 | 9/10 | $1.0 \times 10^9$ | $1.5 \times 10^9$ | 2/4 | 1/4 |
| | | | | $1.0 \times 10^8$ | $1.5 \times 10^8$ | 2/5 | 2/5 |
| $9.0 \times 10^5$ | $1.1 \times 10^6$ | 10/10 | 10/10 | $1.0 \times 10^9$ | $1.5 \times 10^9$ | 3/5 | 0/5 |
| | | | | $1.0 \times 10^8$ | $1.5 \times 10^8$ | 0/5 | 3/5 |
| $9.0 \times 10^4$ | $1.1 \times 10^5$ | 10/10 | 10/10 | $1.0 \times 10^9$ | $1.5 \times 10^9$ | 0/5 | 0/5 |
| | | — | — | $1.0 \times 10^8$ | $1.5 \times 10^8$ | 0/5 | 0/5 |
| Total (all doses) | | | 98/100 | | | | 45/98 |
| | | | | | | | 45.9% |
| Total ($10^7 - 10^9$ doses) | | | 58/60 | | | | 39/58 |
| | | | | | | | 67.2% |

[a] Female BALB/c mice were six to eight weeks of age. χ8918 was grown in LB broth with 0.2% arabinose.
[b] Doses are CFU.

TABLE 6

Oral immunization of mice with χ8956 (ΔP$_{rpoS183}$) and with survivors challenged orally with wild-type-χ3761 thirty days later [a]

| Immunizing dose [b] | | Survivors/ total | | Immunizing dose [b] | | Survivors/ total | |
|---|---|---|---|---|---|---|---|
| Exp. 1 | Exp. 2 | Exp. 1 | Exp. 2 | Exp. 1 | Exp. 2 | Exp. 1 | Exp. 2 |
| 9.4 × 10$^8$ | 1.5 × 10$^9$ | 9/10 | 9/10 | 1.0 × 10$^9$ | 1.5 × 10$^9$ | 0/5 | 4/4 |
|  |  |  |  | 1.0 × 10$^8$ | 1.5 × 10$^8$ | 1/5 | 5/5 |
| 9.4 × 10$^7$ | 1.5 × 10$^8$ | 10/10 | 10/10 | 1.0 × 10$^9$ | 1.5 × 10$^9$ | 0/5 | 5/5 |
|  |  |  |  | 1.0 × 10$^8$ | 1.5 × 10$^8$ | 0/5 | 3/5 |
| 9.4 × 10$^6$ | 1.5 × 10$^7$ | 10/10 | 9/10 | 1.0 × 10$^9$ | 1.5 × 10$^9$ | 2/5 | 5/5 |
|  |  |  |  | 1.0 × 10$^8$ | 1.5 × 10$^8$ | 0/5 | 2/4 |
| 9.4 × 10$^5$ | 1.5 × 10$^6$ | 10/10 | 10/10 | 1.0 × 10$^9$ | 1.5 × 10$^9$ | 0/5 | 4/5 |
|  |  |  |  | 1.0 × 10$^8$ | 1.5 × 10$^8$ | 0/5 | 2/5 |
| 9.4 × 10$^4$ | 1.5 × 10$^5$ | 10/10 | 10/10 | 1.0 × 10$^9$ | 1.5 × 10$^9$ | 0/5 | 0/5 |
|  |  | — | — | 1.0 × 10$^8$ | 1.5 × 10$^8$ | 0/5 | 0/5 |
| Total (all doses) |  |  | 97/100 |  |  |  | 33/97 |
|  |  |  |  |  |  |  | 34.0% |
| Total (10$^7$ – 10$^9$ doses) |  |  | 57/60 |  |  |  | 27/57 |
|  |  |  |  |  |  |  | 47.4% |

[a] Female BALB/c mice were six to eight weeks of age χ8956 was grown in LB broth with 0.2% arabinose.
[b] Doses are in CFU.

The results in Table 7 indicate that χ9021 with the ΔP$_{crp}$527::TT araC P$_{BAD}$ crp deletion-insertion mutation is both highly attenuated and also very immunogenic. Neither of these attributes was altered when the strain was grown in LB broth with or without arabinose.

TABLE 7

Oral immunization of mice with χ9021 (ΔP$_{crp527}$, land with survivors challenged orally with wild-type χ3761 thirty days later [a]

| Immunizing dose [b] | | Survivors/ total | | Challenge dose [b] | | Survivors/ total | |
|---|---|---|---|---|---|---|---|
| Exp. 1 | Exp. 2 | Exp. 1 | Exp. 2 | Exp. 1 | Exp. 2 | Exp. 1 | Exp. 2 |
| 9.5 × 10$^8$ | 1.6 × 10$^9$ | 10/10 | 10/10 | 1.0 × 10$^9$ | 1.5 × 10$^9$ | 5/5 | 5/5 |
|  |  |  |  | 1.0 × 10$^8$ | 1.5 × 10$^8$ | 5/5 | 5/5 |
| 9.5 × 10$^7$ | 1.6 × 10$^8$ | 10/10 | 10/10 | 1.0 × 10$^9$ | 1.5 × 10$^9$ | 5/5 | 5/5 |
|  |  |  |  | 1.0 × 10$^8$ | 1.5 × 10$^8$ | 5/5 | 5/5 |
| 9.5 × 10$^6$ | 1.6 × 10$^7$ | 10/10 | 10/10 | 1.0 × 10$^9$ | 1.5 × 10$^9$ | 4/5 | 5/5 |
|  |  |  |  | 1.0 × 10$^8$ | 1.5 × 10$^8$ | 5/5 | 5/5 |
| 9.5 × 10$^5$ | 1.6 × 10$^6$ | 10/10 | 9/10 | 1.0 × 10$^9$ | 1.5 × 10$^9$ | 5/5 | 3/5 |
|  |  |  |  | 1.0 × 10$^8$ | 1.5 × 10$^8$ | 3/5 | 2/4 |
| 9.5 × 10$^4$ | 1.6 × 10$^5$ | 10/10 | 10/10 | 1.0 × 10$^9$ | — | 4/5 | — |
|  |  |  |  | 1.0 × 10$^8$ | — | 3/5 | — |
| Total (all doses) |  |  | 99/100 |  |  |  | 78/89 |
|  |  |  |  |  |  |  | 87.6% |
| Total (10$^7$ – 10$^9$ doses) |  |  | 60/60 |  |  |  | 59/60 |
|  |  |  |  |  |  |  | 98.3% |

[a] Female BALB/c mice were six to eight weeks of age. χ9021 was grown in LB broth with 0.2% arabinose.
[b] Doses are in CFU.

Alterations in Strains with the ΔP$_{fur}$::TT araC P$_{BAD}$ fur and ΔP$_{phoPQ}$::TT araC P$_{BAD}$ phoPQ Deletion-Insertion Mutations to Increase the Attenuation of the Former and Increase the Immunogenicity of the Latter.

As noted above, χ8848 with the ΔP$_{fur33}$::TT araC P$_{BAD}$ fur mutation was more attenuated when grown in LB broth without arabinose and more virulent when grown in LB broth with 0.2 percent arabinose prior to oral inoculation of mice. This implied that overproduction of Fur, which would require more cell divisions in vivo to dilute out, reduced attenuation without adversely altering immunogenicity in mice surviving immunization. Consequently, two derivatives were constructed in which the ATG start codon for the fur nucleic acid sequence was changed to GTG, and in one of these, the SD sequence was changed from AGGA to AAGG. The structure of these two mutations, ΔP$_{fur77}$::TT araC P$_{BAD}$ fur and ΔP$_{fur81}$::TT araC P$_{BAD}$ fur, are diagrammed in FIG. 8. χ9273 with the ΔP$_{fur77}$::TT araC P$_{BAD}$ fur mutation and χ9269 with the ΔP$_{fur81}$::TT araC P$_{BAD}$ fur mutation both synthesize much less Fur as reveled by western blot analysis when grown in LB broth with 0.2 percent arabinose than does χ8848 with the ΔP$_{fur33}$::TT araC P$_{BAD}$ fur mutation.

It was also noted above that the immunogenicity of χ8918 with the ΔP$_{phoPQ107}$::TT araC P$_{BAD}$ phoPQ mutation was decreased when the strain was grown in LB broth with 0.2 percent arabinose although its attenuation was independent of the arabinose concentration in LB broth. This implied that over production of PhoP and/or PhoQ decreased induction of immunity to challenge. This inference was also supported by studies that demonstrated that χ8918 was less able to colonize Peyer's patches, mesenteric lymph nodes and spleen when grown in LB broth with 0.2 percent arabinose than when grown with no added arabinose. Two derivatives were therefore constructed in which the ATG start codon for the phoP nucleic acid sequence was changed to GTG and in one of these also changed the SD sequence from AGGA to AAGG.

The structure of these two mutations, $\Delta P_{phoPQ173}$::TT araC $P_{BAD}$ phoPQ and $\Delta P_{phoPQ177}$::TT araC $P_{BAD}$ phoPQ, are diagrammed in FIG. 9. χ9382 with the $\Delta P_{phoPQ173}$::TT araC $P_{BAD}$ phoPQ mutation and χ9383 with the $\Delta P_{phoPQ177}$::TT araC $P_{BAD}$ phoPQ mutation both synthesize much less PhoP as reveled by western blot analysis when grown in LB broth with 0.2 percent arabinose than does χ8918 with the $\Delta P_{phoPQ107}$::TT araC $P_{BAD}$ phoPQ mutation.

Table 8 below contains results that demonstrate the high immunogenicity of χ9273 with the $\Delta P_{fur77}$::TT araC $P_{BAD}$ fur mutation and χ9269 with the $\Delta P_{fur81}$::TT araC $P_{BAD}$ fur mutation with χ9269 with the $\Delta P_{fur81}$::TT araC $P_{BAD}$ fur mutation demonstrating much better attenuation when grown in LB broth with 0.2 percent arabinose. The data in Table 8 also indicates that both χ9382 with the $\Delta P_{phoPQ173}$::TT araC $P_{BAD}$ phoPQ mutation and χ9383 with the $\Delta P_{phoPQ177}$::TT araC $P_{BAD}$ phoPQ mutation are completely attenuated when grown in LB broth with 0.2 percent arabinose and display essentially the same immunogenicity that is much improved over that exhibited by χ8918 with the $\Delta P_{phoPQ107}$::TT araC $P_{BAD}$ phoPQ mutation when it is grown in LB broth with 0.2 percent arabinose.

TABLE 8

Oral immunization of mice with strains with modified $\Delta P_{fur}$ and $\Delta P_{phoPQ}$ mutations and with survivors challenged orally with wild-type χ3761 thirty days later.[a]

| Strain[b] | Genotype | Immunizing dose[c] | Survivors/total | Challenge dose[c] | Survivors/total |
|---|---|---|---|---|---|
| χ9273 | $\Delta P_{fur77}$ | $1.5 \times 10^9$ | 6/10 | $1.7 \times 10^9$ | 6/6 |
|  |  | $1.7 \times 10^9$ | 6/10 | $1.6 \times 10^9$ | 6/6 |
| χ9269 | $\Delta P_{fur81}$ | $1.0 \times 10^9$ | 11/15 | $8.7 \times 10^8$ | 11/11 |
|  |  | $1.0 \times 10^8$ | 15/15 | $8.7 \times 10^8$ | 15/15 |
|  |  | $1.8 \times 10^9$ | 10/10 | $1.3 \times 10^9$ | 10/10 |
|  |  | $1.7 \times 10^9$ | 19/20 | $1.6 \times 10^9$ | 19/19 |
| χ9382 | $\Delta P_{phoPQ173}$ | $1.0 \times 10^9$ | 15/15 | $1.8 \times 10^9$ | 11/15 |
|  |  | $1.0 \times 10^8$ | 15/15 | $1.8 \times 10^9$ | 11/15 |
|  |  | $1.0 \times 10^7$ | 15/15 | $1.8 \times 10^9$ | 12/15 |
| χ9383 | $\Delta P_{phoPQ177}$ | $1.1 \times 10^9$ | 15/15 | $1.8 \times 10^9$ | 10/15 |
|  |  | $1.1 \times 10^8$ | 15/15 | $1.8 \times 10^9$ | 11/15 |
|  |  | $1.1 \times 10^7$ | 15/15 | $1.8 \times 10^9$ | 13/15 |

[a]Female BALB/c mice were six to eight weeks of age. Strains were grown in LB broth with no added arabinose or with 0.05% or 0.2% arabinose with no significant differences noted.
[b]χ9382 and χ9383 have the ΔaraBAD23 deletion (Table 1) in addition to the $\Delta P_{phoPQ}$ insertion-deletion mutations the ΔaraBAD23 deletion (Table 5).
[c]Doses are in CFU.

Abilities of Intraperitoneally Administered Strains with araC $P_{BAD}$ Regulated Virulence Nucleic Acid Sequences to Induce Protective Immunity to Oral Challenge with Wild-Type *S. Typhimurium* UK-1.

Although the vaccines were designed for oral administration, it was worthwhile to determine if strains with these mutations, when administered intraperitoneally (i.p.), would also display attenuation and induce immunity to challenge with orally administered wild-type χ3761. The *S. Typhimurium* UK-1 strain χ3761 has an $LD_{50}$ by the i.p. route of less than 10 CFU. Table 9 demonstrates that strains with $\Delta P_{fur}$::TT araC $P_{BAD}$ fur mutations retain considerable virulence by this route of administration although χ9269 with the $\Delta P_{fur81}$::TT araC $P_{BAD}$ fur mutation displays the highest attenuation of the three strains evaluated and yet induces complete protective immunity to all survivors when challenged with about $10^9$ CFU of χ3761. χ8918 with the $\Delta P_{phoPQ107}$::TT araC $P_{BAD}$ phoPQ mutation displays fairly good attenuation by this route. On the other hand, χ8956 with the $\Delta P_{rpoS183}$::TT araC $P_{BAD}$ rpoS mutation and χ9021 with the $\Delta P_{crp527}$::TT araC $P_{BAD}$ crp mutation are the most attenuated and induce a very high level of protective immunity when delivered at i.p doses in the $10^2$ to $10^4$ CFU range (Table 9).

TABLE 9

Intraperitoneal immunization of mice with strains with various deletion-insertion mutations conferring regulated delayed oral attenuation and with survivors orally challenged with wild-type χ3761 thirty days later.

| Strain | Genotype | Immunizing dose[b] | Survivors/total | Challenge dose[b] | Survivors/total |
|---|---|---|---|---|---|
| χ8848 | $\Delta P_{fur33}$ | $1.2 \times 10^4$ | 0/5 | — |  |
|  |  | $1.2 \times 10^3$ | 0/5 | — |  |
|  |  | $1.2 \times 10^2$ | 0/5 | — |  |
|  |  | $1.2 \times 10^1$ | 0/5 | — |  |
| χ9273 | $\Delta P_{fur77}$ | $1.6 \times 10^4$ | 0/5 |  |  |
|  |  | $1.6 \times 10^3$ | 0/5 |  |  |
|  |  | $1.6 \times 10^2$ | 0/5 |  |  |
|  |  | $1.6 \times 10^1$ | 1/5 | $1.6 \times 10^9$ | 1/1 |
| χ9269 | $\Delta P_{fur81}$ | $1.7 \times 10^4$ | 1/10 | $1.6 \times 10^9$ | 1/1 |
|  |  | $1.7 \times 10^3$ | 7/10 | $1.6 \times 10^9$ | 7/7 |
|  |  | $1.7 \times 10^2$ | 4/10 | $1.6 \times 10^9$ | 4/4 |
|  |  | $1.7 \times 10^1$ | 6/10 | $1.6 \times 10^9$ | 6/6 |
| χ8918 | $\Delta P_{phoPQ107}$ | $1.2 \times 10^5$ | 0/5 | — |  |
|  |  | $9.6 \times 10^4$ | 6/10 | $1.5 \times 10^9$ | 4/6 |
|  |  | $1.2 \times 10^4$ | 5/5 | $9.6 \times 10^8$ | 5/5 |
|  |  | $9.6 \times 10^3$ | 8/10 | $1.5 \times 10^9$ | 6/8 |
|  |  | $1.3 \times 10^3$ | 5/5 | $9.6 \times 10^8$ | 2/5 |
|  |  | $9.6 \times 10^2$ | 5/5 | $1.5 \times 10^9$ | 2/5 |
|  |  | $1.2 \times 10^2$ | 5/5 | $9.6 \times 10^8$ | 3/5 |
| χ8956 | $\Delta P_{rpoS183}$ | $1.5 \times 10^4$ | 5/5 | $1.0 \times 10^9$ | 5/5 |
|  |  | $1.5 \times 10^3$ | 5/5 | $1.0 \times 10^9$ | 5/5 |
|  |  | $1.5 \times 10^2$ | 5/5 | $1.0 \times 10^9$ | 3/5 |
|  |  | $1.5 \times 10^1$ | 5/5 | $1.0 \times 10^9$ | 3/5 |
| χ9021 | $\Delta P_{crp527}$ | $1.4 \times 10^5$ | 0/5 | — |  |
|  |  | $1.4 \times 10^4$ | 4/10 | $1.5 \times 10^9$ | 4/4 |
|  |  | $1.4 \times 10^3$ | 10/10 | $1.5 \times 10^9$ | 10/10 |
|  |  | $1.4 \times 10^2$ | 10/10 | $1.5 \times 10^9$ | 10/10 |
|  |  | $1.4 \times 10^1$ | 9/10 | $1.5 \times 10^9$ | 8/9 |

[a]Female BALB/C mice were six to eight weeks of age. All strains were grown in LB broth with 0.2% arabinose.
[b]Doses are in CFU.

Enhanced Control Over araC $P_{BAD}$ Regulated Virulence Nucleic Acid Sequences In Vivo by Inclusion of the $\Delta P_{crp527}$::TT araC $P_{BAD}$ crp Mutation.

Maximum levels of transcription of nucleic acid sequences regulated by the araC $P_{BAD}$ system require not only arabinose to interact with the AraC protein but also the Crp protein (41). Thus the $\Delta P_{crp527}$::TT araC $P_{BAD}$ crp mutation was included in vaccine strains whenever other araC $P_{BAD}$ regulated nucleic acid sequences are included. The benefit of this addition is readily observed by the results previously presented in FIG. 7 that demonstrate this tighter regulation in the absence of arabinose in strains that also have the $\Delta P_{crp527}$::TT araC $P_{BAD}$ crp mutation. This also acts as a backup and should enhance safety and efficacy of vaccine strains.

Means for delay in the in vivo timing of onset of regulated delayed attenuation. As noted by Guzman et al. (32), the inclusion of mutations that abolish utilization of arabinose can prolong expression of nucleic acid sequences under the control of the araC $P_{BAD}$ system. Onset of attenuation can therefore by delayed by including ΔaraBAD23, which prevents use of arabinose retained in the cell cytoplasm at the time of oral immunization, and/or ΔaraE25 that enhances retention of arabinose. These mutations are diagrammed in FIG. 27.

Discussion for Example 2

Four different means have been described to achieve regulated delayed attenuation of *S. Typhimurium* vaccine strains such that vaccines at the time of immunization will be better able to withstand the host defense imposed stresses following oral immunization. Some of these constructs have been modified to optimize attenuation and improve immunogenicity. Although comparative studies with vaccine strains having defined deletion mutations in the fur, phoPQ, rpoS and crp nucleic acid sequences might resolve doubt, such comparative studies become difficult to justify based on animal use. These mutations are being included in strains with multiple attenuating mutations.

REFERENCES FOR EXAMPLE 2

1. Hopkins S, Kraehenbuhl J P, Schodel F, Potts A, Peterson D, de Grandi P, & Nardelli-Haefliger D (1995) A recombinant *Salmonella typhimurium* vaccine induces local immunity by four different routes of immunization. Infect Immun 63: 3279-3286.
2. Nardelli-Haefliger D, Roden R B, Benyacoub J, Sahli R, Kraehenbuhl J P, Schiller J T, Lachat P, Potts A, & De Grandi P (1997) Human papillomavirus type 16 virus-like particles expressed in attenuated *Salmonella typhimurium* elicit mucosal and systemic neutralizing antibodies in mice. Infect Immun 65: 3328-3336.
3. Giannella R A, Broitman S A, & Zamcheck N (1973) Gastric acidity and cholera. Ann Intern Med 78: 780.
4. Foster J W & Spector M P (1995) How *Salmonella* survive against the odds. Annu Rev Microbiol 49: 145-174.
5. Audia J P, Webb C C, & Foster J W (2001) Breaking through the acid barrier: an orchestrated response to proton stress by enteric bacteria. Int J Med Microbiol 291: 97-106.
6. Wilmes-Riesenberg M R, B. Bearson, J. W. Foster, and R. Curtiss, III. (1996) Role of acid tolerance response in virulence of *Salmonella typhimurium*. Infect. Immun 64: 1085-1092.
7. In Soo Lee J L, Holly K Hall, Bradley Bearson, John W Foster (1995) The stationary-phase sigma factor sS (RpoS) is required for a sustained acid tolerance response in virulent *Salmonella typhimurium*. Molecular Microbiology 17: 155-167.
8. Hall H K & Foster J W (1996) The role of fur in the acid tolerance response of *Salmonella typhimurium* is physiologically and genetically separable from its role in iron acquisition. J Bacteriol 178: 5683-5691.
9. Bearson B L, Wilson L, & Foster J W (1998) A low pH-inducible, PhoPQ-dependent acid tolerance response protects *Salmonella typhimurium* against inorganic acid stress. J Bacteriol 180: 2409-2417.
10. Bang I S, Audia J P, Park Y K, & Foster J W (2002) Autoinduction of the ompR response regulator by acid shock and control of the *Salmonella enterica* acid tolerance response. Mol Microbiol 44: 1235-1250.
11. Bang I S, Kim B H, Foster J W, & Park Y K (2000) OmpR regulates the stationary-phase acid tolerance response of *Salmonella enterica* serovar *Typhimurium*. J Bacteriol 182: 2245-2252.
12. Prouty A M & Gunn J S (2000) *Salmonella enterica* serovar *Typhimurium* invasion is repressed in the presence of bile. Infect Immun 68: 6763-6769.
13. van Velkinburgh J C & Gunn J S (1999) PhoP-PhoQ-regulated loci are required for enhanced bile resistance in *Salmonella* spp. Infect Immun 67: 1614-1622.
14. Gunn J S (2000) Mechanisms of bacterial resistance and response to bile. Microbes Infect 2: 907-913.
15. Curtiss R, III & Hassan J O (1996) Nonrecombinant and recombinant avirulent *Salmonella* vaccines for poultry. Vet Immunol Immunopathol 54: 365-372.
16. Bertani G (1951) Studies on lysogenesis. I. The mode of phage liberation by lysogenic *Escherichia coli*. J Bacteriol 62: 293-300.
17. Curtiss R, III (1965) Chromosomal Aberrations Associated with Mutations to Bacteriophage Resistance in *Escherichia coli*. J Bacteriol 89: 28-40.
18. Romeo T & Preiss J (1989) Genetic regulation of glycogen biosynthesis in *Escherichia coli*: in vitro effects of cyclic AMP and guanosine 5'-diphosphate 3'-diphosphate and analysis of in vivo transcripts. J Bacteriol 171: 2773-2782.
19. Lange R & Hengge-Aronis R (1991) Identification of a central regulator of stationary-phase gene expression in *Escherichia coli*. Mol Microbiol 5: 49-59.
20. Hengge-Aronis R & Fischer D (1992) Identification and molecular analysis of glgS, a novel growth-phase-regulated and rpoS-dependent gene involved in glycogen synthesis in *Escherichia coli*. Mol Microbiol 6: 1877-1886.
21. Sambrook J, Fritsch E F, & Maniatis T (1989) (Cold Spring Harbor Lab. Press, Plainview).
22. Roland K, Curtiss R, III, & Sizemore D (1999) Construction and evaluation of a delta cya delta crp *Salmonella typhimurium* strain expressing avian pathogenic *Escherichia coli* O78 LPS as a vaccine to prevent airsacculitis in chickens. Avian Dis 43: 429-441.
23. Miller V L & Mekalanos J J (1988) A novel suicide vector and its use in construction of insertion mutations: osmoregulation of outer membrane proteins and virulence determinants in *Vibrio cholerae* requires toxR. J Bacteriol 170: 2575-2583.
24. Schmieger H (1972) Phage P22-mutants with increased or decreased transduction abilities. Mol Gen Genet 119: 75-88.
25. Schmieger H & Backhaus H (1976) Altered cotransduction frequencies exhibited by HT-mutants of *Salmonella*-phage P22. Mol Gen Genet 143: 307-309.
26. Kang H Y, Dozois C M, Tinge S A, Lee T H, & Curtiss, R., III (2002) Transduction-mediated transfer of unmarked deletion and point mutations through use of counterselectable suicide vectors. J Bacteriol 184: 307-312.
27. Daigle F, Graham J E, & Curtiss, R., III (2001) Identification of *Salmonella typhi* genes expressed within macrophages by selective capture of transcribed sequences (SCOTS). Mol Microbiol 41: 1211-1222.
28. Galan J E & Curtiss R, III (1989) Cloning and molecular characterization of genes whose products allow *Salmonella typhimurium* to penetrate tissue culture cells. Proc Natl Acad Sci USA 86: 6383-6387.
29. Curtiss R, III & Kelly S M (1987) *Salmonella typhimurium* deletion mutants lacking adenylate cyclase and cyclic AMP receptor protein are avirulent and immunogenic. Infect Immun 55: 3035-3043.
30. Gulig P A & Curtiss R, III (1987) Plasmid-associated virulence of *Salmonella typhimurium*. Infect Immun 55: 2891-2901.
31. Kong W, Wanda S-Y, Zhang X, Bollen W, Tinge S A, Roland K L, & Curtiss, R., III (2008) Regulated programmed lysis of recombinant *Salmonella* within host tissues to release protective antigens and confer biological containment. Proc Natl Acad Sci USA accepted.
32. Guzman L M, Belin D, Carson M J, & Beckwith J (1995) Tight regulation, modulation, and high-level expression by vectors containing the arabinose PBAD promoter. J Bacteriol 177: 4121-4130.
33. Loewen P C & Triggs B L (1984) Genetic mapping of katF, a locus that with katE affects the synthesis of a second catalase species in *Escherichia coli*. J Bacteriol 160: 668-675.
34. Nickerson C A & Curtiss R, III (1997) Role of sigma factor RpoS in initial stages of *Salmonella typhimurium* infection. Infect Immun 65: 1814-1823.
35. Buchmeier N A, Libby S J, Xu Y, Loewen P C, Switala J, Guiney D G, & Fang F C (1995) DNA repair is more important than catalase for *Salmonella* virulence in mice. J Clin Invest 95: 1047-1053.
36. Mulvey M R, Switala J, Borys A, & Loewen P C (1990) Regulation of transcription of katE and katF in *Escherichia coli*. J Bacteriol 172: 6713-6720.
37. Lee H C & Bernstein H D (2002) Trigger factor retards protein export in *Escherichia coli*. J Biol Chem 277: 43527-43535.
38. Tu X, Latifi T, Bougdour A, Gottesman S, & E A. G (2006) The PhoP/PhoQ two-component system stabilizes the alternative sigma factor RpoS in *Salmonella enterica*. Proc Natl Acad Sci USA. 103: 13503-13508.
39. Peterson C N, Ruiz N, & Silhavy T J (2004) RpoS proteolysis is regulated by a mechanism that does not require the SprE (RssB) response regulator phosphorylation site. J Bacteriol 186: 7403-7410.
40. Curtiss R. III et al. (2007) Virulence Mechanisms of Bacterial Pathogens (ASM Press, Washington D.C.).
41. Lobell R B & Schleif R F (1991) AraC-DNA looping: orientation and distance-dependent loop breaking by the cyclic AMP receptor protein. J Mol Biol 218: 45-54.

Example 3

Improved Immune Responses Induced by RASVs with Regulated Delayed Attenuation and Regulated Delayed Synthesis of Protective Antigen Generating a *Salmonella* strain that is safe and also retains its immunogenicity is the biggest challenge in the development of live vaccine candidates (1). An ideal *Salmonella* vaccine strain should exhibit wild-type abilities to withstand all stresses (enzymatic, acid, osmotic, ionic, etc.) and host defenses (bile, antibacterial peptides, etc.) encountered following oral or intranasal immunization and should exhibit wild-type abilities to colonize and invade host lymphoid tissues while remaining avirulent. A variety of attenuated *Salmonella* strains have been used as live vaccines to induce mucosal and systemic immunity against either the carrier itself or to a vectored antigen (2). More recently developed *Salmonella* vaccine strains carry defined nonreverting mutations that fall into two general categories: metabolic functions and virulence factors (3). Different means for attenuating *Salmonella* have been investigated to develop ideal immune responses (4, 5). Many previously utilized means for *Salmonella* attenuation either reduced vaccine survival due to host-induced stresses and/or reduced colonization of lymphoid effector tissues leading to less than optimal immunogenicity (6, 7). To circumvent these problems, a system for regulated delayed in vivo expression of attenuation has been developed (8). Thus vaccine strains are phenotypically wild-type for host invasion at the time of immunization and become attenuated after colonization of host tissues (8).

PspA is an important virulence factor found on the surface of all pneumococci (9). It plays a role in colonization of the host and contributes to the ability of pneumococcus to cause invasive disease (10). The N-terminal half of the protein is the α-helical domain which contains protective epitopes based on immunization studies with the full length and truncated PspA fragments (11, 12). Humans naturally infected or colonized with pneumococcus, develop anti-PspA antibodies in both serum and mucosal secretions, with antibody to the α-helical domain of PspA also implicated in preventing pneumococcal carriage.

Previous work has demonstrated that oral vaccination of mice with a Δcrp *Salmonella* vaccine strain expressing a secreted PspA fusion protein could protect the immunized mice from virulent *S. pneumoniae* WU2 challenge (13). The protection rate was about 60% against a 50 $LD_{50}$ challenge (13). To increase the effective protective immunity against *S. pneumoniae*, we designed and constructed a new generation of *Salmonella enterica* serovar *Typhimurium* strains with delayed regulated attenuation (see Example 2) and for one strain with regulated delayed expression of anigen encoding sequences in vivo (Example 1).

In this example, the immunogenicity is evaluated of two new attenuated *S. Typhimurium* strains transformed with $Asd^+$ balanced-lethal plasmids encoding a secreted form of the α-helical region of PspA. Antibody responses, cytokine responses and protective immunity against *S. pneumoniae* WU2 challenge were evaluated. The results attained confirm the hypothesis that vaccine strains with regulated delayed in vivo attenuation including the strain that also exhibited regulated delayed protective antigen synthesis confer a more superior immune response than a vaccine strain with a more traditional means of attenuation.

Materials and Methods for Example 3

Bacterial Strains, Plasmids, Media, and Growth Conditions:

The bacterial strains and plasmids used in this example are listed in Table 1 and 2, respectively. Bacteriophage P22HTint was used for generalized transduction. *S. Typhimurium* cultures were grown at 37° C. in LB broth or on LB agar (14). For animal experiments, plasmid-containing χ9088 and χ9558 cultures were supplemented with 0.2% mannose or 0.2% mannose and 0.05% arabinose, respectively. No additions were made to the media for growing plasmid-containing χ8133 cultures. MacConkey agar (Difco, Detroit, Mich.) supplemented with 1% sugar was used for fermentation assays. DAP was added (50 μg/ml) for the growth of Asd-strains (15). *S. pneumoniae* WU2 was cultured on brain heart infusion agar containing 5% sheep blood or in Todd-Hewitt broth plus 0.5% yeast extract (12).

Strain Construction and Characterization:

MacConkey agar supplemented with 1% maltose was used to confirm the phenotype of crp mutants (13). Chrome Azurol S (CAS) plates were used to confirm the constitutive synthesis of siderophores characteristic of fur mutants (16). The presence of the ΔasdA33 and ΔasdA16 mutations in *Salmonella* was confirmed by inability of the strain to grow on media without DAP (15). Lipopolysaccharide (LPS) profiles of *Salmonella* strains were examined as described (17). Plasmid stability was determined as previously described (18). All plasmids were found to be stable for 50 generations of growth in the presence of DAP.

SDS-PAGE and Immunoblot Analyses:

Protein samples were boiled for 5 min and subsequently separated by SDS-PAGE. For immunoblotting, proteins separated by SDS-PAGE were transferred to nitrocellulose membranes. After blocking membranes with 3% skim milk in 10 mM Tris-0.9% NaCl (pH 7.4), PspA was detected with rabbit polycolonal antibody specific for PspA (University of Alabama at Birmingham) followed by the addition of an AP-conjugated goat anti-rabbit immunoglobulin G (IgG) (Sigma). Immunoreactive bands were visualized by the addition of BCIP/NBT solution (Sigma). The reaction was stopped after 2 min by washing with large volumes of deionized water several times.

Immunization of Mice:

Female BALB/c mice, 6-7 weeks old, were obtained from Charles River Laboratories. All animal procedures were approved by the Arizona State University Animal Care and Use Committee. Mice were acclimated for 7 days before starting experiments.

Recombinant attenuated *Salmonella* vaccine (RASV) strains were grown statically overnight in LB broth containing the appropriate supplements at 37° C. The following day, an overnight culture of 1 ml was inoculated into 100 ml of LB broth containing the appropriate supplements and grown with aeration at 37° C. to an $OD_{600}$ of 0.8 to 0.9. Cells were pelleted by centrifugation at room temperature (6,000×g for 15 min), and the pellet resuspended in 1 ml of buffered saline with gelatin (BSG). To determine the titer of RASV strains used to inoculate mice, dilutions of the RASV strains were plated onto MacConkey agar supplemented with 1% lactose. Mice were orally inoculated with 20 μl of BSG containing $1\times10^9$ CFU of an RASV strain. Blood was obtained by mandibular vein puncture at biweekly intervals. Following centrifugation, the serum was removed from the whole blood and stored at −20° C.

Antigen Preparation:

rPspA protein and *S. Typhimurium* outer membrane proteins (SOMPs) were purified as described (13). *S. Typhimu-*

*rium* LPS was obtained from Sigma. The rPspA clone and purified protein were kind gifts from Dr. Susan Hollingshead at the University of Alabama at Birmingham (19).

Enzyme Linked Immunosorbent Assay (ELISA):

ELISA was used to assay antibodies in serum to *S. Typhimurium* LPS, SOMPs and to rPspA. Polystyrene 96-well flat-bottom microtiter plates (Dynatech Laboratories Inc., Chantilly, Va.) were coated with LPS (100 ng/well; Sigma), SOMP (100 ng/well, our lab), or purified rPspA (100 ng/well). Antigens suspended in sodium carbonate-bicarbonate coating buffer (pH 9.6) were applied with 100-μl volumes in each well. Plates were incubated overnight at 4° C. Free binding sites were blocked with phosphate-buffered saline (pH 7.4) containing 0.1% Tween 20, and 1% bovine serum albumin. A 100-μl volume of series diluted sample was added to individual wells in triplicate and incubated for 1 h at 37° C. Plates were treated with biotinylated goat anti-mouse IgG, IgG1, or IgG2a (Southern Biotechnology Inc., Birmingham, Ala.) Wells were developed with streptavidin-alkaline phosphatase conjugate (Southern Biotechnology) followed by p-nitrophenylphosphate substrate (Sigma) in diethanolamine buffer (pH 9.8). Color development (absorbance) was recorded at 405 nm using an automated ELISA plate (model EL311SX; Biotek, Winooski, Vt.). Absorbance readings 0.1 higher than PBS control values were considered positive reactions.

Passive Transfer of Cells and Sera:

At week 12, sera and spleen cells were harvested from 5 mice per group. The sera were pooled and $CD4^+$ T cells were isolated using T-cell enrichment columns (R&D Systems Inc, Minneapolis, Minn.), according to the manufacturer's instructions. Spleen cells ($1 \times 10^7$) or purified $CD4^+$ T cells ($5 \times 10^6$) were suspended in PBS and injected into the lateral tail veins of naive, syngeneic BALB/c mice. Naïve syngeneic BALB/c mice received 100 μl of serum from a different group of mice through the tail vein. All groups were challenged intraperitoneally after 12 h with $5 \times 10^4$ CFU of *S. pneumoniae* in 200 μl of BSG.

IL-4 and IFN-γ ELISPOTs:

At week 8, spleen cells were harvested from 3 mice of each group. ELISPOTs were performed as previously described (20). Briefly, PVDF membrane plates (Millipore, Bedford, Mass., USA) were pre-wetted with ethyl alcohol, washed with sterile $H_2O$ and coated with 100 μl of mAbs IL-4 or IFN-γ (BD PharMingen, San Diego, Calif.) at 2 μg/ml, in PBS overnight at 4° C. The wells were washed with PBS and blocked with RPMI with 10% FCS. After that, 50 μl cell medium (RPMI-1640 supplemented with 10% FCS, 2 mM L-glutamine, 100 IU/ml penicillin and streptomycin and 1% HEPES, with or without stimuli and 50 μl of cells (100,000 per well) in cell medium were added per well and incubated in the plates overnight in 5% $CO_2$ at 37° C. The next day, the cell suspensions were discarded and the plates washed with PBS. Biotinylated mAb IL-4 or IFN-γ (BD PharMingen, San Diego, Calif.) at 0.5 μg/ml in PBS with 1% FCS was added and incubated at room temperature for 2 h. After washing with PBS, 100 μl/well of avidin peroxidase diluted 1:1000 (v/v) in PBS-T containing 1% FCS were added followed by incubation for 1 hour at room temperature. AEC (3-amina-9-ethycarbazole) substrate was prepared according to manufacturer's (Vector Laboratories, Burlingame, Calif.) specifications, and 100 μl of substrate was added per well. Spots were developed for 15 minutes at room temperature. Plates were dried and analyzed by using an automated CTL ELISPOT Reader System (Cellular Technology LTD, Cleveland, Ohio).

Measurement of Cytokine Concentrations:

Cytokine concentrations were determined using the Bio-Plex Protein Array System (Bio-Rad, Hercules, Calif., USA). Cytokine-specific antibody-coated beads (Bio-Rad) were used for these experiments. The assay quantitates cytokines over a broad range (2-32,000 pg/ml) and eliminates multiple dilutions of high-concentration samples. The samples were prepared and incubated with the antibody-coupled beads for 1 h with continuous shaking. The beads were washed three times with wash buffer to remove unbound protein and then incubated with biotinylated detection cytokine-specific antibody for 1 h with continuous shaking. The beads were washed once more and were then incubated with streptavidin-phycoerythrin for 10 min. After incubation, the beads were washed and resuspended in assay buffer, and the constituents of each well were drawn up into the flow-based Bio-Plex Suspension Array System, which identifies each different color bead as a population of protein and quantifies each protein target based on secondary antibody fluorescence. Cytokine concentrations were automatically calculated by Bio-Plex Manager software using a standard curve derived from a recombinant cytokine standard. Many readings were made on each bead set, further validating the results.

Pneumococcal Challenge:

At week 12 the ability of the *Salmonella*-PspA vaccine to protect immunized mice against *S. pneumoniae* was assessed by intraperitoneal challenge with $5 \times 10^4$ CFU of *S. pneumoniae* WU2 in 200 μl of BSG (21). The 50% lethal dose ($LD_{50}$) of *S. pneumoniae* WU2 in BALB/c mice was $2 \times 10^2$ CFU by intraperitoneal administration. Twenty-four hours after intraperitoneal challenge, mice were marked and bled by mandibular vein puncture, and blood samples with 10-fold serial dilutions in saline were plated on brain heart infusion agar containing 5% sheep blood. Bacterial colonies were enumerated after overnight incubation at 37° C.

Histological Examinations:

After challenge, mice were euthanized just before dying and survivors were euthanized after 15 days of observation. Fixed lung, spleen and liver specimens were embedded in paraffin wax, sectioned, and stained with hematoxylin and eosin (H&E). Micrographs were taken with a digital camera.

Statistical Analysis:

Most data were expressed as means±standard error. The means were evaluated with One-way ANOVA and LSD tests for multiple comparisons among groups. $p < 0.05$ was considered statistically significant.

Regulated Attenuation of fur, crp and pmi in χ9088 ($\Delta P_{fur33}$::TT araC $P_{BAD}$ fur Δpmi-2426 Δ(gmd-fcl)-26 ΔasdA33) and χ9558 (Δpmi-2426 Δ(gmd-fcl)-26 $\Delta P_{fur81}$::TT araC $P_{BAD}$fur $\Delta P_{crp527}$::TT araC $P_{BAD}$crp ΔasdA27::TT araC $P_{BAD}$c2 ΔaraE25 ΔaraBAD23 ΔrelA198::araCP$_{BAD}$lacI TT ΔsopB1925 ΔagfBAC811).

Regulated delayed attenuation attributes distinguish χ9088 and χ9558 from other attenuated *Salmonella* strains due to a unique combination of arabinose-regulated expression of Fur, Crp and mannose-regulated expression of O-antigen synthesis. *Salmonella* with pmi mutations are attenuated and immunogenic (22). Strains with the Δpmi-2426 mutation lack phosphomannose isomerase needed to interconvert fructose-6-P and mannose-6-P but synthesize a complete LPS O-antigen when grown in the presence of mannose (FIG. 30). Note that LPS synthesis is dependent on the addition of mannose when cells are grown in nutrient broth, but there is enough mannose in LB broth to enable O-antigen production.

The other means used to achieve regulated delayed in vivo attenuation was to replace the promoter/operator regions of the fur and crp nucleic acid sequences with the tightly-regulated, arabinose-dependent araC $P_{BAD}$ activator-promoter. (FIG. 31) Growth of these mutant strains in the presence of arabinose leads to transcription of the fur and crp nucleic acid sequences but nucleic acid sequence expression ceases in the absence of arabinose. Since free arabinose is not found in mammalian tissues, the arabinose-regulated fur and crp nucleic acid sequences will not be expressed.

Expression of rPspA in *Salmonella*.

The recombinant plasmid pYA3634 (pBR ori) was constructed for the periplasmic secretion of the a-helical region of the PspARx1 (8) (Table 2). Plasmid pYA3493 (vector control) and pYA3634 (encoding β-lactamase (bla) SS-pspA)

were electroporated into *S. Typhimurium* strains χ8133, χ9088 and χ9558. The RASV electroporants containing pYA3634 expressed a protein with an approximate molecular mass of 37 kDa, the expected size of the Bla SS-PspA fusion protein encoded by pYA3634, that reacts specifically with an anti-PspA polyclonal antibody (FIG. 32). Plasmid stability was evaluated as described in the Material and Methods. Plasmids were maintained and protein expression was shown to be stable when strains were grown in the presence of DAP for 50 nucleic acid sequencerations.

Antibody Responses in Mice after Oral Immunization with the Recombinant *S. enterica* Serovar *Typhimurium* Vaccines.

A dose of RASV χ8133(pYA3634) ($1.9 \times 10^9$ CFU), χ9088 (pYA3634) ($1.7 \times 10^9$ CFU), χ9558(pYA3634) ($1.5 \times 10^9$ CFU), χ8133(pYA3493) ($1.8 \times 10^9$ CFU), χ9088(pYA3493) ($2.0 \times 10^9$ CFU) or χ9558(pYA3493) ($1.5 \times 10^9$ CFU/mouse) was orally administered to 7-week-old female BALB/c mice. Mice were boosted with the same dose of the same strain eight weeks later. All immunized mice survived, and no signs of disease were observed in the immunized mice during the entire experimental period. The antibody responses to *Salmonella* LPS, SOMPs and rPspA in the sera of immunized mice were measured (FIG. 33). High serum IgG titers against all antigens, including PspA, were observed by 2 weeks after the primary immunization. The maximum preboost anti-LPS, —SOMP, and -rPspA IgG levels were detected by 6 weeks post immunization. The serum anti-rPspA IgG antibody levels of χ9558(pYA3634) and χ9088(pYA3634) immunized mice were significantly higher than the levels in χ8133 (pYA3634) immunized mice ($p<0.01$, $p<0.05$).

IgG Isotype Analyses

The types of immune responses to rPspA were further examined by measuring the levels of IgG isotype subclasses IgG1 and IgG2a (FIG. 34). The Th1-helper cells direct cell-mediated immunity and promote class switching to IgG2a, and Th2 cells provide potent help for B-cell antibody production and promote class switching to IgG1 (23, 24). Th1-type dominant immune responses are frequently observed after immunization with attenuated *Salmonella* (25-27). A Th1- and Th2-type mixed response was observed for the rPspA antigen. Although the IgG1 levels were almost the same as IgG2a levels in the early phase, the level of anti-rPspA IgG2a isotype antibodies gradually increased after boosting at 8 weeks. After 12 weeks postimmunization, the ratios of IgG1:IgG2a are 1:8.3 for χ8133(pYA3634) immunized mice, 1:9.4 for χ9088(pYA3634) immunized mice and 1:1.5 for χ9558 (pYA3634) immunized mice. The serum anti-rPspA IgG1 and IgG2a antibody levels of χ9558(pYA3634) and χ9088 (pYA3634) immunized mice are both significantly higher than those of the χ8133(pYA3634) immunized mice ($p<0.01$) (FIG. 34).

Antigen-Specific Stimulation of IL-4 or IFN-g Production.

ELISPOT was used to compare PspA antigen stimulation of IL-4 or IFN-g production by cells from spleens of immunized control mice (FIG. 35). Spleen lymphocytes from χ9088(pYA3634) immunized mice had ($114.0 \pm 28.8$) antigen specific IL-4 secreting cells per $10^6$ cells and ($315.9 \pm 31.5$) antigen specific IFN-g secreting cells per $10^6$ cells which were both significantly higher than those of the spleen lymphocytes from χ8133(pYA3634) immunized mice ($p<0.001$) The spleen lymphocytes from χ9558(pYA3634) immunized mice had ($108.1 \pm 90.25$) antigen specific IL-4 secreting cells per $10^6$ cells and ($280.1 \pm 47.10$) antigen specific IFN-g secreting cells per $10^6$ cells which were also significantly higher than those of the spleen lymphocytes from χ8133(pYA3634) immunized mice ($p<0.001$).

Status of Systemic Cytokine Environment.

At 2 weeks after immunization, sera from each group of mice were subjected to Bio-Plex analyses. The secretion profiles were compared (Table 10). The sera from χ8133 (pYA3634), χ9088(pYA3634), χ9558(pYA3634) immunized mice have increased levels of cytokine concentrations compared with the BSG control group ($p<0.01$). χ9558 (pYA3634) immunized mice have an increased level of cytokines including both Th1 and Th2 cytokines compared with the χ8133(pYA3634) group ($p<0.05$), which suggested that the RASV strains caused mixed Th1 and Th2 responses and our regulated delayed attenuation strain χ9558(pYA3634) stimulated stronger cellular immunity and cytokine secretion than χ8133(pYA3634), which will facilitate antigen presentation and activation of T and B cells.

TABLE 10

S. Typhimurium vaccine strains with regulated delayed attenuation stimulate higher systemic cytokine production

| Mouse groups | Cytokines concentrations (pg/ml) | | | | | | |
|---|---|---|---|---|---|---|---|
| | IL-2 | IL-4 | IL-5 | IL-10 | IL-12 | GM-CSF | TNF-α |
| BSG | $6.5 \pm 0.71$ | $13.4 \pm 1.27$ | $8.5 \pm 1.41$ | $7.8 \pm 1.06$ | $15.0 \pm 0.71$ | $12.5 \pm 1.41$ | $9.9 \pm 0.14$ |
| χ8133 (pYA3493) | $7.3 \pm 0.35$ | $18.3 \pm 0.35$ | $10.2 \pm 1.20$ | $8.5 \pm 0.00$ | $17.7 \pm 0.92$ | $13.8 \pm 1.06$ | $11.3 \pm 0.35$ |
| χ8133 ** (pYA3634) | $12.0 \pm 1.27$ | $27.7 \pm 5.44$ | $21.8 \pm 3.89$ | $21.7 \pm 3.04$ | $42.3 \pm 9.55$ | $28.0 \pm 2.12$ | $32.3 \pm 3.18$ |
| χ9088 (pYA3493) | $9.5 \pm 0.00$ | $27.4 \pm 1.56$ | $17.0 \pm 0.00$ | $14.0 \pm 1.41$ | $29.9 \pm 3.39$ | $20.9 \pm 0.57$ | $18.8 \pm 1.77$ |
| χ9088 ** (pYA3634) | $11.5 \pm 0.71$ | $37.3 \pm 1.41$ | $24.5 \pm 2.12$ | $22.5 \pm 0.71$ | $49.7 \pm 1.20$ | $31.7 \pm 3.75$ | $31.0 \pm 2.12$ |
| χ9558 (pYA3493) | $11.8 \pm 0.35$ | $34.8 \pm 1.06$ | $30.5 \pm 2.12$ | $25.8 \pm 1.06$ | $53.3 \pm 1.41$ | $39.2 \pm 1.02$ | $37.8 \pm 1.06$ |
| χ9558 **# (pYA3634) | $15.0 \pm 1.41$ | $46.3 \pm 1.06$ | $32.0 \pm 1.41$ | $26.5 \pm 1.48$ | $59.0 \pm 8.13$ | $39.8 \pm 7.78$ | $39.7 \pm 3.32$ |

** Compared with BSG group of mice all three vaccine strains stimulate significant higher systemic cytokine production $p < 0.01$.
Compared with χ8133(pYA3634) group of mice, χ9558(pYA3634) group of mice stimulate significantly higher systemic cytokine production $p < 0.05$.

Evaluation of Protective Immunity.

To examine the ability of *Salmonella*-rPspA vaccines to protect against pneumococcal infection, mice were challenged intraperitoneally with $5 \times 10^4$ CFU (250 times the $LD_{50}$) of *S. pneumoniae* WU2 four weeks after they were boosted. Eighty-six percent of the mice immunized with χ9088(pYA3634), seventy-one percent of the mice immunized with χ9558(pYA3634), and twenty-nine percent of the mice immunized with χ8133(pYA3634) were protected from pneumococcal challenge, with statistical significance ($p<0.01$). This challenge dose killed 100% of the non-immunized, and χ8133(pYA3493), χ9088(pYA3493) and χ9558 (pYA3493) immunized mice (Table 11). Following challenge, non-immunized mice, and mice immunized with χ8133(pYA3493) or χ9088(pYA3493) or χ9558(pYA3493) died rapidly.

TABLE 11

Oral immunization with PspA-expressing *Salmonella* strains protects BALB/c mice against i.p. challenge with 5 × $10^4$ CFU of capsular type 3 *S. pneumoniae* WU2

| Vaccine strain[a] | PspA expression[b] | Number of challenged mice | Days to death[c] | Protection rate (%) |
|---|---|---|---|---|
| BSG | NA | 10 | 2, 2, 2, 2, 2, 2, 2, 2, 3, 3 | 0 |
| χ8133(pYA3493) | − | 10 | 2, 2, 2, 2, 2, 2, 2, 2, 2, 2 | 0 |
| χ9088(pYA3493) | − | 10 | 2, 2, 2, 2, 2, 2, 2, 2, 2, 3 | 0 |
| χ9558(pYA3493) | − | 10 | 2, 2, 2, 2, 2, 2, 2, 2, 2, 3 | 0 |
| χ8133(pYA3634) | + | 14 | 2, 2, 2, 2, 2, 2, 2, 2, 2, 3, 3, 3, >15, >15, >15 | 21 |
| χ9088(pYA3634) | + | 14 | 2, 3, >15, >15, >15, >15, >15, >15, >15, >15, >15, >15, >15, >15 | 86* |
| χ9558(pYA3634) | + | 14 | 2, 2, 3, 3, >15, >15, >15, >15, >15, >15, >15, >15, >15, >15 | 71[#] |

[a]Mice were orally immunized twice at 8-weeks intervals with the indicated vaccine strains.
[b]+, PspA expressed; −, PspA not expressed; NA, not applicable.
[c]Four weeks after the second oral immunization, mice were challenged in two experiments with approximately 5 × $10^4$ CFU of *S. pneumoniae* WU2. Both experiments gave similar results, and the data have been pooled for presentation and analysis. The $LD_{50}$ of WU2 in nonimmunized BALB/c mice is 2 × $10^2$ (data not shown).
*p < 0.001 versus survival of mice immunized with the χ8133(pYA3634);
[#] p = 0.001 versus survival of mice immunized with the χ8133(pYA3634).

Passive-Immunization Studies.

A passive-immunization study was conducted to evaluate the roles of antibody and T-cell mediated immunity afforded by immunization of mice with the recombinant attenuated *Salmonella* vaccines. One hundred microliters of pooled sera, spleen lymphocytes ($1 \times 10^7$) or purified CD4+ T cells ($5 \times 10^6$) taken from immunized mice or controls were administered by tail vein injection into groups of 5 naïve mice. This was followed 12 hours later by intraperitoneal challenge with $5 \times 10^4$ CFU WU2. Mice receiving sera or cells transferred from χ8133(pYA3493), χ9088(pYA3493), χ9558(pYA3493) or BSG immunized mice died with a mean time of 2 days (Table 12). The sera transferred from both χ9088(pYA3634) immunized mice and χ9558(pYA3634) immunized mice protected all 5 naïve mice from challenge; while the sera transferred from χ8133(pYA3634) immunized mice protected 4 mice from challenge, the other mouse died 4 days after challenge. Passive transfer of spleen lymphocytes from χ9088(pYA3634) immunized mice protected all 5 naive mice from challenge; spleen lymphocytes from χ9558(pYA3634) immunized mice protected 3 out of 5 mice from challenge; while the spleen cell transfer from χ8133(pYA3634) immunized mice showed no protection. All the mice receiving CD4+ T cells from any group of immunized mice all died in 2 or 3 days (Table 12).

TABLE 12

Passive transfer of pneumococcal immunity by serum or lymphocytes from donors immunized with PspA *Salmonella* vaccines

| Vaccine strain used to immunize donors[a] | % survival of recipients of[b] | | |
|---|---|---|---|
| | Pooled serum[c] | Spleen cells[d] | Purified $CD_4^+$ T cells[e] |
| BSG | 0 | 0 | 0 |
| χ8133(pYA3493) | 0 | 0 | 0 |
| χ9088(pYA3493) | 0 | 0 | 0 |
| χ9558(pYA3493) | 0 | 0 | 0 |
| χ8133(pYA3634) | 80 | 0 | 0 |
| χ9088(pYA3634) | 100 | 100* | 0 |
| χ9558(pYA3634) | 100 | 60[#] | 0 |

[a]Mice were orally immunized at day 0 and boosted 8 weeks later with the indicated vaccine strains. Serum and cells were collected 4 weeks after boosting and transferred to groups of 5 naive mice.
[b]All recipient mice were challenged by i.p with 5 × $10^4$ CFU WU2 at 12 h after transfer. Survival was calculated 15 days postchallenge.
[c]0.1 ml of serum intravenously.
[d]1 × $10^7$ viable spleen cells intravenously.
[e]5 × $10^6$ viable $CD_4^+$ T cells intravenously.
*p < 0.001, compared to groups of mice receiving passive transfer from χ8133(pYA3634) immunized or control donors.
[#]p = 0.001, compared to groups of mice receiving passive transfer from χ8133(pYA3634) immunized or control donors.

Isolation of *S. pneumoniae* from Blood and Histological Examinations of Challenged Mice.

Twenty-four hours after intraperitoneal challenge, each mouse was marked and bled. *S. pneumoniae* was recovered from the blood of mice which showed significant signs of weakness and listlessness and died within 7 days (6833.3±321.5 CFU/ml), but not from mice that appeared to be healthy and survived past 15 days (p<0.001). Histological analyses showed severe tissue damage to the lung tissue in mice that died after challenge (FIG. 56). Gross visual examination of the lungs of the dead mice from challenge but not the survivors' lungs showed lobar regions of consolidation and hemorrhage. Conventional light microscopy of H&E-stained lung tissue samples of dead mice from challenge demonstrated that *S. pneumoniae* caused focal consolidation with extensive mononuclear and polymorphonuclear infiltration and loss of alveolar structure, which are characteristic of pneumonia.

Discussion of Example 3

Few infectious pathogens can match the global impact of *Streptococcus pneumoniae* (*S. pneumoniae*) on illness, complications, sequelae, health care costs, and death (28). *S. pneumoniae* is the most common cause of community-acquired pneumonia, bacterial meningitis, and acute otitis media (29, 30). The current 23-valent polysaccharide vaccine has been shown to prevent pneumococcal pneumonia in immunocompetent young adults, but not in elderly persons (31). A 7-valent conjugated polysaccharide vaccine is licensed for use in children. However, the low serotype coverage, need for repeated doses, and high price, may decrease the usefulness of the conjugate vaccine, especially in the developing world (32). Developing an inexpensive, safe and effective vaccine against this pathogen is still an urgent demand.

The new regulated delayed attenuation strains χ9088(pYA3634) and χ9558(pYA3634) induced stronger immune responses to PspA as judged by PspA-specific serum antibody levels, PspA specific lymphocytes cytokine secretion levels, systemic cytokine secretion levels and protection from virulent *S. pneumoniae* challenge. In this example a 10-fold higher challenge dose of *S. pneumoniae* WU2 was used compared to earlier studies (13), while the protection rate increased more than twenty percent.

Mixed Th1- and Th2-type immune responses were observed for rPspA. The mechanisms stimulating these types of immune responses by the *Salmonella*-rPspA vaccine remain unknown. Host defense against encapsulated bacteria, such as *S. pneumoniae*, depends on the presence of opsonic antibodies specific for capsular polysaccharide (33-35). Therefore, antibody levels measured by ELISA may not adequately reflect the presence of protective antibodies that are capable of triggering leukocyte effector functions (36). Other investigators have suggested that IgG2a is protective during infection with encapsulated bacteria, including pneumococcal infection (36-38). It is possible that under conditions of limiting expression of antibody, in the mouse, IgG2a is highly effective at fixing complement and promoting opsonophagocytosis (39). It is consistent with our result that after boosting, IgG2a becomes the dominant antibody type. Some investigators reported that $CD4^+$ T cells are very important for the protection against virulent *S. pneumoniae* challenge (40-41). Our results showed that $CD4^+$ T cells from both groups of immunized mice did not confer protection. It might be that for our *Salmonella*-rPspA vaccines, PspA specific antibodies are the most important factors in protection. T cells are important in helping the production of effective antibodies (23, 42, 43), but T cells themselves did not have the ability to protect, at least in this experiment.

All the control mice challenged intraperitoneally with *S. pneumoniae* WU2 died of septicemia. In surviving mice from the immunized group no bacteria were recovered from blood and also no signs of lung damage were detected, indicating that these vaccines can protect mice from both fatal bacteremia and the pneumonia caused by *S. pneumoniae*.

Although χ9558(pYA3436) possesses the ΔrelA198::araC $P_{BAD}$ lacI TT deletion-insertion mutation to provide regulated delayed synthesis of the PspA antigen, this feature did not show any benefit to the level of immunogenicity over that induced by χ9088 that does not have this attribute that was shown to be highly beneficial in Example 1. There are two probable reasons for this. First, the segment of the Rx1 PspA specified by pYA3634 is shorter and less stressful on recombinant *Salmonella* than the Rx1 PspA specified by the codon optimized sequence in pYA4088 used in the studies reported in Example 1. Second, χ9558 possesses some 10 genetic alterations and has a genotype almost identical to *S. Typhi* candidate vaccine strains that will soon be evaluated in human volunteers. This is in contrast to the presence of only four genetic alterations in χ9088. The additional mutations in χ9558 are present to render it safe for newborn mice and thus probably result in some degree of overattenuation to reduce immunogenicity. Nevertheless, these constructions are important to evaluate since the historical fact is that almost all single mutations that render *S. Typhimurium* totally avirulent and highly immunogenic in mice when introduced into *S. Typhi* strains and tested in humans are still partially virulent and cause disease. It will thus be important to evaluate isogenic strains that only differ by the presence or absence of the ΔrelA198::araC $P_{BAD}$ lacI TT deletion-insertion mutation. Nevertheless, χ9558(pYA3436) was still far superior to χ8133(pYA3634) in regard to immunogenicity and in inducing protective immunity to pneumococcal challenge.

In conclusion, the results of this example demonstrated that the *Salmonella* vaccine strains χ9088(pYA3436) and χ9558 (pYA3436) featuring the novel regulated delayed in vivo attenuation system are superior not only in inducing PspA specific antibody responses but also in eliciting cellular immunity and cytokine secretion resulting in significant protection of mice against pneumococcal challenge.

REFERENCES FOR EXAMPLE 3

1. Kwon Y M, Cox M M, & Calhoun L N (2007) *Salmonella*-based vaccines for infectious diseases. Expert Review of Vaccines 6: 147-152.
2. Medina E & Guzman C A (2001) Use of live bacterial vaccine vectors for antigen delivery: potential and limitations. Vaccine 19: 1573-1580.
3. Raupach B & Kaufmann S H E (2001) Bacterial virulence, proinflammatory cytokines and host immunity: how to choose the appropriate *Salmonella* vaccine strain? Microbes and Infection 3: 1261.
4. Dunstan S J, Simmons C P, & Strugnell R A (1998) Comparison of the Abilities of Different Attenuated *Salmonella Typhimurium* Strains To Elicit Humoral Immune Responses against a Heterologous Antigen. Infect. Immun. 66: 732-740.
5. Garmory H S, Leary S E C, Griffin K F, Williamson E D, Brown K A, & Titball R W (2003) The Use of Live Attenuated Bacteria as a Delivery System for Heterologous Antigens. Journal of Drug Targeting 11: 471.
6. Hohmann E L, Oletta C A, & Miller S I (1996) Evaluation of a phoP/phoQ-deleted, aroA-deleted live oral *Salmonella typhi* vaccine strain in human volunteers. Vaccine 14: 19-24.
7. Tacket C O, Kelly S M, Schodel F, Losonsky G, Nataro J P, Edelman R, Levine M M, & Curtiss R, III (1997) Safety and immunogenicity in humans of an attenuated *Salmonella typhi* vaccine vector strain expressing plasmid-encoded hepatitis B antigens stabilized by the asd-balanced lethal vector system. Infect Immun 65: 3381-3385.
8. Curtiss R, III, Zhang X, Wanda S Y, Kang H Y, Konjufca V, Li Y, Gunn B, Wang S, Scarpellini G, & Lee. I S (2007) in Virulence Mechanisms of Bacterial Pathogens, ed. K. A. Brogden F C M, N. Cornick, T. B. Stanton, Q. Zhang, L. K. Nolan, and M. J. Wannemuehler (ASM Press, Washington D.C.), pp. 297-313.
9. McDaniel L S, Yother J, Vijayakumar M, McGarry L, Guild W R, & Briles D E (1987) Use of insertional inactivation to facilitate studies of biological properties of pneumococcal surface protein A (PspA). J. Exp. Med. 165: 381-394.
10. Ogunniyi A D, LeMessurier K S, Graham R M A, Watt J M, Briles D E, Stroeher U H, & Paton J C (2007) Contributions of Pneumolysin, Pneumococcal Surface Protein A (PspA), and PspC to Pathogenicity of *Streptococcus pneumoniae* D39 in a Mouse Model. Infect. Immun. 75: 1843-1851.
11. Moore Q C, Bosarge J R, Quin L R, & McDaniel L S (2006) Enhanced protective immunity against pneumococcal infection with PspA DNA and protein. Vaccine 24: 5755.
12. Briles D E, King J D, Gray M A, McDaniel L S, Swiatlo E, & Benton K A (1996) PspA, a protection-eliciting pneumococcal protein: immunogenicity of isolated native PspA in mice. Vaccine 14: 858-867.
13. Kang H Y, Srinivasan J, & Curtiss R, III (2002) Immune Responses to Recombinant Pneumococcal PspA Antigen Delivered by Live Attenuated *Salmonella enterica* Serovar *Typhimurium* Vaccine. Infect. Immun. 70: 1739-1749.
14. Bertani G (1951) STUDIES ON LYSOGENESIS. I. The Mode of Phage Liberation by Lysogenic *Escherichia coli*. J. Bacteriol. 62: 293-300.
15. Nakayama K, Kelly S M, & Curtiss R, III (1988) Construction of an asd+ Expression-Cloning Vector: Stable Maintenance and High Level Expression of Cloned Genes in a *Salmonella* Vaccine Strain. 6: 693-697.
16. Schwyn B & Neilands J B (1987) Universal chemical assay for the detection and determination of siderophores. Analytical Biochemistry 160: 47.
17. Hitchcock P J & Brown T M (1983) Morphological heterogeneity among *Salmonella* lipopolysaccharide chemotypes in silver-stained polyacrylamide gels. J. Bacteriol. 154: 269-277.
18. Konjufca V, Wanda S-Y, Jenkins M C, & Curtiss R, III (2006) A Recombinant Attenuated *Salmonella enterica* Serovar *Typhimurium* Vaccine Encoding Eimeria acervulina Antigen Offers Protection against E. acervulina Challenge. Infect. Immun. 74: 6785-6796.
19. Nabors G S, Braun P A, Herrmann D J, Heise M L, Pyle D J, Gravenstein S, Schilling M, Ferguson L M, Hollingshead S K, Briles D E, et al. (2000) Immunization of healthy adults with a single recombinant pneumococcal 20. Sedgwick J D & Holt P G (1983) A solid-phase immunoenzymatic technique for the enumeration of specific antibody-secreting cells. Journal of Immunological Methods 57: 301.
21. Nayak A R, Tinge S A, Tart R C, McDaniel L S, Briles D E, & Curtiss R, III (1998) A Live Recombinant Avirulent Oral *Salmonella* Vaccine Expressing Pneumococcal Surface Protein A Induces Protective Responses against *Streptococcus pneumoniae*. Infect. Immun. 66: 3744-3751.
22. Collins L V, Attridge S, & Hackett J (1991) Mutations at rfc or pmi attenuate *Salmonella Typhimurium* virulence for mice. Infect. Immun. 59: 1079-1085.
23. DeKruyff R H, Rizzo L V, & Umetsu D T (1993) Induction of immunoglobulin synthesis by CD4+ T cell clones. Seminars in Immunology 5: 421-430.
24. Gor D O, Rose N R, & Greenspan N S (2003) TH1-TH2: a Procrustean paradigm. Nat Immunol 4: 503.
25. Pascual D W, Hone D M, Hall S, van Ginkel F W, Yamamoto M, Walters N, Fujihashi K, Powell R J, Wu S, Vancott J L, et al. (1999) Expression of Recombinant Enterotoxigenic *Escherichia coli* Colonization Factor Antigen I by *Salmonella Typhimurium* Elicits a Biphasic T Helper Cell Response. Infect. Immun. 67: 6249-6256.
26. Pashine A, John B, Rath S, George A, & Bal V (1999) Th1 dominance in the immune response to live *Salmonella Typhimurium* requires bacterial invasiveness but not persistence. Int. Immunol. 11: 481-489.
27. Ramarathinam L, Niesel D W, & Klimpel G R (1993) *Salmonella Typhimurium* induces IFN-gamma production in murine splenocytes. Role of natural killer cells and macrophages. J Immunol 150: 3973-3981.
28. Greenwood B (1999) The epidemiology of pneumococcal infection in children in the developing world. Philos Trans R Soc Lond B Biol Sci 354: 777-785.
29. Del Beccaro M A, Mendelman P M, Inglis A F, Richardson M A, Duncan N O, Clausen C R, & Stull T L (1992) Bacteriology of acute otitis media: a new perspective. J Pediatr 120: 81-84.
30. Schuchat A, Robinson K, Wenger J D, Harrison L H, Farley M, Reingold A L, Lefkowitz L, & Perkins B A (1997) Bacterial meningitis in the United States in 1995. Active Surveillance Team. N Engl J Med 337: 970-976.
31. Ortqvist A, Hedlund J, Burman L A, Elbel E, Hofer M, Leinonen M, Lindblad I, Sundelof B, & Kalin M (1998) Randomised trial of 23-valent pneumococcal capsular polysaccharide vaccine in prevention of pneumonia in middle-aged and elderly people. Swedish Pneumococcal Vaccination Study Group. Lancet 351: 399-403.
32. Hicks L A, Harrison L H, Flannery B, Nadler J L, Schaffner W, Craig A S, Jackson D, Thomas A, Beall B, Lynfield R, et al. (2007) Incidence of pneumococcal disease due to non-pneumococcal conjugate vaccine (PCV7) serotypes in the United States during the era of widespread PCV7 vaccination, 1998-2004. J Infect Dis 196: 1346-1354.
33. Alonso De Velasco E, Dekker B A, Verheul A F, Feldman R G, Verhoef J, & Snippe H (1995) Anti-polysaccharide immunoglobulin isotype levels and opsonic activity of antisera: relationships with protection against *Streptococcus pneumoniae* infection in mice. J Infect Dis 172: 562-565.
34. Matthay K K, Mentzer W C, Wara D W, Preisler H K, Lameris N B, & Ammann A J (1981) Evaluation of the opsonic requirements for phagocytosis of *Streptococcus pneumoniae* serotypes VII, XIV, and XIX by chemiluminescence assay. Infect Immun 31: 228-235.
35. Saeland E, Jakobsen H, Ingolfsdottir G, Sigurdardottir S T, & Jonsdottir I (2001) Serum samples from infants vaccinated with a pneumococcal conjugate vaccine, PncT, protect mice against invasive infection caused by *Streptococcus pneumoniae* serotypes 6A and 6B. J Infect Dis 183: 253-260.
36. Arulanandam B P, Lynch J M, Briles D E, Hollingshead S, & Metzger D W (2001) Intranasal vaccination with pneumococcal surface protein A and interleukin-12 augments antibody-mediated opsonization and protective immunity against *Streptococcus pneumoniae* infection. Infect Immun 69: 6718-6724.
37. Khan M N, Bansal A, Shukla D, Paliwal P, Sarada S K, Mustoori S R, & Banerjee P K (2006) Immunogenicity and protective efficacy of DnaJ (hsp40) of *Streptococcus pneumoniae* against lethal infection in mice. Vaccine 24: 6225-6231.
38. Lefeber D J, Benaissa-Trouw B, Vliegenthart J F, Kamerling J P, Jansen W T, Kraaijeveld K, & Snippe H (2003) Th1-directing adjuvants increase the immunogenicity of oligosaccharide-protein conjugate vaccines related to *Streptococcus pneumoniae* type 3. Infect Immun 71: 6915-6920.
39. Buchanan R M, Arulanandam B P, & Metzger D W (1998) IL-12 Enhances Antibody Responses to T-Independent Polysaccharide Vaccines in the Absence of T and NK Cells. J Immunol 161: 5525-5533.
40. Malley R, Trzcinski K, Srivastava A, Thompson C M, Anderson P W, & Lipsitch M (2005) CD4+ T cells mediate antibody-independent acquired immunity to pneumococcal colonization. PNAS 102: 4848-4853.
41. Van Rossum A M, Lysenko E S, & Weiser J N (2005) Host and bacterial factors contributing to the clearance of colonization by *Streptococcus pneumoniae* in a murine model. Infect Immun 73: 7718-7726.
42. Wu Z Q, Shen Y, Khan A Q, Chu C L, Riese R, Chapman H A, Kanagawa O, & Snapper C M (2002) The mechanism underlying T cell help for induction of an antigen-specific in vivo humoral immune response to intact *Streptococcus pneumoniae* is dependent on the type of antigen. J Immunol 168: 5551-5557.
43. Snapper C M, Shen Y, Khan A Q, Colino J, Zelazowski P, Mond J J, Gause W C, & Wu Z Q (2001) Distinct types of T-cell help for the induction of a humoral immune response to *Streptococcus pneumoniae*. Trends Immunol 22: 308-311.

Example 4

Design and Construction of *S. Typhi* and *S. Paratyphi* a Vaccine Strains with Regulated Delayed Attenuation and Regulated Delayed Synthesis of Plasmid Encoded Protective Antigens Attenuated mutants of *Salmonella enterica* serovar Typhi (*S. Typhi*) and *Salmonella enterica* serovar Typhimurium (*S. Typhimurium*) have been extensively studied as multivalent vectors expressing more than 50 different bacterial, viral and protozoan antigens in preclinical and clinical trials (1-5). Recombinant *S. Typhimurium* vaccines (RASVs) administered orally can colonize the gut-associated lymphoid tissue (GALT) and the secondary lymphatic tissues, including the liver and spleen, and elicit mucosal, humoral and cellular immune responses against *Salmonella* and heterologous antigens during infection of the mouse (1, 2). There is also good reason to consider use of attenuated derivatives of *S. Paratyphi* A as vaccine vectors since infections with this pathogen causing enteric fever have been increasing in recent years due to the cessation in use of the killed TAB vaccine. This has been contributed to by immunization against *S. Typhi* by use of the live Ty21A or conjugate Vi antigen vaccines.

A number of factors may affect the immune response to protective antigens including the ability of vaccine strains to invade and colonize the host GALT, the stability of the plasmid expression system and the antigen sub-cellular location (1, 2, 6). High-level expression of protective antigens by RASV strains often impose an energy demand that decreases the growth, fitness and ability to colonize lymphoid tissues resulting in further attenuation and a reduction in immunogenicity (2, 7, 8). Means have been developed, such as regulated delayed in vivo antigen synthesis (Example 1), to enhance the ability of vaccine strains to efficiently invade and colonize GALT after oral immunization (7-10). Another strategy to improve the immune response is to construct strains with regulated delayed in vivo attenuation such that vaccine strains are better able to withstand the stresses and host defence means that generally reduce survival especially of attenuated vaccine strains. We have addressed this problem by developing means for regulated delayed in vivo attenuations such that vaccine strains are more able to survive these host induced stresses and behave more like wild-type infectious *Salmonella* pathogens at the time of immunization. Thus, the combined use of regulated delayed in vivo attenuation and regulated delayed in vivo synthesis of protective antigens both afford means for the RASV to more efficiently colonize to a higher vaccine cell density effector lymphoid tissues to enhance induction of effective protective immunity.

We have thus constructed *S. Typhimurium* strains to evaluate in mice with a constellation of mutations to not only provide regulated delayed in vivo attenuation and regulated delayed in vivo synthesis of plasmid-specified protective antigens but to also provide inability to establish persistent carrier states, inability to induce fluid secretion in the intestine, and engender safety for newborns. *S. Typhimurium* UK-1 strains with each of the mutations present in some of these strains and not presented in detail in Examples 1 and 2 are listed in Table 13 along with data from infection of female BALB/c mice to indicate the contributions of these mutations to the level of virulence/attenuation. The suicide vectors used to introduce these mutations into *Salmonella* strains are listed in Table 2 and the methods for these constructions are given in Examples 1 and 2.

TABLE 13

Virulence of *S.* Typhimurium UK-1 mutants with single deletion or deletion-insertion mutations

| Strain | Genotype | CFU/dose | Survival/total |
|---|---|---|---|
| χ3761 | Wild-type UK-1 | $4.7 \times 10^8$ | 0/5 |
| | | $4.7 \times 10^7$ | 0/5 |
| | | $4.7 \times 10^5$ | 0/5 |
| | | $4.7 \times 10^4$ | 0/5 |
| | | $4.7 \times 10^3$ | 3/5 |
| χ3761 | Wild-type UK-1 | $1.0 \times 10^6$ | 0/5 |
| | | $1.0 \times 10^5$ | 0/5 |
| | | $1.0 \times 10^4$ | 4/5 |
| | | $1.0 \times 10^3$ | 5/5 |
| χ8767 | ΔaraBAD23 UK-1 | $1.9 \times 10^5$ | 1/5 |
| | | $1.9 \times 10^4$ | 1/5 |
| | | $1.9 \times 10^3$ | 5/5 |
| χ8477 | ΔaraE25 UK-1 | $1.1 \times 10^8$ | 0/4 |
| | | $1.1 \times 10^7$ | 1/4 |
| | | $1.1 \times 10^6$ | 1/4 |
| | | $1.1 \times 10^5$ | 2/4 |
| χ8276 | ΔasdA16 UK-1 | $6.0 \times 10^8$ | 5/5 |
| | | $9.8 \times 10^8$ | 4/4 |
| χ8960 | ΔasdA18::TT araC $P_{BAD}$ c2 UK-1 | $5.5 \times 10^8$ | 5/5 |
| χ8289 | ΔasdA19::TT araC $P_{BAD}$c2 UK-1 | $1.0 \times 10^9$ | 4/4 |
| χ8958 | ΔasdA33 UK-1 | $6.4 \times 10^8$ | 5/5 |
| χ8844 | ΔendA2311 UK-1 | $8.6 \times 10^6$ | 0/4 |
| | | $8.6 \times 10^5$ | 2/4 |
| | | $8.6 \times 10^4$ | 2/2 |
| χ8844 | ΔendA2311 UK-1 | $3.0 \times 10^5$ | 0/2 |
| | | $3.0 \times 10^4$ | 1/2 |

TABLE 13-continued

Virulence of *S.* Typhimurium UK-1 mutants with single deletion or deletion-insertion mutations

| Strain | Genotype | CFU/dose | Survival/total |
|---|---|---|---|
| χ8989 | ΔendA19::araC $P_{BAD}$ lacI TT UK-1 | $1.0 \times 10^6$ | 0/5 |
| | | $1.0 \times 10^5$ | 2/5 |
| | | $1.0 \times 10^4$ | 2/5 |
| χ8831 | Δ(gmd-fcl)-26 UK-1 | $5.9 \times 10^5$ | 1/4 |
| | | $5.9 \times 10^4$ | 4/4 |
| | | $5.9 \times 10^3$ | 4/4 |
| | | $5.9 \times 10^2$ | 4/4 |
| χ8831 | Δ(gmd-fcl)-26 UK-1 | $8.6 \times 10^6$ | 0/4 |
| | | $8.6 \times 10^5$ | 0/4 |
| | | $8.6 \times 10^4$ | 0/4 |
| | | $8.6 \times 10^3$ | 1/4 |
| χ8650 | Δpmi-2426 UK-1 Nutrient Broth | $1.7 \times 10^9$ | 8/8 |
| | | $1.7 \times 10^8$ | 8/8 |
| | | $1.7 \times 10^7$ | 7/8 |
| | | $1.7 \times 10^6$ | 4/4 |
| | | $1.7 \times 10^5$ | 4/4 |
| χ8650 | Δpmi-2426 UK-1 Nutrient Broth + 0.5% mannose + 0.5% glucose | $1.5 \times 10^9$ | 3/8 |
| | | $1.5 \times 10^8$ | 7/8 |
| | | $1.5 \times 10^7$ | 7/8 |
| | | $1.5 \times 10^6$ | 4/4 |
| | | $1.5 \times 10^5$ | 4/4 |
| χ8882 | ΔrelA1123 UK-1 | $8.0 \times 10^7$ | 0/4 |
| | | $8.0 \times 10^6$ | 1/5 |
| | | $8.0 \times 10^5$ | 1/4 |
| | | $8.0 \times 10^4$ | 3/4 |
| | | $8.0 \times 10^3$ | 4/4 |
| χ8990 | ΔrelA196::araC $P_{BAD}$ lacI TT UK-1 | $1.0 \times 10^5$ | 1/5 |
| | | $1.0 \times 10^4$ | 4/5 |
| | | $1.0 \times 10^3$ | 5/5 |
| χ8923 | ΔsopB1925 UK-1 | $1.2 \times 10^7$ | 1/5 |
| | | $1.2 \times 10^6$ | 2/5 |
| | | $1.2 \times 10^5$ | 5/5 |
| | | $1.2 \times 10^4$ | 5/5 |

Strain χ9558 Δpmi-2426 Δ(gmd-fcl)-26 $\Delta P_{fur81}$::TT araC $P_{BAD}$ fur $\Delta P_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811 was used in Example 3 to deliver heterologous antigens such as the *S. pneumoniae* α-helical domain of the Rx1 PspA antigen encoded by pYA3634 either secreted into the extra-cellular environment or displayed on the vaccine carrier surface. Such approaches are based on observations that antigens localized on the surface of *Salmonella* cells or extracellularly secreted produce greater immune responses and protection (6, 11-13). In addition, secretion of heterologous antigens by RASV may decrease the toxicity of the protein to the bacterial vector, facilitate bacterial growth and antigen uptake by antigen-presenting cells (APC) and continuously stimulate the host immune system during the colonization of lymphatic tissues by *Salmonella*, so as to enhance the immune response against the heterologous antigens (5, 14).

*Streptococcus pneumoniae*, a gram-positive human pathogen, causes serious health problems, including community-acquired pneumonia, otitis media, meningitis, and bacteremia in persons of all ages. *S. pneumoniae* is a leading agent of childhood pneumonia worldwide, resulting in about 3 million deaths per year (15). The pneumococcal surface protein A (PspA) and pneumococcal surface protein C (PspC) have been considered as pneumococcal subunit vaccine candidates. PspA and PspC/Hic are expressed in all clinically isolated pneumococcal strains (16-18). Immune responses to PspA and PspC can protect mice against virulent *S. pneumoniae* challenge (6, 17, 19-23).

Toward this end of making a suitable vaccine to prevent pneumococcal disease in newborns and infants, we have introduced the improved $Asd^+$ vector pYA4088 (Example 1) that expresses at high level the longer Rx1 PspA specified by a codon-optimized sequence into χ9558. In addition to repeating the immunogenicity and protection studies described in Example 3 with superior results, we have demonstrated that this recombinant strain can be orally administered to newborn mice only a few hours old at doses of $10^8$ CFU or more with no deaths, disease symptoms or impairment in growth. Furthermore, when the χ9558(pYA4088) strain is inoculated intranasally into six-week old BALB/c mice, there is no colonization of the olfactory lobe or brain and no development of meningitis as found after intranasal inoculation of other *Salmonella* strains.

Based on the above successes, we have generated *S. Typhi* vaccine vectors as listed in Table 1 that have most all of the mutations present in χ9558. Since there has been a lack of success of recombinant attenuated *S. Typhi* vaccines derived from the widely used Ty2 strain, we have generated recombinant strains that have the rpoS mutation in the Ty2 strain replaced with the wild-type rpoS allele and have also derived a vaccine strain from the Chilean clinical isolate ISP1820. χ9639 is the *S. Typhi* Ty2 derived strain that is RpoS and has the genotype $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacI TT ΔaraE25 ΔtviABCDE10 ΔagfBAC811 ΔasdA33 and χ9640 is the Ty2 $RpoS^+$ derivative with the identical genotype as in χ9639. χ9633 is the *S. Typhi* ISP1820 derivative is $RpoS^+$ and has the geneotype $\Delta P_{crp527}$::TT araC $P_{BAD}$ crp $\Delta P_{fur81}$::TT araC $P_{BAD}$ fur Δpmi-2426 Δ(gmd-fcl)-26 ΔsopB1925 ΔrelA198::araC $P_{BAD}$ lacI TT ΔaraE25 ΔaraBAD23 ΔtviABCDE10 ΔagfBAC811 ΔasdA33. χ9639 and χ9640 do not have the ΔaraBAD23 mutation present in χ9633 since the parental Ty2 strain is already unable to use arabinose for growth or as a fermentation substrate. All three strains possess the attenuating ΔtviABCDE10 mutation that eliminates synthesis of the capsular Vi antigen that is unique to *S. Typhi* strains and is not made by *S. Typhimurium*. The Δ(gmd-fcl)-26 and ΔagfBAC811 mutations block synthesis of colanic acid and thin aggregative fimbriae (curli), respectively, that prevent formation of biofilms and preclude persistant colonization of gallstones in the gall bladder. The ΔsopB1925 mutation reduces the potential to induce fluid secretion in the intestinal track and also eliminates a means by which *Salmonella* suppresses induction of immune responses. Thus, this mutation increases the immunogenicity of these *S. Typhi* antigen delivery vaccine vectors.

We have also designed and constructed vaccine vector derivatives in *S. Paratyphi* A and note that χ9857 (Table 1) with the genotype $\Delta P_{crp527}$::TT araC $P_{BAD}$ crp $\Delta P_{fur81}$::TT araC $P_{BAD}$ fur Δpmi-2426 Δ(gmd-fcl)-26 ΔagfBAC811 ΔrelA198::araC $P_{BAD}$ lacI TT ΔsopB1925 ΔaraE25 ΔaraBAD23 ΔasdA33 has much the same properties as χ9558 and the three *S. Typhi* vaccine vectors described above.

REFERENCES FOR EXAMPLE 4

1. Curtiss R. III (2005) in Mucosal Immunology, ed. J. Mestecky M E L, W. Strober, J. Bienenstock, J. R. McGhee, and L. Mayer (ed) (Academic Press, San Diego).
2. Curtiss R, III, Zhang X, Wanda S Y, Kang H Y, Konjufca V, Li Y, Gunn B, Wang S, Scarpellini G, & Lee. I S (2007) in Virulence Mechanisms of Bacterial Pathogens, ed. K. A. Brogden F C M, N. Cornick, T. B. Stanton, Q. Zhang, L. K. Nolan, and M. J. Wannemuehler (ASM Press, Washington D.C.), pp. 297-313.
3. Curtiss R, III, Kelly S M, & Hassan J O (1993) Live oral avirulent *Salmonella* vaccines. Vet. Microbiol. 37: 397-405.
4. Doggett T A & Curtiss R, III (1992) Delivery of antigens by recombinant avirulent *Salmonella* strains. Adv. Exp. Med. Biol. 327: 165-173.
5. Spreng S, Dietrich G, & Weidinger G (2006) Rational design of *Salmonella*-based vaccination strategies. Methods 38: 133-143.
6. Kang H Y & Curtiss R, III, (2003) Immune responses dependent on antigen location in recombinant attenuated *Salmonella typhimurium* vaccines following oral immunization. FEMS Immunol. Med. Microbiol. 37: 99-104.
7. Chatfield S N, Charles I G, Makoff A J, Oxer M D, Dougan G, Pickard D, Slater D, & Fairweather N F (1992) Use of the nirB promoter to direct the stable expression of heterologous antigens in *Salmonella* oral vaccine strains: development of a single-dose oral tetanus vaccine. Biotechnology (NY) 10: 888-892.
8. Roberts M, Li J, Bacon A, & Chatfield S (1998) Oral vaccination against tetanus: comparison of the immunogenicities of *Salmonella* strains expressing fragment C from the nirB and htrA promoters. Infect. Immun. 66: 3080-3087.
9. Curtiss R, II, S-Y. Wanda, X. Zhang, B. Gunn. (2007) *Salmonella* vaccine vectors displaying regulated delayed in vivo attenuation to enhance immunogenicity, abstr. E-061, p 278. Abstr. 107th Gen. Meet. Am. Soc. Microbiol. American Society for Microbiology, Washington, D.C.
10. Wang S, Y. Li, G. Scarpellini, W. Kong, Curtiss R, III (2007) *Salmonella* vaccine vectors displaying regulated delayed antigen expression in vivo to enhance immunogenicity, Abstr. E-064, p 278. Abstr. 107th Gen. Meet. Am. Soc. Microbiol. American Society for Microbiology, Washington, D.C.
11. Kaufmann S H & Hess J (1999) Impact of intracellular location of and antigen display by intracellular bacteria: implications for vaccine development. Immunol. Lett. 65: 81-84.
12. Hess J, Gentschev I, Miko D, Wetzel M, Ladel C, Goebel W, & Kaufmann S H (1996) Superior efficacy of secreted over somatic antigen display in recombinant *Salmonella* vaccine induced protection against listeriosis. Proc. Natl. Acad. Sci. USA 93: 1458-1463.
13. Hess J, Grode L, Gentschev I, Fensterle J, Dietrich G, Goebel W, & Kaufmann S H (2000) Secretion of different listeriolysin cognates by recombinant attenuated *Salmonella typhimurium*: superior efficacy of haemolytic over non-haemolytic constructs after oral vaccination. Microbes Infect. 2: 1799-1806.
14. Gentschev I, Glaser I, Goebel W, McKeever D J, Musoke A, & Heussler V T (1998) Delivery of the p67 sporozoite antigen of *Theileria parva* by using recombinant *Salmonella dublin*: secretion of the product enhances specific antibody responses in cattle. Infect. Immun. 66: 2060-2064.
15. Greenwood B (1999) The epidemiology of pneumococcal infection in children in the developing world. Philos. Trans. R. Soc. Lond. B. Biol. Sci. 354: 777-785.
16. Iannelli F, Oggioni M R, & Pozzi G (2002) Allelic variation in the highly polymorphic locus pspC of *Streptococcus pneumoniae*. Gene 284: 63-71.
17. Brooks-Walter A, Briles D E, & Hollingshead S K (1999) The pspC gene of *Streptococcus pneumoniae* encodes a polymorphic protein, PspC, which elicits cross-reactive antibodies to PspA and provides immunity to pneumococcal bacteremia. Infect. Immun. 67: 6533-6542.
18. Hollingshead S K, Becker R, & Briles D E (2000) Diversity of PspA: mosaic genes and evidence for past recombination in *Streptococcus pneumoniae*. Infect. Immun. 68: 5889-5900.
19. Briles D E, Hollingshead S K, King J, Swift A, Braun P A, Park M K, Ferguson L M, Nahm M H, & Nabors G S (2000) Immunization of humans with recombinant pneumococcal surface protein A (rPspA) elicits antibodies that passively protect mice from fatal infection with *Streptococcus pneumoniae* bearing heterologous PspA. J. Infect. Dis. 182: 1694-1701.
20. Briles D E, Hollingshead S K, Nabors G S, Paton J C, & Brooks-Walter A (2000) The potential for using protein vaccines to protect against otitis media caused by *Streptococcus pneumoniae.* Vaccine 19 Suppl 1: S87-S95.
21. Briles D E, King J D, Gray M A, McDaniel L S, Swiatlo E, & Benton K A (1996) PspA, a protection-eliciting pneumococcal protein: immunogenicity of isolated native PspA in mice. Vaccine 14: 858-867.
22. Kang H Y, Srinivasan J, & Curtiss R, III, (2002) Immune responses to recombinant pneumococcal PspA antigen delivered by live attenuated *Salmonella enterica* serovar Typhimurium vaccine. Infect. Immun. 70: 1739-1749.
23. Nayak A R, Tinge S A, Tart R C, McDaniel L S, Briles D E, & Curtiss R, III, (1998) A live recombinant avirulent oral *Salmonella* vaccine expressing pneumococcal surface protein A induces protective responses against *Streptococcus pneumoniae.* Infect. Immun. 66: 3744-3751.

Example 5

Biological Containment

Live attenuated pathogens such as *Salmonella enterica* have been developed as homologous vaccines to protect against *Salmonella* infections and as carriers of heterologous antigens because of their capacity for efficient mucosal antigen delivery (1, 2). A variety of attenuating mutations and antibiotic-free balanced-lethal plasmid stabilization systems has been developed for this purpose (1, 3-5). However, biological containment systems are required to address the potential risk posed by the unintentional release of these genetically modified organisms into the environment, a subject of considerable concern (6, 7). Such release can lead to unintentional immunizations and the possible transfer of cloned genes that might represent virulence attributes in some cases. A number of mutations have been identified in *S. Typhimurium*, including shdA, misL and ratB, that reduce environmental shedding in mice without negatively influencing immunogenicity (8). While these mutations lead to a reduction in fecal shedding, it is not clear how long these strains will persist in the environment. Therefore, more effective systems need to be developed. Our approach has been to develop a biological containment system that will allow the vaccine strain time to colonize the host lymphoid tissues, a requirement for inducing a robust immune response (9, 10) and eventually lead to cell death by lysis, thus preventing spread of the vaccine strain into the environment.

The intracellular location of antigens in a recombinant attenuated *Salmonella* vaccine (RASV) can significantly influence the level of induced immune response upon immunization (11). Thus, if the antigen is retained in the cytoplasm and must be released by the actions of the immunized host, the immune response to the antigen is not as strong as when the antigen is secreted (11, 12). We hypothesize that the release of an expressed antigen by a RASV delivery strain within the lymphoid tissues of an immunized animal by programmed lysis would further enhance the immune response to the expressed antigen.

In this example, a RASV programmed bacterial lysis system vectoring the β-lactamase-PspA fusion protein was constructed. It was previously shown that this fusion protein is directed to the periplasm, but only about 10 to 20% is released into the extracellular environment (13). This new system combines the features of a previously described antigen expression plasmid with a novel programmed bacterial lysis system designed to release antigen into the host tissues to induce an efficacious immune response and to provide biological containment of the RASV.

Materials and Methods for Example 5

Bacterial Strains, Plasmids, Media, and Growth Conditions:

Bacterial strains and plasmids used in this example are listed in Tables 1 and 2, respectively. *S. Typhimurium* strains with asdA gene deletions were grown at 37° C. in LB broth or on LB agar (14) supplemented with 50 µg/ml DAP (3). Transformants containing araC $P_{BAD}$ asdA murA plasmids were selected on LB agar plates containing 0.2% arabinose. We used 0.02% arabinose in LB broth cultures to prevent pH changes in the medium caused by metabolism of arabinose that may affect the physiology of the bacterial cells. LB agar containing 5% sucrose, no sodium chloride, was used for sacB gene-based counterselection in allelic exchange experiments (15). For mouse inoculation, *Salmonella* strains were grown with aeration after inoculated with a 1/20 dilution of a non-aerated static overnight culture.

Strain Characterization:

Vaccine strains were compared with vector controls for stability of plasmid maintenance, arabinose-dependent growth and antigen synthesis. Molecular genetic attributes were confirmed by PCR with appropriate primers. Lipopolysaccharide (LPS) profiles of *Salmonella* strains were examined by described methods (16). For detection of PspA in RASV, 12 µl or 2 µl of cultures at an $OD_{600}$ of 0.8 were subjected to SDS-PAGE or immunoblot analysis, respectively.

Construction of a Regulated Programmed Lysis *S. Typhimurium* Vaccine Host-Vector System:

The $\Delta P_{murA7}$::araC $P_{BAD}$ murA deletion-insertion mutation was constructed by standard methods and introduced into wild-type strain χ3761 to yield χ8645. The ΔasdA19::araC $P_{BAD}$ c2 deletion-insertion mutation was introduced into χ8645 by P22HT int transduction from χ8290 (ΔasdA19::TT araC $P_{BAD}$ c2). As described in Example 4 and presented in Table 13, these two types of mutations render *Salmonella* totally avirulent. However, as noted in the Background to the Invention, the $\Delta P_{murA7}$::araC $P_{BAD}$ murA deletion-insertion mutation represents an example of a mutation conferring a regulated delayed attenuation phenotype since a strain with this mutation would be expected to grow and divide a generation or two before undergoing muramic acid-less death by lysis. The ΔendA2311, Δ(gmd-fcl)-26 and ΔrelA1123 mutations were added sequentially using suicide vectors (see Table 2) resulting in vaccine strain χ8937. The presence of mutations and absence of suicide vector sequences were confirmed by PCR using suitable primer sets (Table 14). The primers and steps used to construct plasmids are described as follows. The *E. coli* B/r araC $P_{BAD}$ activator-promoter was derived from pBAD18 (17). The *E. coli* K-12 araC $P_{BAD}$ activator-promoter was PCR amplified using primers araC-NsiI and EaraBAD-EcoRI from strain χ289. The SD-GTG mutation in pYA3530 was introduced into the asdA gene by PCR. The ATG-murA gene was amplified by PCR from *E. coli* K-12 strain χ289 (glnV42λ⁻T3ʳ) using primers EmurA-EcoRI 5' and EmurA-EcoRI 3', then the ATG start codon of the murA gene was changed to GTG by PCR. The P22 $P_R$ promoter was derived from plasmid pMEG104. The $P_{trc}$-5ST1T2-$P_{BR}$ ori fragment came from plasmid pYA3342. The fragment including in-frame fusion of the rPspA Rx1 (α-helical region of PspA from amino acid residue 3 to 257 of mature $PspA_{Rx1}$) to the β-lactamase signal sequence was derived from pYA3634 (18). Expression of the rPspA Rx1 antigen was verified by SDS-PAGE and western blot analysis with the anti-PspA monoclonal antibody Xi126 (19).

TABLE 14

Primers used in this example

| Primer Name | Sequence |
|---|---|
| A. Construction of plasmid pYA3681 | |
| *GTG asd* | |
| GTG asd 5' | cag gaa aaa aac gct gtg aaa aat gtt gg |
| GTG asd 3' | gtc ctt ttt ttg cga cac ttt tta caa cc |
| *araC P$_{BAD}$ GTG asd* | |
| araC-SmaI | cga ccc ggg atc gat ctg tgc ggt att tca cac cg |
| asd-SmaI | gca ccc ggg tcg aca gat cct tgg cgg cga gaa ag |
| *araC* P$_{BAD}$ (from χ289)* | |
| EaraC-NsiI | cca atg cat aat gtg cct gtc aaa tgg |
| EaraBAD-EcoRI | cgg aat tcg cta gcc caa aaa aac g |
| *MurA* | |
| EmurA-EcoRI 5' | cgg aat tct gag aac aaa cta aat gg |
| EmurA-EcoRI 3' | cgg aat tct tat tcg cct ttc aca cgc |
| *GTG murA* | |
| EMGTGRV-NcoI | cat gcc atg gag ctc ggt acc cgg gga t |
| EMGTG-NcoI-EcoRI | cat gcc atg gaa ttc tga gaa caa act aag tgg ata aat ttc gtg ttc ag |
| *P$_{trc}$-PBR ori cassette* | |
| P$_{trc}$-PmeI | agc ttt gtt taa acg gat ctt ccg gaa gac ctt cca ttc |
| XbaI-pBR | gct cta gac tgt cag acc aag ttt act cat a |
| *Synthetic rrfG TT* | |
| rrfG TT | aac tgc agt cta gat tat gcg aaa ggc cat cct gac gga tgg cct ttt tgt tta aac gga tcc gc |

| Primer Name | Sequence |
|---|---|
| B. Construction of plasmid pYA3685 | |
| NcoI-bla-PspA | cat gcc atg ggt att caa cat ttc cgt gtc gcc ctt att c |
| SmaI-TAA-PspA | tcc ccc ggg cta tta ttc tac att att gtt ttc T |
| C. Construction of suicide vectors | |
| *ΔrelA1123* | |
| relA C-SphI | aca tgc atg ccc aga tat ttt cca gat ctt cac |
| relA C-EcoRI | cgg aat tca ccc cag aca gta atc atg tag cgg |
| relA N-EcoRI | cgg aat tca gg gac cag gcc tac cga ag |
| relA N-BamHI | cgg gat ccg agg gcg ttc cgg cgc tgg tag aa |
| *Δ(gmd-fcl)-26* | |
| wcaF-XbaI | gct cta gat cct caa ata gtc ccg tta gg |
| wcaF-SmaI | tcc ccc ggg caa aat att gta tcg ctg g |
| gmm-SphI | gca cgc atg ctc agg cag gcg taa atc gct ct |
| gmm-XbaI | cct cta gac aat gtt ttt acg tca gga aga tt |
| *ΔendA2311* | |
| endAN- BamHI | cgg gat ccg cta cga atc cgc ctc aac |
| endAN-HindIII | ccc aag ctt agc aaa acg agc cgc aa cg |
| endAC-HindIII | ccc aag ctt cct aca cta gcg gga ttc ttg |
| endAC-SphI | aca tgc atg ccg cag cgc tca gag |

Strain Characterization:

Vaccine strains were compared with vector controls for stability of plasmid maintenance, arabinose-dependent growth and antigen synthesis. Molecular genetic attributes were confirmed by PCR with appropriate primers. Lipopolysaccharide (LPS) profiles of *Salmonella* strains were examined by described methods (16). For detection of PspA in RASV, 12 µl or 2 µl of cultures at an $OD_{600}$ of 0.8 were subjected to SDS-PAGE or immunoblot analysis, respectively.

Examination of Cell Lysis In Vitro:

Overnight cultures of strains were grown in LB broth supplemented with 0.002% arabinose. We used 0.002% arabinose to prevent the accumulation of arabinose within bacterial cells to allow us to detect cell lysis during the short time frame used for this experiment. Cultures were diluted 1:400 into fresh pre-warmed LB broth supplemented with or without 0.02% arabinose β-galactosidase activity in supernatant and cell-pellet fractions were assayed at indicated time points as described (20).

Colonization of Mice with the Regulated Programmed Lysis *Salmonella* Vaccine Strain:

Seven-week-old female BALB/c mice (3 mice for each time point) were deprived of food and water for 4 h before oral administration of *Salmonella* vaccine strains. These strains were grown with aeration in LB broth supplemented with 0.02% arabinose to an optical density at 600 nm ($OD_{600}$) of 0.85 from a non-aerated static overnight culture. $1.3 \times 10^9$ CFU of χ8937(pYA3681) in 20 µl of phosphate-buffered saline containing 0.01% gelatin (BSG) was orally administered to the mice at the back of the mouth with a pipette tip. Food and water were returned to the animals 30 to 45 min later. Mice were euthanized at indicated times and their Peyer's patches, spleens, and livers were collected aseptically. Tissues were homogenized and plated on LB agar with 0.2% arabinose to evaluate colonization and persistence, and onto LB agar plates without arabinose to screen for arabinose-independent mutants.

Immunization of Mice:

Groups of 5 seven-week-old female BALB/c mice were orally vaccinated with either $1.3 \times 10^9$ CFU *S. Typhimurium* vaccine strain χ8937(pYA3685) (expressing rPspA Rx1) or $1.1 \times 10^9$ CFU host-vector controls χ8937(pYA3681) as described above. A second oral dose of $1.2 \times 10^9$ CFU χ8937 (pYA3685) or $1.1 \times 10^9$ CFU χ8937(pYA3681) was given one week later. The immunized mice were monitored for 60 days for evidence of illness by observing them daily for evidence of diarrhea, ruffled (ungroomed) fur, or irritability. None of these symptoms of infection were observed in any of the mice. Blood was collected at weeks 2, 4, 6, 8 after immunization. Serum fractions were stored at −20° C. Vaginal secretion specimens were collected by wash with 50 µl BSG, solid material was removed by centrifugation and secretion samples were stored at −20° C. (21).

Antigen Preparation:

rPspA Rx1 protein and *S. Typhimurium* SOMPs were purified as described (13).

Enzyme Linked Immunosorbent Assay (ELISA):

The procedures used for detection of antibody have been described elsewhere (13, 22). Briefly, polystyrene 96-well flat-bottom microtiter plates (Nunc, Roskilde, Denmark) were coated with *S. Typhimurium* SOMPs (100 ng/well) or purified rPspA Rx1 (100 ng/well). Antigens suspended in sodium carbonate-bicarbonate coating buffer (pH 9.6) were applied with 100 µl volumes in each well. Vaginal secretions obtained from the same experimental group were pooled and diluted 1:10, and sera were diluted 1:1280 for detection of IgG and 1:400 for IgG1 and IgG2a, respectively. A 100 µl volume of diluted sample was added to individual wells in duplicate. Plates were treated with biotinylated goat anti-mouse IgG, IgG1, or IgG2a (Southern Biotechnology Inc., Birmingham) for sera and IgA for vaginal secretions.

Statistical Analysis:

Most data were expressed as means±standard error. The means were evaluated with One-way ANOVA and LSD tests for multiple comparisons among groups. $p<0.05$ was considered statistically significant.

Construction of a Regulated Programmed Lysis System.

Diaminopimelic acid (DAP) and muramic acid are essential components of the peptidoglycan layer of the bacterial cell wall (23). The asdA gene encodes an enzyme essential for DAP synthesis and the murA gene encodes the first enzyme in muramic acid synthesis (24, 25). To test the feasibility of an arabinose-regulated asdA-based lysis system, we introduced the ΔasdA16 deletion mutation into *S. Typhimurium* UK-1 resulting in strain χ8276. We then introduced plasmid pYA3450, which carries the asdA gene with an ATG start codon transcribed from the $P_{BAD}$ promoter which is activated by the AraC protein in the presence of arabinose (26), into χ8276 to yield χ8276(pYA3450). However, we found that growth of this strain was not arabinose-dependent, indicating that the level of residual transcription from the $P_{BAD}$ promoter in the absence of arabinose was sufficient to produce enough Asd for growth. In addition, χ8276(pYA3450) also retained wild-type virulence in mice. To reduce translational efficiency, we changed the asdA start codon from ATG to GTG, generating plasmid pYA3530. The GTG start codon significantly decreased the level of Asd expression (FIG. 37A). However, strain χ8276(pYA3530) still exhibited arabinose-independent growth and did not lyse in media devoid of arabinose. This problem was overcome by additional modifications described below, including addition of the murA gene.

Unlike lethal asdA deletions, which can be overcome by the addition of DAP to the growth medium, murA deletions, also lethal, cannot be overcome by nutritional supplements. Therefore, a conditional-lethal murA mutation was created by replacing the chromosomal murA promoter with the araC $P_{BAD}$ activator-promoter. We introduced the $\Delta P_{murA7}$::araC $P_{BAD}$ murA mutation into wild-type *S. Typhimurium* resulting in strain χ8645. To evaluate the predicted arabinose-dependent murA transcription, the strain was inoculated with and without arabinose into several media containing nutritional components that are likely to be encountered by a vaccine strain, including 1% rodent chow, 1% chicken feed or 1% chicken breast meat in minimal medium (27). As expected, growth was not only dependent on the presence of arabinose, but bacterial titers dropped in the absence of arabinose, indicative of cell lysis (FIG. 37B). These results confirm that the $\Delta P_{murA7}$::araC $P_{BAD}$ murA mutation confers a regulated delayed attenuation phenotype since some growth was possible prior to onset of death by lysis.

We combined the asdA and murA systems, providing redundant mechanisms to ensure cell death. However, as described above, we first needed to reduce the amount of Asd produced from our plasmid. The araC $P_{BAD}$ promoter-activator we used for all the previously described constructs was derived from an *E. coli* B/r strain (17). We discovered that when we substituted the araC $P_{BAD}$ promoter-activator from *E. coli* K-12 strain χ289, transcription from the plasmid was more tightly regulated and arabinose-dependent growth was achieved. We then inserted a murA gene in between the $P_{BAD}$ promoter and the asdA gene to further decrease the transcription level of asdA. Finally, we introduced P22 $P_R$, a C2-regulated promoter, with opposite polarity at the 3' end of the asd gene to interfere with transcription of the plasmid asdA and murA genes and to direct synthesis of antisense mRNA to block translation of mRNA transcribed from these genes during programmed lysis when arabinose is absent. Transcription terminators (TT) flank all plasmid domains so that expression in one domain does not affect the transcriptional activities of any other domain. The resulting plasmid was designated pYA3681 (FIG. 14).

Figure 38A:
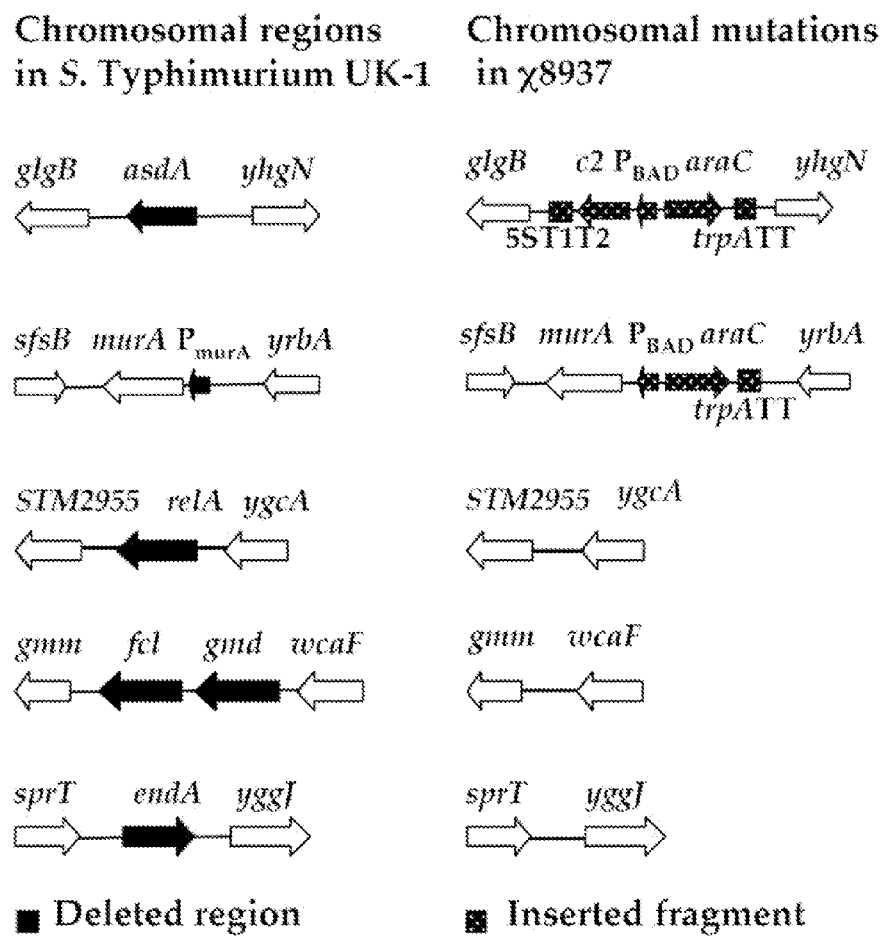
Figure 38B:
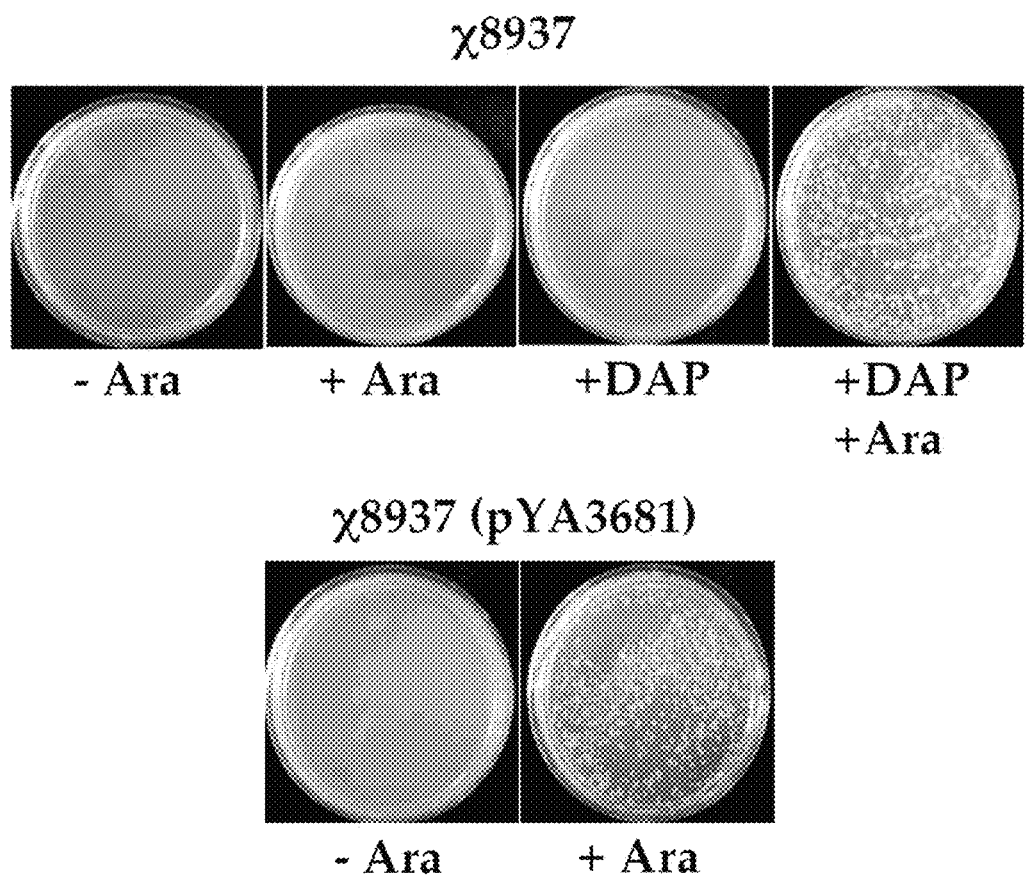

The host strain for this system was constructed by introducing a ΔasdA mutation into the ΔP$_{murA7}$::araC P$_{BAD}$ murA mutant strain χ8645. To facilitate regulation of P22 P$_R$ in plasmid pYA3681, we introduced the ΔasdA19 deletion/insertion mutation, in which the P22 phage C2 repressor gene under transcriptional control of the P$_{BAD}$ promoter was inserted into the ΔasdA16 deletion (FIG. 38A). Three additional mutations designed to enhance lysis and facilitate antigen delivery were also included in this strain (FIG. 38A). The Δ(gmd-fcl)-26 mutation deletes genes encoding enzymes for GDP-fucose synthesis, thereby precluding the formation of colanic acid, a polysaccharide made in response to stress associated with cell wall damage (28). This mutation was included because we have observed that under some conditions, asdA mutants can survive if they produce copious amounts of colanic acid (29). Therefore, by deleting the genes required for colanic acid synthesis, we circumvent this possibility. The ΔrelA1123 mutation uncouples cell wall-less death from dependence on protein synthesis to further ensure that the bacteria do not survive in vivo or after excretion and to allow for maximum antigen production in the face of amino acid starvation resulting from a lack of aspartate semi-aldehyde synthesis due to the asdA mutation (30, 31). This regulated lysis system S. Typhimurium strain also has potential for use as a DNA vaccine delivery vector. Therefore, we included a ΔendA mutation which eliminates the periplasmic endonuclease I enzyme (32), to increase plasmid survival upon its release into the host cell. The resulting strain, χ8937 (ΔasdA19::araC P$_{BAD}$ c2 ΔP$_{murA7}$::araC P$_{BAD}$ murA Δ(gmd-fcl)-26 ΔrelA1123 ΔendA2311), requires both arabinose and DAP for growth (FIG. 38B).

pYA3681 was introduced into S. Typhimurium χ8937. Growth of the resulting strain χ8937(pYA3681) required arabinose (FIG. 38B). The plasmid was stably maintained for 50 or more generations when grown in the presence of arabinose and DAP. In the presence of arabinose, the plasmid-encoded copies of asdA and murA and the chromosomally encoded copies of murA and c2 are transcribed from their respective P$_{BAD}$ promoters, allowing for bacterial growth and repression of the P22 P$_R$ promoter by C2 (FIG. 39). In the absence of arabinose, the P$_{BAD}$ promoters cease to be active, with no further synthesis of Asd and MurA or C2. The concentrations of Asd, MurA and C2 decrease due to cell division. The decreased concentration of Asd and MurA leads to reduced synthesis of DAP and muramic acid and imbalanced synthesis of the peptidoglycan layer of the cell wall. As the C2 concentration drops, P22 P$_R$ is derepressed resulting in P$_R$-directed synthesis of anti-sense mRNA which blocks translation of residual asdA and murA mRNA. These concerted activities lead to cell lysis.

Regulated Programmed Lysis and Biological Containment Properties after Colonization of Lymphoid Tissues.

The regulated lysis vaccine strain χ8937(pYA3681) grew well in LB broth supplemented with 0.02% arabinose, but began to die after one hour of incubation in LB broth without arabinose (FIG. 40A). To evaluate cell lysis, release of the cytoplasmic enzyme β-galactosidase into culture supernatants was used as an indicator. The atrB13::MudJ allele which directs constitutive expression of β-galactosidase (13) was transduced into S. Typhimurium wild-type as a non-lysis control and into vaccine strain χ8937, resulting in strains χ9379 and χ9380, respectively. We then introduced plasmid pYA3681 into χ9380 to yield χ9380(pYA3681). The ratio of β-galactosidase activity in the supernatant (released β-galactosidase) or cell pellet (retained cell-associated β-galactosidase) versus total β-galactosidase activity (supernatant plus cell pellet) indicated the extent of cell lysis. Release of β-galactosidase by strain χ9380(pYA3681) occurred only in medium lacking arabinose (FIG. 40B). Conversely, the amount of cell-associated β-galactosidase decreased over time when χ9380(pYA3681) was grown in medium without arabinose, but no decrease was seen in media containing arabinose. β-galactosidase release was not observed when the wild-type control strain χ9379 was grown without arabinose. These results are consistent with our expectations for the arabinose-regulated cell lysis phenotype.

To evaluate virulence, BALB/c mice were orally inoculated with doses in excess of $10^9$ CFU of the host-vector strain χ8937(pYA3681), a dose 50,000 times the LD$_{50}$ of the wild-type parent strain, χ3761. During the 30 days observation period after dosing, we observed no deaths or signs of illness in any of the mice. Colonization by strain χ8937(pYA3681) was evaluated in eight-week old female mice orally inoculated with $10^9$ CFU. The strain transiently colonized lymphoid tissues (FIG. 40C) and no bacteria were recovered by four weeks post-inoculation. No arabinose-independent Salmonella mutants were recovered at any time during this experiment. These results indicate that a wild-type Salmonella strain engineered with this programmed lysis system is attenuated and is efficiently cleared from the host following colonization of lymphoid tissues.

Construction of the rPspA Rx1-Expressing Plasmid.

Figure 41C:
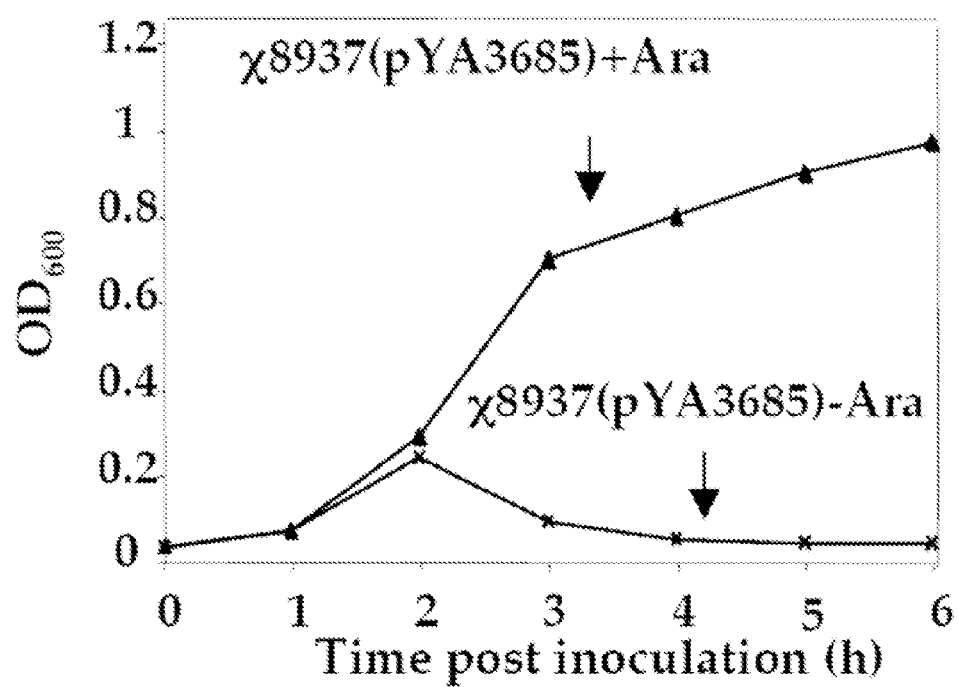

It was previously shown that a recombinant protein fusing the first 35 amino acids of β-lactamase to the α-helical region of PspA (rPspA Rx1) is highly immunogenic when delivered by a recombinant avirulent S. Typhimurium (13). We utilized a similar fusion to evaluate the ability of our regulated lysis strain to deliver an antigen to host tissues. A DNA fragment encoding the in-frame fusion of the β-lactamase leader sequence from plasmid pBR322 to rPspA Rx1 (α-helical region of PspA from amino acid residue 3 to 257 of mature PspA$_{Rx1}$) was inserted into pYA3681 to yield pYA3685 (FIG. 41A). The nucleic acid encoding the antigen is constitutively expressed from the P$_{trc}$ promoter. Production of rPspA Rx1 in S. Typhimurium χ8937(pYA3685) grown in media with arabinose was detected by western blot analysis with the anti-PspA monoclonal antibody (FIG. 41B), and we confirmed that the fraction of antigen secreted to the periplasm was similar to that reported previously (13). The strain did not grow on LB agar without arabinose and expression of the recombinant antigen did not interfere with programmed lysis when χ8937(pYA3685) was grown in LB broth without arabinose (FIG. 41C).

Immune Responses in Mice after Oral Immunization with the Regulated Programmed Lysis Host-Vector System.

The antibody responses to Salmonella outer membrane proteins (SOMPs) and to the foreign antigen rPspA Rx1 in sera and vaginal secretions of the immunized mice were measured (FIG. 42). The maximum serum IgG response to PspA was observed at 6 weeks and responses at all time points were significantly greater than in the control group, where no response was detected (p<0.05) (FIG. 42A). The anti-SOMP IgG response was slower to develop in mice vaccinated with χ8937(pYA3685) than in the control group, with significant differences between groups at weeks 2 and 6 (p<0.05). This could be a result of differences in the ability of the two strains to survive systemically brought about by the antigen load in χ8937(pYA3685). However, both χ8937(pYA3681) and χ8937(pYA3685) elicited equivalent anti-SOMP IgA responses in vaginal secretions, with no significant differences between groups after two weeks, while rPspA Rx1-specific IgA was detected only in samples from mice immunized with vaccine strain χ8937(pYA3685) (p<0.05) (FIG. 42B).

IgG Isotype Analyses

The type of immune responses to SOMPs and the rPspA Rx1 were further examined by measuring the levels of IgG isotype subclasses IgG2a and IgG1 (FIG. 43). The Th1-helper cells direct cell-mediated immunity and promote class switching to IgG2a, and Th2 cells provide potent help for B-cell antibody production and promote class switching to IgG1 (33). IgG2a isotype dominant responses were observed for the SOMP antigens indicating that the vaccine induced a strong cellular immune response against Salmonella. In contrast to the strong Th1 responses to SOMPs, a Th1- and Th2-type mixed response was observed for the rPspA Rx1 antigen (FIG. 43).

Discussion of Example 5

Our long-term goals are to develop RASVs for oral administration, protecting humans and animals against a variety of mucosal pathogens. Immunization with live *Salmonella* vaccines introduces the potential for release of the bacteria into the environment, possibly leading to unintended immunizations. The objective of this example was to construct and evaluate a biological containment system that would be consistent with the requirements for efficacious vaccination, in particular, colonization of host lymphoid tissues for an amount of time sufficient for optimal antigen delivery. RASV are capable of delivering a variety of bacterial, viral, fungal, and parasitic antigens thereby eliciting humoral and cellular immunity in the immunized host (1, 34-36). Immune responses, especially antibody responses, are enhanced when the antigen is released into the extracellular environment as opposed to being sequestered in the bacterial cytoplasm (11, 12).

These considerations led us to develop a RASV containment/delivery system capable of releasing antigen by cell lysis within the immunized animal. We utilized the tightly regulated araC $P_{BAD}$ activator-promoter system to construct a strain/plasmid system that directs regulated arabinose-dependent, programmed lysis. An arabinose-regulated cell lysis system should not be undermined by release into the environment, where stream and groundwater levels of arabinose are in the sub-micromolar range (37). Studies in our laboratory have shown that in our *Salmonella* strains, $P_{BAD}$ is not activated by 13 µM (0.0002%) arabinose (S. Wang, personal communication).

We chose the asdA gene as the primary driver of cell lysis, since it is known that, unlike some lethal mutations, a lack of Asd not only results in cell death, but also cell lysis (38). To further facilitate containment, we also included the murA gene in our scheme. The plasmid copy of murA was derived from *E. coli* to reduce the potential for recombination with the *S. Typhimurium* chromosomal copy, a possible escape strategy for the cell. Finally, we included the P22 $P_R$ promoter driving transcription of anti-sense mRNA to silence any residual mRNA transcripts that may arise from the plasmid copies of asdA or murA in the absence of arabinose. In our system, the C2 repressor, which inhibits P22 $P_R$ transcription, is only synthesized in the presence of arabinose. Thus, in the arabinose-limiting environment in host tissues, C2 is not made and anti-sense mRNA is transcribed.

The data of this example show that the system we have devised results in cell lysis in the absence of arabinose and clearance of the strain from host tissues. More importantly, our strain was fully capable of delivering a test antigen and inducing a robust immune response comparable to that of a vaccine strain without this containment system, thereby demonstrating that this system has all the features required for biological containment of a RASV. This plasmid-host system of regulated delayed lysis in vivo depends on regulated delayed shut off in the synthesis of enzymes essential for peptidoglycan synthesis results in complete avirulence in the complete absence of any other attenuating mutations. As such this is another means to confer a regulated delayed attenuation phenotype.

This system can be modified to suit a number of different needs for antigen delivery. We can add mutations that will delay lysis to allow additional time for the RASV to colonize host tissues. For example, we have deleted additional genes from the arabinose operon to prevent arabinose metabolism, thereby maintaining an effective arabinose concentration in the cytoplasm for a longer period of time. Strains with these arabinose gene deletions are currently being evaluated for use as antigen or DNA delivery vectors.

The regulated lysis system also has potential as a DNA vaccine vector delivery system. An asdA deletion mutant of *Shigella flexneri* has been used to deliver DNA in animals (39), but the immune responses were weak, presumably because the cells did not persist long enough to efficiently invade host tissues. A ΔasdA mutant of *E. coli* has also been used to deliver DNA in tissue culture (40). However, our system, whether used for *Shigella*, *E. coli* or *Salmonella* (41), provides the vaccine with adequate time to establish itself in host tissues before lysis occurs, thereby enhancing the probability of efficient DNA delivery.

Lastly, this system could be modified to provide effective biological containment for genetically engineered bacteria used for a diversity of purposes in addition to vaccines

REFERENCES FOR EXAMPLE 5

1. Cárdenas L, Clements J D (1992) Oral immunization using live attenuated *Salmonella* spp. as carriers of foreign antigens. *Clin. Microbiol. Rev.* 5: 328-42.
2. Curtiss R, III (2005) in Mucosal Immunology, eds Mestecky J et al (Academic Press, San Diego), pp 1009-1037.
3. Nakayama K, Kelly S M, Curtiss R, III (1988) Construction of an Asd+ expression-cloning vector: stable maintenance and high level expression of cloned genes in a *Salmonella* vaccine strain. *Bio/Technology* 6: 693-697.
4. Galen J E et al. (1999) Optimization of Plasmid Maintenance in the Attenuated Live Vector Vaccine Strain *Salmonella typhi* CVD 908-htrA. *Infect. Immun.* 67: 6424-6433.
5. Garmory H S et al. (2005) Antibiotic-free plasmid stabilization by operator-repressor titration for vaccine delivery by using live *Salmonella enterica* serovar *Typhimurium*. *Infect. Immun.* 73:2005-2011.
6. Davison J E (2002) Towards safer vectors for the field release of recombinant bacteria. *Environ. Biosafety Res.* 1: 9-18.
7. Kotton C N, Hohmann E L (2004) Enteric pathogens as vaccine vectors for foreign antigen delivery. *Infect. Immun.* 72: 5535-5547.
8. Abd El Ghany M et al. (2007) Candidate live, attenuated *Salmonella enterica* serotype *Typhimurium* vaccines with reduced fecal shedding are immunogenic and effective oral vaccines. *Infect. Immun.* 75: 1835-1842.
9. Curtiss R, Iii, Doggett T, Nayak A, Srinivasan J (1996) in *Essentials of mucosal immunology*, eds Kagnoff M F, Kiyono H (Academic Press, San Diego), pp 499-511.
10. Medina E, Guzman C A (2001) Use of live bacterial vaccine vectors for antigen delivery: potential and limitations. *Vaccine* 19: 1573-1580.
11. Kang H Y, Curtiss R, III (2003) Immune responses dependent on antigen location in recombinant attenuated *Salmonella typhimurium* vaccines following oral immunization. *FEMS Immunol. Med. Microbiol. Lett.* 37: 99-104.
12. Hess J et al. (1996) Superior efficacy of secreted over somatic antigen display in recombinant *Salmonella* vaccine induced protection against listeriosis. *Proc. Natl. Acad. Sci. U.S.A.* 93: 1458-63.
13. Kang H Y, Srinivasan J, Curtiss R, III (2002) Immune responses to recombinant pneumococcal PspA antigen delivered by live attenuated *Salmonella enterica* serovar *Typhimurium* vaccine. *Infect. Immun.* 70: 1739-49.
14. Bertani G (1951) Studies on lysogenesis. I. The mode of phage liberation by lysogenic *Escherichia coli*. *J. Bacteriol.* 62: 293-300.
15. Gay P, Le Coq D, Steinmetz M, Berkelman T, Kado C I (1985) Positive selection procedure for entrapment of insertion sequence elements in gram-negative bacteria. *J. Bacteriol.* 164:918-921.

16. Hitchcock P J, Brown T M (1983) Morphological heterogeneity among *Salmonella* lipopolysaccharide chemotypes in silver-stained polyacrylamide gels. *J. Bacteriol.* 154: 269-277.
17. Guzman L M, Belin D, Carson M J, Beckwith J (1995) Tight regulation, modulation, and high-level expression by vectors containing the arabinose $P_{BAD}$ promoter. *J. Bacteriol.* 177: 4121-4130.
18. Curtiss R, III et al. (2007) in *Virulence Mechanisms of Bacterial Pathogens*, eds Brogden K A (ASM Press, Washington D.C.), pp 297-313.
19. McDaniel L S, Scott G, Kearney, J F, Briles D E (1984) Monoclonal antibodies against protease sensitive pneumococcal antigens can protect mice from fatal infection with *Streptococcus pneumoniae*. *J. Exp. Med.* 160: 386-397.
20. Miller J H (1972) in Experiments in Molecular Genetics (Cold Spring Harbor Lab. Press, Plainview).
21. Zhang X, Kelly S M, Bollen W S, Curtiss R, III (1997) Characterization and immunogenicity of *Salmonella typhimurium* SL1344 and UK-1 crp and cdt deletion mutants. *Infect. Immun.* 65: 5381-5387.
22. Nayak A R et al. (1998) A live recombinant avirulent oral *Salmonella* vaccine expressing pneumococcal surface protein A induces protective responses against *Streptococcus pneumoniae*. *Infect. Immun.* 66: 3744-3751.
23. Van Heijenoort J (1994) in *Bacterial Cell Wall*, eds Ghuysen J M, Hackenbeck R (Elsevier, Amsterdam), pp 39-54.
24. Black S, Wright N G (1955) Aspartic β-semialdehyde dehydrogenase and aspartic β-semialdehyde. *J. Biol. Chem.* 213: 39-50.
25. Brown E D, Vivas E I, Walsh C T, Kolter R (1995) MurA (MurZ), the enzyme that catalyzes the first committed step in peptidoglycan biosynthesis, is essential in *Escherichia coli*. *J. Bacteriol.* 177: 4194-4197.
26. Lee N L, Gieliw W O, Wallace R G (1981) Mechanism of araC autoregulation and the domains of two overlapping promoters, $P_C$ and $P_{BAD}$, in the L-arabinose regulatory region of *Escherichia coli*. *Proc. Natl. Acad. Sci. U.S.A.* 78: 752-756.
27. Curtiss R, III (1965) Chromosomal aberrations associated with mutations to bacteriophage resistance in *Escherichia coli*. *J. Bacteriol.* 89: 28-40.
28. Whitfield C (2006) Biosynthesis and assembly of capsular polysaccharides in *Escherichia coli*. *Annu Rev. Biochem.* 75: 39-68.
29. Curtiss R, III et al. (1976) in *Recombinant Molecules: Impact on Science and Society*, eds Beers R F, Jr, Bassett E G (Raven Press, New York), pp 45-56.
30. Török I, Kari C (1980) Accumulation of ppGpp in a relA mutant of *Escherichia coli* during amino acid starvation. *J. Biol. Chem.* 255: 3838-3840.
31. De Groote M A, Testerman T, Xu Y, Stauffer G, Fang F C (1996) Homocysteine antagonism of nitric oxide-related cytostasis in *Salmonella typhimurium*. *Science* 272: 414-417.
32. Dubnau D (1999) DNA uptake in bacteria. *Annu. Rev. Microbiol.* 53: 217-244.
33. Spellberg B, Edwards J E, Jr (2001) Type 1/type 2 immunity in infectious diseases. *Clin. Infect. Dis.* 32: 76-102.
34. Formal S B et al. (1981) Construction of a potential bivalent vaccine strain: introduction of *Shigella sonnei* form I antigen genes into the galE *Salmonella typhi* Ty21a typhoid vaccine strain. *Infect. Immun.* 34: 746-750.
35. Curtiss R, III et al. (1994) Recombinant *Salmonella* vectors in vaccine development. *Dev Biol Stand.* 82: 23-33.
36. Curtiss R, III (2002) Bacterial infectious disease control by vaccine development. *J. Clin. Investig.* 110: 1061-1066.
37. Cheng X, Kaplan L A (2003) Simultaneous analyses of neutral carbohydrates and amino sugars in freshwaters with HPLC-PAD. *J. Chromatogr. Sci.* 41: 434-438.
38. Loessner H, Endmann A, Rhode M, Curtiss R, III, Weiss S (2006) Differential effect of auxotrophies on the release of macromolecules by *Salmonella enterica* vaccine strains. *FEMS Microbiol. Lett.* 265: 81-88.
39. Sizemore D R, Branstrom A A, Sadoff J C (1997) Attenuated bacteria as a DNA delivery vehicle for DNA-mediated immunization. *Vaccine* 15: 804-7.
40. Grillot-Courvalin C, Goussard S, Huetz F, Ojcius D M, Courvalin P (1998) Functional gene transfer from intracellular bacteria to mammalian cells. *Nat. Biotechnol.* 16: 862-866.
41. Loessner H, Weiss S (2004) Bacteria-mediated DNA transfer in gene therapy and vaccination. *Expert. Opin. Biol. Ther.* 4: 157-68

Example 6

Preparation of Vaccine Product

Master seed and working seed banks of each vaccine organism in separate vials have been prepared for frozen storage in vegetable-based cryopreservative. Purity of the seed banks was established following standard operating procedures Full characterization of the seed banks includes phenotypic evaluation on selective media, PCR, antigenic agglutination, colorimetric assays, LPS gel analysis, production of catalase to reveal the RpoS phenotype and demonstrated to reflect the correct and anticipated phenotype and genotype of the three vaccine strains. Antibiotic sensitivity testing has confirmed that these strains are sensitive to ciprofloxacin, ampicillin, ceftriaxone, trimethoprim/sulfamethoxazole (Table 15). Ampicillin, ciprofloxacin, ceftriaxone and trimethoprim/sulfamethoxazole are typically tested for minimum inhibitory concentrations (MICs) for *Salmonella*.

TABLE 15

Minimum inhibitory concentrations of antibiotics for RASV-Sp strains.

| | *Salmonella* Typhi strain (μg/ml) | | |
|---|---|---|---|
| Antibiotic | χ9633 (pYA4088) | χ9639 (pYA4088) | χ9640 (pYA4088) |
| ampicillin | <2 | <2 | <2 |
| ciprofloxacin | <0.25 | <0.25 | <0.25 |
| ceftriaxone | <0.25 | <1 | <1 |
| trimethroprim-sulfamethoxazole | <20 | <20 | <20 |

The vials of vaccine Working Seed are maintained frozen in designated boxes and entered into the freezers' inventory logs. The Working Seed vials are stored in duplicate freezers maintained between −65° and −75° C. Vaccine stability is determined by titration of representative vials of each of the RASV-Sp Master and Working Seed banks at 0, 3, 6, 12, 24 months and every 6 months thereafter. Table 16 shows the stability of the RASV-Sp Master Seed and Working Seed stocks as determined by quarterly viable titration.

TABLE 16

| Stability of RASV-Sp Master Seed (MS) and Working Seed (WS) banks | | | | | | |
|---|---|---|---|---|---|---|
| Date of | χ9633(pYA4088) CFU/ml | | χ9639(pYA4088) CFU/ml | | χ9640(pYA4088) CFU/ml | |
| Titer | MS | WS | MS | WS | MS | WS |
| Nov. 17, 2007 | $1.95 \times 10^{10}$ | $3.20 \times 10^{10}$ | $1.60 \times 10^{10}$ | $2.63 \times 10^{10}$ | $1.76 \times 10^{10}$ | $3.00 \times 10^{10}$ |
| Feb. 22, 2008 | $1.98 \times 10^{10}$ | $3.40 \times 10^{10}$ | $1.66 \times 10^{10}$ | $3.20 \times 10^{10}$ | $1.69 \times 10^{10}$ | $3.53 \times 10^{10}$ |
| May 17, 2008 | $1.62 \times 10^{10}$ | $4.23 \times 10^{10}$ | $1.58 \times 10^{10}$ | $3.08 \times 10^{10}$ | $1.54 \times 10^{10}$ | $3.01 \times 10^{10}$ |
| Sep. 8, 2008 | $1.44 \times 10^{10}$ | $2.70 \times 10^{10}$ | $1.11 \times 10^{10}$ | $3.55 \times 10^{10}$ | $1.43 \times 10^{10}$ | $1.30 \times 10^{10}$ |

Live, whole bacteria constitute the unformulated active immunogenic substance that when fermented in permissive conditions will be formulated with sterile PBS pH 7.4 to produce the final vaccine product.

The final vaccine products will be prepared on the day of administration to the volunteers in the clinical trial to optimize immunogenicity and fitness of the strains.

Briefly, a 37° C. overnight culture of each vaccine strain is prepared from a frozen vial of RASV-Sp Working Seed. The next morning, the cultures are subcultured 1:20 into fresh, prewarmed media and shaken gently at 37° C. to an optical density (OD) at 600 nm ideally between 2.0-2.3. The cells are harvested by centrifugation and resuspended gently in sterile PBS to the final dosage prescribed. Data collected from production runs of the vaccine dosages conducted prior to the start of the clinical trial will be used to correlate the $OD_{600}$ of the final PBS cell suspension to CFU/ml (GCGH-ASU-SOP-096-00, see CMC section of the IND application). This data will be used to confirm the target range of the final dosage prior to releasing the vaccine dosages to the clinic.

Table 17 shows the production record of three consecutive dosages of the RASV-Sp inocula for producing 10-ml final liquid dosages of live vaccine for oral administration to adult volunteers. The data provide assurance that the RASV-Sp vaccine inocula can be consistently produced within the target range of the dosage required on the start date of the clinical trial.

TABLE 17

| RASV-Sp final dosage preparation record | | | | |
|---|---|---|---|---|
| Production date | RASV-Sp Strain | Harvest $OD_{600}$ | Hours to culture harvest | Vaccine Dosage/ 10 ml[1] |
| Aug. 11, 2008 | χ9633(pYA4088) | 2.83 | 4 h 37 min | $2.14 \times 10^7$ |
| | χ9639(pYA4088) | 2.20 | 4 h 24 min | $3.04 \times 10^7$ |
| | χ9640(pYA4088) | 2.38 | 4 h | $2.30 \times 10^7$ |
| Aug. 19, 2008 | χ9633(pYA4088) | 2.11 | 3 h 58 min | $1.14 \times 10^7$ |
| | χ9639(pYA4088) | 2.08 | 4 h 40 min | $2.22 \times 10^7$ |
| | χ9640(pYA4088) | 2.14 | 3 h 57 min | $1.29 \times 10^7$ |
| Aug. 21, 2008 | χ9633(pYA4088) | 2.15 | 3 h 48 min | $1.37 \times 10^7$ |
| | χ9639(pYA4088) | 2.01 | 4 h 30 min | $2.09 \times 10^7$ |
| | χ9640(pYA4088) | 2.14 | 3 h 42 min | $1.51 \times 10^7$ |

[1]Each lot produced passed purity and identity testing following standard operating procedures.

Formulation

The human fasting stomach can reach pH levels as low as 1.5. Low pH tolerance of the RASV-Sp strains was tested after suspending cells in medium at pH 7, 4.5 or 3 for 1 hour at 37° C. Viability of the samples after incubation was assessed by plate counts. Data shown are the average number of CFU/ml recovered. In these studies, we included the parental wild-type *S. Typhi* strains χ3744 (ISP1820), χ3769 (Ty2) and χ8438 (Ty2 $RpoS^+$). We also included an attenuated *S. Typhi* ISP1820 strain (χ8110) that had been used in a previous trial in which reactogenicity was observed. In all cases, the vaccine constructions χ9633(pYA4088), χ9639(pYA4088) and χ9640(pYA4088) were more acid sensitive than their wild-type parents or than the attenuated ISP1820 strain χ8110 (FIG. 44).

The PBS used as the diluent is unlikely to provide sufficient buffering activity. Since the stomach pH rises dramatically upon ingestion of food, we plan to increase the stomach pH of volunteers by administering Ensure nutrition shakes prior to administering the vaccine dosages. FIG. 45 shows the stability after one hour of the RASV-Sp vaccines suspended in three different flavors of Ensure® nutrition shake.

Stability of RASV-Sp Strains

The RASV-Sp vaccine dosages maintain a stable titer suspended in the PBS at room temperature for a period of less than 2 hours. FIG. 46 shows that the initial cell suspensions hold titers near $1\times10^{10}$ CFU for up to an hour and then maintain stably after dilution in PBS for an additional hour. The RASV-Sp final dosages will be administered to volunteers within two hours of resuspension in PBS to ensure optimal immunogenicity.

Example 7

Nonclinical Studies

It should be noted that *S. Typhi* is an obligate human pathogen and no animal models are available for a full evaluation of the *S. Typhi*-based vaccines. Inoculation of newborn mice with high doses of wild-type virulent strains of *S. Typhi*, even when modified to express the *S. Typhimurium* virulence plasmid needed by *S. Typhimurium* to cause disseminated disease in mice, fails to infect or cause any signs of disease or any weight loss. We constructed, in parallel of the engineering of *S. Typhi, S. Typhimurium* strains bearing essentially identical mutations as the *S. Typhi*-based vaccines for pre-clinical safety and immunogenicity evaluation in mice.

Safety of *S. Typhimurium* χ9558(pYA4088) in Newborn Mice.

A relevant safety test was to evaluate the safety in newborn and infant mice of *S. Typhimurium* strain χ9558(pYA4088) [(Δpmi-2426 Δ(gmd-fcl)-26 $\Delta P_{fur81}$::TT araC $F_{BAD}$ fur $\Delta P_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811], which carries mutations nearly identical to the *S. Typhi* vaccine strains and the same plasmid to enable PspA expression. Newborn mice are highly susceptible to wild-type *S. Typhimurium* infection and succumb at oral doses lower than 100 CFU.

Newborn and infant mice were orally inoculated with 5 μl containing $1\text{-}3\times10^8$ CFU of the strain χ9558(pYA4088) at 0, 2, 4 or 7 days of age. Table 18 shows the health status and survivors over a 10-week period. No disease symptoms or death occurred in any of the mice at any time after oral inoculation with over $10^6$ times the wild-type $LD_{50}$.

TABLE 18

Safety of χ9558(pYA4088) in newborn/infant BALB/c mice

| Age of mice (days) | Oral dosage CFU | Health status 10 weeks post-vaccination | Survivors/total |
|---|---|---|---|
| 0 | $1.0 \times 10^8$ | Healthy | 9/9 |
| 2 | $1.2 \times 10^8$ | Healthy | 12/12 |
| 4 | $3.0 \times 10^8$ | Healthy | 11/11 |
| 7 | $3.5 \times 10^8$ | Healthy | 13/13 |

The oral $LD_{50}$ for the wild-type parent strain χ3761 is less than 100 CFU.

Distribution of *S. Typhimurium* χ9558(pYA4088) in Tissues of Newborn Mice

Colonization of tissues from newborn and infant mice was evaluated 3 and 7 days after oral inoculation with the *S. Typhimurium* strain χ9558(pYA4088). Homogenized tissue samples from euthanized mice were spread onto agar plates and CFU/g enumerated. In addition, samples of homogenized tissues were also subjected to enrichment culture to reveal presence or absence of *Salmonella*. Table 19 shows the tissue distribution of the attenuated *S. Typhimurium* strain χ9558(pYA4088) in newborn mice to 7 days of age.

The levels of colonization of the intestinal tract by *S. Typhimurium* χ9558(pYA4088) were quite good. In this regard, it should be noted that isolation of Peyer's patch tissue in these infant mice to determine *Salmonella* titers is not feasible. Titers in liver and spleen were lower than expected but this was interpreted as an indication of the safety of χ9558(pYA4088) for newborn and infant mice.

These data in Table 16 and Table 17 show that the attenuated *S. Typhimurium* vaccine strain with mutations nearly identical to the *S. Typhi* vaccine strains is safe for newborn and infant mice. Therefore, it can be extrapolated from these data that these mutations provide an equivalent level of safety to the *S. Typhi* vaccines.

TABLE 20

Safety of *S. Typhi* χ9633(pYA4088), χ9639(pYA4088) and χ9640(pYA4088) in newborn mice

| Strain | Oral dosage (CPU) | Health status 6-weeks post-inoculation | Survivors/total |
|---|---|---|---|
| χ9633(pYA4088) | $1.2 \times 10^9$ | healthy | 3/3 |
| χ9639(pYA4088) | $6.0 \times 10^8$ | healthy | 3/3 |
| χ9640(pYA4088) | $7.5 \times 10^8$ | healthy | 3/3 |

Distribution of *S. Typhi* Strains in Tissues of Newborn Mice.

Although *S. Typhi* can invade murine cells with low efficiency (compared to *S. Typhimurium*), they do not survive well or multiply and quickly decline in titer following oral administration. For this reason, the ability of *S. Typhi* to colonize (or not colonize) murine tissues is not necessarily indicative of the ability of the strain to colonize human tissue. However, the distribution of *S. Typhi* cells in tissues from newborn mice was evaluated as an addition to the data from the *S. Typhimurium* RASV-Sp strain χ9558(pYA4088) (see Table 19).

Colonization was assessed 3 and 7 days after oral inoculation with the *S. Typhi* vaccine and wild-type strains. The attenuated ISP1820 strain used in a previous trial (χ8110) and the typhoid vaccine strain Ty21a were also included for comparative purposes. Homogenized tissue samples from euthanized mice were spread onto agar plates and CFU/g enumerated. In addition, samples of homogenized tissues were also subjected to enrichment culture to reveal the presence or absence of *Salmonella*. FIG. 47 shows the distribution of the *S. Typhi* vaccine and wild-type strains in the intestine, spleen and liver tissues 3 and 7 days after inoculation. Data shown are the geometric means±standard deviations of two separate colonization experiments.

TABLE 19

Colonization data of χ9558(pYA4088) in tissues (CFU/gram) 3 and 7 days post inoculation in infant mice

| Age of Mice (day) | Oral dosage (CFU) | Number of mice | Spleen (CFU/g) Day 3 | Spleen (CFU/g) Day 7 | Liver (CFU/g) Day 3 | Liver (CFU/g) Day 7 | Intestine* (CFU/g) Day 3 | Intestine* (CFU/g) Day 7 |
|---|---|---|---|---|---|---|---|---|
| 0 | $1.0 \times 10^8$ | 1 | <10 | $5.9 \times 10^3$ | <10 | $6.8 \times 10^3$ | $2.7 \times 10^6$ | $6.3 \times 10^4$ |
|  |  | 2 | <10 | $7.3 \times 10^3$ | <10 | $5.0 \times 10^4$ | $5.9 \times 10^5$ | $3.1 \times 10^5$ |
|  |  | 3 | <10 | $2.4 \times 10^3$ | $3.0 \times 10^3$ | $2.5 \times 10^4$ | $1.6 \times 10^6$ | $2.4 \times 10^5$ |
| 2 | $1.2 \times 10^8$ | 1 | $0 \ll 10$ | $1.1 \times 10^3$ | $2.9 \times 10^3$ | $1.1 \times 10^3$ | $6.1 \times 10^5$ | $5.0 \times 10^5$ |
|  |  | 2 | $0 \ll 10$ | $1.4 \times 10^3$ | $5.9 \times 10^2$ | $1.7 \times 10^3$ | $2.3 \times 10^5$ | $5.4 \times 10^3$ |
|  |  | 3 | $2.5 \times 10^3$ | $1.7 \times 10^3$ | $5.7 \times 10^3$ | $3.3 \times 10^3$ | $2.7 \times 10^6$ | $3.1 \times 10^5$ |
| 4 | $3.0 \times 10^8$ | 1 | $3.3 \times 10^3$ | <10 | $5.2 \times 10^3$ | <10 | $1.1 \times 10^8$ | $5.4 \times 10^6$ |
|  |  | 2 | <10 | $8.5 \times 10^3$ | $2.4 \times 10^3$ | $8.0 \times 10^3$ | $1.1 \times 10^8$ | $1.8 \times 10^7$ |
|  |  | 3 | $8.1 \times 10^4$ | $2.7 \times 10^3$ | $1.2 \times 10^4$ | $2.1 \times 10^4$ | $7.1 \times 10^6$ | $2.8 \times 10^7$ |
| 7 | $3.5 \times 10^8$ | 1 | <10 | <10 | $2.4 \times 10^2$ | <10 | $7.0 \times 10^6$ | $1.5 \times 10^7$ |
|  |  | 2 | <10 | <10 | $5.0 \times 10^2$ | <10 | $1.1 \times 10^7$ | $6.0 \times 10^6$ |
|  |  | 3 | <10 | <10 | $3.2 \times 10^2$ | <10 | $1.8 \times 10^7$ | $3.9 \times 10^6$ |

*: Entire small intestine and contents

Evaluation of Safety of *S. Typhi* Vaccine Strains in Young Mice.

Newborn mice (<24 h) were each orally inoculated with 10 µl containing $1 \times 10^9$ CFU of each of the *S. Typhi* vaccine strains. Table 20 shows the health status and survivors over a six-week period. No disease symptoms or death occurred in any of the mice at any time after oral inoculation.

These data demonstrate that the mutant vaccine candidate *S. Typhi* strains colonize mouse tissues no better than the wild-type parental strains. The additional strains Ty21a and χ8110 showed similarly poor levels of colonization. These results were not unexpected, since mice are unable to support an infection with *S. Typhi* strains even when infected soon after birth.

Reactogenicity of PBS Diluent with and without *S. Typhi*

The general safety test as directed in 21 CFR 610.11 was performed to address concerns raised of the possibility that residual media components might be reactogenic in volunteers.

The RASV-Sp PBS cell suspensions were filter-sterilized and these cell-free solutions, along with sterile PBS and sterile growth medium were injected intraperitonneally into mice and guinea pigs. The weight, health and general well-being of study animals were monitored daily for 7 days. At the conclusion of the study, animals were euthanized and necropsied, and observable differences of the internal organs (including alterations in size, shape, coloration and vascularization) were photographed for comparative analysis.

All animals survived for the duration of the general safety test (7 days after injection). No unexpected or nonspecific responses were observed with any of the RASV-Sp strains as compared to the PBS controls. The average weights for each group throughout the course of the study are shown in FIGS. 48A and B. For each group, the animals weigh the same or more on Day 7 than they did on the day of injection.

No diminishment of the health and general well-being, and no change in the character of internal organs of mice and guinea pigs were noted.

These data provide evidence to support the conclusion that the trace amount of residual media components present in the final vaccine preparation is unlikely to be reactogenic in human volunteers.

Immunogenicity Assessment of *S. Pneumoniae* Antigen

The immunogenicity of the PspA antigen of *S. pneumoniae* was assessed using the Asd$^+$ plasmid vector pYA3634. The pYA3634 plasmid is a precursor of pYA4088 and encodes aa 3-257 of the PspA-Rx1 protein (pYA4088 spans aa 3-285) (See FIG. 49). Cultures of the RASV-Sp strains grown in the presence of arabinose synthesize the LacI repressor at high levels to repress transcription from $P_{trc}$ on the Asd$^+$ plasmid vector pYA3634 to minimize synthesis of PspA until after immunization when the vaccine strain is already colonizing internal lymphoid tissues. 0.05% arabinose and 0.2% mannose were used to prepare *S. Typhimurium* χ9558(pYA3634) (Δpmi-2426 Δ(gmd-fcl)-26 $\Delta P_{fur81}$::TT araC $P_{BAD}$ fur $\Delta P_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811) to evaluate relative IgG response to PspA-Rx1 expressed from χ9558(pYA3634) in BALB/c mice compared to χ9088(pYA3634) ($\Delta P_{fur33}$::TT araC $P_{BAD}$ fur Δpmi-2426 Δ(gmd-fcl)-26 ΔasdA33) and χ8133 (pYA3634) (Δcya-27 Δcrp-27 ΔasdA16). Groups of 7-week-old female BALB/c mice were orally administered approximately $10^9$ CFU of each strain and boosted with the same dose at 8 weeks. Blood was obtained by mandibular vein puncture with heparinized capillary tubes at biweekly intervals. ELISA was performed to determine IgG antibody titers to PspA, *S. Typhimurium* LPS. FIG. 50 shows total serum IgG titers to the PspA protein and to *S. Typhimurium* LPS.

Four weeks after the second oral immunization, mice were challenged in two experiments with approximately $5\times10^4$ CFU of *S. pneumoniae* WU2. Both experiments gave similar results, and the data have been pooled for presentation and analysis. This challenge dose resulted in the deaths of 100% of the unvaccinated mice, with a mean time to death of 2-3 days.

The percent protection rate and the number of days of survival after challenge with virulent *S. pneumoniae* strain WU2 are shown in FIG. 51. Seventy-one percent of the mice immunized with χ9558(pYA3634) were protected from pneumococcal challenge. This is significantly higher than the level of protection observed for the Δcya Δcrp strain χ8133 (pYA3634) (p=0.0063).

Passive Transfer of Pneumococcal Immunity.

An experiment to demonstrate passive-antibody transfer of protective immunity to pneumococcal challenge was conducted in mice. Mice were orally inoculated with $1\times10^9$ CFU of a RASV-Sp strain containing either the empty vector pYA3493 or the vector pYA3634 and boosted with the same strain and dose 8 weeks after primary immunization. At week 12, sera from immunized mice were collected and pooled.

Naïve, syngeneic BALB/c mice received 100 μl in the tail vein of undiluted serum from pooled serum of immunized mice. All groups were challenged intraperitoneally 12 h later with *S. pneumoniae* WU2. The percent survival of mice receiving pooled serum was assessed 15 days after challenge with *S. pneumoniae* WU2. Table 21 shows the percent survival of mice that were protected by passive-antibody transfer from challenge with more than 250 $LD_{50}$ doses of the virulent *S. pneumoniae* WU2.

Sera from mice immunized with *S. Typhimurium* χ9558 (pYA3634) passively protected 100% of mice challenged with over 250 $LD_{50}$ doses of the virulent *S. pneumoniae* WU2.

TABLE 21

Passive transfer of pneumococcal immunity by serum from donors immunized with *S.* Typhimurium vaccines expressing PspA

| Donors immunized with vaccine strain | Strain expresses PspA | No. of mice | Volume of the donor serum (μl) administered IV | % survival of pooled serum recipients[1] |
|---|---|---|---|---|
| Saline control | — | 5 | 100 | 0 |
| χ8133(pYA3493) Δcya-27 Δcrp-27 ΔasdA16 | No | 5 | 100 | 0 |
| χ9088(pYA3493) Δpmi-2426 Δ(gmd-fcl)-26 $\Delta P_{fur81}$::TT araC $P_{BAD}$ fur ΔasdA33 | No | 5 | 100 | 0 |
| χ9558(pYA3493) Δpmi-2426 Δ(gmd-fcl)-26 $\Delta P_{fur33}$::TT araC $P_{BAD}$ fur $\Delta P_{crp527}$::TT araC $P_{BAD}$ crp ΔasdA27::TT araC $P_{BAD}$ c2 ΔaraE25 ΔaraBAD23 ΔrelA198::araC $P_{BAD}$ lacI TT ΔsopB1925 ΔagfBAC811 | No | 5 | 100 | 0 |
| χ8133(pYA3634) | Yes | 5 | 100 | 80 |
| χ9088(pYA3634) | Yes | 5 | 100 | 100 |
| χ9558(pYA3634) | Yes | 5 | 100 | 100 |

[1]Mice were challenged IP 12 h after receiving donor immune serum with >250 $LD_{50}$ doses of *S. pneumoniae* WU2

Immunogenicity of χ9633(pYA4088), χ9639(pYA4088), and χ9640(pYA4088) in Female 6- to 7-Week-Old BALB/c Mice.

The ability of the *S. Typhi* RASV-Sp strains administered intranasally to BALB/c to induce serum antibody titers to PspA was assessed (GCGH-ASU-SOP-074-00, see CMC section of the IND application). Mice were inoculated intranasally with 10 μl of approximately $10^9$ CFU of a RASV strain with either the empty vector pYA3493 or the PspA+ vector pYA4088. Sera were collected 2, 4, 6 and 8 weeks after vaccination and anti-PspA, -LPS and -OMP IgG titers determined by ELISA.

It should be noted that this type of immunogenicity assay has been used by others even though we believe it is of marginal value. This is because *S. Typhi* (wild-type or mutant) is unable to successfully invade and persist in murine cells or lymphoid tissues as is *S. Typhimurium*. FIGS. 52A-C show the total IgG response to PspA, LPS and OMP from sera collected over an 8-week period after intranasal administration of the RASV strains with the PspA plasmid pYA4088 or the empty vector pYA3493. All RASV strains harboring either pYA3493 or pYA4088 equally induced significant anti-LPS and anti-OMP IgG titers as soon as two weeks post-inoculation. PspA IgG titers gradually increased over the eight-week period from mice administered the RASV-Sp strains. Although the group size was small, the RASV-Sp Ty2 RpoS$^+$ strain χ9640(pYA4088) induced a slightly higher anti-PspA IgG titer than the ISP1820 derivative χ9633(pYA4088). Complement Deposition Assay and Passive Protection of Mice Using Serum from Human Vaccine Volunteers.

Sera from the vaccine volunteers which test positive for PspA will be evaluated for their ability to passively protect mice from pneumococcal infection. Passive transfer of protective immunity to pneumococcal challenge will be demonstrated by transfer of pre- and post-immune serum and the antibodies it contains to naive unimmunized mice followed by intravenous challenge with virulent S. pneumoniae.

As an additional measure of the protective capacity of the anti-PspA response in volunteers, sera may be further evaluated by the complement deposition assay. This test will quantitatively evaluate the ability of antibody in pre- and post-immune sera to facilitate deposition of complement C3 onto S. pneumoniae. Immunization of humans with PspA has been shown to lead to elevated levels of antibody to PspA, increases in the ability of the sera to mediate complement deposition on S. pneumoniae, and increases in the ability of human sera to protect mice from fatal pneumococcal infection. The deposition of complement on S. pneumoniae has been shown to correlate inversely with the ability of S. pneumoniae to cause invasive disease.

Example 8

Non-Clinical Assessment of Safety

Additional safety tests were conducted to address concerns raised regarding the apparent lack of adequate safety data for the ISP1820 derivative strain χ9633(pYA4088). Another ISP1820 derivative, χ8110 Δcfs), (Δcya-27 Δcrp-pabA-40 Δcfs), was shown to be safe in Phase I clinical trials. To bridge the previous human data with χ8110 to the present vaccine candidate χ9633(pYA4088), additional safety data were generated to demonstrate that χ9633(pYA4088) is equivalent to or more attenuated than χ8110 as evaluated by survival in human blood and peripheral blood monocytes. Comparisons to the Ty21a vaccine Vivotif® which is the gold standard for live Salmonella vaccine safety were also included in the following non-clinical assessment of safety.
Survival of RASV-Sp Strains in Human Blood The bactericidal effects of heat-treated and untreated whole blood were compared by incubating the RASV-Sp strains and wild-type S. Typhi counterparts in the presence of normal whole blood (GCGH-ASU-SOP-081-01, see CMC section of the IND application).

Approximately 1×10$^6$ CFU of each RASV-Sp strain, χ8110, Ty21a and their wild-type counterparts were added to duplicate 1.5 ml blood aliquots from volunteers. Blood was collected in accordance with the ASU human use protocol #0804002872. Survival of the Salmonella strains was assayed in blood that had been heat inactivated (HI) by incubation at 55° C. for one hour prior to inoculation, or in untreated, active (A) blood. Viability of the Salmonella strains was measured by plating samples on permissive media 0, 3, 6 and 18 hours after inoculation. FIG. 53 shows the geometric mean of the CFU recovered of at least 3 trials±the standard deviation.

The RASV-Sp candidates are severely attenuated in their ability to survive in whole human blood as compared to wild-type S. Typhi and χ8110. Vaccine strain levels drop below the threshold of detection within 3 hours and the strains did not regrow at the later timepoints of the assay. This is in contrast to χ3744, χ3769 and χ8110, which are not only present at significantly higher levels, but also replicate in the blood at the later timepoints of the assay. The RASV-Sp candidates, including the ISP1820 derivative χ9633 (pYA4088), are as attenuated as Ty21a and more attenuated than the ISP1820 RASV χ8110 used in a previous clinical trial.
Sensitivity of RASV-Sp Strains to Native Guinea Pig Serum Complement.

The bactericidal properties of guinea pig serum complement were determined for the RASV-Sp strains and their wild-type counterparts. Guinea pig complement was used for this assay because of its high level of bacteriocidal activity.

The S. Typhi strains χ3744 (wild-type ISP1820), χ3769 (wild-type Ty2), χ8438 (RpoS$^+$ wild-type Ty2), χ9633 (pYA4088), χ9639(pYA4088) and χ9640(pYA4088) were prepared following GCGH-ASU-SOP-062-01 Preparation of RASV-Sp dosages for adult volunteers. The sensitivity of the cells to complement was assayed following GCGH-ASU-SOP-091-00 Resistance of RASV-Sp strains to guinea pig complement. Strains were assayed in PBS only, complement (purified from guinea pig serum) only, and complement with anti-S. Typhi O-antigen D$_1$ opsonizing antibody. Reactions were incubated for 3 hours at 37° C., and then the viability of the Salmonella strains was measured by plating on permissive media. Data shown in FIG. 54 represent the average CFU/ml.

Both the wild-type Salmonella Typhi strains and the RASV-Sp strains are sensitive to killing by complement in the presence of Salmonella Typhi O-antigen specific D$_1$ antibody. The vaccine strains are killed to a moderately higher degree than the wild-type strains. In the absence of S. Typhi-specific antibody, the wild-type strains are resistant to complement-mediated killing. However, the RASV-Sp strains exhibit a high level of sensitivity to complement-mediated killing even in the absence of opsonizing antibody.
Survival of RASV-Sp Strains in Peripheral Human Mononuclear Cells.

Rubin et al. demonstrated that in patients with typhoid fever, circulating S. Typhi cells are associated with mononuclear cell-platelet fraction of whole blood. Because this serovar does not typically cause disease in mice or other animals, the development of rapid ex-vivo assays using freshly elutriated peripheral blood mononuclear cells (PBMCs) have been demonstrated as reliable tools for determining attenuation of S. Typhi for vaccine research and development.

Figure 55A:
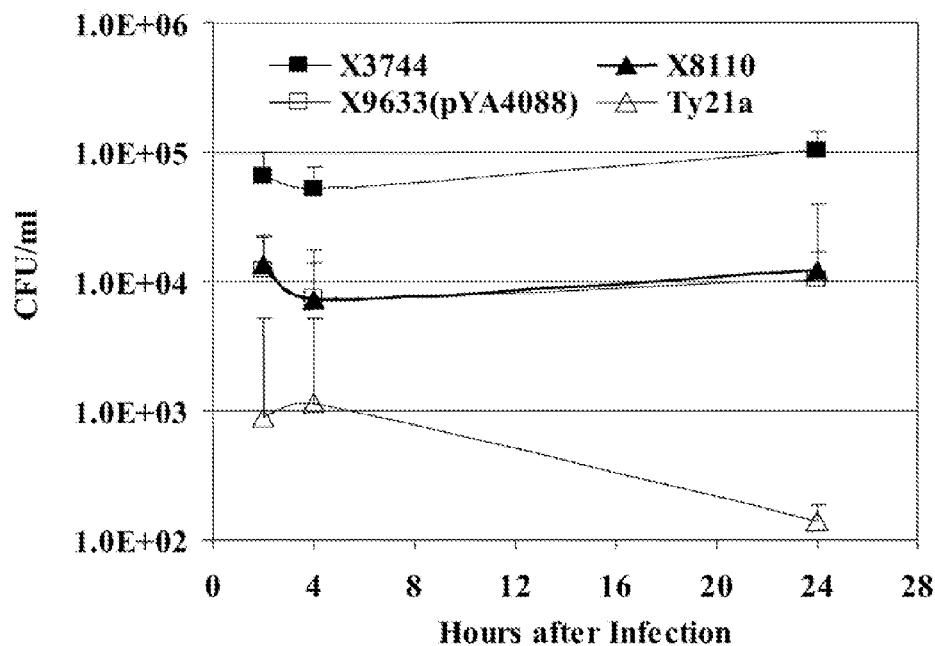
Figure 55B:
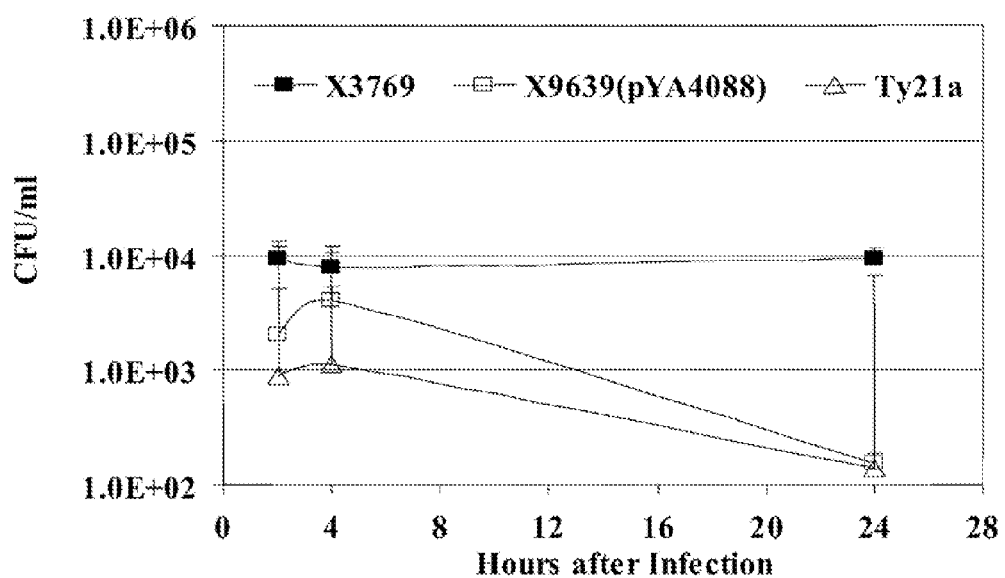
Figure 55C:
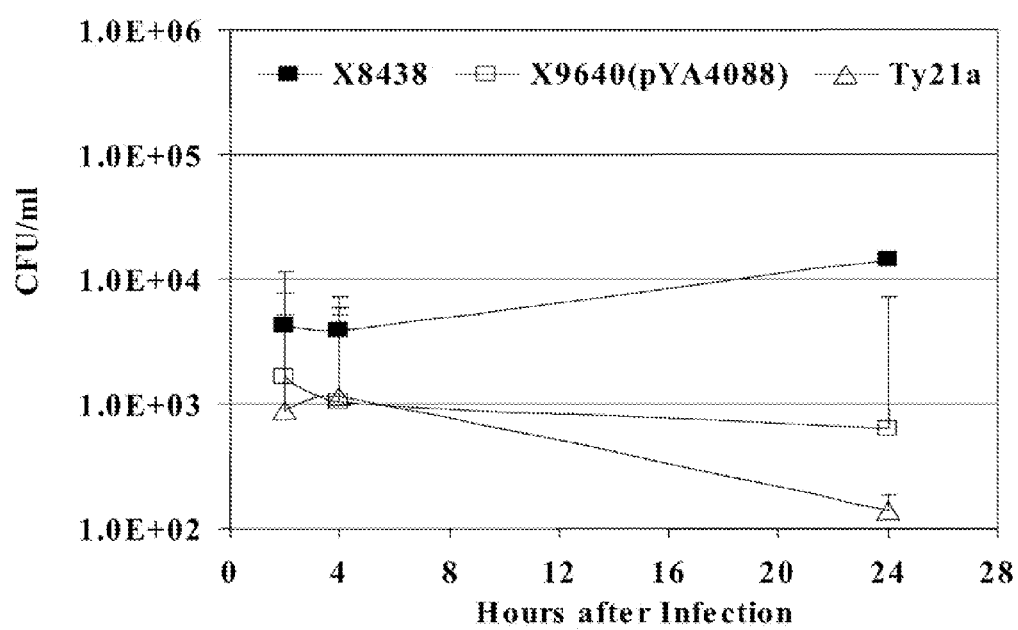

PBMCs derived from blood of 3 different volunteers were elutriated following GCGH-ASU-SOP-082-01 Survival of RASV-Sp strains in peripheral human mononuclear cells. After incubation of PBMCs and bacteria in 24-well culture plates for 1, 3 and 23 additional hours, PBMCs were lysed and cell lysates were plated onto permissive media to determine viable CFU. Survivability of the RASV-Sp strains χ9633 (pYA4088), χ9639(pYA4088) and χ9640(pYA4088) compared to χ8110 (ISP1820 Δcya-27 Δcrp-pabA-40 Δcfs), Ty21a and to wild-type S. Typhi χ3744 (wild-type ISP1820), χ3769 (wild-type Ty2), χ8438 (RpoS$^+$ wild-type Ty2) are shown in FIGS. 55A-C. The data shown are the geometric means±standard deviations of three separate assays.

The peripheral blood mononuclear cell assay used to measure the invasion and persistence of the S. Typhi strains readily distinguished between virulent S. Typhi and the attenuated RASV-Sp strains and Ty21a, known to survive poorly both in vitro and in vivo. The wild-type Ty2 and ISP1820 strains invaded and persisted at a significantly higher rate than the RASV-Sp strains and Ty21a (p<0.05).

Both χ9639(pYA4088) and Ty21a were the least fit to survive and persist in PBMCs compared to the wild-type Ty2 RpoS$^-$ strain (p=0.0022 and 0.0022 at 24 hours, respectively), which may be a consequence of possessing the rpoS mutation. These results are consistent with the RpoS$^-$ phenotype in that null mutants are susceptible to killing by macrophage and exhibit increased sensitivity to environmental stress.

The ISP1820 derivative χ9633(pYA4088) was equivalent to χ8110 in surviving within PBMCs at 2, 4 and 24 hours (p=1.00, 0.505 and 0.878, respectively) and both strains were significantly reduced in their ability to invade and persist within PBMCs compared to the wild-type ISP1820 at all timepoints.

Together these data demonstrate further safety of the RASV-Sp strains. Additionally the ability of the ISP1820 derivative χ9633(pYA4088) to invade to a lesser degree than the wild-type ISP1820 but persist at a low level in PBMCs demonstrates that this strain is not compromised to reach host target cells to deliver the PspA for antigen processing.

Taken collectively, the RASV-Sp strains are adequately attenuated due to their extreme sensitivity to complement-mediated killing, their poor survival in whole human blood and in fresh elutriated peripheral blood mononuclear cells. The ISP1820 derivative χ9633(pYA4088), although sufficiently attenuated by the data presented here, may display the best attributes for antigen presentation to the appropriate antigen-presenting cells of the host immune system.

RASV-Sp Shedding and Survival in Human Stool

A consequence of oral administration of live *Salmonella* vaccine organisms is that they can be shed transiently in the stool of vaccine recipients. An important aspect of the potential impact of environmental release of a live vaccine is to evaluate the duration, rate of shedding and the survival rate. Endeavors to develop live vaccines that reduce shedding have been met with variable success. The licensed live oral typhoid vaccine, serovar Typhi Ty21a, is shed at low rates in the stools of most vaccinees for 1 to 4 days. Ideally, it is desirable to limit the number of genetically modified microorganisms entering the environment, without decreasing vaccine immunogenicity or efficacy.

An initial assessment of the duration of shedding following oral inoculation was conducted in 6-week old adult mice. The *S. Typhi* RASV-Sp strains χ9633(pYA4088), χ9639 (pYA4088), and χ9640(pYA4088), the *S. Typhimurium* RASV-Sp counterpart χ9558(pYA4088) and the *S. Typhi* wild-type strains χ3744, χ3769 and χ8438 were grown. Approximately $1\times10^9$ CFU of each strain was administered orally to groups of 3 mice. Shedding was monitored for 6 days after inoculation by homogenizing fecal pellets and plating on selectively differential media. The data shown in Table 22 represent the average number of CFU/ml detected for each group. None of the *S. Typhi* strains (wild-type or RASV-Sp) were detected more than 3 hours following the inoculation. The *S. Typhimurium* RASV-Sp strain χ9558(pYA4088) was also not detected after the initial day of inoculation. These data indicate that significant levels of vaccine organism shedding are confined to the initial day of immunization. Low-level shedding (less than $10^3$ CFU/ml) may occur for a slightly longer period.

TABLE 22

Fecal shedding of RASV-Sp strains and S. Typhi wild-type strains following oral inoculation of mice.

| Strain | 3 Hours (CFU/ml) | 18 Hours (CFU/ml) | Day 2 (CFU/ml) | Day 4 (CFU/ml) | Day 6 (CFU/ml) |
|---|---|---|---|---|---|
| χ9558(pYA4088) | $1.7\times10^7$ | $<10^3$ | $<10^3$ | $<10^3$ | $<10^3$ |
| χ3744 | $1.7\times10^7$ | $<10^3$ | $<10^3$ | $<10^3$ | $<10^3$ |
| χ9633(pYA4088) | $8.0\times10^6$ | $<10^3$ | $<10^3$ | $<10^3$ | $<10^3$ |
| χ3769 | $1.0\times10^7$ | $<10^3$ | $<10^3$ | $<10^3$ | $<10^3$ |
| χ9639(pYA4088) | $1.6\times10^7$ | $<10^3$ | $<10^3$ | $<10^3$ | $<10^3$ |
| χ8438 | $1.8\times10^7$ | $<10^3$ | $<10^3$ | $<10^3$ | $<10^3$ |
| χ9640(pYA4088) | $1.6\times10^6$ | $<10^3$ | $<10^3$ | $<10^3$ | $<10^3$ |

Limit of detection for this assay was $10^3$ CFU/ml

Since *S. Typhi* is unable to efficiently attach to and invade to the intestinal epithelial cells of mice, the results of the previous study may not accurately represent the duration of shedding from a human host. In order to gather data about the competitive fitness of the strains in the human intestinal environment, the RASV-Sp and wild-type *S. Typhi* strains were evaluated in anaerobic human stool samples. Viability of the *S. Typhi* strains was assessed by plating dilutions onto selective media 1, 3, 7 and 10 days after inoculation of fresh stool suspensions with approximately $1\times10^8$ CFU/ml. Inoculated samples were incubated at 37° C. in an anaerobic environment. The limit of detection for recovering the *S. Typhi* strains was $10^4$ CFU/ml.

FIG. 56 shows the survival of the *S. Typhi* wild-type χ3744 (wild-type ISP1820), χ3769 (wild-type Ty2), χ8438 ($RpoS^+$ wild-type Ty2) and RASV-Sp strains χ9633(pYA4088), χ9639(pYA4088) and χ9640(pYA4088) in human stool over the 10-day period of evaluation. The RASV-Sp strains were not recoverable 24 hours after inoculation of the stool samples and remained below the threshold of detection ($10^4$ CFU) throughout the remainder of the study. The wild-type strains, however, persisted through day 3 at measurable titers above $10^4$ CFU and then fell below the level of detection through day 10 of the study.

These data represent the worst case scenario as the RASV-Sp strains were prepared in this study to allow the regulated-delayed expression of the near wild-type attributes that would endow the strains with characteristics that would make them most fit for survival. In reality, once ingested by volunteers, the strains will eventually lose and no longer display these protective attributes due to the absence of exogenous arabinose and mannose and would rapidly succumb to the harsh and competitive environment present in stool.

Survival of *S. Typhi* in Canal Water, Chlorinated Water and Sewage

The aim of this study was to compare the survivability of the RASV-Sp strains and *S. Typhi* wild-type counterparts in several conditions that mimic the environment and to address concerns regarding the impact of releasing live attenuated, genetically-modified organisms into the environment.

Three environmental conditions were prepared to serve as test material for assessing survivability of the *S. Typhi* strains. Chlorinated water was prepared to contain approximately 3 to 5 ppm chlorine. The *S. Typhi* test strains were washed twice to remove residual media and approximately $1\times10^8$ CFU of each strain were added to triplicate tubes containing the test solution. Raw sewage was retrieved from a local waste water treatment plant in Phoenix, Ariz. Untreated canal water was collected from the Phoenix metropolitan area. Viability of the *S. Typhi* strains was assessed by plating dilutions onto selective media 1, 3, 7 and 10 days after inoculation of the triplicate test solutions with approximately $1\times10^8$ CFU/ml. The limit of detection for recovering the *S. Typhi* strains was $10^4$ CFU/ml.

FIG. 57A-C shows the survival of the *S. Typhi* wild-type χ3744 (wild-type ISP1820), χ3769 (wild-type Ty2), χ8438 ($RpoS^+$ wild-type Ty2) and RASV-Sp strains χ9633 (pYA4088), χ9639(pYA4088) and χ9640(pYA4088) in the environmental test solutions. The RASV-Sp and wild-type strains were extremely sensitive to chlorinated water experiencing several logs of killing after a 30-minute exposure (FIG. 57A). The RASV-Sp strains were less fit than the wild-type strains to persist in canal water decreasing more than 3 logs in titer over the 10-day evaluation period (FIG. 57B). Titers of the RASV-Sp strains in raw sewage dropped steadily decreasing more than 3 logs in titer over the 10-day period (FIG. 57C). These data show that the RASV-Sp strains did not display any enhanced attributes to survive in these environmental test solutions over the Ty2 or ISP1820 wild-type strains.

In summary, the data show that the RASV-Sp strains do not have a competitive advantage in chlorinated water, untreated surface water or sewage over naturally-occurring organisms and are no more likely to persist in these conditions than the wild-type *Salmonella Typhi*.

Example 9

Response to *S. Typhi* Vaccines in Adult Mice Immunized by Intranasal Response Immune Response to *S. Typhi* Vaccines in Adult Mice Immunized by Intranasal Response.

Adult BALB/c mice (7 weeks) were inoculated intranasally with approximately $1 \times 10^9$ CFU of RAStyV strains carrying either rPspA expression plasmid pYA4088 or control plasmid pYA3493 in 10 μl, and boosted with the same dose of the same strain six weeks later. Sera were collected 2, 4, 6 and 8 weeks after vaccination and serum IgG responses to rPspA, *S. Typhi* LPS and *S. Typhi* OMPs were measured by ELISA. This experiment was performed twice, with each group (8 mice) receiving approximately the same dose of vaccine. Sera from all mice in a group were pooled for analysis. Absorbance levels of a secondary anti-mouse antibody conjugated to HRP was recorded at 405 nm using an automated ELISA plate reader (model EL311SX; Biotek, Winooski, Vt.). Absorbance readings that were 0.1 higher than PBS control values were considered positive. The results from both experiments were similar and have been pooled for analysis.

Figure 58A:
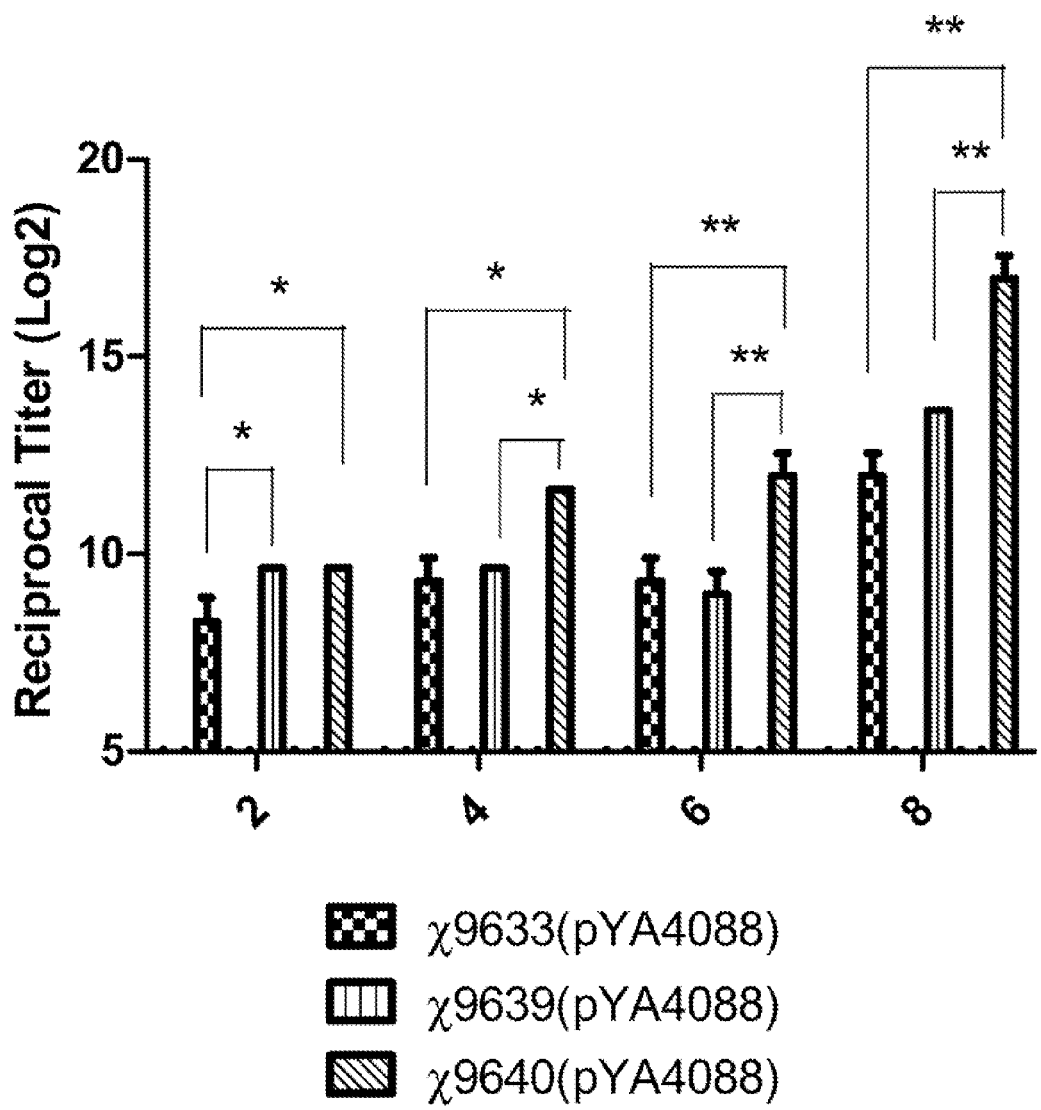
Figure 58B:
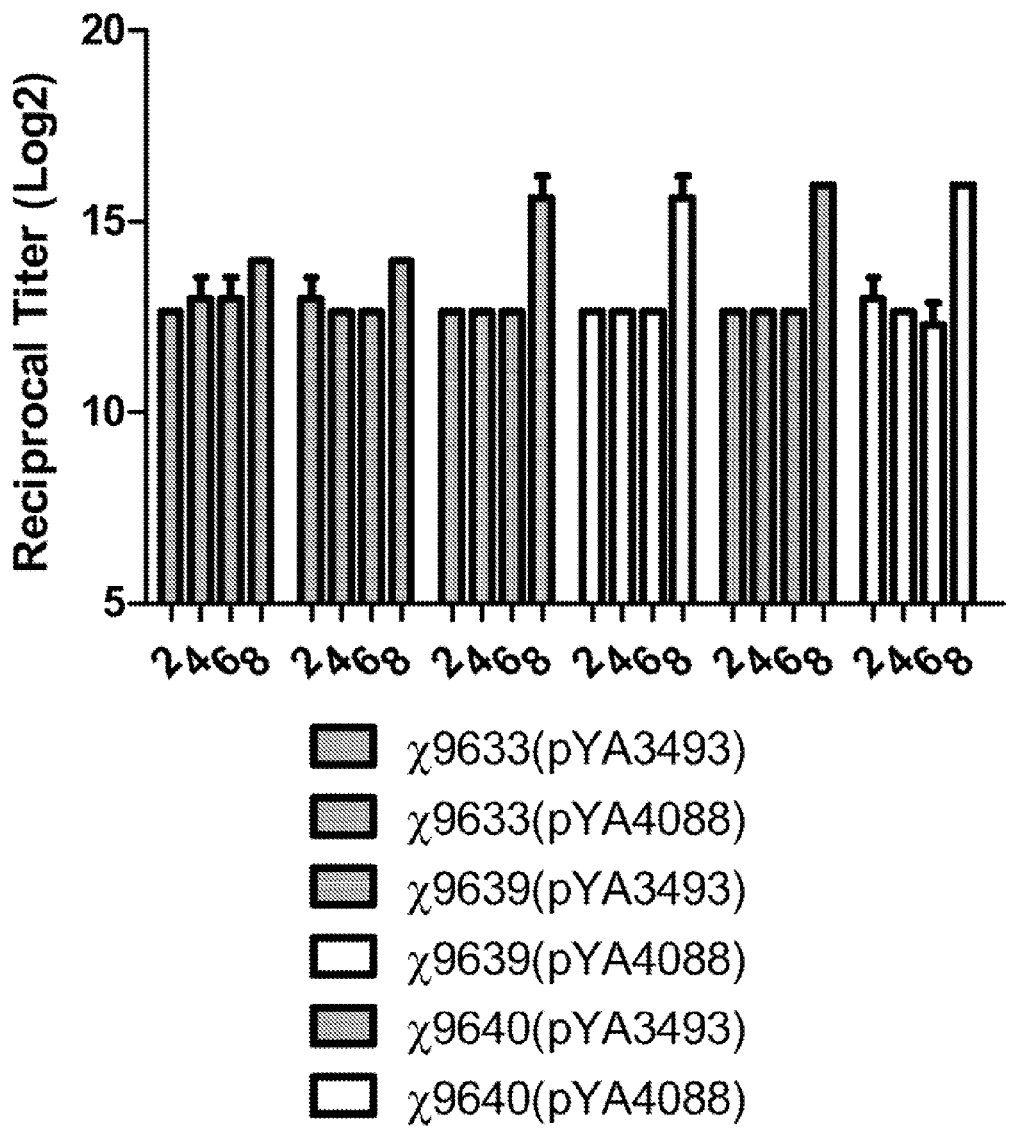
Figure 58C:
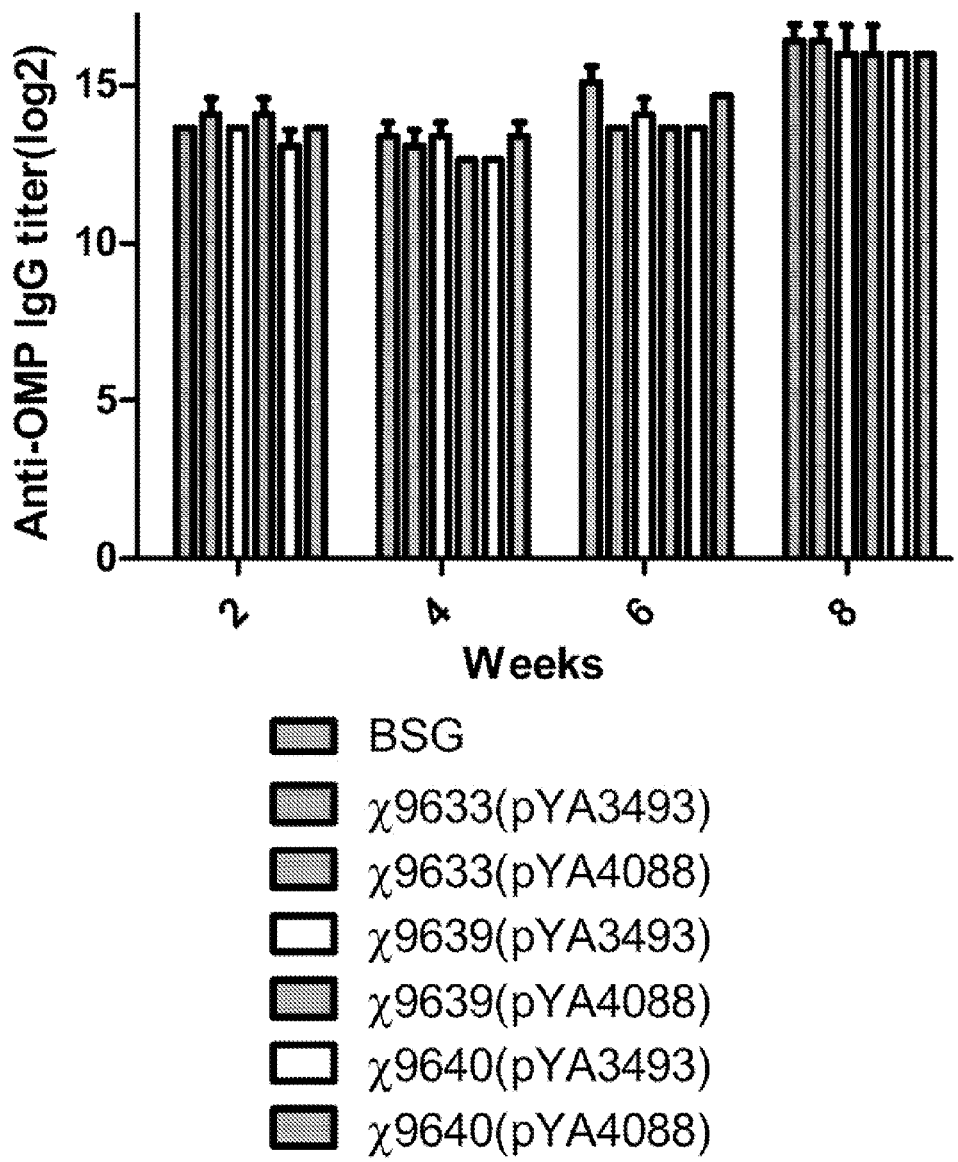

Results: All mice immunized with strains expressing pspA developed anti-PspA antibodies (FIG. 58A). Anti-PspA titers were boosted after the second immunization at 6 weeks. Strain χ9640(pYA4088) (Ty2 RpoS$^+$) induced a significantly higher anti-rPspA IgG titer in mice than those of either the ISP1820 derivative χ9633(pYA4088), or the Ty2 derivative χ9639(pYA4088) at all time points (P<0.01). After boosting, the anti-rPspA IgG antibody levels in χ9639(pYA4088) immunized mice were significantly higher than the mice immunized with χ9633(pYA4088) (P<0.05). No anti-PspA IgG was detected in mice immunized with PBS or strains carrying pYA3493.

All RAStyV strains induced significant anti-LPS titers (FIG. 58B) and OMPs (FIG. 58C) as early as two weeks post inoculation. After the second immunization, significant boosting of serum antibody responses to LPS and OMPs was observed (P<0.01).

Figure 58D:
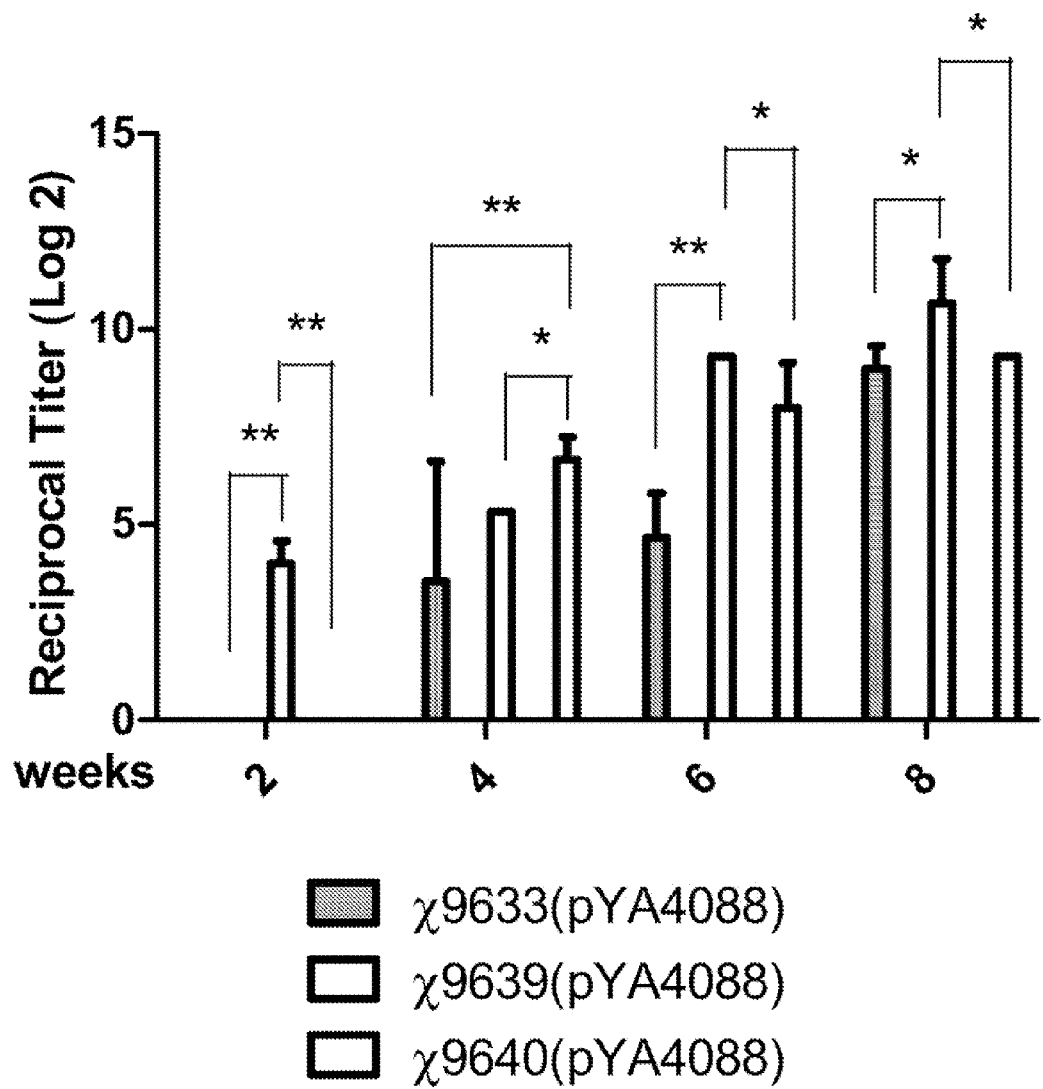

Mucosal IgA anti-PspA responses were slow to develop, but reached high titers after boosting (FIG. 58D).

Protection of Adult Mice Immunized with *S. Typhi* Vaccines Against Challenge with Virulent *S. pneumoniae*.

Method: At week 10, mice were challenged by intraperitoneal injection with $1.0 \times 10^4$ CFU of *S. pneumoniae* WU2 (50 LD$_{50}$) in 100 μl BSG. Challenged mice were monitored daily for 30 days.

Result: All mice immunized with three *S. Typhi* vaccine strains expressing pspA were significantly protected compared with controls (FIG. 41). The protection afforded by the Ty2 derivatives, χ9639 (pYA4088) and χ9640 (pYA4088) was significantly greater than that the protective effects of χ9633 (pYA4088) (\*\*, P<0.01).

Example 10

Comparative Phase I Protocol to Test Safety and Immunogenicity in Adult Volunteers of Three Recombinant Attenuated *Salmonella Typhi* Vaccine Vectors Producing *Streptococcus pneumoniae* Surface Protein Antigen PspA This trial was conducted in compliance with the protocol, International Conference on Harmonisation Good Clinical Practice E6 (ICH-GCP) and the applicable Food and Drug Administration and other Department of Health and Human Services regulatory requirements. Study design is summarized below and in FIG. 59.

Objectives:

Objective 1.

To evaluate maximum safe tolerable single dose levels of the three recombinant attenuated *S. Typhi* vaccine vectors (χ9639(pYA4088) *S. Typhi* Ty2 RpoS$^-$, χ9640(pYA4088) *S. Typhi* Ty2 RpoS$^+$ and χ9633(pYA4088) *S. Typhi* ISP1820) using dose escalation studies in healthy adult volunteers.

Objective 2.

To evaluate immunogenicity of the three recombinant attenuated *S. Typhi* vaccine vectors [χ9639(pYA4088) *S. Typhi* Ty2 RpoS$^-$, χ9640(pYA4088) *S. Typhi* Ty2 RpoS$^+$ and χ9633(pYA4088) *S. Typhi* ISP1820] with regard to their abilities to induce mucosal and systemic antibody and cellular immune responses to the *S. pneumoniae* PspA antigen and to *Salmonella* LPS and outer membrane protein (OMP) antigens.

Study Outcome Measures

Primary Outcome Measures:

Safety and tolerability will be measured by assessment of reactogenicity and Adverse Events following vaccination. Escalation to the next dose level will occur only after review of the safety data from day 28 post-inoculation of the previous Arm.

Secondary Outcome Measures:

Immunogenicity testing will include antibody and/or cellular responses to vaccine at Days 0, 7, 28, 84 and 168.

Hypotheses Tested

The recombinant attenuated χ9639(pYA4088) *S. Typhi* Ty2 RpoS$^-$, χ9640(pYA4088) *S. Typhi* Ty2 RpoS$^+$ and χ9633 (pYA4088) *S. Typhi* ISP1820 vaccine vectors will be safe when given orally to healthy adult human volunteers.

The χ9640(pYA4088) *S. Typhi* Ty2 RpoS$^+$ recombinant attenuated vaccine vector will induce higher titers of antibodies to the *Streptococcus pneumoniae* PspA antigen than will the parental χ9639(pYA4088) *S. Typhi* Ty2 RpoS$^-$ vector.

The χ9633(pYA4088) *S. Typhi* ISP1820 recombinant attenuated vaccine vector will induce higher titers of antibodies to the *Streptococcus pneumoniae* PspA antigen than will either the parental χ9639(pYA4088) *S. Typhi* Ty2 RpoS$^-$ or 9640(pYA4088) *S. Typhi* Ty2 RpoS$^+$ vaccine.

Study Design

The study was a dose escalating study divided into four Arms (1-4). Each Arm will consist of 3 groups (A-C) of 5 healthy young adults 18-40 years of age and each group (A-C) will be administered one of three different vaccine vectors. Each subject will receive an oral dose of vaccine on day 0 and be followed closely to determine the safety, tolerability and immunogenicity of the vector. The vaccine vector found to be both safe and immunogenic with maximum immunogenicity and ease of genetic manipulation will be selected as the parent for second generation vaccine vectors to deliver multiple *S. pneumoniae* protective antigens.

Arm 1 will evaluate the attenuated strains of χ9639 (pYA4088) *S. Typhi* Ty2 RpoS$^-$, χ9640(pYA4088) *S. Typhi* Ty2 RpoS$^+$ and χ9633(pYA4088) *S. Typhi* ISP1820 in an initial single oral dose ($10^7$ CFU), evaluating safety and immunogenicity of the recombinant attenuated strains. An escalation in dose will proceed only after demonstrating the safety and tolerability of the lower vaccine dose through Day 28.

Arm 2 will evaluate an escalation of dose ($10^8$ CFU) for safety and immunogenicity in 3 groups of 5 new volunteers. An escalation dose will proceed only after demonstrating the safety and tolerability of the lower vaccine dose through Day 28.

Arm 3 will evaluate an escalation of dose ($10^9$ CFU) for safety and immunogenicity in 3 groups of 5 new volunteers. An escalation dose will proceed only after demonstrating the safety and tolerability of the lower vaccine dose through Day 28.

Arm 4 will evaluate an escalation of dose ($10^{10}$ CFU) for safety and immunogenicity in 3 groups of 5 new volunteers. This is the highest dose to be tested The dose escalation schedule is provided below:

TABLE 23

Vaccination Schedule
Vaccine Groups and Dose

| (n = 5/group) | A<br>χ9639(pYA4088)<br>Ty2 RpoS$^-$ | B<br>χ9640(pYA4088)<br>Ty2 RpoS$^+$ | C<br>χ9633(pYA4088)<br>ISP1820 |
|---|---|---|---|
| Arm 1 | $10^7$ CFU | $10^7$ CFU | $10^7$ CFU |
| Arm 2 | $10^8$ CFU | $10^8$ CFU | $10^8$ CFU |
| Arm 3 | $10^9$ CFU | $10^9$ CFU | $10^9$ CFU |
| Arm 4 | $10^{10}$ CFU | $10^{10}$ CFU | $10^{10}$ CFU |

The study will enroll Arms 1 through Arms 4 in succession as data are reviewed following each Arm and the Safety Monitoring Committee (SMC) authorizes the next Arm to enroll based on review of 28-day safety data including final blood and stool culture results obtained from previous Arm. This review cycle allows for an interval of a minimum of 35 days of review of all data from the current Arm, after enrollment of the last subjects in the current Arm, before proceeding to the next higher dosage Arm of the study.

Maximum Limit of Tolerability and Dose Escalation of a Specific Strain

Escalation to the next dose level of any of the three vaccine vectors will occur only if the safety data in the preceding dose level cohort for a specific vaccine are acceptable to the SMC and the PI. Escalation to higher dose levels for each of the three vaccines shall proceed in this manner until the highest dose level is reached, or dose-limiting toxicity (maximum limit of tolerability) prevents further dose escalation. Dose escalation of a specific strain shall not proceed in the event that: 3 or more individuals within 1 dose level develop the same severe laboratory abnormality and the abnormality is deemed medically significant by the SMC and is determined to be associated with vaccine; or if 2 or more individuals develop a severe systemic reaction that is determined to be associated with the vaccine; or if 1 individual develops an SAE determined to be associated with vaccine.

Subject Selection Criteria

Volunteers will be healthy 18-40 year old male or non-pregnant female adults who fully understand the purpose and details of the study. Subject exclusion criteria include history of *Salmonella* infection or vaccination, and a history of pneumococcal vaccine.

What is claimed is:

1. A recombinant bacterium capable of the regulated expression of at least one nucleic acid sequence encoding an antigen of interest, wherein the bacterium comprises:
   (a) at least one chromosomally integrated nucleic acid sequence encoding a repressor operably linked to a regulatable promoter wherein the nucleic acid sequence encoding the repressor and/or promoter have been modified from the wild-type nucleic acid sequence so as to optimize the expression level of the nucleic acid sequence encoding the repressor, and;
   (b) a vector comprising a nucleic acid sequence encoding at least one antigen of interest operably linked to a promoter regulated by the repressor, such that the expression of the nucleic acid sequence encoding the antigen is repressed during in vitro growth of the bacterium, but the bacterium is capable of high level expression of the nucleic acid sequence encoding the antigen in a host; and
   (c) the mutation $\Delta P_{crp}$::TT araC $P_{BAD}$ crp.

2. The recombinant bacterium of claim 1, wherein the repressor is selected from the group consisting of LacI, C2, and C1.

3. The recombinant bacterium of claim 1, wherein the bacterium comprises at least two chromosomally integrated nucleic acid sequences, wherein at least one chromosomally integrated nucleic acid sequence encodes a repressor operably linked to a regulatable promoter selected from the group consisting of $P_{rhaBAD}$, $P_{xylAB}$, and $P_{xylFGH}$, and the second chromosomally integrated nucleic acid sequence encodes a repressor operably linked to a regulatable promoter.

4. The recombinant bacterium of claim 3, wherein the repressors are independently selected from the group consisting of LacI, C2, and C1.

5. The recombinant bacterium of claim 1, wherein the codons of the nucleic acid sequence encoding the repressor have been modified so as to optimize the expression level of the nucleic acid sequence encoding the repressor.

6. The recombinant bacterium of claim 1, wherein the repressor comprises a modified Shine-Dalgarno sequence and optimized codons so as to optimize the expression level of the nucleic acid sequence encoding the repressor.

7. The recombinant bacterium of claim 1, wherein the vector is a plasmid.

8. The recombinant bacterium of claim 1, wherein the nucleic acid encoding an antigen of interest is operably linked to a promoter regulated by a repressor selected from the group consisting of LacI, C1, and C2.

9. The recombinant bacterium of claim 1, wherein the nucleic acid encoding an antigen of interest is operably linked to a $P_{trc}$ promoter.

10. The recombinant bacterium of claim 1, wherein the antigen is toxic.

11. The recombinant bacterium of claim 1, wherein the vector further comprises a nucleic acid sequence encoding a secretion signal for the antigen of interest.

12. The recombinant bacterium of claim 1, wherein the bacterium elicits a protective immune response in the host.

13. The recombinant bacterium of claim 1, wherein the bacterium comprises more than one means of attenuation.

14. The recombinant bacterium of claim 1, wherein the repressor is LacI; the $P_{xylFGH}$, the vector is a plasmid; and the nucleic acid encoding an antigen of interest is operably linked to the $P_{trc}$ promoter.

15. A vaccine composition comprising the recombinant bacterium of claim 1.

16. A method for eliciting an immune response in a host, the method comprising administering to the host an effective amount of a vaccine composition comprising a recombinant bacterium of claim 1.

\* \* \* \* \*

SEQUENCE LISTING

<160> NUMBER OF SEQ ID NOS: 58

<210> SEQ ID NO 1
<211> LENGTH: 15
<212> TYPE: DNA
<213> ORGANISM: Artificial Sequence
<220> FEATURE:
<223> OTHER INFORMATION: SALMONELLA

<400> SEQUENCE: 1
agggtggtga atgtg                                                     15

<210> SEQ ID NO 2
<211> LENGTH: 15
<212> TYPE: DNA
<213> ORGANISM: Artificial Sequence
<220> FEATURE:
<223> OTHER INFORMATION: SALMONELLA

<400> SEQUENCE: 2
aggatggtga atatg                                                     15

<210> SEQ ID NO 3
<211> LENGTH: 14
<212> TYPE: DNA
<213> ORGANISM: Artificial Sequence
<220> FEATURE:
<223> OTHER INFORMATION: SALMONELLA

<400> SEQUENCE: 3
aggatggtga atag                                                      14

<210> SEQ ID NO 4
<211> LENGTH: 15
<212> TYPE: DNA
<213> ORGANISM: Artificial Sequence
<220> FEATURE:
<223> OTHER INFORMATION: SALMONELLA

<400> SEQUENCE: 4
agggtggtga atgtg                                                     15

<210> SEQ ID NO 5
<211> LENGTH: 15
<212> TYPE: DNA
<213> ORGANISM: Artificial Sequence
<220> FEATURE:
<223> OTHER INFORMATION: SALMONELLA

<400> SEQUENCE: 5
aggatggtga atatg 15

<210> SEQ ID NO 6
<211> LENGTH: 15
<212> TYPE: DNA
<213> ORGANISM: Artificial Sequence
<220> FEATURE:
<223> OTHER INFORMATION: SALMONELLA

<400> SEQUENCE: 6
aggatggtga atatg 15

<210> SEQ ID NO 7
<211> LENGTH: 1094
<212> TYPE: DNA
<213> ORGANISM: Artificial Sequence
<220> FEATURE:
<223> OTHER INFORMATION: SALMONELLA

<400> SEQUENCE: 7

```
agggtggtga atgtgaaacc agtaacgtta tacgatgtcg cagagtatgc cggtgtctct    60
tatcagaccg tttccgcgt ggtgaaccag gccagccacg ttctgcgaaa acgcgggaaa   120
aagtggaagc ggcgatggcg gagctgaatt acattcccaa ccgcgtggca caacaactgg   180
cgggcaaaca gtcgttgctg attggcgttg ccacctccag tctggccctg cacgcgccgt   240
cgcaaattgt cgcggcgatt aaatctcgcg ccgatcaact gggtgccagc gtggtggtgt   300
cgatggtaga acgaagcggc gtcgaagcct gtaaagcggc ggtgcacaat cttctcgcgc   360
aacgcgtcag tgggctgatc attaactatc cgctggatga ccaggatgcc attgctgtgg   420
aagctgcctg cactaatgtt ccggcgttat ttcttgatgt ctctgaccag acacccatca   480
acagtattat tttctcccat gaagacggta cgcgactggg cgtggagcat ctggtcgcat   540
tgggtcacca gcaaatcgcg ctgttagcgg gcccattaag ttctgtctcg gcgcgtctgc   600
gtctggctgg ctggcataaa tatctcactc gcaatcaaat tcagccgata gcggaacggg   660
aaggcgactg gagtgccatg tccggttttc aacaaaccat gcaaatgctg aatgagggca   720
tcgttcccac tgcgatgctg gttgccaacg atcagatggc gctgggcgca atgcgcgcca   780
ttaccgagtc cgggctgcgc gttggtgcgg atatctcggt agtgggatac gacgataccg   840
aagacagctc atgttatatc ccgccgttaa ccaccatcaa acaggatttt cgcctgctgg   900
ggcaaaccag cgtggaccgc ttgctgcaac tctctcaggg ccaggcggtg aagggcaatc   960
agctgttgcc cgtctcactg gtaaaaagaa aaaccaccct ggcgcccaat acgcaaaccg  1020
cctctccccg cgcgttggcc gattcattaa tgcagctggc acgacaggtt tcccgactgg  1080
aaagcgggca gtga                                                   1094
```

<210> SEQ ID NO 8
<211> LENGTH: 1094
<212> TYPE: DNA
<213> ORGANISM: Artificial Sequence
<220> FEATURE:

<223> OTHER INFORMATION: SALMONELLA

<400> SEQUENCE: 8

| aggatggtga atatgaaacc agtaacgtta tacgatgtcg cagagtatgc cggtgtctct | 60 |
| tatcagaccg tttccgcgt ggtgaaccag gccagccacg ttctgcgaaa acgcgggaaa | 120 |
| aagtggaagc ggcgatggcg gagctgaatt acattcccaa ccgcgtggca caacaactgg | 180 |
| cgggcaaaca gtcgttgctg attggcgttg ccacctccag tctggccctg cacgcgccgt | 240 |
| cgcaaattgt cgcggcgatt aaatctcgcg ccgatcaact gggtgccagc gtggtggtgt | 300 |
| cgatggtaga acgaagcggc gtcgaagcct gtaaagcggc ggtgcacaat cttctcgcgc | 360 |
| aacgcgtcag tgggctgatc attaactatc cgctggatga ccaggatgcc attgctgtgg | 420 |
| aagctgcctg cactaatgtt ccggcgttat ttcttgatgt ctctgaccag acacccatca | 480 |
| acagtattat tttctcccat gaagacggta cgcgactggg cgtggagcat ctggtcgcat | 540 |
| tgggtcacca gcaaatcgcg ctgttagcgg gcccattaag ttctgtctcg gcgcgtctgc | 600 |
| gtctggctgg ctggcataaa tatctcactc gcaatcaaat tcagccgata gcggaacggg | 660 |
| aaggcgactg gagtgccatg tccggttttc aacaaaccat gcaaatgctg aatgagggca | 720 |
| tcgttcccac tgcgatgctg gttgccaacg atcagatggc gctgggcgca atgcgcgcca | 780 |
| ttaccgagtc cgggctgcgc gttggtgcgg atatctcggt agtgggatac gacgataccg | 840 |
| aagacagctc atgttatatc ccgccgttaa ccaccatcaa acaggattt cgcctgctgg | 900 |
| ggcaaaccag cgtggaccgc ttgctgcaac tctctcaggg ccaggcggtg aagggcaatc | 960 |
| agctgttgcc cgtctcactg gtaaaaagaa aaaccaccct ggcgcccaat acgcaaaccg | 1020 |
| cctctccccg cgcgttggcc gattcattaa tgcagctggc acgacaggtt tcccgactgg | 1080 |
| aaagcgggca gtga | 1094 |

<210> SEQ ID NO 9
<211> LENGTH: 1094
<212> TYPE: DNA
<213> ORGANISM: Artificial Sequence
<220> FEATURE:
<223> OTHER INFORMATION: SALMONELLA

<400> SEQUENCE: 9

| aggatggtga atatgaaacc agtaacgtta tacgatgtcg cagagtatgc cggtgtctct | 60 |
| tatcagaccg tttccgcgt ggtgaaccag gccagccacg ttctgcgaaa acgcgtgaaa | 120 |
| aagtggaagc ggcgatggcg gagctgaatt acattccgaa ccgcgtggca caacaactgg | 180 |
| cgggcaaaca gtcgttgctg attggcgttg ccacctccag tctggccctg cacgcgccgt | 240 |
| cgcaaattgt cgcggcgatt aaatctcgcg ccgatcaact gggtgccagc gtggtggtgt | 300 |
| cgatggtaga acgtagcggc gtcgaagcct gtaaagcggc ggtgcacaat cttctcgcgc | 360 |
| aacgcgtcag tgggctgatc attaactatc cgctggatga ccaggatgcc attgctgtgg | 420 |
| aagctgcctg cactaatgtt ccggcgttat ttcttgatgt ctctgaccag acaccgatca | 480 |
| acagtattat tttctcccat gaagacggta cgcgtctggg cgtggagcat ctggtcgcat | 540 |
| tgggtcacca gcaaatcgcg ctgttagcgg gcccattaag ttctgtctcg gcgcgtctgc | 600 |
| gtctggctgg ctggcataaa tatctcactc gcaatcaaat tcagccgatc gcggaacgtg | 660 |
| aaggcgactg gagtgccatg tccggttttc aacaaaccat gcaaatgctg aatgagggca | 720 |
| tcgttccgac tgcgatgctg gttgccaacg atcagatggc gctgggcgca atgcgcgcca | 780 |
| ttaccgagtc cgggctgcgc gttggtgcgg atatctcggt agtgggttac gacgataccg | 840 |

```
aagacagctc atgttatatc ccgccgttaa ccaccatcaa acaggatttt cgcctgctgg     900
ggcaaaccag cgtggaccgc ttgctgcaac tctctcaggg ccaggcggtg aagggcaatc     960
agctgttgcc cgtctcactg gtaaaacgta aaccaccct ggcgcccaat acgcaaaccg    1020
cctctccgcg cgcgttggcc gattcattaa tgcagctggc acgtcaggtt tcccgtctgg    1080
aaagcgggca gtga                                                     1094
```

<210> SEQ ID NO 10
<211> LENGTH: 360
<212> TYPE: PRT
<213> ORGANISM: Artificial Sequence
<220> FEATURE:
<223> OTHER INFORMATION: SALMONELLA

<400> SEQUENCE: 10

```
Val Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
                20                  25                  30

Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
        50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
                100                 105                 110

Asn Leu Leu Ala Gln Arg Val Ser Gly Leu Ile Ile Asn Tyr Pro Leu
            115                 120                 125

Asp Asp Gln Asp Ala Ile Ala Val Glu Ala Ala Cys Thr Asn Val Pro
        130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
```

```
            305                 310                 315                 320
Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

<210> SEQ ID NO 11
<211> LENGTH: 19
<212> TYPE: DNA
<213> ORGANISM: Artificial Sequence
<220> FEATURE:
<223> OTHER INFORMATION: SALMONELLA

<400> SEQUENCE: 11
aggagactta actatgaat                                                  19

<210> SEQ ID NO 12
<211> LENGTH: 19
<212> TYPE: DNA
<213> ORGANISM: Artificial Sequence
<220> FEATURE:
<223> OTHER INFORMATION: SALMONELLA

<400> SEQUENCE: 12
aggagactta actatgaat                                                  19

<210> SEQ ID NO 13
<211> LENGTH: 21
<212> TYPE: DNA
<213> ORGANISM: Artificial Sequence
<220> FEATURE:
<223> OTHER INFORMATION: SALMONELLA

<400> SEQUENCE: 13
taaggaggtt aactatgaa t                                                21

<210> SEQ ID NO 14
<211> LENGTH: 21
<212> TYPE: DNA
<213> ORGANISM: Artificial Sequence
<220> FEATURE:
<223> OTHER INFORMATION: SALMONELLA

<400> SEQUENCE: 14
taaggaggtt aactatgaa a                                                21

<210> SEQ ID NO 15
<211> LENGTH: 651
<212> TYPE: DNA
<213> ORGANISM: Artificial Sequence
<220> FEATURE:
<223> OTHER INFORMATION: SALMONELLA

<400> SEQUENCE: 15
atgaatacac aattgatggg tgagcgtatt cgcgctcgaa gaaaaaaact caagattaga    60
caagccgctc ttggtaagat ggtgggagtg tctaatgttg caatatcgca atgggagcgc   120
tcggagactg agccaaatgg ggagaacctg ttggcacttt cgaaggctct tcagtgctcc   180
cctgactatt tgctgaaagg agatttaagc cagacaaacg ttgcctatca tagtaggcat   240
gagccaagag gatcataccc tcttatcagt tgggtaagcg cagggcaatg gatggaagct   300
```

```
gtagaacctt atcacaagcg cgcgatagag aactggcacg acaccactgt agattgttca    360
gaagattcat tttggcttga tgtccaaggt gactctatga cagcaccggc agggttaagc    420
attccagaag gaatgataat tctggttgat cccgaagtcg aaccaagaaa cggcaagctg    480
gttgttgcaa aattagaagg tgaaaacgag gccacattca aaaaattagt tatggatgca    540
ggccgaaagt ttttaaaacc attaaaccca caatatccga tgatagaaat caacggaaac    600
tgcaaaatca ttggcgtagt tgttgacgca aaactcgcaa atcttccata a             651
```

<210> SEQ ID NO 16
<211> LENGTH: 651
<212> TYPE: DNA
<213> ORGANISM: Artificial Sequence
<220> FEATURE:
<223> OTHER INFORMATION: SALMONELLA

<400> SEQUENCE: 16

```
atgaatacac aattgatggg tgagcgtatt cgcgctcgtc gtaaaaaact caagattcgt     60
caagccgctc ttggtaagat ggtgggtgtg tctaatgttg caatctcgca atgggagcgc    120
tcggagactg agccaaatgg ggagaacctg ttggcacttt cgaaggctct tcagtgctcc    180
cctgactatt tgctgaaagg tgatttaagc cagacaaacg ttgcctatca tagtcgtcat    240
gagccacgtg gttcataccc tcttatcagt tgggtaagcg cagggcaatg gatggaagct    300
gtagaacctt atcacaagcg cgcgatcgag aactggcacg acaccactgt agattgttca    360
gaagattcat tttggcttga tgtccaaggt gactctatga cagcaccggc agggttaagc    420
attccagaag gtatgatcat tctggttgat ccggaagtcg aaccacgtaa cggcaagctg    480
gttgttgcaa aattagaagg tgaaaacgag gccacattca aaaaattagt tatggatgca    540
ggccgtaagt ttttaaaacc attaaaccca caatatccga tgatcgaaat caacggtaac    600
tgcaaaatca ttggcgtagt tgttgacgca aaactcgcaa atcttccata a             651
```

<210> SEQ ID NO 17
<211> LENGTH: 216
<212> TYPE: PRT
<213> ORGANISM: Artificial Sequence
<220> FEATURE:
<223> OTHER INFORMATION: SALMONELLA

<400> SEQUENCE: 17

```
Met Asn Thr Gln Leu Met Gly Glu Arg Ile Arg Ala Arg Lys Lys Leu
 1               5                  10                  15

Lys Leu Ile Arg Gln Ala Ala Leu Gly Lys Met Val Gly Val Ser Asn
             20                  25                  30

Val Ala Ile Ser Gln Trp Glu Arg Ser Glu Thr Glu Pro Asn Gly Glu
         35                  40                  45

Asn Leu Leu Ala Leu Ser Lys Ala Leu Gln Cys Ser Pro Asp Tyr Leu
     50                  55                  60

Leu Lys Gly Asp Leu Ser Gln Thr Asn Val Ala Tyr His Ser Arg His
 65                  70                  75                  80

Glu Pro Arg Gly Ser Tyr Pro Leu Ile Ser Trp Val Ser Ala Gly Gln
                 85                  90                  95

Trp Met Glu Ala Val Glu Pro Tyr His Lys Arg Ala Ile Glu Asn Trp
            100                 105                 110

His Asp Thr Thr Val Asp Cys Ser Glu Asp Ser Phe Trp Leu Asp Val
        115                 120                 125

Gln Gly Asp Ser Met Thr Ala Pro Ala Gly Leu Ser Ile Pro Glu Gly
```

```
                130                 135                 140
Met Ile Ile Leu Val Asp Pro Glu Val Glu Pro Arg Asn Gly Lys Leu
145                 150                 155                 160

Val Val Ala Lys Leu Glu Gly Glu Asn Glu Ala Thr Phe Lys Lys Leu
                165                 170                 175

Val Met Asp Ala Gly Arg Lys Phe Leu Lys Pro Leu Asn Pro Gln Tyr
            180                 185                 190

Pro Met Ile Glu Ile Asn Gly Asn Cys Lys Ile Ile Gly Val Val Val
        195                 200                 205

Asp Ala Lys Leu Ala Asn Leu Pro
    210                 215

<210> SEQ ID NO 18
<211> LENGTH: 112
<212> TYPE: DNA
<213> ORGANISM: Artificial Sequence
<220> FEATURE:
<223> OTHER INFORMATION: SALMONELLA

<400> SEQUENCE: 18
tttatccata agattagcgg atcctacctg acgcttttta tcgcaactct ctactgtttc      60
tccatacccg ttttttgggg ctagcctcga gggtacctaa ggaggtttaa ct             112

<210> SEQ ID NO 19
<211> LENGTH: 112
<212> TYPE: DNA
<213> ORGANISM: Artificial Sequence
<220> FEATURE:
<223> OTHER INFORMATION: SALMONELLA

<400> SEQUENCE: 19
tttatccata agattagcgg atcctacctg acgcttttta tcgcaactct ctataatttc      60
tccatacccg ttttttgggg ctagcctcga gggtacctaa ggaggtttaa ct             112

<210> SEQ ID NO 20
<211> LENGTH: 60
<212> TYPE: DNA
<213> ORGANISM: Artificial Sequence
<220> FEATURE:
<223> OTHER INFORMATION: SALMONELLA

<400> SEQUENCE: 20
atgaatacac aattgatggg tgagcgtatt cgcgctcgtc gtaaaaaact caagattcgt      60

<210> SEQ ID NO 21
<211> LENGTH: 60
<212> TYPE: DNA
<213> ORGANISM: Artificial Sequence
<220> FEATURE:
<223> OTHER INFORMATION: SALMONELLA

<400> SEQUENCE: 21
atgaatacac aattgatggg tgagcgtatt cgcgctcgtc gtaaaaaact caagattcgt      60

<210> SEQ ID NO 22
<211> LENGTH: 20
<212> TYPE: PRT
<213> ORGANISM: Artificial Sequence
<220> FEATURE:
<223> OTHER INFORMATION: SALMONELLA

<400> SEQUENCE: 22
```

Met Asn Thr Gln Leu Met Gly Glu Arg Ile Arg Ala Arg Arg Lys Lys
1               5                   10                  15

Leu Lys Ile Arg
            20

<210> SEQ ID NO 23
<211> LENGTH: 20
<212> TYPE: PRT
<213> ORGANISM: Artificial Sequence
<220> FEATURE:
<223> OTHER INFORMATION: SALMONELLA

<400> SEQUENCE: 23

Met Lys Thr Gln Leu Met Gly Glu Arg Ile Arg Ala Arg Arg Lys Lys
1               5                   10                  15

Leu Lys Ile Arg
            20

<210> SEQ ID NO 24
<211> LENGTH: 23
<212> TYPE: DNA
<213> ORGANISM: Artificial Sequence
<220> FEATURE:
<223> OTHER INFORMATION: SALMONELLA

<400> SEQUENCE: 24
aggacagatt ccgcatgact gac                                         23

<210> SEQ ID NO 25
<211> LENGTH: 23
<212> TYPE: DNA
<213> ORGANISM: Artificial Sequence
<220> FEATURE:
<223> OTHER INFORMATION: SALMONELLA

<400> SEQUENCE: 25
aggacagatt ccgcgtgact gac                                         23

<210> SEQ ID NO 26
<211> LENGTH: 23
<212> TYPE: DNA
<213> ORGANISM: Artificial Sequence
<220> FEATURE:
<223> OTHER INFORMATION: SALMONELLA

<400> SEQUENCE: 26
aaggcagatt ccgcgtgact gac                                         23

<210> SEQ ID NO 27
<211> LENGTH: 23
<212> TYPE: DNA
<213> ORGANISM: Artificial Sequence
<220> FEATURE:
<223> OTHER INFORMATION: SALMONELLA

<400> SEQUENCE: 27
agggagaaga gatgatgcgc gta                                         23

<210> SEQ ID NO 28
<211> LENGTH: 23
<212> TYPE: DNA
<213> ORGANISM: Artificial Sequence
<220> FEATURE:
<223> OTHER INFORMATION: SALMONELLA

<400> SEQUENCE: 28
agggagaaga ggtggtgcgc gta                                      23

<210> SEQ ID NO 29
<211> LENGTH: 23
<212> TYPE: DNA
<213> ORGANISM: Artificial Sequence
<220> FEATURE:
<223> OTHER INFORMATION: SALMONELLA

<400> SEQUENCE: 29
aaggcgaaga ggtggtgcgc gta                                      23

<210> SEQ ID NO 30
<211> LENGTH: 23
<212> TYPE: DNA
<213> ORGANISM: Artificial Sequence
<220> FEATURE:
<223> OTHER INFORMATION: SALMONELLA

<400> SEQUENCE: 30
aaggcgaaga ggtgatgcgc gta                                      23

<210> SEQ ID NO 31
<211> LENGTH: 20
<212> TYPE: DNA
<213> ORGANISM: Artificial Sequence
<220> FEATURE:
<223> OTHER INFORMATION: SALMONELLA

<400> SEQUENCE: 31
aaggcgagat gatgcgcgta                                          20

<210> SEQ ID NO 32
<211> LENGTH: 26
<212> TYPE: DNA
<213> ORGANISM: Artificial Sequence
<220> FEATURE:
<223> OTHER INFORMATION: SALMONELLA

<400> SEQUENCE: 32
aaggcctcga agagatgatg cgcgta                                   26

<210> SEQ ID NO 33
<211> LENGTH: 114
<212> TYPE: DNA
<213> ORGANISM: Artificial Sequence
<220> FEATURE:
<223> OTHER INFORMATION: SALMONELLA

<400> SEQUENCE: 33
attcatagtt aagtcatctt aaataaactt gactaaagat tcctttagta gataatttaa    60
gtgttcttta atttcggagc gagtctatgt ggatggagta agacgmtggc aatt         114

<210> SEQ ID NO 34
<211> LENGTH: 105
<212> TYPE: DNA
<213> ORGANISM: Artificial Sequence
<220> FEATURE:
<223> OTHER INFORMATION: SALMONELLA

<400> SEQUENCE: 34
cctggtacct aggcctctag ataaataaaa gcagtttaca actcctagaa ttgtgaatat    60
attatcacaa ttctaggata gaataataaa agatctctgc agggc                   105

<210> SEQ ID NO 35
<211> LENGTH: 34
<212> TYPE: DNA
<213> ORGANISM: Artificial Sequence
<220> FEATURE:
<223> OTHER INFORMATION: SALMONELLA

<400> SEQUENCE: 35
agaggtaccc tcgaggctag cccaaaaaaa cggg                                    34

<210> SEQ ID NO 36
<211> LENGTH: 34
<212> TYPE: DNA
<213> ORGANISM: Artificial Sequence
<220> FEATURE:
<223> OTHER INFORMATION: SALMONELLA

<400> SEQUENCE: 36
tggtctagag tcaagccgtc aattgtctga ttcg                                    34

<210> SEQ ID NO 37
<211> LENGTH: 30
<212> TYPE: DNA
<213> ORGANISM: Artificial Sequence
<220> FEATURE:
<223> OTHER INFORMATION: SALMONELLA

<400> SEQUENCE: 37
ggaattctca ctgcccgctt tccagtcggg                                         30

<210> SEQ ID NO 38
<211> LENGTH: 38
<212> TYPE: DNA
<213> ORGANISM: Artificial Sequence
<220> FEATURE:
<223> OTHER INFORMATION: SALMONELLA

<400> SEQUENCE: 38
ccgctcgaga gggtggtgaa tgtgaaacca gtaacgtt                                38

<210> SEQ ID NO 39
<211> LENGTH: 39
<212> TYPE: DNA
<213> ORGANISM: Artificial Sequence
<220> FEATURE:
<223> OTHER INFORMATION: SALMONELLA

<400> SEQUENCE: 39
cccaagcttg agctcgaggg cgttccggcg ctggtagaa                               39

<210> SEQ ID NO 40
<211> LENGTH: 29
<212> TYPE: DNA
<213> ORGANISM: Artificial Sequence
<220> FEATURE:
<223> OTHER INFORMATION: SALMONELLA

<400> SEQUENCE: 40
gaagatctaa gggaccaggc ctaccgaag                                          29

<210> SEQ ID NO 41
<211> LENGTH: 35
<212> TYPE: DNA
<213> ORGANISM: Artificial Sequence
<220> FEATURE:
<223> OTHER INFORMATION: SALMONELLA

```
<400> SEQUENCE: 41
cggaattcac cccagacagt aatcatgtag cggct                              35

<210> SEQ ID NO 42
<211> LENGTH: 31
<212> TYPE: DNA
<213> ORGANISM: Artificial Sequence
<220> FEATURE:
<223> OTHER INFORMATION: SALMONELLA

<400> SEQUENCE: 42
cgggtacccc agatattttc cagatcttca c                                  31

<210> SEQ ID NO 43
<211> LENGTH: 30
<212> TYPE: DNA
<213> ORGANISM: Artificial Sequence
<220> FEATURE:
<223> OTHER INFORMATION: SALMONELLA

<400> SEQUENCE: 43
ggaattctca ctgcccgctt tccagtcggg                                    30

<210> SEQ ID NO 44
<211> LENGTH: 38
<212> TYPE: DNA
<213> ORGANISM: Artificial Sequence
<220> FEATURE:
<223> OTHER INFORMATION: SALMONELLA

<400> SEQUENCE: 44
ccgctcgaga ggatggtgaa tatgaaacca gtaacgtt                           38

<210> SEQ ID NO 45
<211> LENGTH: 30
<212> TYPE: DNA
<213> ORGANISM: Artificial Sequence
<220> FEATURE:
<223> OTHER INFORMATION: SALMONELLA

<400> SEQUENCE: 45
tctccggtag ccagtcagtc taaagctgag                                    30

<210> SEQ ID NO 46
<211> LENGTH: 76
<212> TYPE: DNA
<213> ORGANISM: Artificial Sequence
<220> FEATURE:
<223> OTHER INFORMATION: SALMONELLA

<400> SEQUENCE: 46
ctaattcagc ttttttagca gcaatagttt tctctaaacc ttctttaaag tagtcttcta   60
cattattgtt ttcttc                                                   76

<210> SEQ ID NO 47
<211> LENGTH: 30
<212> TYPE: DNA
<213> ORGANISM: Artificial Sequence
<220> FEATURE:
<223> OTHER INFORMATION: SALMONELLA

<400> SEQUENCE: 47
tctccggtag ccagtcagtc taaagctgag                                    30
```

```
<210> SEQ ID NO 48
<211> LENGTH: 63
<212> TYPE: DNA
<213> ORGANISM: Artificial Sequence
<220> FEATURE:
<223> OTHER INFORMATION: SALMONELLA

<400> SEQUENCE: 48
tgctttctta aggtcagctt cagttttttc taattcagct tttttagcag caatagtttt    60
ctc                                                                  63

<210> SEQ ID NO 49
<211> LENGTH: 28
<212> TYPE: DNA
<213> ORGANISM: Artificial Sequence
<220> FEATURE:
<223> OTHER INFORMATION: SALMONELLA

<400> SEQUENCE: 49
ggaattctct ccggtagcca gtcagtct                                       28

<210> SEQ ID NO 50
<211> LENGTH: 34
<212> TYPE: DNA
<213> ORGANISM: Artificial Sequence
<220> FEATURE:
<223> OTHER INFORMATION: SALMONELLA

<400> SEQUENCE: 50
ttcaagctta ttatgctttc ttaaggtcag cttc                                34

<210> SEQ ID NO 51
<211> LENGTH: 34
<212> TYPE: DNA
<213> ORGANISM: Artificial Sequence
<220> FEATURE:
<223> OTHER INFORMATION: SALMONELLA

<400> SEQUENCE: 51
gggaattccg atgagtaaag gagaagaact tttc                                34

<210> SEQ ID NO 52
<211> LENGTH: 35
<212> TYPE: DNA
<213> ORGANISM: Artificial Sequence
<220> FEATURE:
<223> OTHER INFORMATION: SALMONELLA

<400> SEQUENCE: 52
cggtgcaagc ttattatttg tatagttcat ccatg                               35

<210> SEQ ID NO 53
<211> LENGTH: 22
<212> TYPE: DNA
<213> ORGANISM: Artificial Sequence
<220> FEATURE:
<223> OTHER INFORMATION: SALMONELLA

<400> SEQUENCE: 53
cgggatcctg gtagggaacg ac                                             22

<210> SEQ ID NO 54
<211> LENGTH: 34
<212> TYPE: DNA
<213> ORGANISM: Artificial Sequence
```

```
<220> FEATURE:
<223> OTHER INFORMATION: SALMONELLA

<400> SEQUENCE: 54
gatgccatgg tttaaactat attcagcaaa tgcg                                    34

<210> SEQ ID NO 55
<211> LENGTH: 35
<212> TYPE: DNA
<213> ORGANISM: Artificial Sequence
<220> FEATURE:
<223> OTHER INFORMATION: SALMONELLA

<400> SEQUENCE: 55
gatgccatgg tctgtttcct cgtcttactc catcc                                   35

<210> SEQ ID NO 56
<211> LENGTH: 23
<212> TYPE: DNA
<213> ORGANISM: Artificial Sequence
<220> FEATURE:
<223> OTHER INFORMATION: SALMONELLA

<400> SEQUENCE: 56
acatgcatgc ggacgatcga taa                                                23

<210> SEQ ID NO 57
<211> LENGTH: 39
<212> TYPE: DNA
<213> ORGANISM: Artificial Sequence
<220> FEATURE:
<223> OTHER INFORMATION: SALMONELLA

<400> SEQUENCE: 57
cccaagcttg agctcgaggg cgttccggcg ctggtagaa                               39

<210> SEQ ID NO 58
<211> LENGTH: 31
<212> TYPE: DNA
<213> ORGANISM: Artificial Sequence
<220> FEATURE:
<223> OTHER INFORMATION: SALMONELLA

<400> SEQUENCE: 58
cgggtacccc agatattttc cagatcttca c                                       31
```